United States Patent
Vendeville

(10) Patent No.: US 11,136,321 B2
(45) Date of Patent: Oct. 5, 2021

(54) TRICYCLIC COMPOUNDS

(71) Applicant: ALIGOS THERAPEUTICS, INC., South San Francisco, CA (US)

(72) Inventor: Sandrine Vendeville, Brussels (BE)

(73) Assignee: Aligos Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 16/885,128

(22) Filed: May 27, 2020

(65) Prior Publication Data

US 2020/0407361 A1     Dec. 31, 2020

Related U.S. Application Data

(60) Provisional application No. 62/854,597, filed on May 30, 2019.

(51) Int. Cl.
*C07D 471/14*     (2006.01)
*A61K 31/519*     (2006.01)

(52) U.S. Cl.
CPC .................. *C07D 471/14* (2013.01)

(58) Field of Classification Search
CPC ..... C07D 471/14; A61K 31/519; A61P 31/20; A61P 31/12
USPC .......................................... 544/251; 514/257
See application file for complete search history.

(56) References Cited

FOREIGN PATENT DOCUMENTS

| WO | WO 2008/090379 | 7/2008 |
|----|----|----|
| WO | WO 2008/157273 | 12/2008 |
| WO | WO 2015/065338 | 5/2015 |

OTHER PUBLICATIONS

Fang, Z., et al., "Discovery of pyrazolo [1, 5-a] pyrimidine-3-carbonitrile derivatives as a new class of histone lysine demethylase 4D (KDM4D) inhibitors" Bioorganic & Medicinal Chemistry Letters (2017) 27(14):3201-3204.
International Search Report and Written Opinion dated Aug. 3, 2020 for PCT Application No. PCT/US2020/034746, filed May 27, 2020.

*Primary Examiner* — Charanjit Aulakh
(74) *Attorney, Agent, or Firm* — Knobbe Martens Olson & Bear LLP

(57) ABSTRACT

Provided herein are compounds of Formula (I), or pharmaceutically acceptable salts thereof, pharmaceutical compositions that include a compound described herein (including pharmaceutically acceptable salts of a compound described herein) and methods of synthesizing the same. Also provided herein are methods of treating diseases and/or conditions with a compound of Formula (I), or a pharmaceutically acceptable salt thereof.

20 Claims, No Drawings

Specification includes a Sequence Listing.

TRICYCLIC COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application No. 62/854,597, filed May 30, 2019.

BACKGROUND

Field

The present application relates to the fields of chemistry, biochemistry and medicine. Disclosed herein are compounds of Formula (I), or pharmaceutically acceptable salt thereof, pharmaceutical compositions that include a compound described herein (including pharmaceutically acceptable salts of a compound described herein) and methods of synthesizing the same. Also disclosed herein are methods of treating diseases and/or conditions with a compound of Formula (I), or a pharmaceutically acceptable salt thereof.

Description

The hepatitis B virus (HBV) is a DNA virus and a member of the Hepadnaviridae family. HBV infects more than 300 million worldwide, and is a causative agent of liver cancer and liver disease such as chronic hepatitis, cirrhosis, and hepatocellular carcinoma. Although there are approved drugs for treating HBV, by either boosting the immune system or slowing down the replication of the HBV virus, HBV continues to be a problem due to the drawbacks associated with each of the approved drugs.

REFERENCE TO SEQUENCE LISTING

The present application is filed with a Sequence Listing in Electronic format. The Sequence Listing is provided as a file entitled ALIG026_replacement.txt, created Sep. 16, 2020, which is approximately 2 kb in size. The information in the electronic format of the sequence listing is incorporated herein by reference in its entirety.

SUMMARY

Some embodiments disclosed herein relate to a compound of Formula (I), or a pharmaceutically acceptable salt thereof.

Some embodiments disclosed herein relate to a pharmaceutical composition that can contain an effective amount of a compound of Formula (I), or a pharmaceutically acceptable salt thereof.

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication HBV and/or HDV.

These are other embodiments are described in greater detail below.

DETAILED DESCRIPTION

HBV is a partially double-stranded circular DNA of about 3.2 kilobase (kb) pairs, and is classified into eight genotypes, A to H. The HBV replication pathway has been studied in great detail. T. J. Liang, Hepatology (2009) 49(5 Suppl): S13-S21. On part of replication includes the formation of the covalently closed circular (cccDNA) form. The presence of the cccDNA gives rise to the risk of viral reemergence throughout the life of the host organism. HBV carriers can transmit the disease for many years. An estimated 300 million people are living with hepatitis B virus infection, and it is estimated that over 750,000 people worldwide die of hepatitis B each year. In addition, immunosuppressed individuals or individuals undergoing chemotherapy are especially at risk for reactivation of a HBV infection. HBV can be acute and/or chronic. Acute HBV infection can be either asymptomatic or present with symptomatic acute hepatitis.

HBV can be transmitted by blood, semen, and/or another body fluid. This can occur through direct blood-to-blood contact, unprotected sex, sharing of needles, and from an infected mother to her baby during the delivery process. The HBV surface antigen (HBsAg) is most frequently used to screen for the presence of this infection. Currently available medications do not cure a HBV and/or HDV infection. Rather, the medications suppress replication of the virus.

The hepatitis D virus (HDV) is a DNA virus, also in the Hepadnaviridae family of viruses. HDV can propagate only in the presence of HBV. The routes of transmission of HDV are similar to those for HBV. Transmission of HDV can occur either via simultaneous infection with HBV (coinfection) or in addition to chronic hepatitis B or hepatitis B carrier state (superinfection). Both superinfection and coinfection with HDV results in more severe complications compared to infection with HBV alone. These complications include a greater likelihood of experiencing liver failure in acute infections and a rapid progression to liver cirrhosis, with an increased risk of developing liver cancer in chronic infections. In combination with hepatitis B, hepatitis D has the highest fatality rate of all the hepatitis infections, at 20%. There is currently no cure or vaccine for hepatitis D.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from deuterium, alkyl, alkenyl, alkynyl, cycloalkyl, cycloalkenyl, aryl, heteroaryl, heterocyclyl, aryl (alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$—, $(CH_3)_2CHCH_2$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2, 3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "(heterocyclyl)alkyl" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—). A lower alkylene group can be substituted by replacing one or more hydrogen of the lower alkylene group with a substituent(s) listed under the definition of "optionally substituted" and/or by substituting both hydrogens on the same carbon with a cycloalkyl group

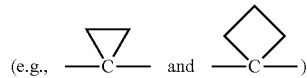

or a monocyclic heterocyclyl (such as

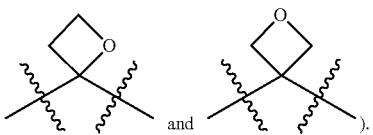 [SMILES: *C1(*)CCO1 ; *C1(*)COC1]

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "alkoxyalkyl" refers to an alkyl group in which one or more of the hydrogen atoms are replaced by a alkoxy group. Exemplary alkoxyalkyl groups include but are not limited to, methoxymethyl, ethoxymethyl, methoxyethyl and ethoxyethyl. An alkoxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein each X is a halogen.

A "trihalomethanesulfonamido" group refers to an "$X_3CS(O)_2N(R_A)$—" group wherein each X is a halogen, and $R_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(=O)N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(=O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(=S)—N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(=S)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(=O)N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(=O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1(protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

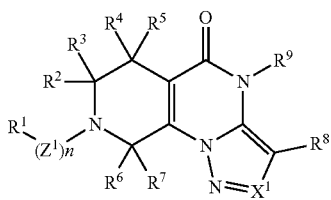

(I)

wherein: n can be 0 or 1; $Z^1$ can be —C(=O)—, —NH—C(=O)— or —O—C(=O)—; $R^1$ can be selected from an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^2$ and $R^3$ can be independently selected from hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^4$ and $R^5$ can be independently selected from hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^6$ and $R^7$ can be independently selected from hydrogen, an unsubstituted $C_{1-4}$ alkyl and an unsubstituted $C_{1-4}$ haloalkyl; $R^8$ can be selected from hydrogen, an unsubstituted $C_{1-4}$ alkyl, an unsubstituted $C_{2-4}$ alkenyl, an unsubstituted $C_{2-4}$ alkynyl, an unsubstituted $C_{1-4}$ haloalkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl), an optionally substituted heterocyclyl($C_{1-4}$ alkyl), an optionally substituted N-amido, an optionally substituted N-sulfonamido, —$NR^{10}R^{11}$ and —$C(=O)NR^{12}R^{13}$; $R^9$ can be selected from hydrogen, an unsubstituted $C_{1-4}$ alkyl, an optionally substituted monocyclic $C_{4-6}$ cycloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^{10}$ and $R^{12}$ can be independently hydrogen or an unsubstituted $C_{1-4}$ alkyl; $R^{11}$ and $R^{13}$ can be independently selected from hydrogen, an unsubstituted $C_{1-4}$ alkyl, an unsubstituted $C_{1-4}$ haloalkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl) and an optionally substituted heterocyclyl($C_{1-4}$ alkyl); or $R^{10}$ and $R^{11}$ can be taken together along with the nitrogen to which $R^{10}$ and $R^{11}$ are attached to form an optionally substituted 4- to 8-membered monocyclic heterocyclyl, an optionally substituted 8- to 13-membered fused-bicyclic heterocyclyl or an optionally substituted 7- to 13-membered spiro-bicyclic heterocyclyl; $R^{12}$ and $R^{13}$ can be taken together along with the nitrogen to which $R^{12}$ and $R^{13}$ are attached to form an optionally substituted 4- to 8-membered monocyclic heterocyclyl, an optionally substituted 8- to 13-membered fused-bicyclic heterocyclyl or an optionally substituted 7- to 13-membered spiro-bicyclic heterocyclyl; $R^2$ and $R^3$ can be taken together along with the carbon to which $R^2$ and $R^3$ are attached to form an optionally substituted monocyclic $C_{3-6}$ cycloalkyl or an optionally substituted 3 to 6 member monocyclic heterocyclyl; or $R^4$ and $R^5$ can be taken together along with the carbon to which $R^4$ and $R^5$ are attached to form an optionally substituted monocyclic $C_{3-6}$ cycloalkyl or an optionally substituted 3 to 6 member monocyclic heterocyclyl; or $R^2$ and $R^4$ can be taken together along with the carbons to which $R^2$ and $R^4$ are each attached to form an optionally monocyclic $C_{5-7}$ cycloalkyl or an optionally substituted 5 to 7 member monocyclic heterocyclyl; or $R^3$ and $R^5$ can be taken together along with the carbons to which $R^3$ and $R^5$ are each attached to form an optionally monocyclic $C_{5-7}$ cycloalkyl or an optionally substituted 5 to 7 member monocyclic heterocyclyl; or $R^6$ and $R^7$ can be taken together along with the carbon to which $R^6$ and $R^7$ are attached to form an optionally substituted monocyclic $C_{3-4}$ cycloalkyl, an optionally substituted oxetane or an optionally substituted thietane; and $X^1$ can be N or $CR^{14}$, wherein $R^{14}$ can be hydrogen, cyano, an unsubstituted $C_{1-4}$ alkyl, a substituted $C_{1-4}$ alkyl or an optionally substituted aryl($C_{1-4}$ alkyl), wherein the substituted $C_{1-4}$ alkyl is substituted one or more times with a substituents selected from cyano, halogen, hydroxy and an unsubstituted $C_{1-4}$ alkoxy.

Some embodiments disclosed herein relate to a compound of Formula (I), or a pharmaceutically acceptable salt thereof, wherein: n can be 0 or 1; $Z^1$ can be —C(=O)—, —NH—C(=O)— or —O—C(=O)—; $R^1$ can be selected from an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^2$ and $R^3$ can be independently selected from hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^4$ and $R^5$ can be independently selected from hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^6$ and $R^7$ can be independently selected from hydrogen, an unsubstituted $C_{1-4}$ alkyl and an unsubstituted $C_{1-4}$ haloalkyl; $R^8$ can be selected from hydrogen, an unsubstituted $C_{1-4}$ alkyl, an unsubstituted $C_{1-4}$ haloalkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl), an optionally substituted heterocyclyl($C_{1-4}$ alkyl), —$NR^{10}R^{11}$ and —C(=O)$NR^{12}R^{13}$; $R^9$ can be selected from hydrogen, an unsubstituted $C_{1-4}$ alkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^{10}$ and $R^{12}$ can be independently hydrogen or an unsubstituted $C_{1-4}$ alkyl; $R^{11}$ and $R^{13}$ can be independently selected from hydrogen, an unsubstituted $C_{1-4}$ alkyl, an unsubstituted $C_{1-4}$ haloalkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl) and an optionally substituted heterocyclyl($C_{1-4}$ alkyl); or $R^{10}$ and $R^{11}$ can be taken together along with the nitrogen to which $R^{10}$ and $R^{11}$ are attached to form an optionally substituted 4- to 8-membered monocyclic heterocyclyl, an optionally substituted 8- to 13-membered fused-bicyclic heterocyclyl or an optionally substituted 7- to 13-membered spiro-bicyclic heterocyclyl; $R^{12}$ and $R^{13}$ can be taken together along with the nitrogen to which $R^{12}$ and $R^{13}$ are attached to form an optionally substituted 4- to 8-membered monocyclic heterocyclyl, an optionally substituted 8- to 13-membered fused-bicyclic heterocyclyl or an optionally substituted 7- to 13-membered spiro-bicyclic heterocyclyl; $R^2$ and $R^3$ can be taken together along with the carbon to which $R^2$ and $R^3$ are attached to form an optionally substituted monocyclic $C_{3-6}$ cycloalkyl or an optionally substituted 3 to 6 member monocyclic heterocyclyl; or $R^4$ and $R^5$ can be taken together along with the carbon to which $R^4$ and $R^5$ are attached to form an optionally substituted monocyclic $C_{3-6}$ cycloalkyl or an optionally substituted 3 to 6 member monocyclic heterocyclyl; or $R^2$ and $R^4$ can be taken together along with the carbons to which $R^2$ and $R^4$ are each attached to form an optionally monocyclic $C_{5-7}$ cycloalkyl or an optionally substituted 5 to 7 member monocyclic heterocyclyl; or $R^3$ and $R^5$ can be taken together along with the carbons to which $R^3$ and $R^5$ are each attached to form an optionally monocyclic $C_{5-7}$ cycloalkyl or an optionally substituted 5 to 7 member monocyclic heterocyclyl; or $R^6$ and $R^7$ can be taken together along with the carbon to which $R^6$ and $R^7$ are attached to form an optionally substituted monocyclic $C_{3-4}$ cycloalkyl, an optionally substituted oxetane or an optionally substituted thietane; and $X^1$ can be N or $CR^{14}$, wherein $R^{14}$ can be hydrogen, cyano, an unsubstituted $C_{1-4}$ alkyl, a substituted $C_{1-4}$ alkyl or an optionally substituted aryl($C_{1-4}$ alkyl), wherein the substituted $C_{1-4}$ alkyl can be substituted one or more times with a substituents selected from cyano, halogen, hydroxy and an unsubstituted $C_{1-4}$ alkoxy.

A variety of moieties can be present for $Z^1$ and $R^1$. In some embodiments, n can be 0; and $R^1$ can be selected from an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl) such that Formula (I), and pharmaceutically acceptable salts thereof can be Formula (Ia), or a pharmaceutically acceptable salt thereof. In other embodiments, n can be 1; $Z^1$ can be —C(=O)—, —NH—C(=O)— or —O—C(=O)—; and $R^1$ can be selected from an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl). As shown below, when $Z^1$ is —C(=O)—, —NH—C(=O)— or —O—C(=O)—, Formula (I) can be Formula (Ib), (Ic) or (Id), or a pharmaceutically acceptable salt thereof, respectively. As described herein, n can be 0 and $R^1$ can be an optionally substituted heteroaryl or an optionally substituted heterocyclyl. An example of n being 0; and $R^1$ being an optionally substituted heteroaryl or an optionally substituted heterocyclyl is

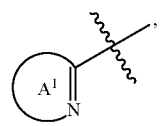

wherein Ring $A^1$ can be an optionally substituted bicyclic heteroaryl or an optionally substituted bicyclic heterocyclyl such that Formula (I), and pharmaceutically acceptable salts thereof can be Formula (Ie), or a pharmaceutically acceptable salt thereof.

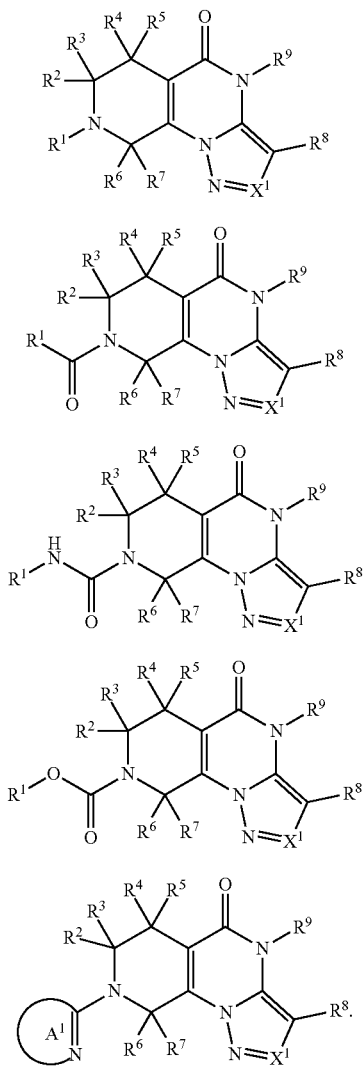

In some embodiments, $X^1$ can be N (nitrogen). In other embodiments, $X^1$ can be CH. In still other embodiments, $X^1$ can be $CR^{14}$, wherein $R^{14}$ can be cyano, an unsubstituted $C_{1-4}$ alkyl or a substituted $C_{1-4}$ alkyl, wherein the substituted $C_{1-4}$ alkyl is substituted one or more times with a substituents selected from cyano, halogen, hydroxy and an unsubstituted $C_{1-4}$ alkoxy. In still other embodiments, $X^1$ can be $CR^{14}$, wherein $R^{14}$ can be an optionally substituted aryl($C_{1-4}$ alkyl).

Various cyclic moieties can be present for $R^1$. In some embodiments, $R^1$ can be an optionally substituted aromatic carbocyclic moiety, for example an optionally substituted aryl. For example, $R^1$ can be an optionally substituted phenyl. In some embodiments, $R^1$ can be an unsubstituted phenyl. In other embodiments, $R^1$ can be a substituted phenyl. When $R^1$ is a substituted phenyl, the phenyl can be mono-substituted. The mono-substituted phenyl can be a para-substituted phenyl, a meta-substituted phenyl or an ortho-substituted phenyl. The substituted phenyl can be substituted by multiple moieties, such as 2, 3 or 4 or more times. In some embodiments, $R^1$ can be a di-substituted phenyl. When more than one moiety is present, the moieties can be the same or different moieties can be different. In some embodiments, $R^1$ can be an unsubstituted or substituted naphthyl.

As described herein, $R^1$ can be a monocyclic or multicyclic (for example, a bicyclic) moiety that includes one or more heteroatoms in the ring(s). In some embodiments, $R^1$ can be an optionally substituted heteroaryl. In some embodiments, $R^1$ can be an unsubstituted or a substituted monocyclic heteroaryl. For example, $R^1$ can be a 5-membered or 6-membered monocyclic heteroaryl, wherein the heteroaryl ring can be unsubstituted or substituted. In other embodiments, $R^1$ can be an unsubstituted or a substituted bicyclic heteroaryl. The bicyclic heteroaryl can be an unsubstituted or a substituted 9-membered or an unsubstituted or a substituted 10-membered heteroaryl. The heteroaryl can include one or more heteroatoms, such as N (nitrogen), O (oxygen) and/or S (sulfur).

In some embodiments, $R^1$ can be an optionally substituted heterocyclyl. The heterocyclyl can be a monocyclic heterocyclyl or a bicyclic heterocyclyl. In some embodiments, $R^1$ can be an unsubstituted or a substituted monocyclic heterocyclyl, such as an unsubstituted or a substituted 5-membered or an unsubstituted or a substituted 6-membered monocyclic heterocyclyl. In other embodiments, $R^1$ can be an unsubstituted or a substituted bicyclic heterocyclyl, including an unsubstituted or a substituted 9-membered or an unsubstituted or a substituted 10-membered heterocyclyl. The number and types of heteroatoms that can be present in a heterocyclyl for $R^1$ can vary. For example, 1, 2, 3 or more than 3 heteroatoms, such as N (nitrogen), O (oxygen) and/or S (sulfur), can be present in a heterocyclyl of $R^1$.

In some embodiments, n can be 0; and $R^1$ can be

wherein Ring $A^1$ can be an optionally substituted bicyclic heteroaryl. In other embodiments, $R^1$ can be

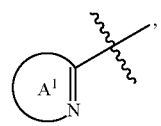

wherein Ring $A^1$ can be an optionally substituted bicyclic heterocyclyl. In some embodiments, Ring $A^1$ can be an optionally substituted nitrogen-containing, 9-membered bicyclic heteroaryl. In other embodiments, Ring $A^1$ can be an optionally substituted nitrogen-containing, 10-membered bicyclic heteroaryl. In still other embodiments, Ring $A^1$ can be an optionally substituted nitrogen-containing, 9-membered bicyclic heterocyclyl. In yet still other embodiments, Ring $A^1$ can be an optionally substituted nitrogen-containing, 10-membered bicyclic heterocyclyl.

In some embodiments, $R^1$ can be a nitrogen-containing, bicyclic heteroaryl or a nitrogen-containing, bicyclic heterocyclyl. In some embodiments, $R^1$ can be selected from an unsubstituted or a substituted [5,5] bicyclic heteroaryl, an unsubstituted or a substituted [5,6] bicyclic heteroaryl, an unsubstituted or a substituted [6,5] bicyclic heteroaryl, an unsubstituted or a substituted [6,6] bicyclic heteroaryl, an unsubstituted or a substituted [5,5] bicyclic heterocyclyl, an unsubstituted or a substituted [5,6] bicyclic heterocyclyl, an unsubstituted or a substituted [6,5] bicyclic heterocyclyl and an unsubstituted or a substituted [6,6] bicyclic heterocyclyl. In some embodiments, $R^1$ can have the general structure

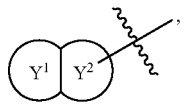

wherein Ring $Y^2$ indicates the point of attachment to the remaining portion of Formula (I); and wherein Ring $Y^1$ and Ring $Y^2$ can be independently selected from phenyl, furan, furazan, thiophene, phthalazine, pyrrole, oxazole, 1,2,3-oxadiazole, 1,2,4-oxadiazole, thiazole, 1,2,3-thiadiazole, 1,2,4-thiadiazole, imidazole, pyrazole, isoxazole, isothiazole, triazole, thiadiazole, tetrazole, pyridine, pyridazine, pyrimidine, pyrazine, 1,2,3-triazine, 1,2,4-triazine, 1,2,3,4-tetrazine, 2H-1,2-oxazine, hexahydro-1,3,5-triazine, imidazoline, imidazolidine, isoxazoline, isoxazolidine, oxazoline, oxazolidine, thiazoline, thiazolidine, morpholine, piperidine, piperazine, pyrrolidine, pyrazoline, pyrazolidine and thiamorpholine, wherein Ring $Y^1$ and Ring $Y^2$ can be each optionally substituted. In some embodiments, Ring $Y^1$ can be selected from an optionally substituted phenyl, an optionally substituted pyridine, an optionally substituted pyridazine, an optionally substituted pyrimidine, an optionally substituted pyrazine, an optionally substituted 1,2,3-triazine, an optionally substituted 1,2,4-triazine and an optionally substituted 1,2,3,4-tetrazine. In some embodiments, Ring $Y^2$ can be selected from an optionally substituted phenyl, an optionally substituted pyridine, an optionally substituted pyridazine, an optionally substituted pyrimidine, an optionally substituted pyrazine, an optionally substituted 1,2,3-triazine, an optionally substituted 1,2,4-triazine and an optionally substituted 1,2,3,4-tetrazine. In other embodiments, Ring $Y^2$ can be selected from an optionally substituted furan, an optionally substituted thiophene, an optionally substituted pyrrole, an optionally substituted oxazole, an optionally substituted thiazole, an optionally substituted imidazole, an optionally substituted pyrazole, an optionally substituted isoxazole and an optionally substituted isothiazole.

A variety of cyclic groups described herein for $R^1$ can be attached via a $C_{1-4}$ alkyl linker. In some embodiments, $R^1$ can be an optionally substituted aryl($C_{1-4}$ alkyl), for example, an optionally substituted benzyl. In other embodiments, $R^1$ can be an optionally substituted heteroaryl($C_{1-4}$ alkyl). In still other embodiments, $R^1$ can be an optionally substituted heterocyclyl($C_{1-4}$ alkyl). Examples of heteroaryls and heterocyclyls are described herein, and include those of the previous paragraph. As described herein, the linker can include 1 to 4 carbons. The aryl, heteroaryl, heterocyclyl and $C_{1-4}$ alkyl of aryl($C_{1-4}$ alkyl), heteroaryl($C_{1-4}$ alkyl) and heterocyclyl($C_{1-4}$ alkyl) can be each unsubstituted or unsubstituted. When the $C_{1-4}$ alkyl linker is substituted, one or more hydrogens can be replaced with a moiety, such as those provided in the definition of "optionally substituted," and/or two or more hydrogens can be taken together along with the carbon to which the hydrogens are attached to form an optionally substituted $C_{3-4}$ cycloalkyl or an optionally substituted 3-, 4- or 5-membered heterocyclyl. In some embodiments, the $C_{1-4}$ alkyl linker of aryl($C_{1-4}$ alkyl), heteroaryl ($C_{1-4}$ alkyl) and heterocyclyl($C_{1-4}$ alkyl) can be substituted with one or more moieties selected from halogen (such as F), cyano, $C_{1-2}$ haloalkyl (for example, $CF_3$), OH, an unsubstituted $C_{1-4}$ alkoxy and an unsubstituted C-amido (such as —C(=O)NH$_2$, —C(=O)NH($C_{1-4}$ alkyl) and —C(=O)N ($C_{1-4}$ alkyl)$_2$). In some embodiments, the $C_{1-4}$ alkyl linker for $R^1$ can be —CH$_2$—, —CH$_2$CH$_2$—, —CH(CH$_3$)CH$_2$—, —CH$_2$CH$_2$CH$_2$—, —CH$_2$CH$_2$CH$_2$CH$_2$—,

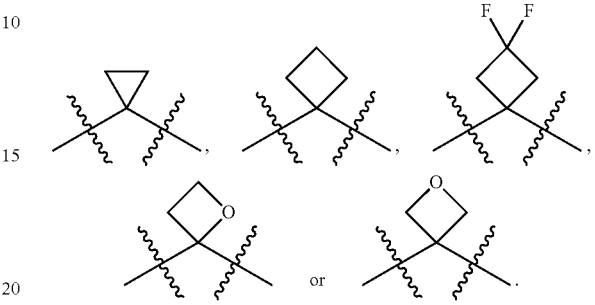

As described herein, the $R^1$ groups can be unsubstituted or substituted. When $R^1$ is substituted, a variety of substituents can be present on a $R^1$ group described herein. In some embodiments, $R^1$ can be substituted with one or more substituents selected from deuterium, halogen (such as F, Cl and/or Br), cyano, an unsubstituted $C_{1-6}$ alkyl (for example, methyl, ethyl, n-propyl, isopropyl, n-butyl, iso-butyl, sec-butyl, tert-butyl, pentyl (straight-changed or branched) and hexyl (straight-chained or branched)), an unsubstituted $C_{2-4}$ alkenyl, an unsubstituted $C_{2-4}$ alkynyl, an unsubstituted monocyclic $C_{3-6}$ cycloalkyl, a halo-substituted monocyclic $C_{3-6}$ cycloalkyl, an unsubstituted $C_{1-6}$ haloalkyl (such as —CHF$_2$, —CH$_2$F, —CF$_3$, —CHClF, —CH$_2$Cl, —CHCl$_2$ and —CCl$_3$), an unsubstituted $C_{1-6}$ alkoxy (for example, methoxy, ethoxy, isopropoxy, n-butoxy, sec-butoxy, isobutoxy and tert-butoxy), an unsubstituted $C_{1-6}$ haloalkoxy (for example, (such as —OCHF$_2$, —OCH$_2$F and —OCF$_3$), an unsubstituted acyl (for example, —C(=O)—$C_{1-4}$ alkyl), an unsubstituted C-amido (such as —C(=O)NH$_2$, —C(=O) NH($C_{1-4}$ alkyl) and —C(=O)N($C_{1-4}$ alkyl)$_2$), an unsubstituted sulfonyl (such as —S(=O)$_2$—$C_{1-4}$ alkyl), an unsubstituted amino, a mono-substituted amine (for example, an mono-alkyl substituted amine) and a di-substituted amine (such as a di-alkyl substituted amine).

Exemplary $R^1$ groups include, but are not limited to, the following:

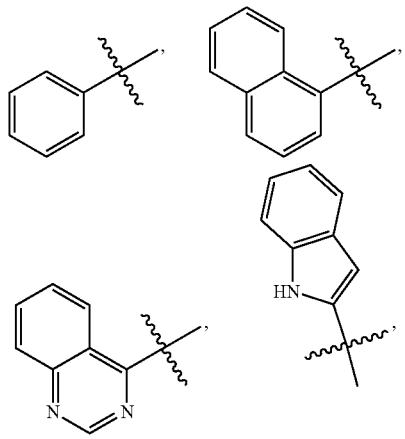

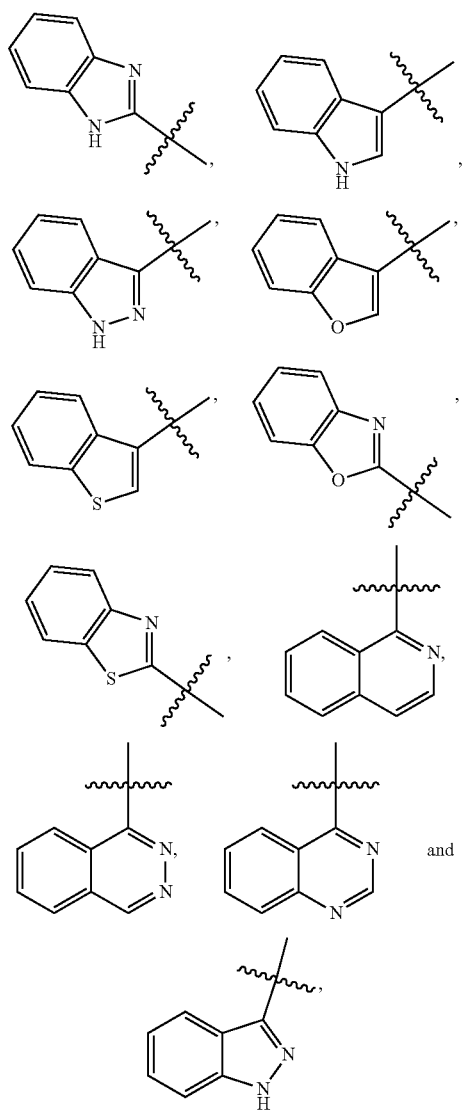
wherein each of these moieties can be unsubstituted or substituted. Examples of substituted R¹ groups include
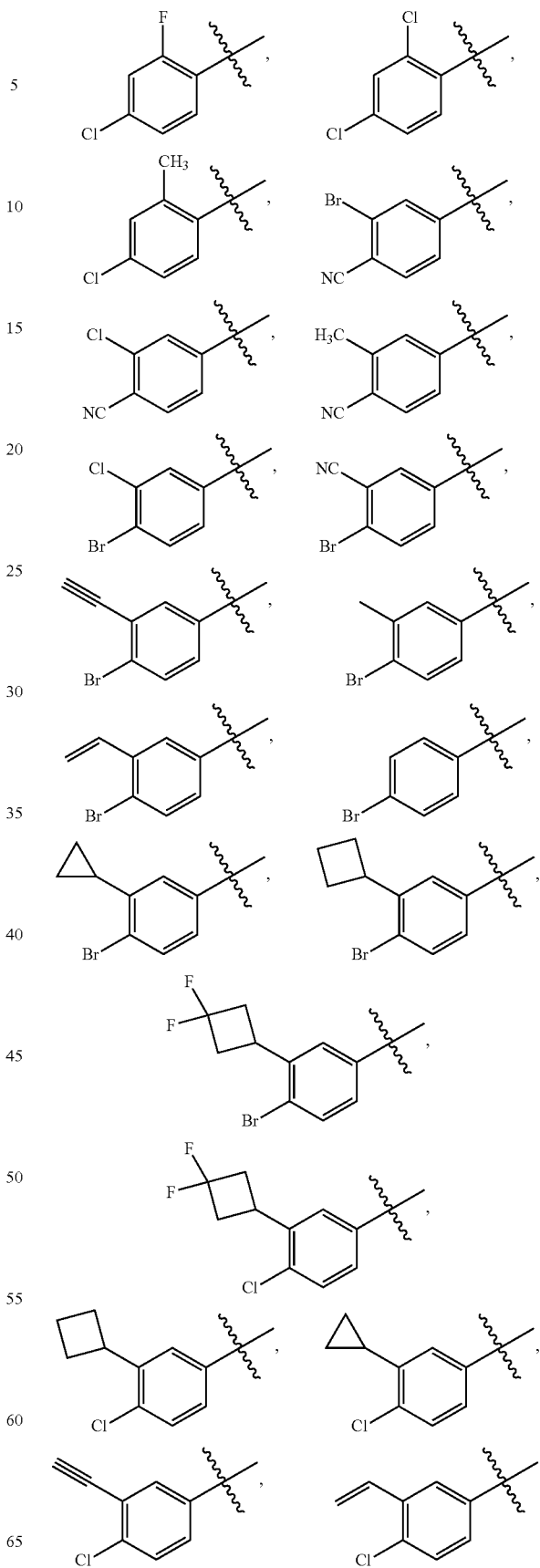

-continued

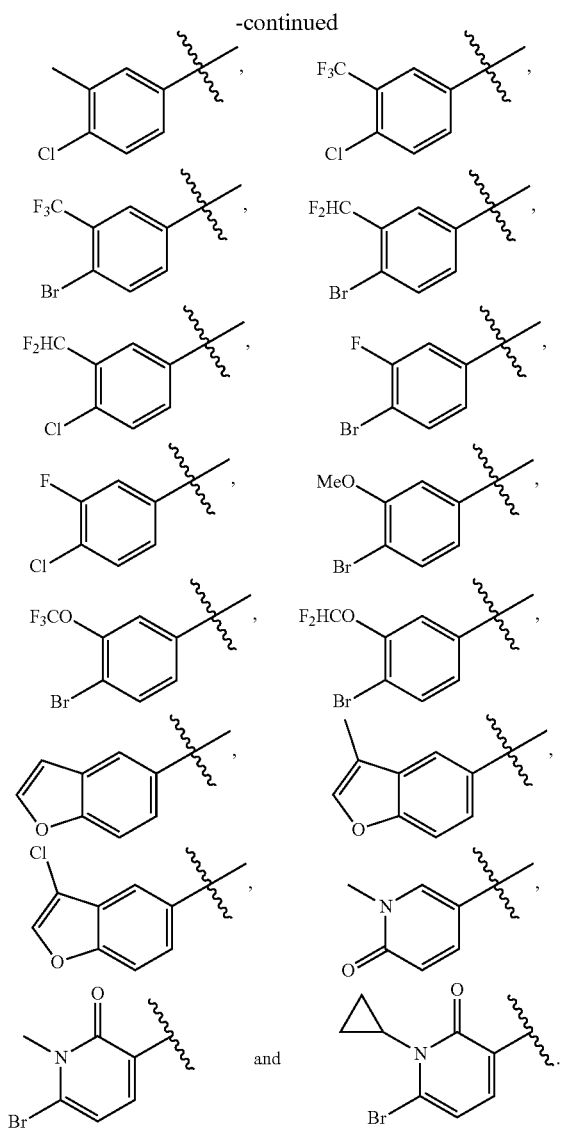

and

As provided herein, $R^8$ can be selected from hydrogen, an unsubstituted $C_{1-4}$ alkyl, an unsubstituted $C_{2-4}$ alkenyl, an unsubstituted $C_{2-4}$ alkynyl, an unsubstituted $C_{1-4}$ haloalkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl), an optionally substituted heterocyclyl ($C_{1-4}$ alkyl), an optionally substituted N-amido, an optionally substituted N-sulfonamido, —$NR^{10}R^{11}$ and —$C(=O)NR^{12}R^{13}$. In some embodiments, $R^8$ can be hydrogen. In other embodiments, $R^8$ can be an unsubstituted $C_{1-4}$ alkyl, such as methyl, ethyl, n-propyl, isopropyl, n-butyl, isobutyl, sec-butyl and tert-butyl. In still other embodiments, $R^8$ can be an unsubstituted $C_{1-4}$ haloalkyl. Exemplary unsubstituted $C_{1-4}$ haloalkyls include —$CF_3$, —$CHF_2$, —$CHClF$, —$CCl_3$ and —$CHCl_2$.

As provided herein, $R^8$ can be an unsaturated hydrocarbon. In some embodiments, $R^8$ can be an unsubstituted $C_{2-4}$ alkenyl. For example, $R^8$ can be —$CH=CH_2$, —$CH_2CH=CH_2$, —$CH_2CH_2CH=CH_2$ or —$CH_2CH(CH_3)CH=CH_2$. In other embodiments, $R^8$ can be an unsubstituted $C_{2-4}$ alkenyl, such as ethynyl and propynyl.

Several cyclic moieties can be present at $R^8$. For example, in some embodiments, $R^8$ can be an optionally substituted cycloalkyl or an optionally substituted cycloalkenyl. The optionally substituted cycloalkyl and the optionally substituted cycloalkenyl can be monocyclic, such as an optionally substituted $C_{3-6}$ cycloalkyl or an optionally substituted $C_{3-6}$ cycloalkenyl. Alternatively, the optionally substituted cycloalkyl and/or the optionally substituted cycloalkenyl can be multicyclic, for example, an optionally substituted fused-bicyclic cycloalkyl, an optionally substituted fused-bicyclic cycloalkenyl, an optionally substituted spiro-bicyclic cycloalkyl and an optionally substituted spiro-bicyclic cycloalkenyl. In other embodiments, $R^8$ can be an optionally substituted aryl, an optionally substituted heteroaryl or an optionally substituted heterocyclyl. Exemplary $R^8$ aryls, heteroaryls and heterocyclyls include, but are not limited to, phenyl, 5-membered monocyclic heteroaryls, 6-membered monocyclic heteroaryls, 5-membered monocyclic heterocyclyls and 6-membered monocyclic heterocyclyls, wherein each of the aforementioned moieties can be unsubstituted or substituted. The heteroatom(s) that can be present in an optionally substituted heteroaryl and an optionally substituted heterocyclyl for $R^8$ include N (nitrogen), O (oxygen) and/or S (sulfur).

The cyclic moieties described herein for $R^8$ can be attached via a $C_{1-4}$ alkyl linker, such as those described herein. In some embodiments, $R^8$ can be an optionally substituted cycloalkyl($C_{1-4}$ alkyl). In other embodiments, $R^8$ can be an optionally substituted cycloalkenyl($C_{1-4}$ alkyl). In still other embodiments, $R^8$ can be an optionally substituted aryl($C_{1-4}$ alkyl). In yet still other embodiments, $R^8$ can be an optionally substituted heteroaryl($C_{1-4}$ alkyl). In some embodiments, $R^8$ can be an optionally substituted heterocyclyl($C_{1-4}$ alkyl). The cycloalkyls, cycloalkenyls, aryls, heteroaryls and heterocyclyls can be monocyclic or bicyclic (for example, fused bicyclic). For example, $R^8$ can be an optionally substituted monocyclic $C_{3-6}$ cycloalkyl($C_{1-4}$ alkyl), an optionally substituted monocyclic $C_{3-6}$ cycloalkenyl($C_{1-4}$ alkyl), an optionally substituted benzyl, an optionally substituted monocyclic heteroaryl($C_{1-4}$ alkyl) (such as a 5-membered monocyclic heteroaryl($C_{1-4}$ alkyl) or 6-membered monocyclic heteroaryl($C_{1-4}$ alkyl)) or an optionally substituted monocyclic heterocyclyl($C_{1-4}$ alkyl) (such as a 5-membered monocyclic heterocyclyl($C_{1-4}$ alkyl) or 6-membered monocyclic heterocyclyl($C_{1-4}$ alkyl)).

The $C_{1-4}$ alkyls of cycloalkyl($C_{1-4}$ alkyl), cycloalkenyl ($C_{1-4}$ alkyl), aryl($C_{1-4}$ alkyl), heteroaryl($C_{1-4}$ alkyl) and heterocyclyl($C_{1-4}$ alkyl) can be unsubstituted or substituted. When the $C_{1-4}$ alkyl is substituted, one or more hydrogens can be replaced with a moiety, such as those provided in the definition of "optionally substituted," and/or two or more hydrogens can be taken together along with the carbon to which the hydrogens are attached to form an optionally substituted $C_{3-4}$ cycloalkyl or an optionally substituted 3-, 4- or 5-membered heterocyclyl. In some embodiments, the $C_{1-4}$ alkyl linker of cycloalkyl($C_{1-4}$ alkyl), cycloalkenyl($C_{1-4}$ alkyl), aryl($C_{1-4}$ alkyl), heteroaryl($C_{1-4}$ alkyl) and heterocyclyl($C_{1-4}$ alkyl) can be substituted with one or more moieties selected from halogen (such as F), cyano, $C_{1-2}$ haloalkyl (for example, $CF_3$), OH, an unsubstituted $C_{1-4}$ alkoxy and an unsubstituted C-amido (such as —$C(=O)NH_2$, —$C(=O)NH(C_{1-4}$ alkyl) and —$C(=O)N(C_{1-4}$ alkyl)$_2$). Exemplary linkers that can attached the cyclic moieties for $R^8$ include, but are not limited to, —CH$_2$—, —CH$_2$CH$_2$—, —CH(CH$_3$) CH$_2$—, —CH$_2$CH$_2$CH$_2$—, —CH$_2$CH$_2$CH$_2$CH$_2$—,

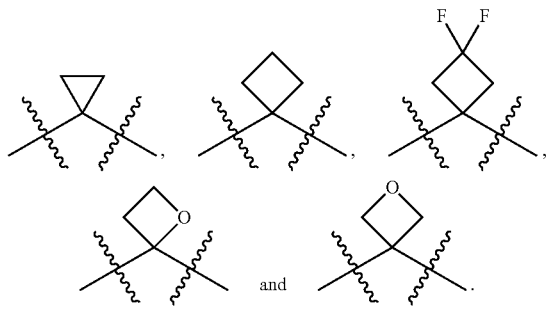

In some embodiments, R$^8$ can be an optionally substituted N-amido. In other embodiments, R$^8$ can be an optionally substituted N-sulfonamido. An N-amido can have the structure RC(=O)N(R$_A$)— in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). In some embodiments, R$^8$ can be an unsubstituted or a substituted —NHC(=O)R$^{A1}$, wherein R$^{A1}$ can be C$_{1-4}$ alkyl, C$_{2-4}$ alkenyl, C$_{2-4}$ alkynyl, C$_{3-8}$ cycloalkyl, C$_{3-8}$ cycloalkenyl, aryl, heteroaryl, heterocyclyl, aryl(alkyl), heteroaryl(alkyl) or heterocyclyl (alkyl). An N-sulfonamido can have the structure RSO$_2$N (R$_A$)— in which R and R$_A$ can be independently hydrogen, alkyl, alkenyl, alkynyl, cycloalkyl, cycloalkenyl, aryl, heteroaryl, heterocyclyl, aryl(C$_{1-4}$ alkyl), heteroaryl(C$_{1-4}$ alkyl) or heterocyclyl(C$_{1-4}$ alkyl). In some embodiments, R$^8$ can be an unsubstituted or a substituted —NHS(=O)$_2$R$^{B1}$, wherein R$^{B1}$ can be C$_{1-4}$ alkyl, C$_{2-4}$ alkenyl, C$_{2-4}$ alkynyl, C$_{3-8}$ cycloalkyl, C$_{3-8}$ cycloalkenyl, aryl, heteroaryl, heterocyclyl, aryl(C$_{1-4}$ alkyl), heteroaryl(C$_{1-4}$ alkyl) or heterocyclyl(C$_{1-4}$ alkyl).

For R$^{A1}$ and R$^{B1}$, the C$_{1-4}$ alkyl can be an unsubstituted or a substituted C$_{1-4}$ alkyl, the C$_{2-4}$ alkenyl can be an unsubstituted or a substituted C$_{2-4}$ alkenyl, the C$_{2-4}$ alkynyl can be an unsubstituted or a substituted C$_{2-4}$ alkynyl, the C$_{3-8}$ cycloalkyl can be a monocyclic or a bicyclic cycloalkyl that can be unsubstituted or substituted, the C$_{3-8}$ cycloalkenyl can be a monocyclic or a bicyclic cycloalkenyl that can be unsubstituted or substituted, the aryl can be a monocyclic or a bicyclic aryl that can be unsubstituted or substituted, the heteroaryl can be a monocyclic or a bicyclic heteroaryl that can be unsubstituted or substituted, the heterocyclyl can be a monocyclic or a bicyclic heterocyclyl that can be unsubstituted or substituted, the aryl(C$_{1-4}$ alkyl) can be a monocyclic or a bicyclic aryl(C$_{1-4}$ alkyl) that can be unsubstituted or substituted, the heteroaryl(C$_{1-4}$ alkyl) can be a monocyclic or a bicyclic heteroaryl(C$_{1-4}$ alkyl) that can be unsubstituted or substituted, and the heterocyclyl(C$_{1-4}$ alkyl) can be a monocyclic or a bicyclic heterocyclyl (C$_{1-4}$ alkyl) that can be unsubstituted or substituted. Examples of suitable R$^{A1}$ and R$^{B1}$ ring moieties include, but are not limited to, an unsubstituted or a substituted phenyl, an unsubstituted or a substituted naphthyl, an unsubstituted or a substituted heteroaryl (such as a 5- or 6-membered monocyclic heteroaryl or a 9- or 10-membered bicyclic heteroaryl that includes 1, 2 or 3 heteroatoms independently selected from O, S and N), an unsubstituted or a substituted heterocyclyl (for example, a 5- or 6-membered monocyclic heterocyclyl or a 9- or 10-membered bicyclic heterocyclyl that includes 1, 2 or 3 heteroatoms independently selected from O, S and N), an unsubstituted or a substituted benzyl, an unsubstituted or a substituted monocyclic or bicyclic heteroaryl(C$_{1-4}$ alkyl) and an unsubstituted or a substituted monocyclic or bicyclic heterocyclyl(C$_{1-4}$ alkyl). In some embodiments, the unsubstituted or a substituted monocyclic heteroaryl(C$_{1-4}$ alkyl) for R$^{A1}$ and/or R$^{B1}$ can be a 5- or 6-membered monocyclic heteroaryl or a 9- or 10-membered bicyclic heteroaryl that includes 1, 2 or 3 heteroatoms independently selected from O, S and N; and the C$_{1-4}$ alkyl linker can be —CH$_2$— or —CH(CH$_3$)—. In some embodiments, the unsubstituted or a substituted monocyclic heterocyclyl (C$_{1-4}$ alkyl) for R$^{A1}$ and/or R$^{B1}$ can be a 5- or 6-membered monocyclic heterocyclyl or a 9- or 10-membered bicyclic heterocyclyl that includes 1, 2 or 3 heteroatoms independently selected from O, S and N; and the C$_{1-4}$ alkyl linker can be —CH$_2$— or —CH(CH$_3$)—. In some embodiments, R$^{A1}$ and/or R$^{B1}$ can be independently methyl, ethyl, n-propyl, isopropyl, n-butyl, isobutyl, sec-butyl or tert-butyl.

In some embodiments, R$^8$ can be —NR$^{10}$R$^{11}$. In other embodiments, R$^8$ can be —C(=O)NR$^{12}$R$^{13}$. In some embodiments, R$^{10}$ can be hydrogen. In other embodiments, R$^{10}$ can be optionally substituted C$_{1-4}$ alkyl. In some embodiments, R$^{12}$ can be hydrogen. In other embodiments, R$^{12}$ can be optionally substituted C$_{1-4}$ alkyl. For example, R$^{10}$ and/or R$^{12}$ can be methyl, ethyl, n-propyl, iso-propyl, n-butyl, iso-butyl, sec-butyl or tert-butyl.

In some embodiments, R$^{11}$ can be hydrogen. In other embodiments, R$^{11}$ can be an unsubstituted C$_{1-4}$ alkyl. In still other embodiments, R$^{11}$ can be an unsubstituted C$_{1-4}$ haloalkyl. As described herein, R$^{11}$ can be various carbocyclic, heteroaryl or heterocyclic groups. In some embodiments, R$^{11}$ can be an optionally substituted cycloalkyl, for example, an optionally substituted C$_{3-8}$ cycloalkyl. In other embodiments, R$^{11}$ can be an optionally substituted cycloalkenyl, such as an optionally substituted C$_{3-8}$ cycloalkenyl. In some embodiments, R$^{11}$ can be an optionally substituted aryl. For example, R$^{11}$ can be an unsubstituted or a substituted phenyl. In still other embodiments, R$^{11}$ can be an optionally substituted heteroaryl. The heteroaryl for R$^{11}$ can be an optionally substituted monocyclic heteroaryl (such as an optionally substituted 5- or 6-membered monocyclic heteroaryl) or an optionally substituted bicyclic heteroaryl (for example, an optionally substituted 9- or 10-membered bicyclic heteroaryl). In some embodiments, R$^{11}$ can be an optionally substituted heterocyclyl.

A variety cyclic groups can be attached via a C$_{1-4}$ alkyl linker for R$^{11}$. Examples of C$_{1-4}$ alkyl linkers are described herein and include —CH$_2$—, —CH$_2$CH$_2$—, —CH(CH$_3$) CH$_2$—, —CH$_2$CH$_2$CH$_2$—, —CH$_2$CH$_2$CH$_2$CH$_2$—,

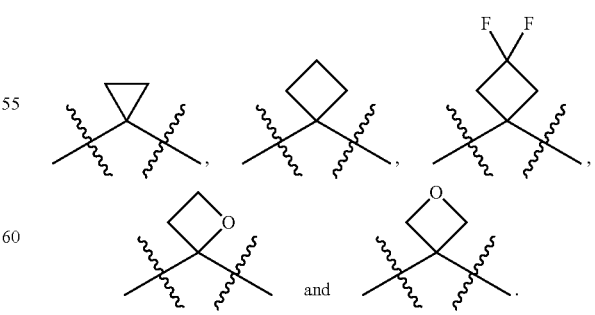

As shown and described herein, the C$_{1-4}$ alkyl linkers for R$^{11}$ can be unsubstituted or substituted. When the C$_{1-4}$ alkyls for R$^{11}$ are substituted, one or more hydrogens can be replaced with a moiety, such as those provided in the definition of "optionally substituted," and/or two or more hydrogens can be taken together along with the carbon to which the hydrogens are attached to form an optionally substituted $C_{3-4}$ cycloalkyl or an optionally substituted 3-, 4- or 5-membered heterocyclyl. In some embodiments, the $C_{1-4}$ alkyl linker for the $R^{11}$ groups can be substituted with one or more moieties selected from halogen (such as F), cyano, $C_{1-2}$ haloalkyl (for example, $CF_3$), OH, an unsubstituted $C_{1-4}$ alkoxy and an unsubstituted C-amido (such as —C(═O)$NH_2$, —C(═O)NH($C_{1-4}$ alkyl) and —C(═O)N($C_{1-4}$ alkyl)$_2$). In some embodiments, $R^{11}$ can be an optionally substituted cycloalkyl($C_{1-4}$ alkyl), such as an optionally substituted monocyclic $C_{3-8}$ cycloalkyl($C_{1-4}$ alkyl). In other embodiments, $R^{11}$ can be an optionally substituted cycloalkenyl($C_{1-4}$ alkyl), such as an optionally substituted monocyclic $C_{3-8}$ cycloalkenyl($C_{1-4}$ alkyl). In still other embodiments, $R^{11}$ can be an optionally substituted aryl($C_{1-4}$ alkyl). As an example, $R^{11}$ can be an optionally substituted benzyl. In yet still other embodiments, $R^{11}$ can be an optionally substituted heteroaryl($C_{1-4}$ alkyl). In some embodiments, $R^{11}$ can be an optionally substituted heterocyclyl($C_{1-4}$ alkyl). The heteroaryl of the optionally substituted heteroaryl($C_{1-4}$ alkyl) can be an optionally substituted monocyclic heteroaryl (such as a 5- or 6-membered monocyclic heteroaryl) or an optionally substituted bicyclic heteroaryl (such as a 9- or 10-membered bicyclic heteroaryl).

In some embodiments, $R^{10}$ and $R^{11}$ can be taken together along with the nitrogen to which $R^{10}$ and $R^{11}$ are attached to form an optionally substituted 4 to 8 member monocyclic heterocyclyl. In other embodiments, $R^{10}$ and $R^{11}$ can be taken together along with the nitrogen to which $R^{10}$ and $R^{11}$ are attached to form an optionally substituted 8 to 13 membered fused-bicyclic heterocyclyl. In still other embodiments, $R^{10}$ and $R^{11}$ can be taken together along with the nitrogen to which $R^{10}$ and $R^{11}$ are attached to form an optionally substituted 7 to 13 membered spiro-bicyclic heterocyclyl. The 4 to 8 member monocyclic heterocyclyl, 8 to 13 membered fused-bicyclic heterocyclyl and/or 7 to 13 membered spiro-bicyclic heterocyclyl can include one or more ring nitrogens.

As described herein, $R^{13}$ can be cyclic and non-cyclic moieties. In some embodiments, $R^{13}$ can be hydrogen. In other embodiments, $R^{13}$ can be an unsubstituted $C_{1-4}$ alkyl. In still other embodiments, $R^{13}$ can be an unsubstituted $C_{1-4}$ haloalkyl. Various carbocyclic, heteroaryl or heterocyclic groups are suitable for $R^{13}$. In some embodiments, $R^{13}$ can be an optionally substituted cycloalkyl, for example, an optionally substituted $C_{3-8}$ cycloalkyl. In other embodiments, $R^{13}$ can be an optionally substituted cycloalkenyl, such as an optionally substituted $C_{3-8}$ cycloalkenyl. In some embodiments, $R^{13}$ can be an optionally substituted aryl. For example, $R^{13}$ can be an unsubstituted or a substituted phenyl. In still other embodiments, $R^{13}$ can be an optionally substituted heteroaryl. The heteroaryl for $R^{13}$ can be an optionally substituted monocyclic heteroaryl (such as an optionally substituted 5- or 6-membered monocyclic heteroaryl) or an optionally substituted bicyclic heteroaryl (for example, an optionally substituted 9- or 10-membered bicyclic heteroaryl). In some embodiments, $R^{13}$ can be an optionally substituted heterocyclyl.

As described herein, $R^{13}$ can be an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl) or an optionally substituted heterocyclyl($C_{1-4}$ alkyl). Various $C_{1-4}$ alkyls are described herein for an optionally substituted cycloalkyl ($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl) and/or an optionally substituted heterocyclyl($C_{1-4}$ alkyl) are described herein. For example, the $C_{1-4}$ alkyl of an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl) and/or an optionally substituted heterocyclyl($C_{1-4}$ alkyl) can be selected from —$CH_2$—, —$CH_2CH_2$—, —$CH(CH_3)CH_2$—, —$CH_2CH_2CH_2$—, —$CH_2CH_2CH_2CH_2$—,

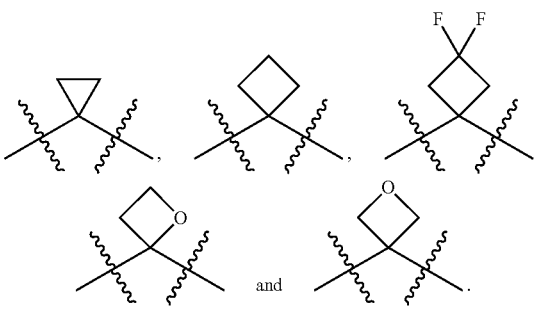

As shown and described herein, the $C_{1-4}$ alkyl linkers for $R^{13}$ can be unsubstituted or substituted. When the $C_{1-4}$ alkyls for $R^{13}$ are substituted, one or more hydrogens can be replaced with a moiety, such as those provided in the definition of "optionally substituted," and/or two or more hydrogens can be taken together along with the carbon to which the hydrogens are attached to form an optionally substituted $C_{3-4}$ cycloalkyl or an optionally substituted 3-, 4- or 5-membered heterocyclyl. In some embodiments, the $C_{1-4}$ alkyl linker for the $R^{13}$ groups can be substituted with one or more moieties selected from halogen (such as F), cyano, $C_{1-2}$ haloalkyl (for example, $CF_3$), OH, an unsubstituted $C_{1-4}$ alkoxy and an unsubstituted C-amido (such as —C(═O)$NH_2$, —C(═O)NH($C_{1-4}$ alkyl) and —C(═O)N($C_{1-4}$ alkyl)$_2$).

In some embodiments, $R^{13}$ can be an optionally substituted cycloalkyl($C_{1-4}$ alkyl), such as an optionally substituted monocyclic $C_{3-8}$ cycloalkyl($C_{1-4}$ alkyl). In other embodiments, $R^{13}$ can be an optionally substituted cycloalkenyl($C_{1-4}$ alkyl), such as an optionally substituted monocyclic $C_{3-8}$ cycloalkenyl($C_{1-4}$ alkyl). In some embodiments, $R^{13}$ can be an optionally substituted aryl($C_{1-4}$ alkyl). As an example, $R^{13}$ can be an optionally substituted benzyl. In other embodiments, $R^{13}$ can be an optionally substituted heteroaryl($C_{1-4}$ alkyl). In still other embodiments, $R^{13}$ can be an optionally substituted heterocyclyl($C_{1-4}$ alkyl). The heteroaryl of the optionally substituted heteroaryl($C_{1-4}$ alkyl) can be an optionally substituted monocyclic heteroaryl (such as a 5- or 6-membered monocyclic heteroaryl) or an optionally substituted bicyclic heteroaryl (such as a 9- or 10-membered bicyclic heteroaryl).

In some embodiments, $R^{12}$ and $R^{13}$ can be taken together along with the nitrogen to which $R^{12}$ and $R^{13}$ are attached to form an optionally substituted 4 to 8 member monocyclic heterocyclyl. In other embodiments, $R^{12}$ and $R^{13}$ can be taken together along with the nitrogen to which $R^{10}$ and $R^{11}$ are attached to form an optionally substituted 8 to 13 membered fused-bicyclic heterocyclyl. In still other embodiments, $R^{12}$ and $R^{13}$ can be taken together along with the nitrogen to which $R^{10}$ and $R^{11}$ are attached to form an optionally substituted 7 to 13 membered spiro-bicyclic heterocyclyl. The 4 to 8 member monocyclic heterocyclyl, 8 to 13 membered fused-bicyclic heterocyclyl and/or 7 to 13 membered spiro-bicyclic heterocyclyl can include one or more ring nitrogens.

In some embodiments, $R^{10}$ can be hydrogen; and $R^{11}$ can be a non-hydrogen moiety described herein. For example, $R^8$ can be —NH (an unsubstituted $C_{1-4}$ alkyl) or —NH (an optionally substituted phenyl). In some embodiments, when $X^1$ is $CR^{14}$, then $R^8$ can be —$NR^{10}R^{11}$. In other embodiments, when $X^1$ is $CR^{14}$, then $R^8$ can be —C(=O)$NR^{12}R^{13}$. As an example, $X^1$ can be $CR^{14}$, wherein $R^8$ can be —C(=O)$NHR^{13}$ and $R^{13}$ can be a group described herein. In still other embodiments, when $X^1$ is N, then $R^8$ can be an unsubstituted $C_{1-4}$ alkyl or an unsubstituted $C_{1-4}$ haloalkyl. In yet still other embodiments, when $X^1$ is N, then $R^8$ can be an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl) or an optionally substituted heterocyclyl($C_{1-4}$ alkyl).

Non-limiting examples of $R^8$, $R^{11}$ and $R^{13}$ groups include the following:

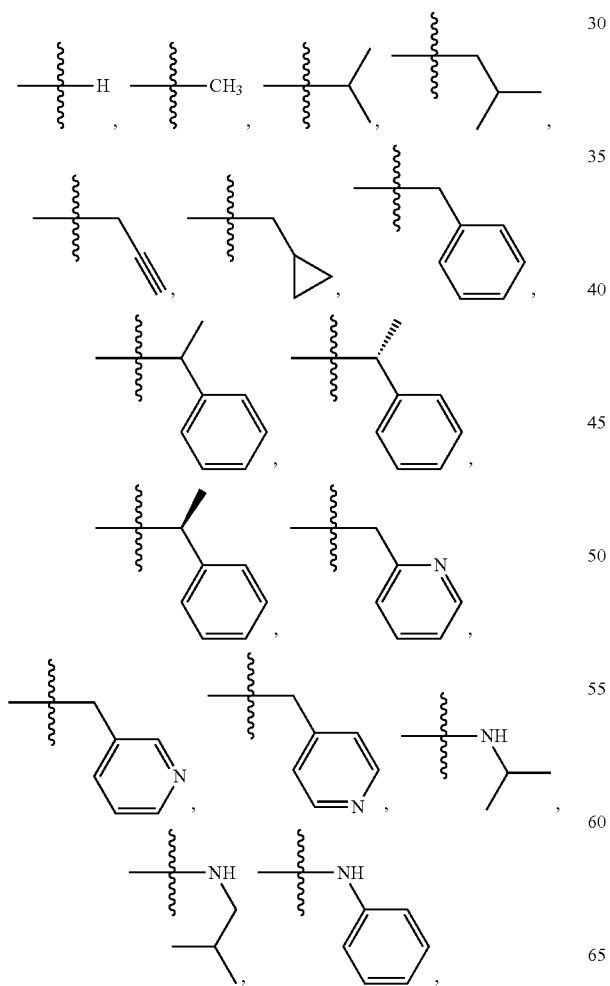

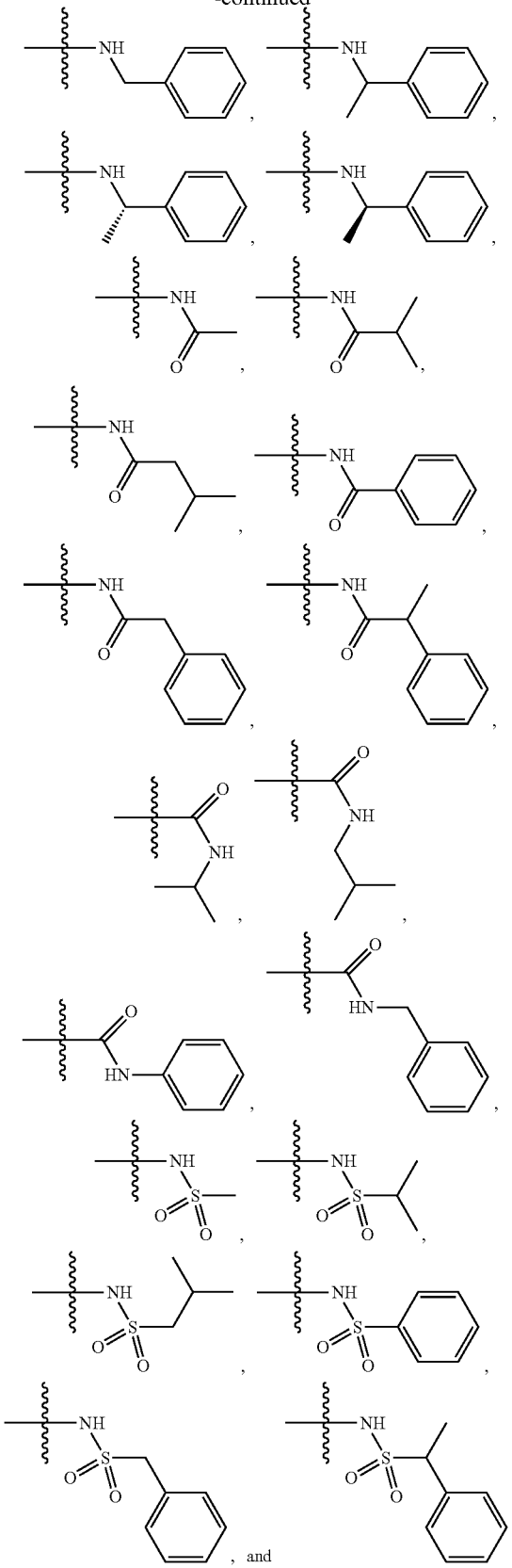

Each of the rings shown above (for example, phenyl, pyridinyl and cyclopropyl) can be unsubstituted or substituted. In some embodiments, when substituted, one or more of the following groups can be present: halogen, cyano, an unsubstituted $C_{1-4}$ alkyl, an unsubstituted $C_{2-4}$ alkenyl, an unsubstituted $C_{2-4}$ alkynyl, an unsubstituted $C_{1-4}$ alkoxy, an unsubstituted $C_{1-4}$ haloalkyl, an unsubstituted $C_{1-4}$ haloalkoxy, an optionally substituted $C_{3-6}$ cycloalkyl, an optionally substituted heteroaryl (for example, an optionally substituted monocyclic heteroaryl including 5- and 6-membered monocyclic heteroaryls that have one or more heteroatoms independently selected from O, S and N), an optionally substituted heterocyclyl (such as an optionally substituted monocyclic heterocyclyl including 5- and 6-membered monocyclic heterocyclyls that have one or more heteroatoms independently selected from O, S and N), —O—CH$_2$—C(=O)NH$_2$, —O—CH$_2$—C(=O)NH (an unsubstituted $C_{1-4}$ alkyl) and —O—CH$_2$—C(=O)N (an unsubstituted $C_{1-4}$ alkyl)$_2$.

Various groups can be present for $R^9$, including hydrogen, an unsubstituted $C_{1-4}$ alkyl, an optionally substituted monocyclic $C_{4-6}$ cycloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl). In some embodiment, $R^9$ can be hydrogen. In other embodiments, $R^9$ can be an unsubstituted $C_{1-4}$ alkyl, including methyl, ethyl, n-propyl, isopropyl, n-butyl, isobutyl, sec-butyl and tert-butyl. In still other embodiments, $R^9$ can be an optionally substituted monocyclic $C_{4-6}$ cycloalkyl, for example, an unsubstituted or a substituted cyclobutyl, an unsubstituted or a substituted cyclopentyl or an unsubstituted or a substituted cyclohexyl.

A variety of cyclic groups can be directly attached to the nitrogen to which $R^9$ is attached or the cyclic groups can be attached via a $C_{1-4}$ linker. In some embodiment, $R^9$ can be an optionally substituted aryl, for example, an optionally substituted phenyl or an optionally substituted naphthyl. In some embodiment, $R^9$ can be an optionally substituted heteroaryl. In other embodiments, $R^9$ can be an optionally substituted heterocyclyl. The heteroaryl can be a monocyclic or bicyclic heteroaryl (such as a fused bicyclic heteroaryl). For example, $R^9$ can be an unsubstituted or a substituted monocyclic 5-membered heteroaryl, an unsubstituted or a substituted monocyclic 6-membered heteroaryl, an unsubstituted or a substituted bicyclic 9-membered heteroaryl or an unsubstituted or a substituted bicyclic 10-membered heteroaryl. As additional examples, $R^9$ can be an unsubstituted or a substituted monocyclic 5-membered heterocyclyl, an unsubstituted or a substituted monocyclic 6-membered heterocyclyl, an unsubstituted or a substituted bicyclic 9-membered heterocyclyl or an unsubstituted or a substituted bicyclic 10-membered heterocyclyl.

In some embodiments, $R^9$ can be an optionally substituted aryl($C_{1-4}$ alkyl). In other embodiments, $R^9$ can be an optionally substituted heteroaryl($C_{1-4}$ alkyl). In still other embodiments, $R^9$ can be an optionally substituted heterocyclyl($C_{1-4}$ alkyl). The $C_{1-4}$ alkyl linkers for $R^9$ can be unsubstituted or substituted. When the $C_{1-4}$ alkyl linkers are substituted, one or more hydrogens can be replaced with a moiety, such as those provided in the definition of "optionally substituted," and/or two or more hydrogens can be taken together along with the carbon to which the hydrogens are attached to form an optionally substituted $C_{3-4}$ cycloalkyl or an optionally substituted 3-, 4- or 5-membered heterocyclyl. In some embodiments, the $C_{1-4}$ alkyl linker for the $R^9$ groups can be substituted with one or more moieties selected from halogen (such as F), cyano, $C_{1-2}$ haloalkyl (for example, $CF_3$), OH, an unsubstituted $C_{1-4}$ alkoxy (for example, methoxy, ethoxy, n-propoxy, iso-propoxy, n-butoxy, iso-butoxy, sec-butoxy and tert-butoxy) and an unsubstituted C-amido (such as —C(=O)NH$_2$, —C(=O)NH($C_{1-4}$ alkyl) and —C(=O)N($C_{1-4}$ alkyl)$_2$). Exemplary $C_{1-4}$ alkyl linkers include, but are not limited to, —CH$_2$—, —CH$_2$CH$_2$—, —CH$_2$CH$_2$CH$_2$—, —CH$_2$CH$_2$CH$_2$CH$_2$—, —CH(CH$_3$)CH$_2$—,

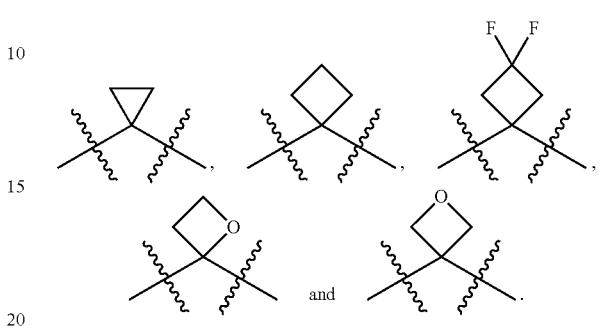

In some embodiments, $R^9$ can be an unsubstituted benzyl. In other embodiments, $R^9$ can be a substituted benzyl. The heteroaryls and heterocyclyls that can be present for $R^9$ and attached via a $C_{1-4}$ alkyl linker include monocyclic and bicyclic heteroaryls and heterocyclyls. In some embodiments, $R^9$ can be an unsubstituted or a substituted monocyclic 5-membered heteroaryl or an unsubstituted or a substituted monocyclic 6-membered heteroaryl. In other embodiments, $R^9$ can be an unsubstituted or a substituted bicyclic 9-membered heteroaryl or an unsubstituted or a substituted bicyclic 10-membered heteroaryl. In still other embodiments, $R^9$ can be an unsubstituted or a substituted monocyclic 5-membered heterocyclyl or an unsubstituted or a substituted monocyclic 6-membered heterocyclyl. In yet still other embodiments, $R^9$ can be an unsubstituted or a substituted bicyclic 9-membered heterocyclyl or an unsubstituted or a substituted bicyclic 10-membered heterocyclyl, for example, an unsubstituted or a substituted fused-bicyclic 9-membered heterocyclyl or an unsubstituted or a substituted fused-bicyclic 10-membered heterocyclyl.

A variety of groups can substitute a $R^9$ group described herein. For example, $R^9$ can be substituted one or more times with a group selected from deuterium, halogen (such as F, Cl and/or Br), cyano, an unsubstituted $C_{1-6}$ alkyl (for example, methyl, ethyl, n-propyl, isopropyl, n-butyl, iso-butyl, sec-butyl, tert-butyl, pentyl (straight-changed or branched) and hexyl (straight-chained or branched)), an unsubstituted $C_{1-6}$ haloalkyl (such as —CHF$_2$, —CH$_2$F, —CF$_3$, —CHClF, —CH$_2$Cl, —CHCl$_2$ and —CCl$_3$), an unsubstituted $C_{1-6}$ alkoxy (for example, methoxy, ethoxy, isopropoxy, n-butoxy, sec-butoxy, isobutoxy and tert-butoxy), an unsubstituted acyl (such as —C(=O)—$C_{1-4}$ alkyl), an unsubstituted C-amido (such as —C(=O)NH$_2$, —C(=O)NH($C_{1-4}$ alkyl) and —C(=O)N($C_{1-4}$ alkyl)$_2$), an unsubstituted sulfonyl (such as —S(=O)$_2$—$C_{1-4}$ alkyl), an unsubstituted S-sulfonamido (such as —S(=O)$_2$NH$_2$, —S(=O)$_2$NH($C_{1-4}$ alkyl) and —S(=O)$_2$N($C_{1-4}$ alkyl)$_2$), an unsubstituted amino, a mono-substituted amine (for example, an mono-alkyl substituted amine), a di-substituted amine (for example, a di-alkyl substituted amine) and an unsubstituted or a substituted monocyclic heteroaryl (such as an unsubstituted or a substituted monocyclic 5- or 6-membered heteroaryl, including an unsubstituted or a substituted monocyclic 5- or 6-membered heteroaryl containing 1 or 2 heteroatoms independently selected from O, S and N).

Examples of $R^9$ groups include the following:
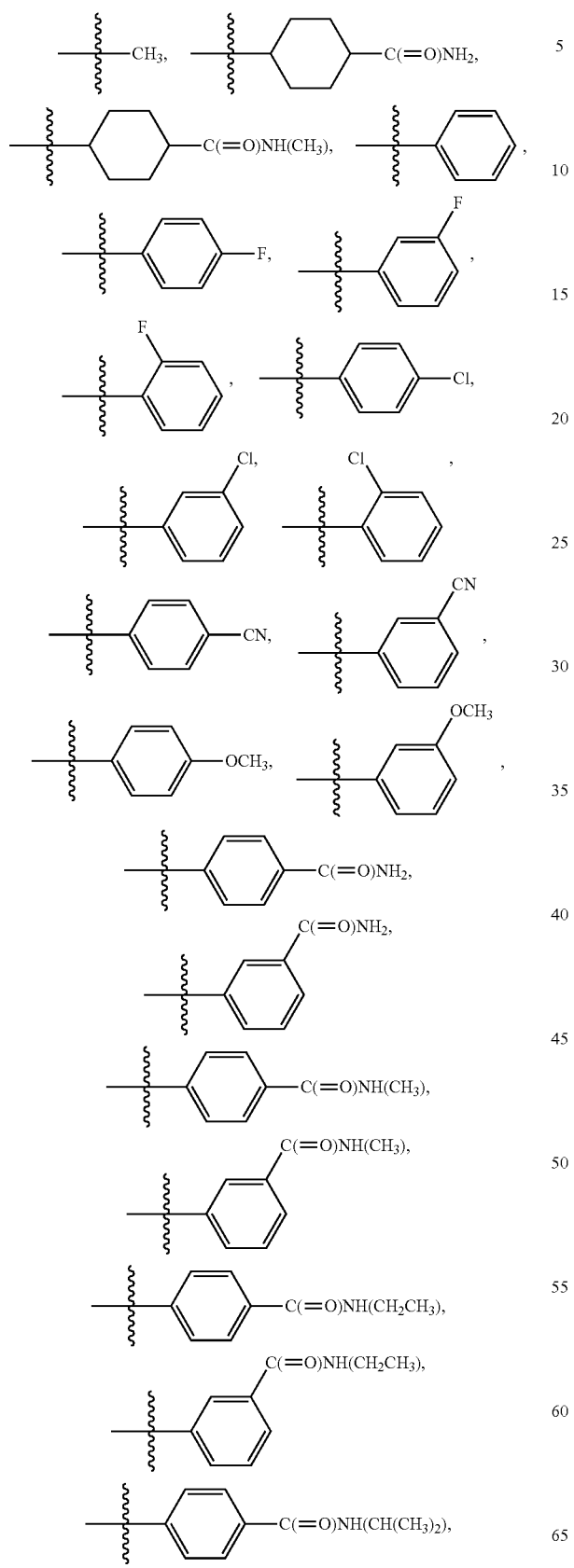
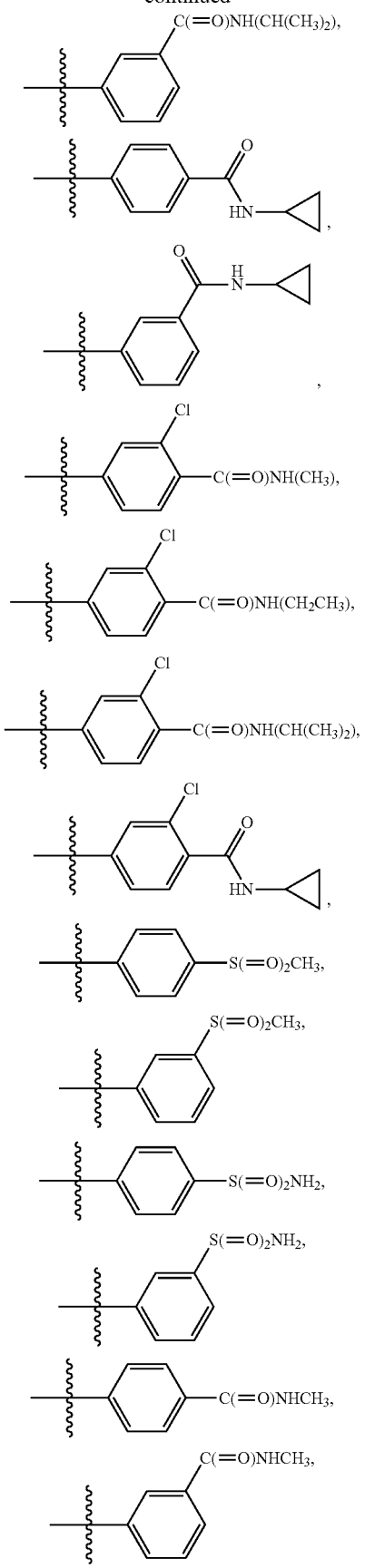

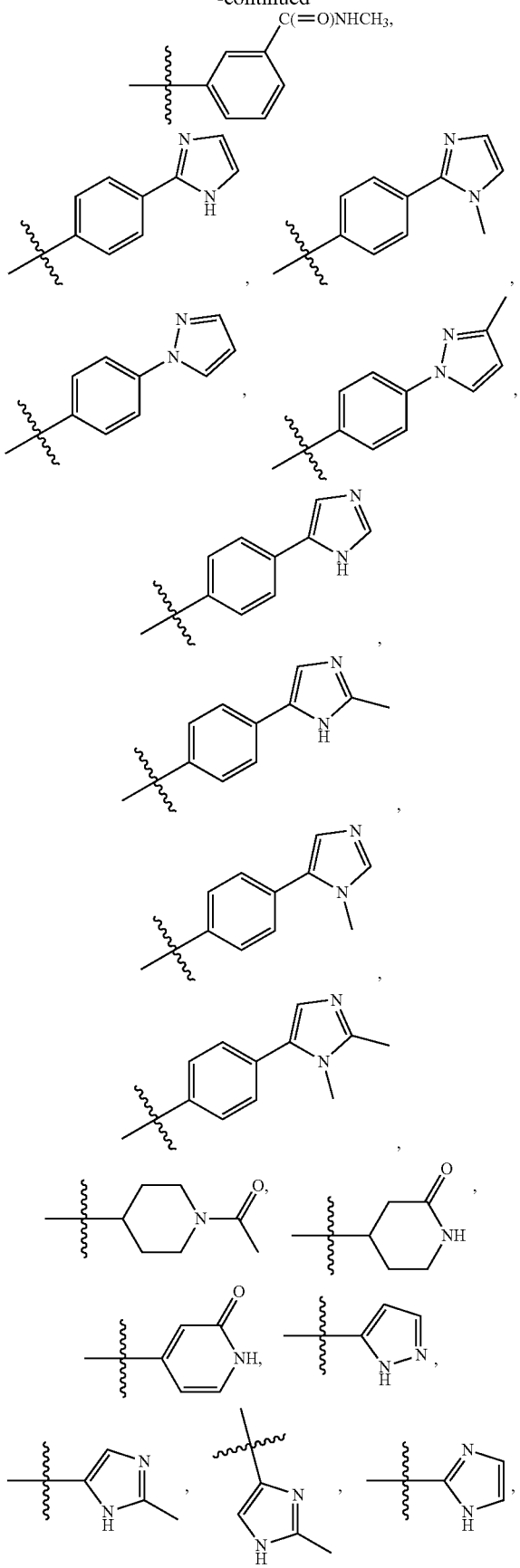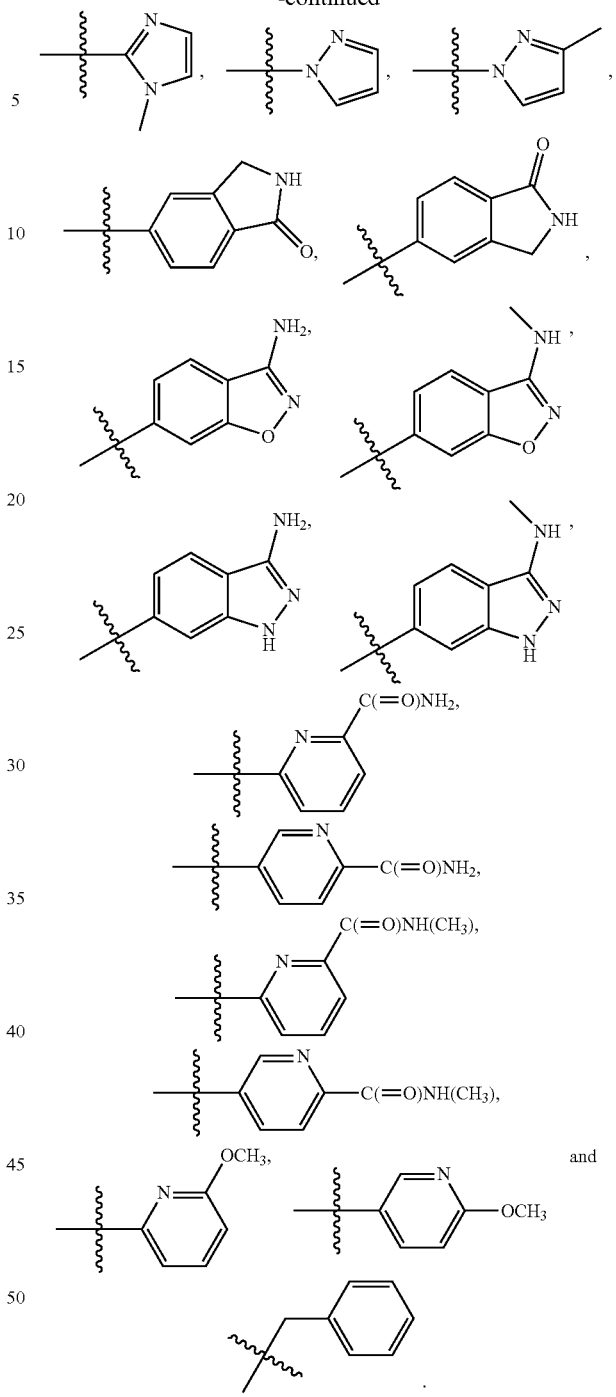

As provided herein, both hydrogen and non-hydrogen moieties can be present on the piperazine ring of a compound of Formula (I), or a pharmaceutically acceptable salt thereof. In some embodiments, $R^2$ can be hydrogen. In other embodiments, $R^2$ can be an unsubstituted $C_{1-4}$ alkyl. In still other embodiments, $R^2$ can be an unsubstituted $C_{1-4}$ haloalkyl. For example, $R^2$ can be methyl, ethyl, n-propyl, iso-propyl, n-butyl, iso-butyl, sec-butyl, tert-butyl, —CHF$_2$, —CH$_2$F, —CF$_3$, —CH$_2$Cl, —CHCl$_2$ and —CCl$_3$. In yet still other embodiments, $R^2$ can be an optionally substituted aryl, an optionally substituted heteroaryl or an optionally substituted heterocyclyl. In some embodiments, $R^2$ can be an optionally substituted aryl($C_{1-4}$ alkyl), an optionally substituted heteroaryl($C_{1-4}$ alkyl) or an optionally substituted heterocyclyl($C_{1-4}$ alkyl). Exemplary $R^2$ groups include, but are not limited to, an optionally substituted phenyl, an optionally substituted benzyl, an optionally substituted monocyclic heteroaryl (an optionally substituted 5- or 6-membered monocyclic heteroaryl) or an optionally substituted monocyclic heterocyclyl (an optionally substituted 5- or 6-membered monocyclic heterocyclyl).

As with $R^2$, $R^3$ can be hydrogen or non-hydrogen moieties as described herein. In some embodiments, $R^3$ can be hydrogen. In other embodiments, $R^3$ can be an unsubstituted $C_{1-4}$ alkyl, such as those described herein. In still other embodiments, $R^3$ can be an unsubstituted $C_{1-4}$ haloalkyl, for example, —$CHF_2$, —$CH_2F$, —$CF_3$, —$CH_2Cl$, —$CHCl_2$ and —$CCl_3$. In yet still other embodiments, $R^3$ can be an optionally substituted aryl, an optionally substituted heteroaryl or an optionally substituted heterocyclyl. In some embodiments, $R^3$ can be an optionally substituted aryl($C_{1-4}$ alkyl), an optionally substituted heteroaryl($C_{1-4}$ alkyl) or an optionally substituted heterocyclyl($C_{1-4}$ alkyl). In other embodiments, $R^3$ can be an optionally substituted phenyl, an optionally substituted monocyclic heteroaryl or an optionally substituted monocyclic heterocyclyl. In other embodiments, $R^2$ and $R^3$ can be taken together along with the carbon to which $R^2$ and $R^3$ are attached to form an optionally substituted monocyclic $C_{3-6}$ cycloalkyl or an optionally substituted 3 to 6 member monocyclic heterocyclyl. For example, $R^2$ and $R^3$ can be taken together along with the carbon to which $R^2$ and $R^3$ are attached to form an optionally substituted cyclopropyl, an optionally substituted cyclobutyl, an optionally substituted cyclopentyl, an optionally substituted cyclohexyl, an optionally substituted oxetane, an optionally substituted thietane, an optionally substituted thietane oxide or an optionally substituted thietane dioxide.

Each of $R^4$ and $R^5$ can be independently hydrogen or selected from the non-hydrogen moieties described herein. In some embodiments, $R^4$ can be hydrogen. In other embodiments, $R^4$ can be an unsubstituted $C_{1-4}$ alkyl, such as methyl, ethyl, n-propyl, iso-propyl, n-butyl, iso-butyl, sec-butyl and tert-butyl. In still other embodiments, $R^4$ can be an unsubstituted $C_{1-4}$ haloalkyl. Exemplary unsubstituted $C_{1-4}$ haloalkyls are described herein, and include —$CHF_2$, —$CH_2F$, —$CF_3$, —$CH_2Cl$, —$CHCl_2$ and —$CCl_3$. In yet still other embodiments, $R^4$ can be an optionally substituted aryl, an optionally substituted heteroaryl or an optionally substituted heterocyclyl. In some embodiments, $R^4$ can be an optionally substituted aryl($C_{1-4}$ alkyl), an optionally substituted heteroaryl($C_{1-4}$ alkyl) or an optionally substituted heterocyclyl ($C_{1-4}$ alkyl). For example, $R^4$ can be an optionally substituted phenyl, an optionally substituted benzyl, an optionally substituted monocyclic heteroaryl (an optionally substituted 5- or 6-membered monocyclic heteroaryl) or an optionally substituted monocyclic heterocyclyl (an optionally substituted 5- or 6-membered monocyclic heterocyclyl).

In some embodiments, $R^5$ can be hydrogen. In other embodiments, $R^5$ can be an unsubstituted $C_{1-4}$ alkyl. In still other embodiments, $R^5$ can be an unsubstituted $C_{1-4}$ haloalkyl. Exemplary unsubstituted $C_{1-4}$ alkyls and unsubstituted $C_{1-4}$ haloalkyls are described herein and include those described with respect to $R^4$. In yet still other embodiments, $R^5$ can be an optionally substituted aryl (such as an optionally phenyl), an optionally substituted heteroaryl (such as an optionally substituted monocyclic heteroaryl) or an optionally substituted heterocyclyl (for example, an optionally substituted monocyclic heterocyclyl). The heteroaryl and heterocyclyl can include 3, 4, 5 or 6 ring(s) atoms and include 1, 2 or 3 heteroatoms such as N (nitrogen), O (oxygen) and S (sulfur). In some embodiments, $R^5$ can be an optionally substituted aryl($C_{1-4}$ alkyl), an optionally substituted heteroaryl($C_{1-4}$ alkyl) or an optionally substituted heterocyclyl($C_{1-4}$ alkyl). For example, $R^5$ can be an unsubstituted or a substituted benzyl, an unsubstituted or a substituted 5-membered monocyclic heteroaryl, an unsubstituted or a substituted 6-membered monocyclic heteroaryl, an unsubstituted or a substituted 5-membered monocyclic heterocyclyl or an unsubstituted or a substituted 6-membered monocyclic heterocyclyl. In some embodiments, $R^4$ and $R^5$ can be taken together along with the carbon to which $R^4$ and $R^5$ are attached to form an optionally substituted monocyclic $C_{3-6}$ cycloalkyl or an optionally substituted 3 to 6 member monocyclic heterocyclyl. Exemplary monocyclic $C_{3-6}$ cycloalkyls and 3 to 6 member monocyclic heterocyclyls include, but are limited to, the following: cyclopropyl, cyclobutyl, cyclopentyl, cyclohexyl, oxetane, thietane, thietane oxide and thietane dioxide, each of the aforementioned can be optionally substituted.

In some embodiments, $R^3$ and $R^5$ can be taken together along with the carbons to which $R^3$ and $R^5$ are each attached to form an optionally substituted monocyclic $C_{5-7}$ cycloalkyl. In other embodiments, $R^3$ and $R^5$ can be taken together along with the carbons to which $R^3$ and $R^5$ are each attached to form an optionally substituted 5 to 7 member monocyclic heterocyclyl. In some embodiments, $R^2$ and $R^4$ can be taken together along with the carbons to which $R^2$ and $R^4$ are each attached to form an optionally monocyclic $C_{5-7}$ cycloalkyl. In other embodiments, $R^2$ and $R^4$ can be taken together along with the carbons to which $R^2$ and $R^4$ are each attached to form an optionally substituted 5 to 7 member monocyclic heterocyclyl. Exemplary 5 to 7 member monocyclic heterocyclyls include, but are not limited to, tetrahydrofuran, pyrrolidine, piperidine and tetrahydro-2H-pyran.

In some embodiments, $R^6$ can be hydrogen. In other embodiments, $R^6$ can be an unsubstituted $C_{1-4}$ alkyl. In still other embodiments, $R^6$ can be an unsubstituted $C_{1-4}$ haloalkyl. Suitable unsubstituted $C_{1-4}$ alkyls and unsubstituted $C_{1-4}$ haloalkyls include methyl, ethyl, n-propyl, iso-propyl, n-butyl, iso-butyl, sec-butyl, tert-butyl, —$CHF_2$, —$CH_2F$, —$CF_3$, —$CH_2Cl$, —$CHCl_2$ and —$CCl_3$.

In some embodiments, $R^7$ can be hydrogen. In other embodiments, $R^7$ can be an unsubstituted $C_{1-4}$ alkyl, such as methyl, ethyl, n-propyl, iso-propyl, n-butyl, iso-butyl, sec-butyl or tert-butyl. In still other embodiments, $R^7$ can be an unsubstituted $C_{1-4}$ haloalkyl, for example, —$CHF_2$, —$CH_2F$, —$CF_3$, —$CH_2Cl$, —$CHCl_2$ and —$CCl_3$. In some embodiments, $R^6$ and $R^7$ are taken together along with the carbon to which $R^6$ and $R^7$ are attached to form an unsubstituted monocyclic $C_{3-4}$ cycloalkyl. In other embodiments, $R^6$ and $R^7$ are taken together along with the carbon to which $R^6$ and $R^7$ are attached to form a substituted monocyclic $C_{3-4}$ cycloalkyl. In still other embodiments, $R^6$ and $R^7$ are taken together along with the carbon to which $R^6$ and $R^7$ are attached to form an unsubstituted oxetane or an unsubstituted thietane. In yet still other embodiments, $R^6$ and $R^7$ are taken together along with the carbon to which $R^6$ and $R^7$ are attached to form a substituted oxetane or a substituted thietane.

In some embodiments, $R^2$, $R^3$, $R^4$, $R^5$, $R^6$ and $R^7$ can be each hydrogen. In other embodiments, at least one of $R^2$, $R^3$, $R^4$, $R^5$, $R^6$ and $R^7$ can be a non-hydrogen group, such as those described herein in the previous paragraphs. In some embodiments, $R^2$ can be a non-hydrogen moiety; and $R^3$, $R^4$ and $R^5$ can be each hydrogen. For example, $R^2$ can be an unsubstituted $C_{1-4}$ alkyl; and $R^3$, $R^4$ and $R^5$ can be each hydrogen. In other embodiments, $R^2$, $R^3$, $R^4$ and $R^5$ can be each hydrogen, and $R^6$ and $R^7$ are taken together along with the carbon to which $R^6$ and $R^7$ are attached to form an optionally substituted monocyclic $C_{3-4}$ cycloalkyl. In still other embodiments, $R^2$, $R^3$, $R^4$ and $R^5$ can be each hydrogen, and $R^6$ and $R^7$ are taken together along with the carbon to which $R^6$ and $R^7$ are attached to form an unsubstituted or a substituted oxetane or an unsubstituted or a substituted thietane. In some embodiments, a compounds of Formula (I), or a pharmaceutically acceptable salt thereof, can be a compound of Formula (Ib), wherein $R^2$ can be hydrogen or an unsubstituted $C_{1-4}$ alkyl; $R^3$, $R^4$ and $R^5$ can be each hydrogen; and $R^1$ can be a substituted phenyl; $X^1$ can be CH.

Examples of compounds of Formula (I) include the following:

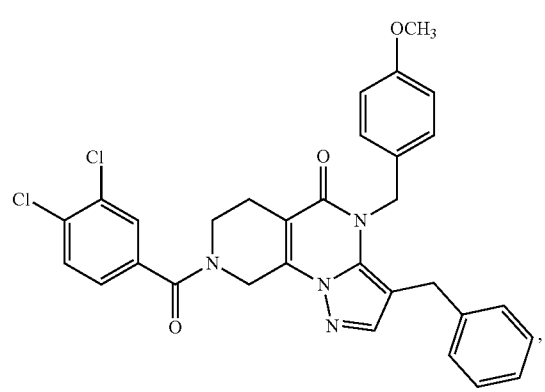

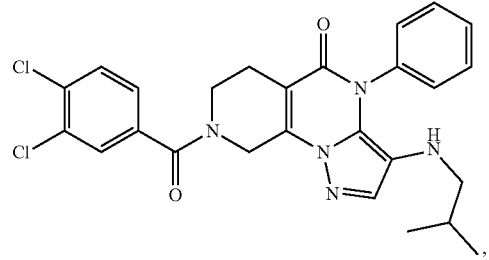

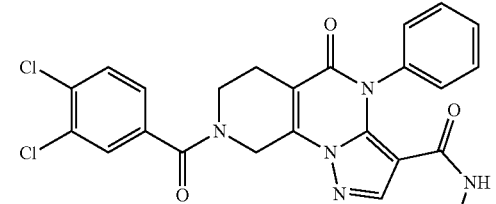

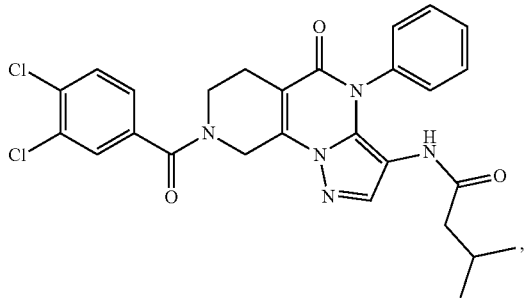

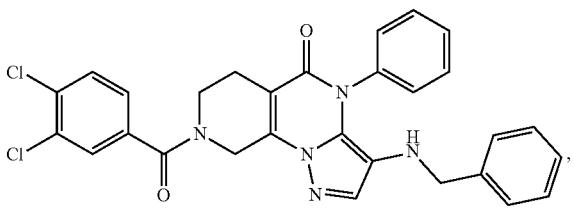

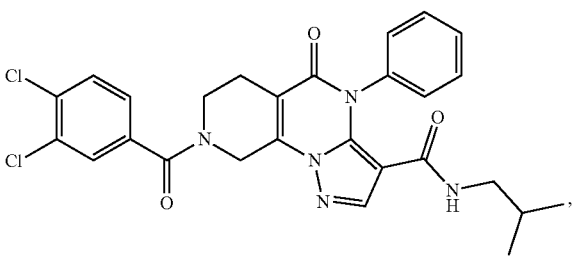

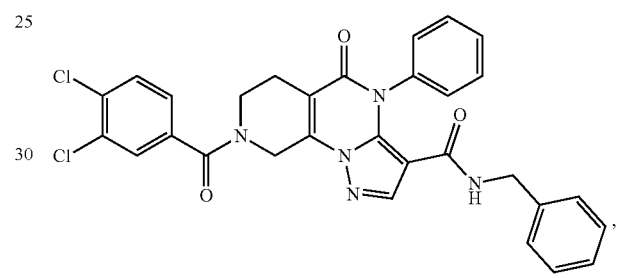

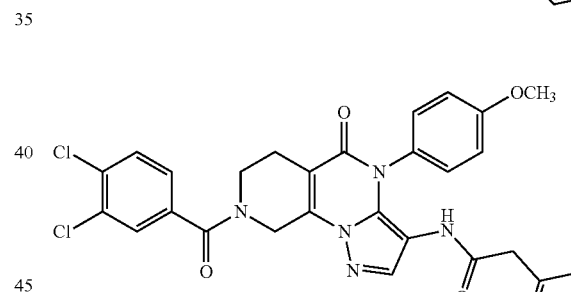

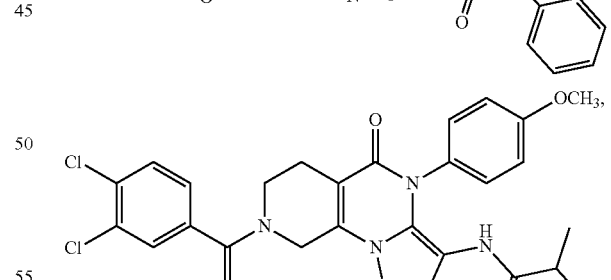

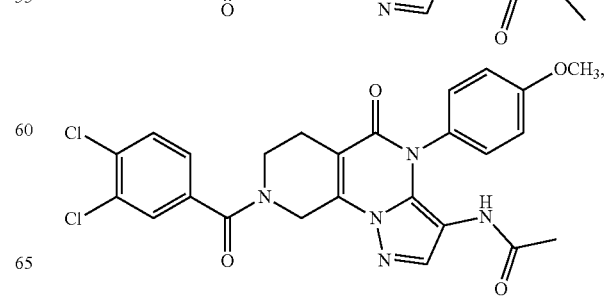

37
-continued
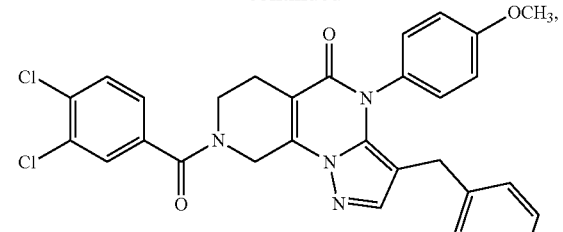
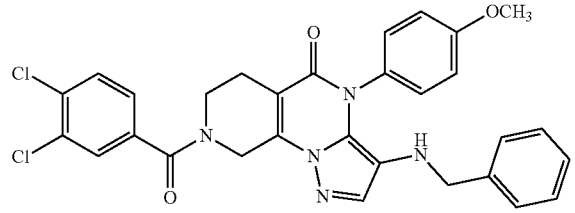
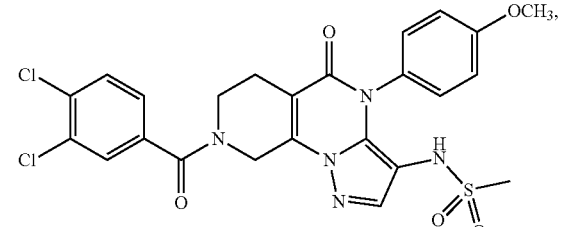
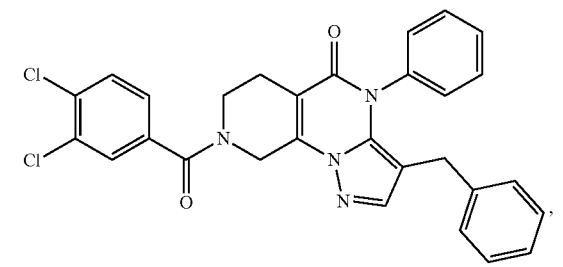
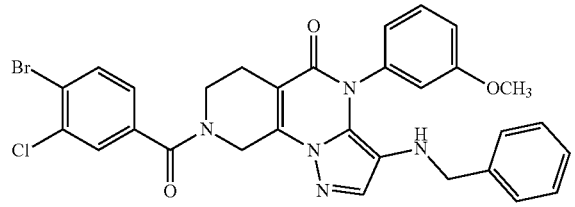
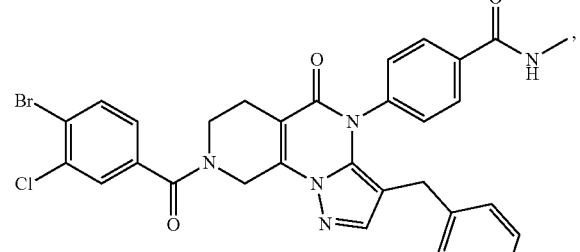
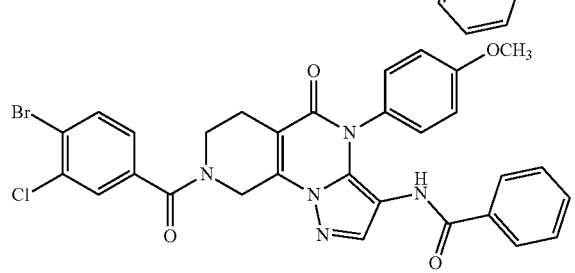
38
-continued
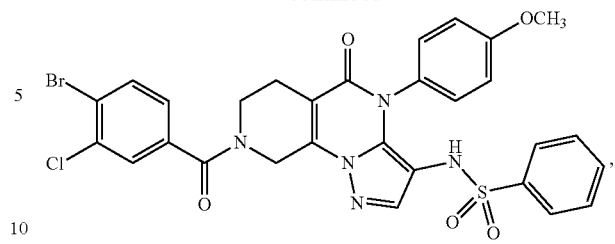
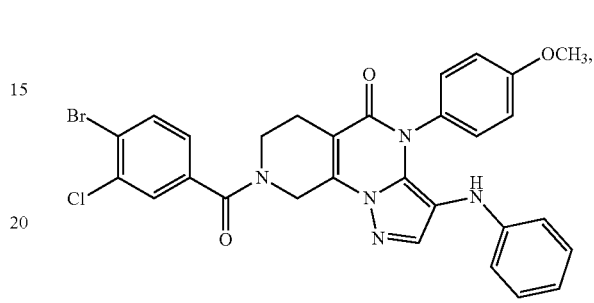
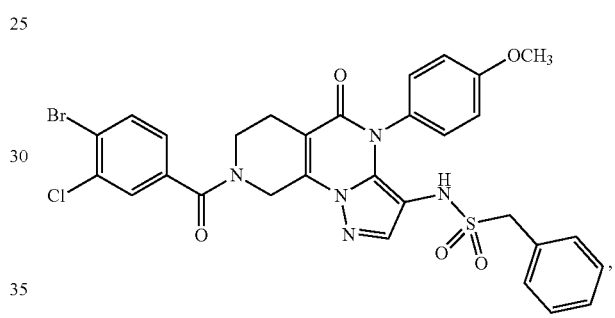
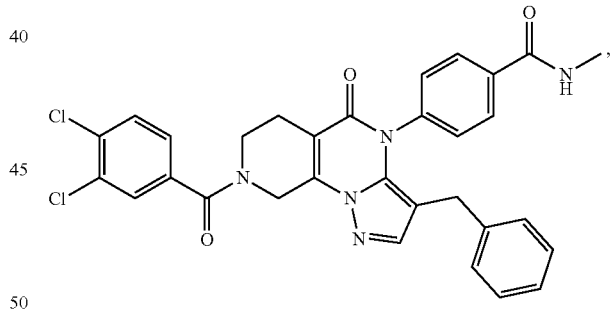
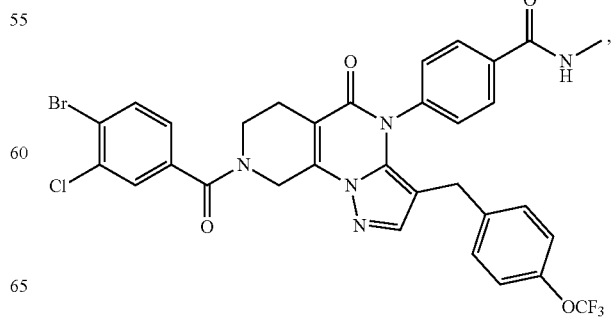

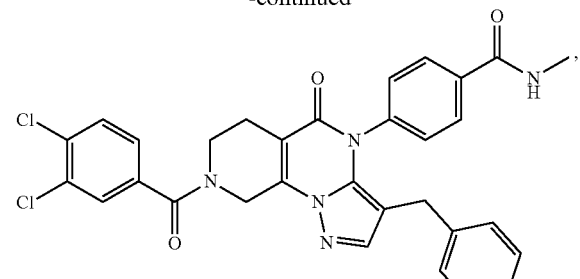
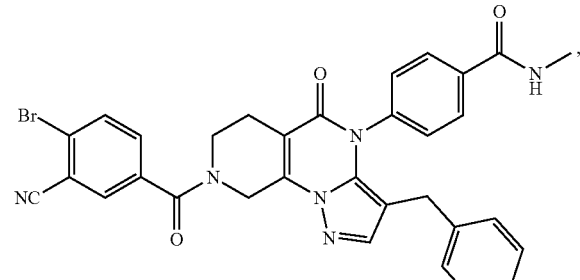
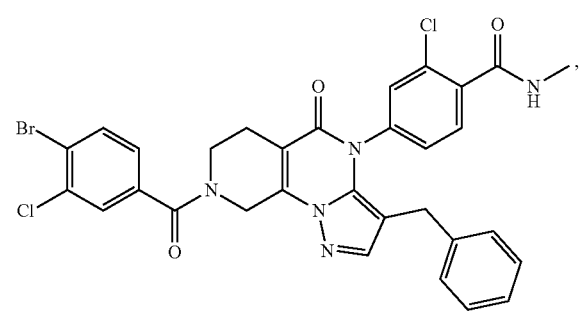
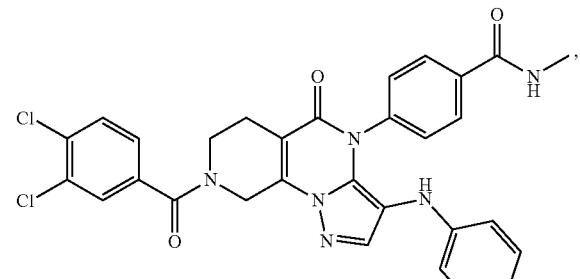
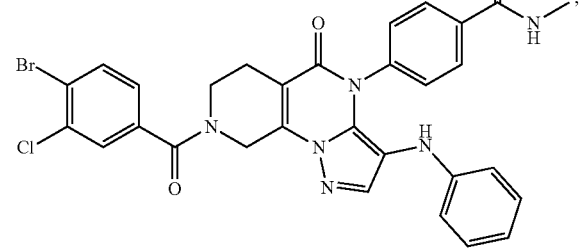
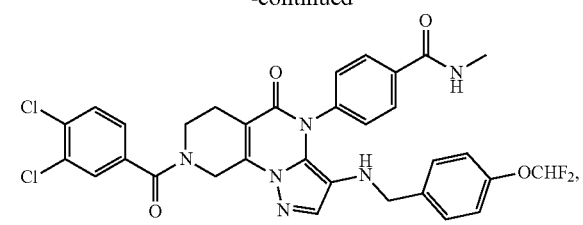
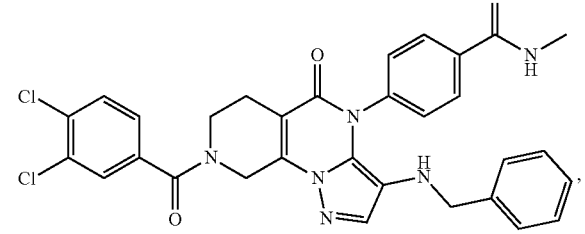
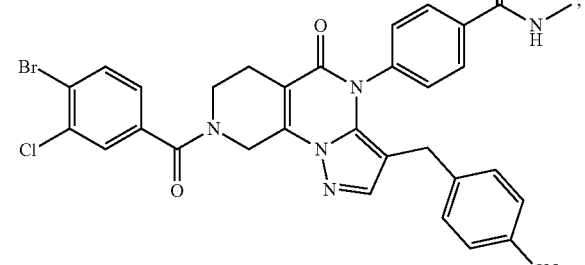
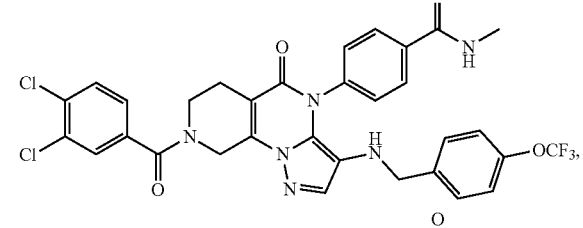
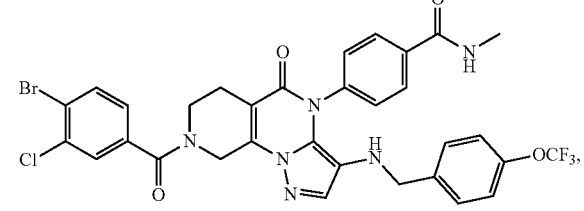
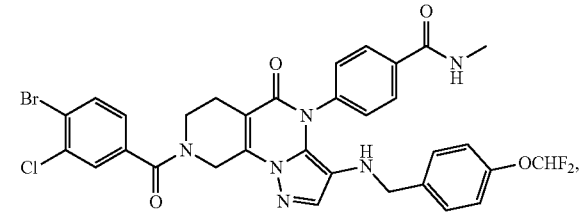
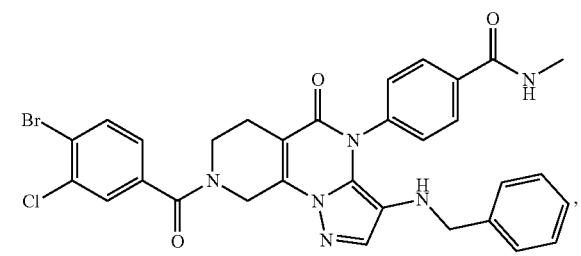

41
-continued
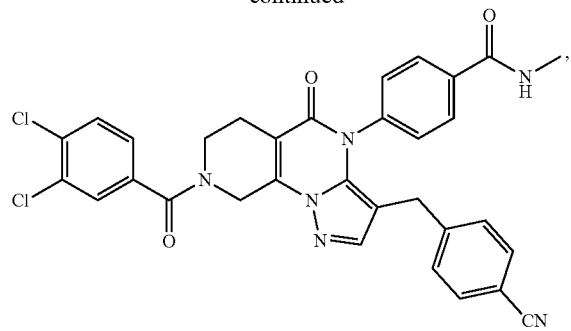
42
-continued
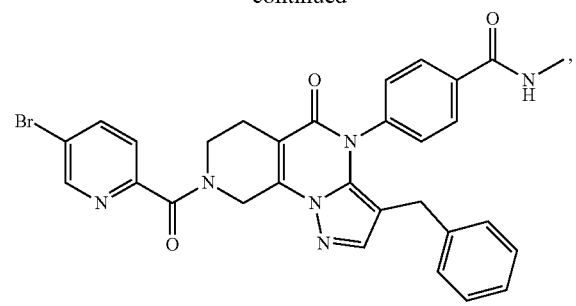

43
-continued
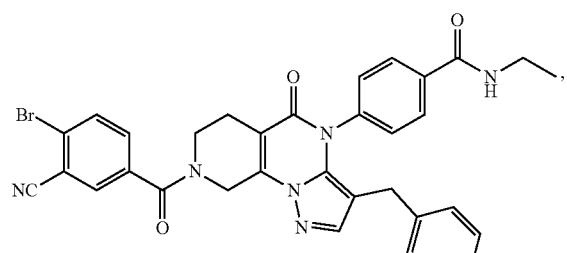
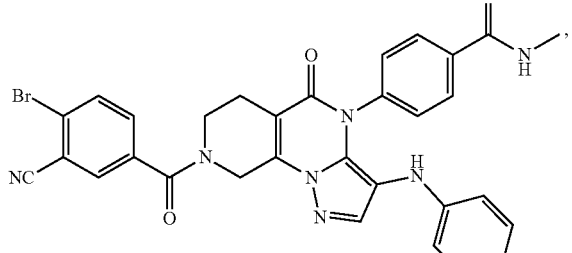
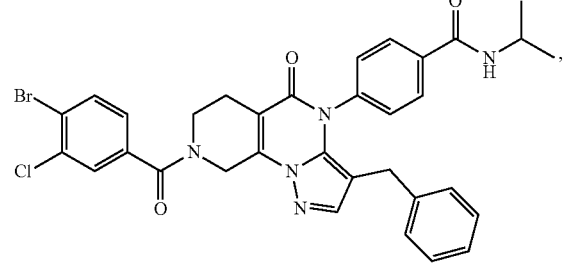
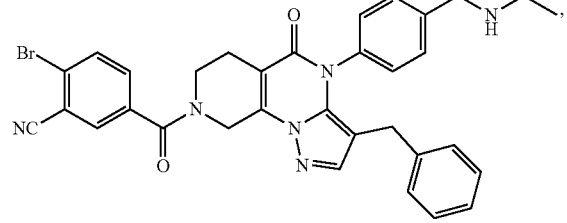
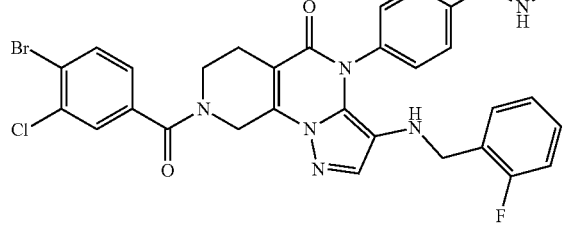
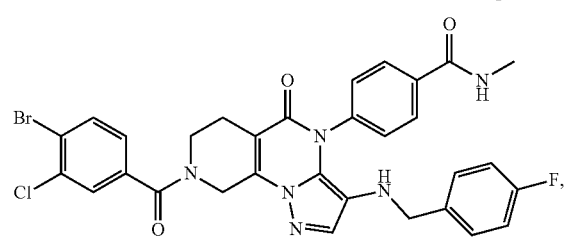
44
-continued
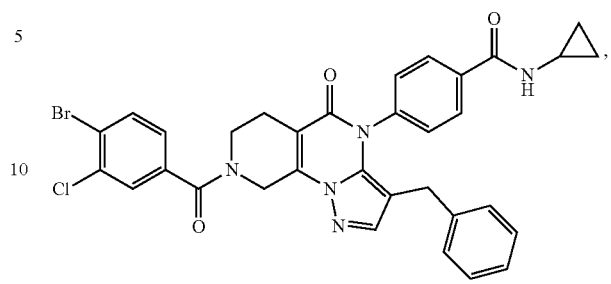
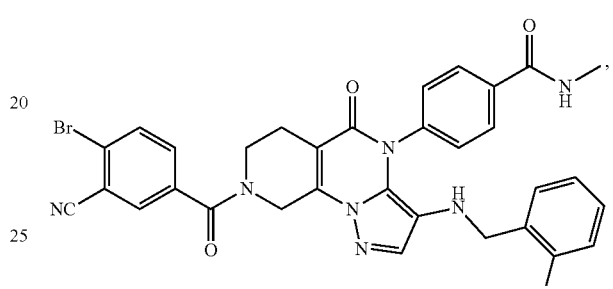
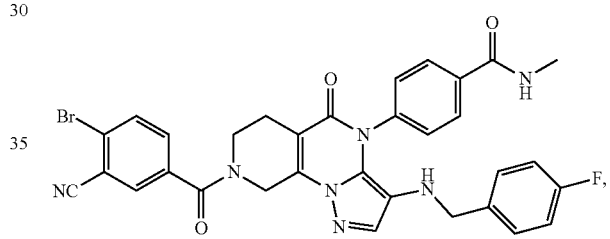
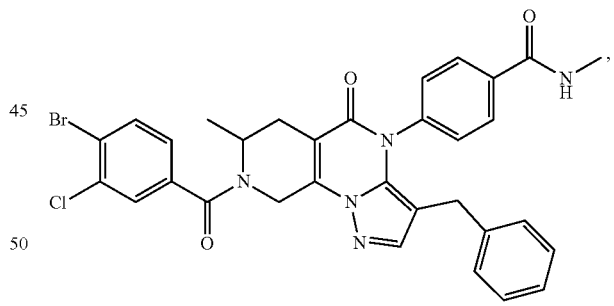
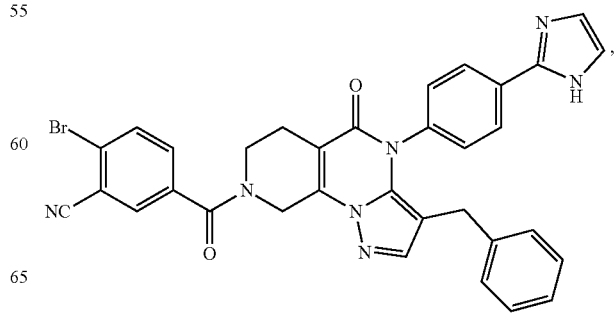

45
-continued
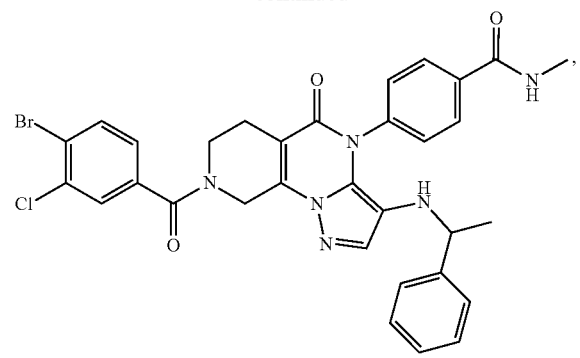
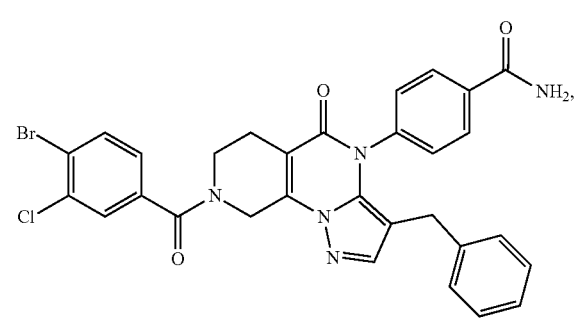
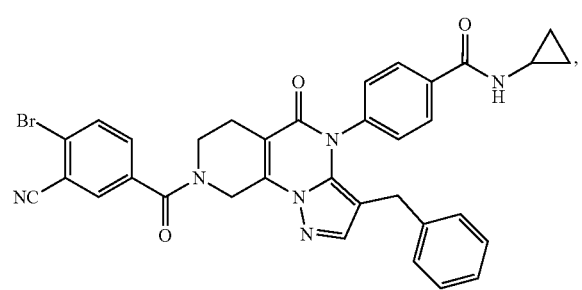
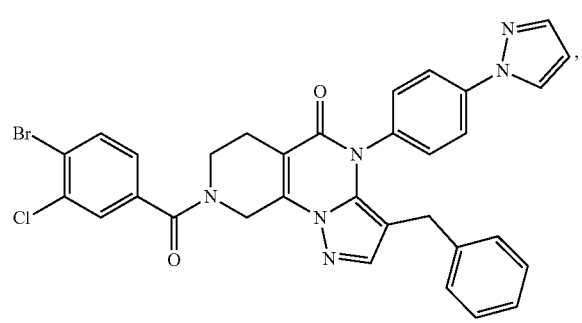
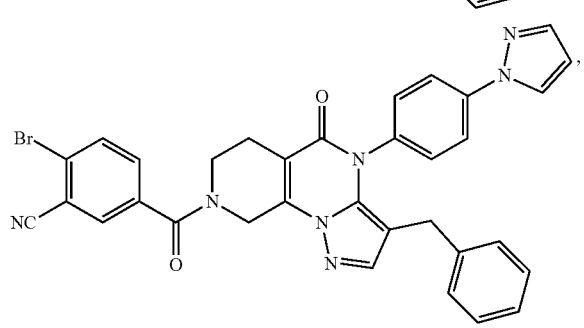
46
-continued
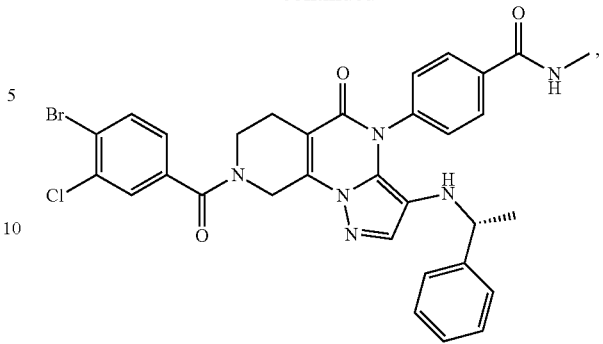
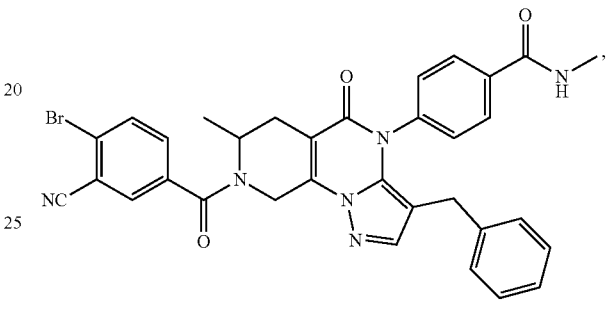
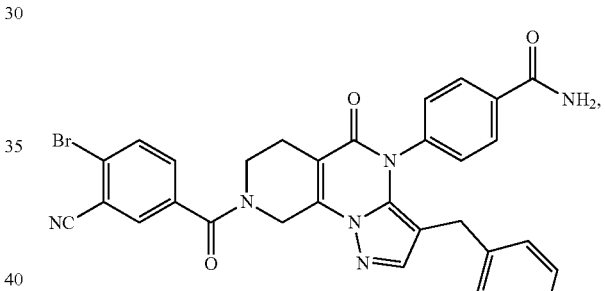
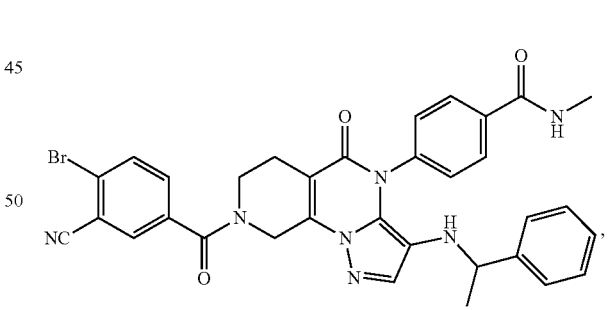
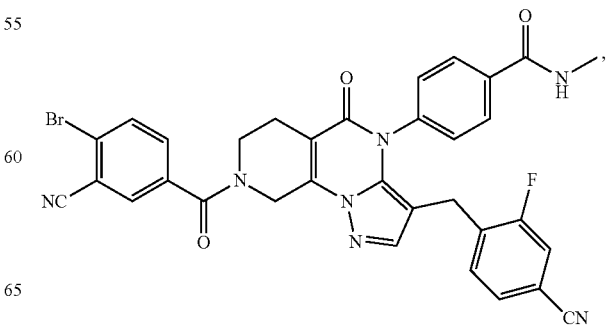

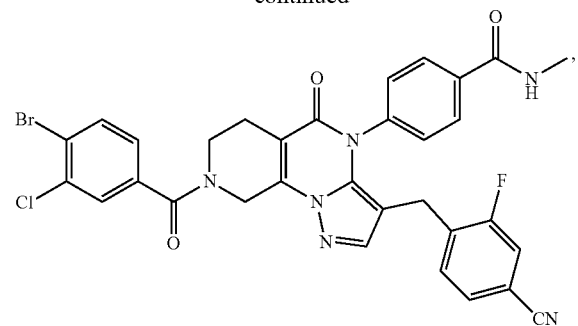
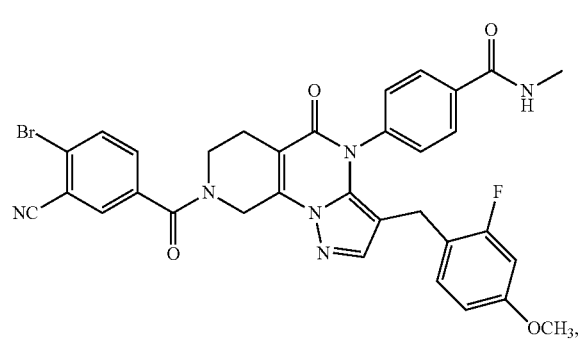
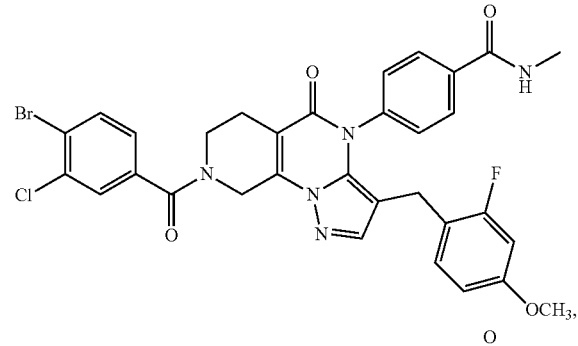
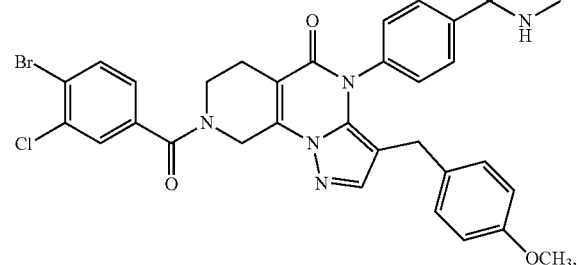
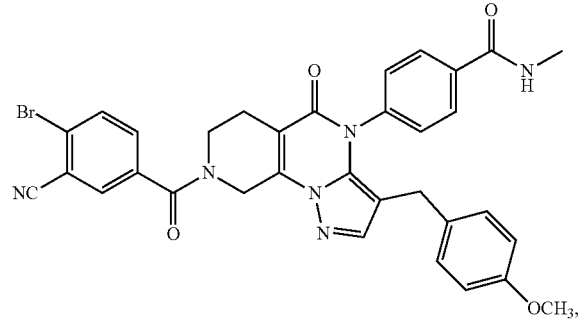
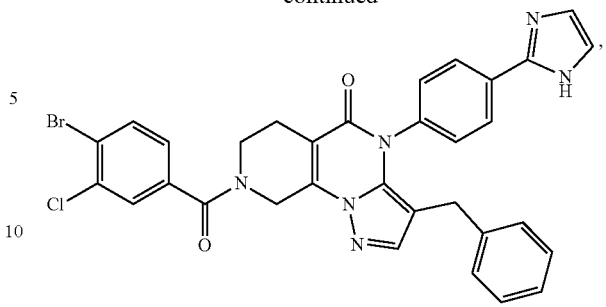
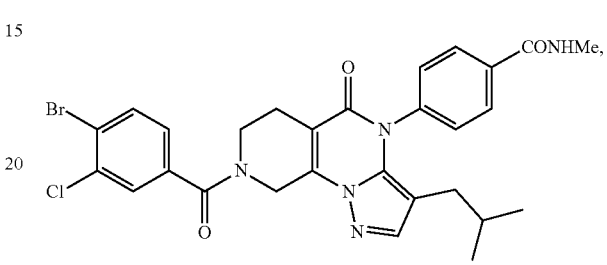
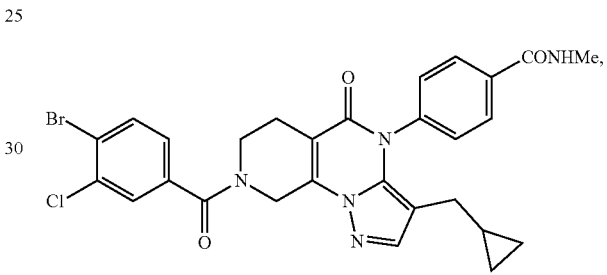
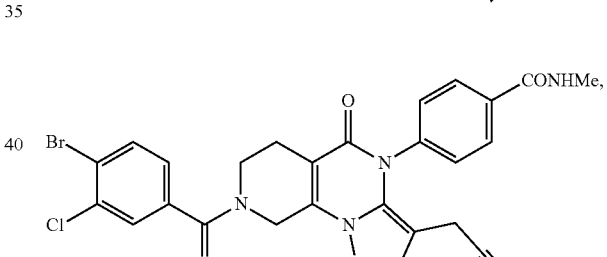
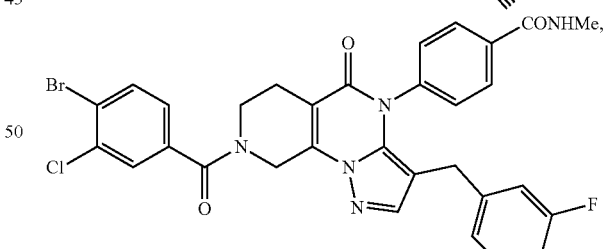
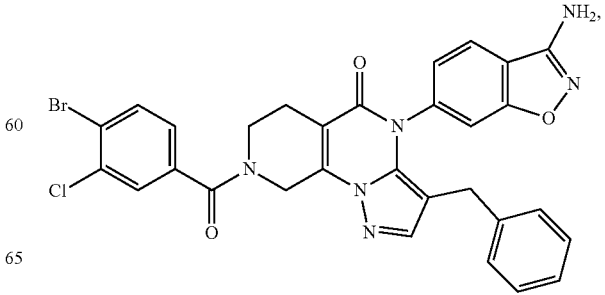

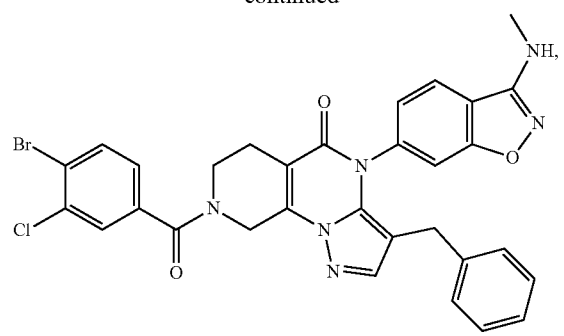
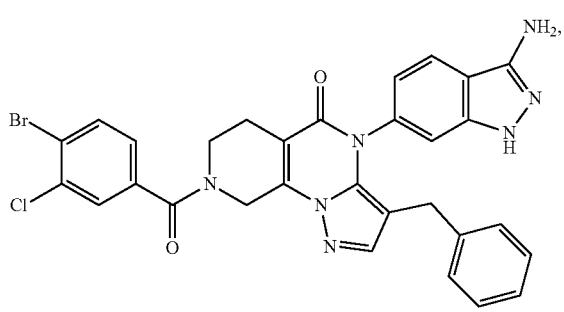
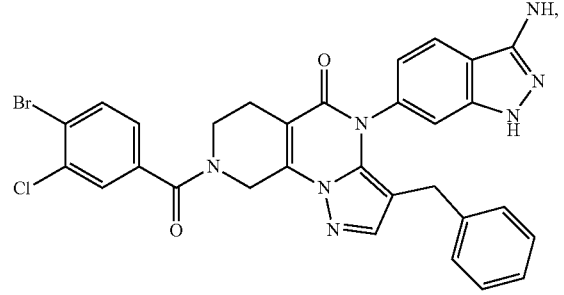
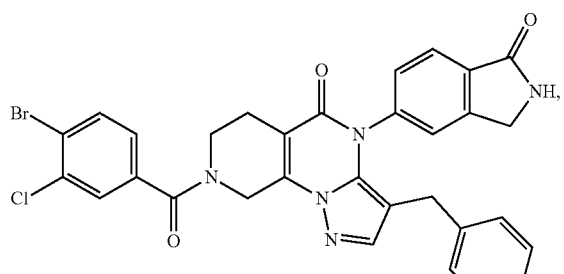
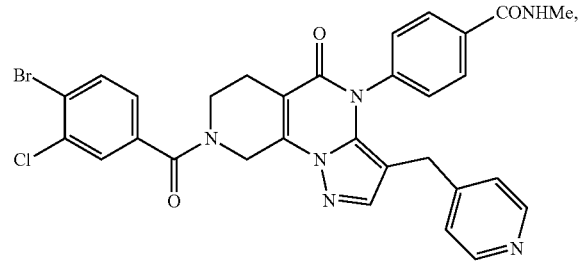
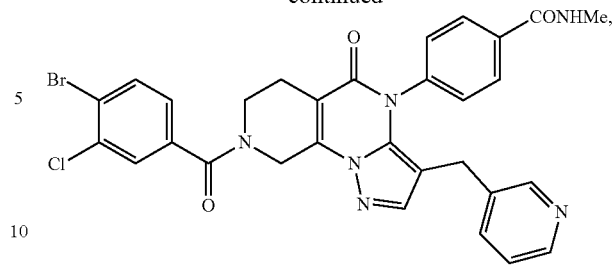
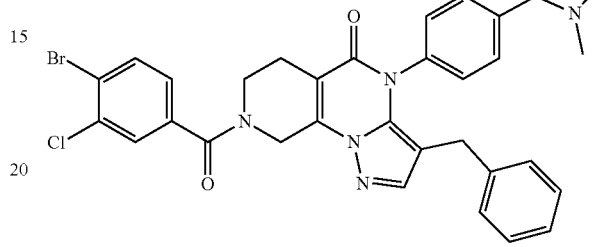
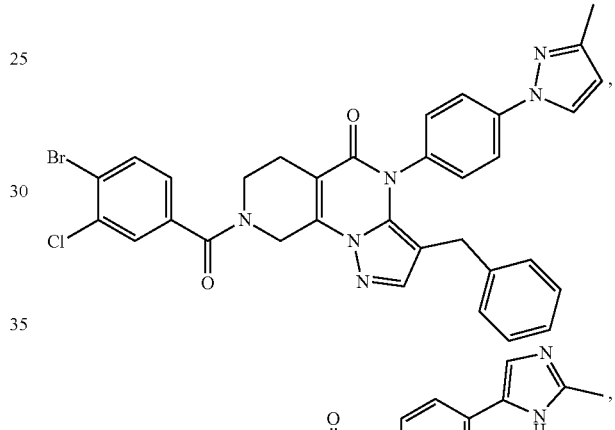
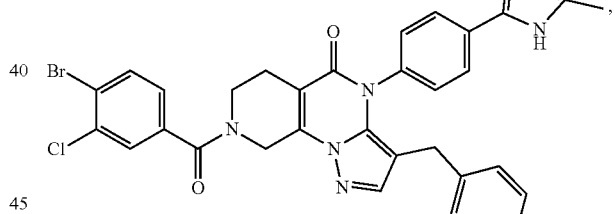
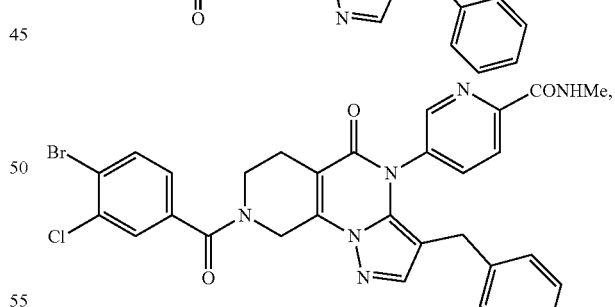
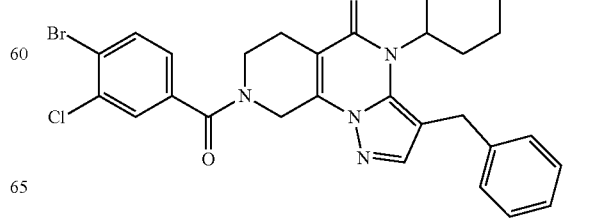

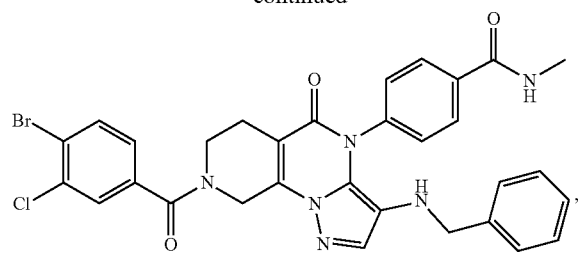
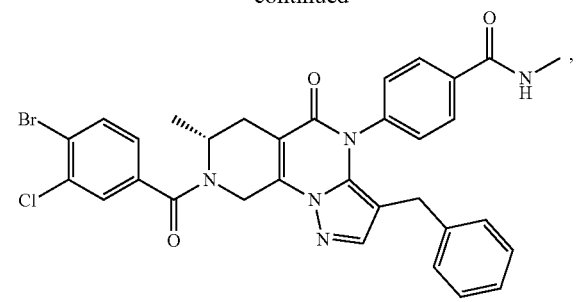
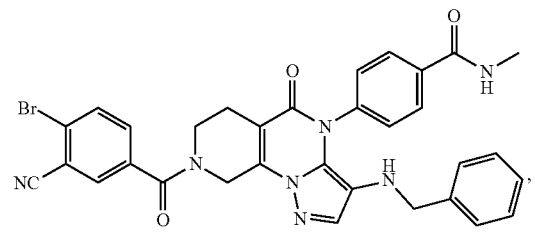
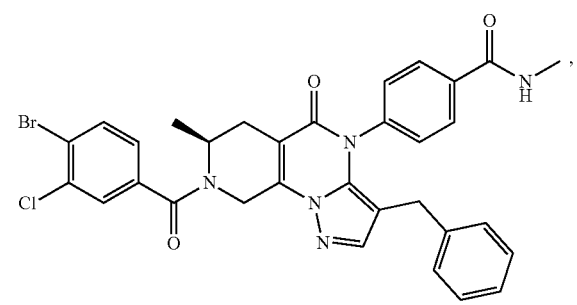
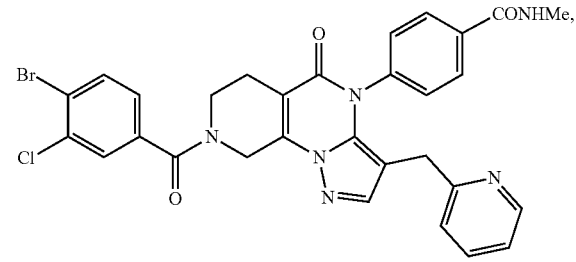
or a pharmaceutically acceptable salt of any of the foregoing.
Additional examples of compounds of Formula (I) include the following:
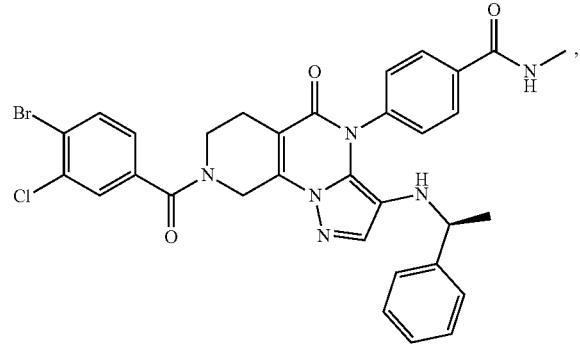
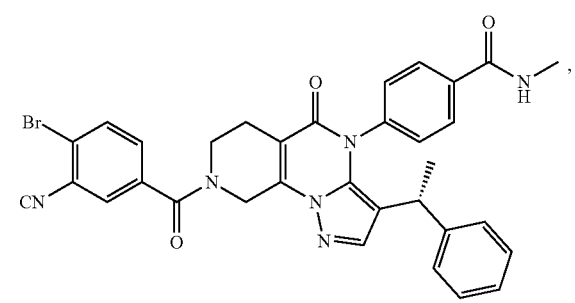
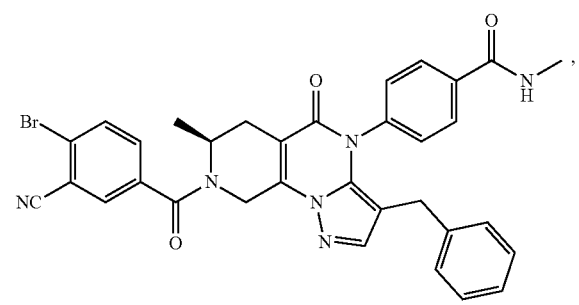
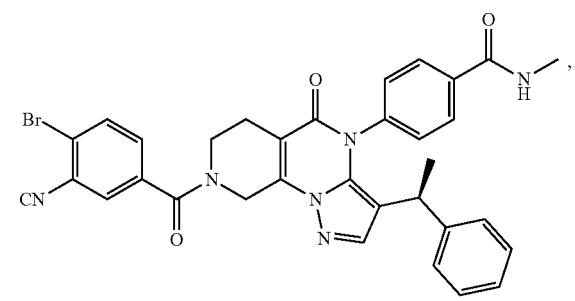
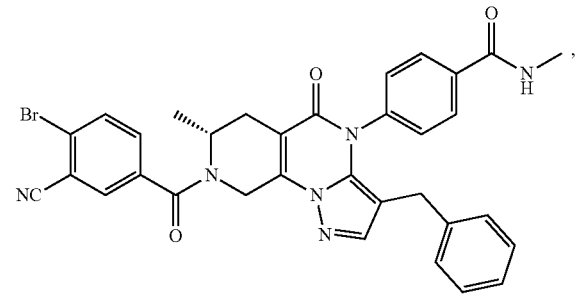

-continued

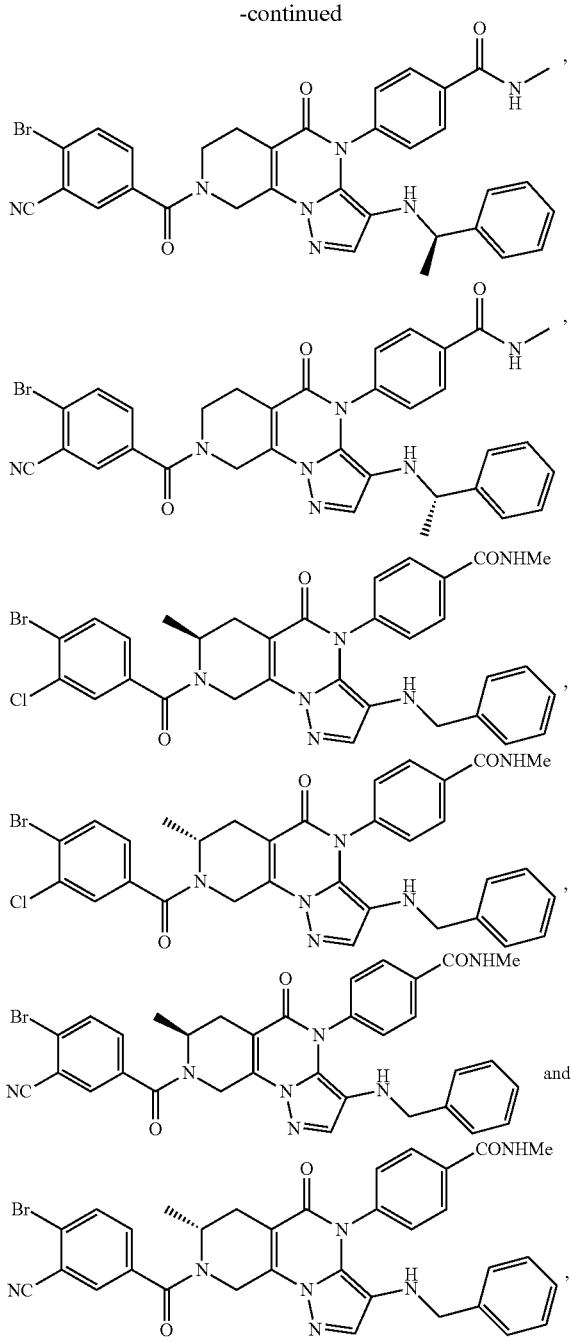

or a pharmaceutically acceptable salt of any of the foregoing.

Synthesis

Compounds of Formula (I) along with those described herein may be prepared in various ways. General synthetic routes for preparing compounds of Formula (I) are shown and described herein along with some examples of starting materials used to synthesize compounds described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme 1

Compounds of Formula (I) can be prepared from a Boc intermediate of Formula (II). The Boc group can be cleaved using acidic conditions, for example, in presence of HCl in a suitable solvent (such as 1,4-dioxane) or in presence of cupper triflate. The coupling of the intermediate of Formula (III) with a suitable agent can afford a compound of Formula (I), or a pharmaceutically acceptable salt thereof. As an example, compounds of Formula (I) along with pharmaceutically acceptable salts thereof, wherein $Z^1$ represents —NH—C(=O)— and n=1, can be obtained by reacting a compound of Formula (III) with a phenyl carbamate of formula $R^1$—NH—C(=O)—O-phenyl or with an isocyanate of general formula $R^1$—N=C=O, in presence of a suitable base in a suitable solvent. An example of a suitable base is triethylamine and an example of suitable solvent is acetonitrile.

Other compounds of Formula (I) along with pharmaceutically acceptable salts thereof, wherein $Z^1$ represents —C(=O)— and n=1, can be obtained by reacting a compound of Formula (III) with an acyl chloride of general formula $R^1$—C(=O)—Cl in presence of a base in a suitable solvent. Other compounds of Formula (I) and pharmaceutically acceptable salts thereof, wherein $Z^1$ represents —C(=O)— and n=1, can be obtained by reacting compound of Formula (III) with an carboxylic acid of formula $R^1$—C(=O)—OH in presence of an amide coupling agent (such as HATU) in a suitable solvent. Other compounds of Formula (I) together with pharmaceutically acceptable salts thereof can be prepared from a compound of Formula (III) using methods known in the art.

Scheme 2

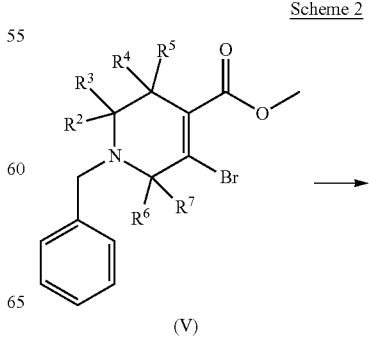

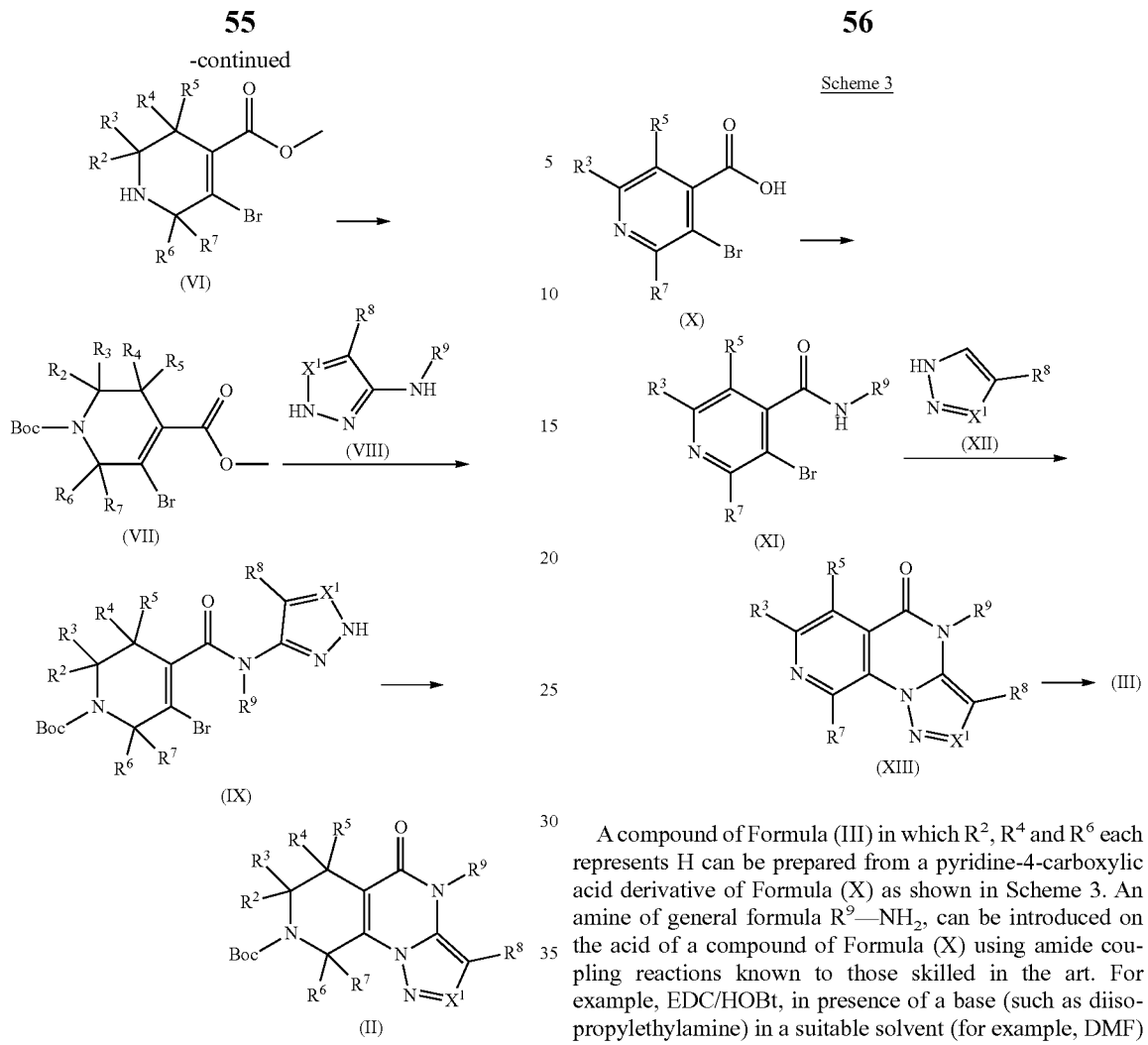

Compounds of Formula (II) can be prepared by various methods known in the art. As an example, a general synthesis of compounds of Formula (II) is depicted in Scheme 2. The benzyl derivative of Formula (V) can be debenzylated by methods known in the art, for example, using chloroethylchloroformate in a suitable solvent (such as dichloroethane) followed by treatment with methanol to give a compound of Formula (VI). A Boc group can be introduced on the nitrogen of a compound of Formula (VI) using (Boc)$_2$O in the presence of a suitable base (such as trimethylamine) in a suitable solvent (such as dichloromethane) to afford a compound of Formula (VII). If desired, protecting groups can be introduced and cleaved appropriately during the synthetic steps of Scheme 2. The coupling of the ester of Formula (VII) with a heterocycle of Formula (VIII) can be achieved in presence of a base, for example, lithium hexamethyldisilazide in a suitable solvent (such as tetrahydrofurane) to obtain a compound of Formula (IX). In some embodiments, a compound of Formula (VIII) (wherein $X^1$ can be $CR^{14}$) can be an optionally substituted amino pyrazole. Cyclisation of a compound of Formula (IX) can be achieved by using methods known in the art. For example, a compound of Formula (IX) can be reacted with a base (such as potassium carbonate) in presence of cupper in a suitable solvent (such as DMF) to afford a compound of Formula (II).

A compound of Formula (III) in which $R^2$, $R^4$ and $R^6$ each represents H can be prepared from a pyridine-4-carboxylic acid derivative of Formula (X) as shown in Scheme 3. An amine of general formula $R^9$—$NH_2$, can be introduced on the acid of a compound of Formula (X) using amide coupling reactions known to those skilled in the art. For example, EDC/HOBt, in presence of a base (such as diisopropylethylamine) in a suitable solvent (for example, DMF) to afford a compound of Formula (XI). The coupling of a compound of Formula (XII) with a compound of Formula (XI) can be achieved by methods known in the art. As an example, a compound of Formula (XII) can be reacted with a compound of Formula (XI) to yield a compound of Formula (XIII) utilizing the following conditions: 1,10-phenanthroline, CuI and a base (such as sodium ethoxide) in a suitable solvent (such as DMF) in the presence of oxygen. A compound of Formula (XII), wherein $X^1$ can be $CR^{14}$, can be an optionally substituted pyrazole. The reduction of the pyridyl cycle in a compound of Formula (XIII) can be achieved by hydrogenation in presence of a suitable catalyst, such as platinum dioxide, in a suitable solvent, such as methanol, to afford a compound of Formula (III) in which $R^2$, $R^4$ and $R^6$ each represent H.

Alternatively, the reduction of the pyridyl moiety of a compound of Formula (XIII) can be achieved in several steps. For example, a compound of Formula (XIII) can be alkylated with 3,4-dimethoxy benzylbromide in a suitable solvent (such as acetonitrile) to afford a pyridinium intermediate that can be isolated, and then reduced with sodium triacetoxyborohydride in a suitable solvent (such as 1,2-dichloroethane). The dimethoxybenzyl group can be cleaved using procedures known to those skilled in the art. Exemplary procedures include using chloroethylchloroformate in a suitable solvent (such as 1,2-dichloroethane) followed by a treatment with methanol to obtain a compound of Formula (III) in which $R^2$, $R^4$ and $R^6$ each represent H.

Scheme 4

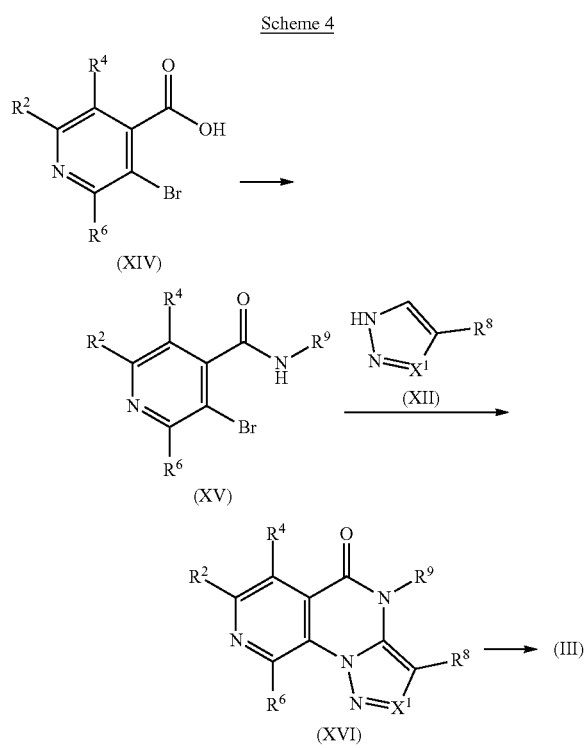

A compound of Formula (III), wherein $R^3$, $R^5$ and $R^7$ each represent H, can be prepared from a compound of Formula (XIV) as shown in Scheme 4 using methods known to those skilled in the art.

Scheme 5

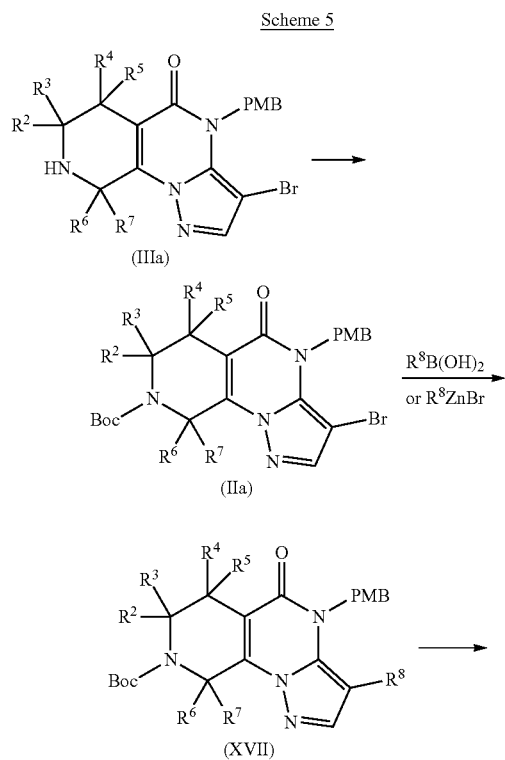

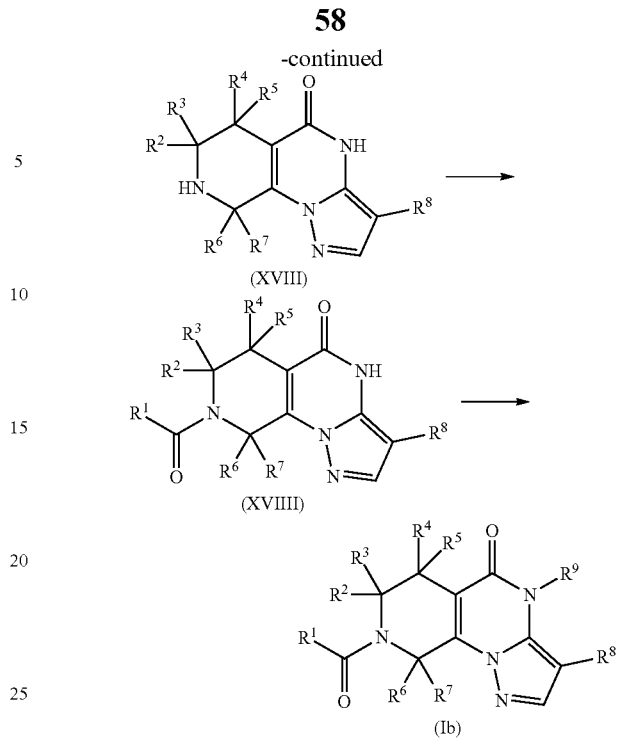

Alternatively a compound of Formula (Ib) in which $R^8$ can be an unsubstituted $C_{1-4}$ alkyl, an unsubstituted $C_{2-4}$ alkenyl, an unsubstituted $C_{1-4}$ haloalkyl, an optionally substituted aryl, an optionally substituted heteroaryl, an optionally substituted cycloalkyl($C_{1-4}$ alkyl), an optionally substituted cycloalkenyl($C_{1-4}$ alkyl), an optionally substituted aryl ($C_{1-4}$ alkyl), an optionally substituted heteroaryl($C_{1-4}$ alkyl), and an optionally substituted heterocyclyl($C_{1-4}$ alkyl), can be prepared as described in Scheme 5, from intermediate (IIIa). Intermediate (IIIa) can be synthesized as provided in Scheme 3, using 4-methoxybenzylamine as $R^9NH_2$ in step 1, and 4-bromo-1H-pyrazole as the compound of Formula (XII) in the second step. Subsequent introduction of the Boc protecting group using conditions known in the art (such as reaction with $Boc_2O$ in presence of TEA in DCM), can provide a compound of Formula (IIa). Reaction of intermediate (IIa) with a compound of Formula $R^8B(OH)_2$, or the corresponding boronic ester, in presence of a palladium catalyst (such as Pd(dppf)Cl$_2$ or Pd(PPh$_3$)$_4$ or Pd(OAc)$_2$ with XPhos) and a base (for example, cesium carbonate or sodium carbonate) in a suitable solvent (such as dioxane) under heating conditions, can provide a compound of Formula (XVII).

Alternatively a compound of Formula $R^8BF_3K$ can also be used to introduce $R^8$ on intermediate (IIa), in the presence of a catalyst, such as Pd(dtbpf)Cl$_2$, and a base (for example, potassium phosphate) in a solvent, such as dioxane/water. A compound of Formula $R^8ZnBr$ can be also be used, in the presence of Pd(OAc)$_2$ and XPhos in THF to provide a compound of Formula (XVII). After removal of the Boc and PMB protecting groups under acidic conditions (such as TFA) the compound of Formula (XVIII) can be coupled to a compound of Formula $R^1COOH$, using coupling conditions known in the art (for example, EDCI, HOBt, DIEA in a suitable solvent such as DMF) to give a compound of Formula (XVIIII). Reaction of a compound of Formula (XVIIII) with a compound of Formula $R^9B(OH)_2$ in presence of a copper-based agent like Cu(OTf)$_2$ or Cu(OAc)$_2$ and a base (such as pyridine or trimethylamine) in a solvent (for example, DMF or DCM) can provide a compound of Formula (Ib). Other conditions to substitute a lactam known in the art may also be used to introduce a R⁹ moiety.

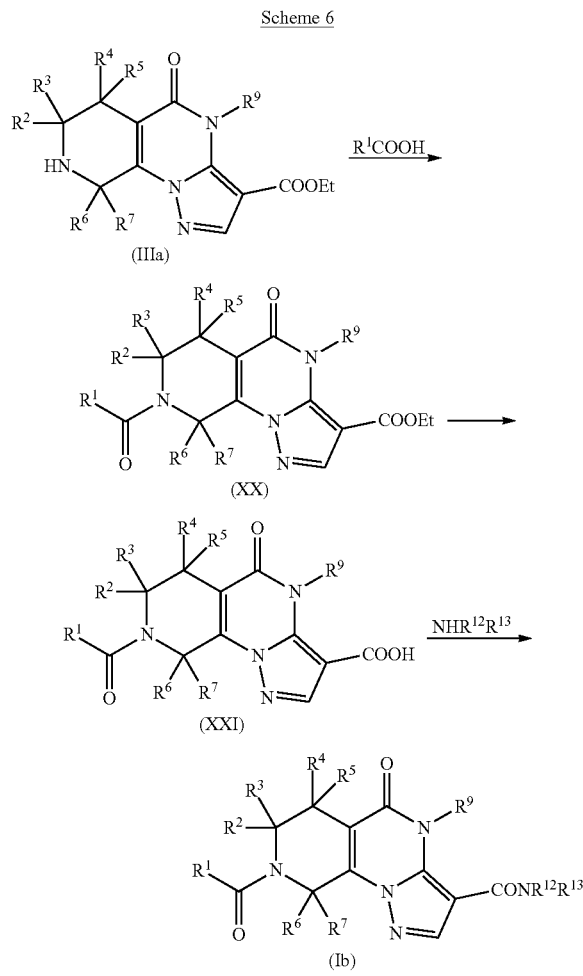

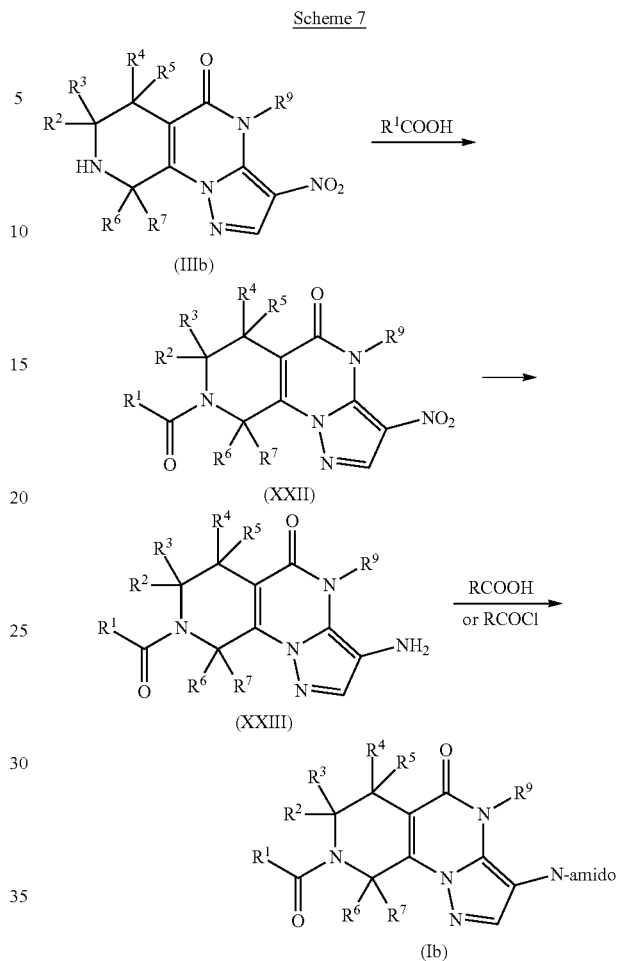

A compound of Formula (Ib) in which $R^8$ is an amide of general formula —CONR$^{12}$R$^{13}$ can be prepared from a compound of Formula (IIIa) as shown in Scheme 6. Synthesis of a compound of Formula (IIIa) can be carried out as depicted in scheme 3, using ethyl 1H-pyrazole-4-carboxylate as the compound of formula (XII) in the second step. Acylation of a compound of Formula (IIIa) to give a compound of Formula (XX) can be achieved with an acyl chloride of general formula R$^1$—C(═O)—Cl in presence of a base in a suitable solvent, or with a carboxylic acid of formula R$^1$—C(═O)—OH in presence of an amide coupling agent (such as HATU, or EDCI/HOBt) and a suitable base (such as DIEA) in a suitable solvent (such as DMF). Other compounds of Formula (XX) can be prepared from a compound of Formula (IIIa) using methods known in the art. Subsequently a carboxylic acid derivative of Formula (XXI) can be obtained from (XX) by reaction with BBr$_3$ in DCM. Compounds of Formula (Ib) can then be obtained by reacting a compound of Formula (XXI) with an amine of general formula NHR$^{12}$R$^{13}$, under acylation conditions known in the art, such as EDCI/HOBt in the presence of a suitable base (such as DIEA) in a suitable solvent (such as DMF).

A compound of Formula (Ib) in which $R^8$ is an optionally substituted N-amido can be prepared from a compound of Formula (IIIb) as shown in Scheme 7. Synthesis of a compound of Formula (IIIb) can be carried out as depicted in Scheme 3, using 4-nitro-1H-pyrazole as the compound of formula (XII) in the second step. Acylation of a compound of Formula (IIIb) to give a compound of Formula (XXII) can be achieved with an acyl chloride of general formula R$^1$—C(═O)—Cl in presence of a base in a suitable solvent, or with a carboxylic acid of formula R$^1$—C(═O)—OH in presence of an amide coupling agent (such as HATU, or EDCI/HOBt) and a suitable base (such as DIEA) in a suitable solvent (such as DMF). Other compounds of Formula (XXII) can be prepared from a compound of Formula (Mb) using methods known in the art. Subsequently the nitro group of the derivative of Formula (XXII) can be reduced to obtain a compound of Formula (XXIII) using, for example, iron in presence of ammonium chloride, in a suitable solvent (such as ethanol). Compounds of Formula (Ib) can be obtained by reacting a compound of Formula (XXIII) with an acyl chloride of general formula R—C(═O)—Cl in presence of a base in a suitable solvent, or with a carboxylic acid of formula R—C(═O)—OH in presence of an amide coupling agent (such as HATU, or EDCI/HOBt) and a suitable base (such as DIEA) in a suitable solvent (such as DMF). Other compounds of Formula (Ib) can be prepared from a compound of Formula (XXIII) using methods known in the art.

Scheme 8

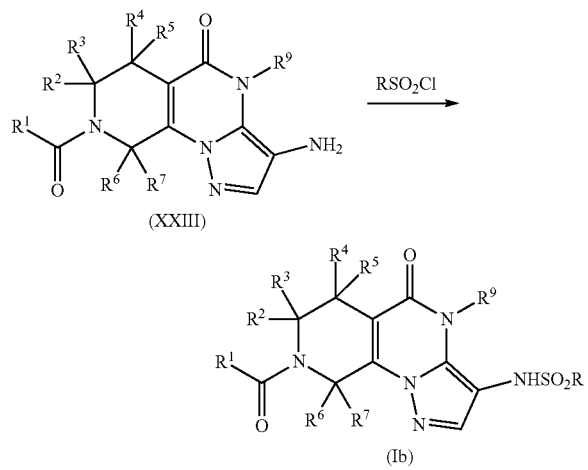

A compound of Formula (Ib) in which R⁸ is an optionally substituted sulfonamido can be prepared from a compound of Formula (XXIII) and a sulfonyl chloride derivative of general formula RSO₂Cl, in the presence of a base (such as TEA) in a suitable solvent (such as DCM), as shown in Scheme 8.

Scheme 9

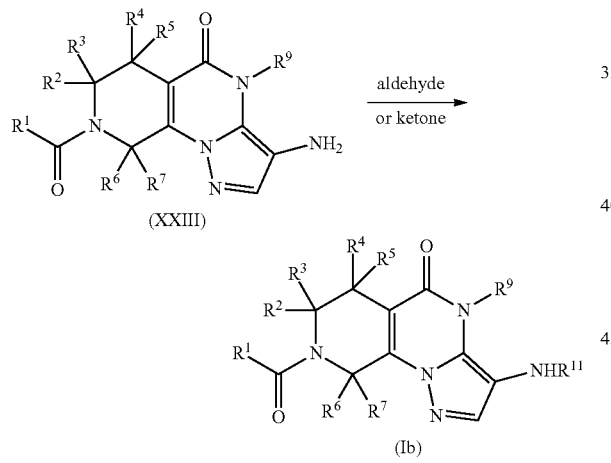

A compound of Formula (Ib) in which R⁸ is a mono-substituted amine of general formula —NHR¹¹ (in which R¹¹ can be an unsubstituted $C_{1-4}$ alkyl, an unsubstituted $C_{1-4}$ haloalkyl, an optionally substituted cycloalkyl, an optionally substituted cycloalkenyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl) and an optionally substituted heterocyclyl($C_{1-4}$ alkyl)) can be prepared from a compound of Formula (XXIII) using reductive amination conditions by reacting an aldehyde or ketone with a compound of Formula (XXIII), followed by the addition of a reducing agent (such as STAB) in a suitable solvent (such as DCE), as shown in Scheme 9.

Scheme 10

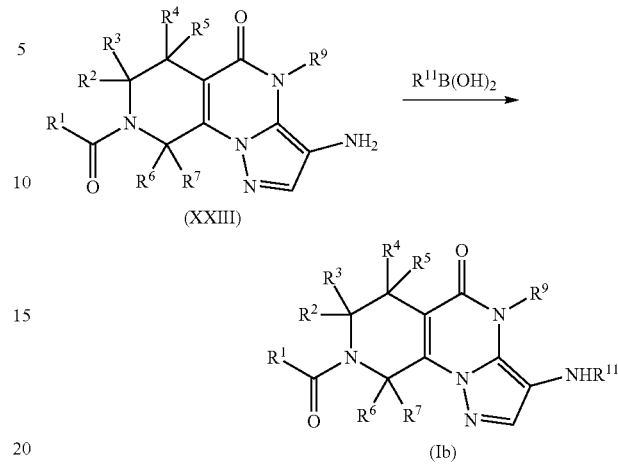

A compound of Formula (Ib) in which R⁸ is a mono-substituted amine of general formula —NHR¹¹ (in which R¹¹ can be an optionally substituted aryl or an optionally substituted heteroaryl) can be prepared from a compound of Formula (XXIII) and a boronic acid derivative of general formula R¹¹B(OH)₂, in presence of a copper-based reagent (such as Cu(OAc)₂) and pyridine, in a suitable solvent (such as DCM) as shown in Scheme 10.

Scheme 11

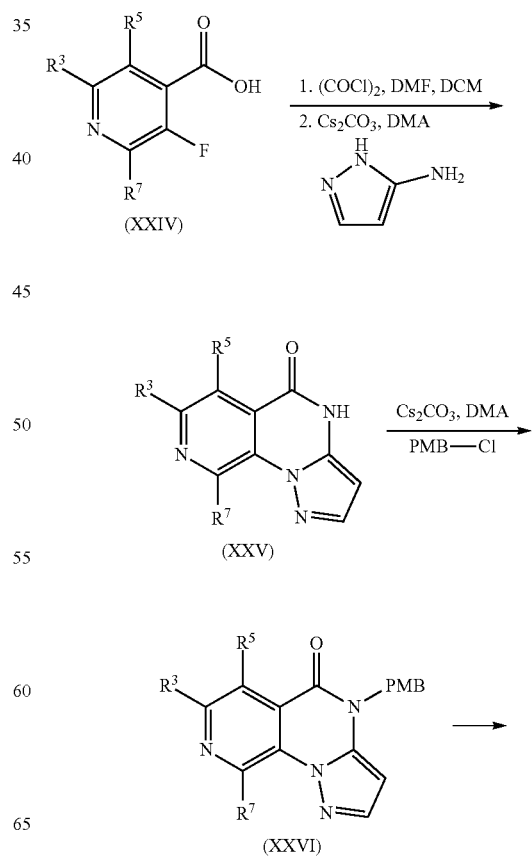

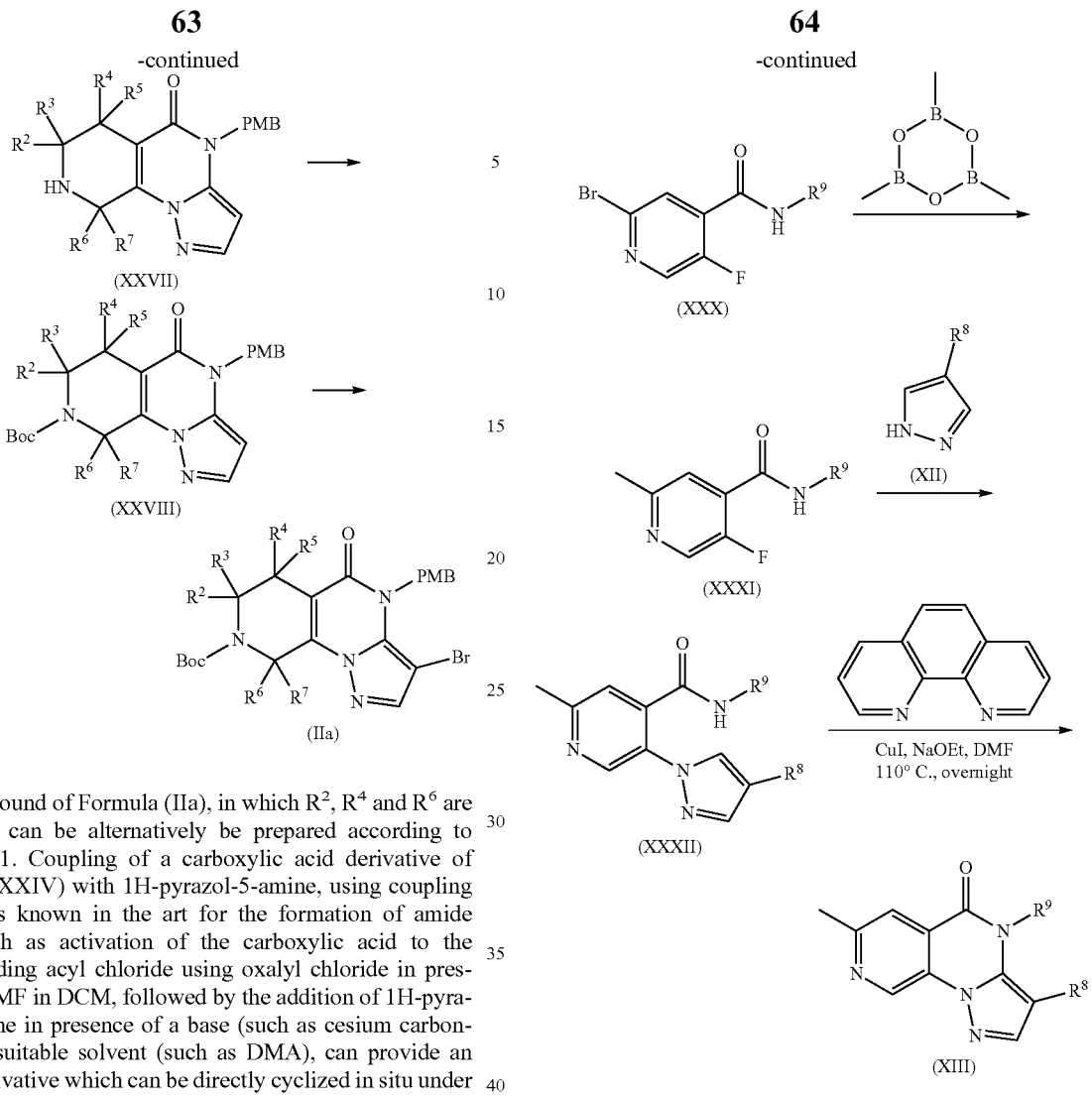

A compound of Formula (IIa), in which $R^2$, $R^4$ and $R^6$ are hydrogen, can be alternatively be prepared according to Scheme 11. Coupling of a carboxylic acid derivative of Formula (XXIV) with 1H-pyrazol-5-amine, using coupling procedures known in the art for the formation of amide bond, such as activation of the carboxylic acid to the corresponding acyl chloride using oxalyl chloride in presence of DMF in DCM, followed by the addition of 1H-pyrazol-5-amine in presence of a base (such as cesium carbonate) in a suitable solvent (such as DMA), can provide an amide derivative which can be directly cyclized in situ under heating conditions to give a compound of Formula (XXV). Subsequently, alkylation of a compound of Formula (XXV) can be performed using a base (such as cesium carbonate) and an alkylating agent (such as PMB-Cl) in a suitable solvent (such as DMA) to give a compound of Formula (XXVI).

A compound of Formula (XXVIII) in which $R^2$, $R^4$ and $R^6$ are hydrogen, can be obtained by reduction of a compound of Formula (XXVI) using, for example, catalytic hydrogenation with Pd(OH)$_2$ in AcOH, followed by the introduction of a Boc protecting group, using conditions known in the art, such as reaction with Boc$_2$O in presence of TEA in DCM. Bromination of a compound of Formula (XXVIII) using, for example, NBS in DMF, can provide a compound of Formula (IIa) in which $R^2$, $R^4$ and $R^6$ are hydrogen.

Scheme 12

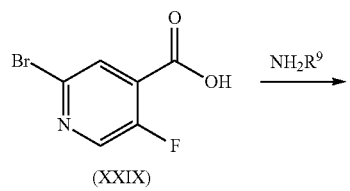

An intermediate of Formula (XIII), in which $R^3$ is methyl, and $R^5$ and $R^7$ are each hydrogen, can alternatively be synthesized as depicted in Scheme 12. An amine of general Formula $R^9$—NH$_2$, can be introduced on the acid of a compound of Formula (XXIX) using amide coupling reactions known to those skilled in the art. For example, EDC/HOBt, in presence of a base (such as diisopropylethylamine) in a suitable solvent (for example, DMF) to afford a compound of Formula (XXX). This latter compound can then be reacted with 2,4,6-trimethyl-1,3,5,2,4,6-trioxatriborinane, in presence of a palladium catalyst (such as Pd(dppf)Cl$_2$) and a base (such as potassium carbonate) in a suitable solvent (such as dioxane) to give a compound of Formula (XXXI). Further, reaction of a compound of Formula (XXXI) with an optionally substituted pyrazole (XII), in presence of a suitable base (such as potassium carbonate) in a solvent (for example, DMSO) can provide a compound of Formula (XXXII), which can be cyclized to afford a compound of Formula (XIII) in presence of 1,10-phenanthroline, CuI and a base (such as sodium ethoxide) in a suitable solvent (such as DMF) in the presence of oxygen.

Pharmaceutical Compositions

Some embodiments described herein relate to a pharmaceutical composition, that can include an effective amount of a compound described herein (e.g., a compound, or a pharmaceutically acceptable salt thereof, as described herein) and a pharmaceutically acceptable carrier, excipient or combination thereof. A pharmaceutical composition described herein is suitable for human and/or veterinary applications.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Proper formulation is dependent upon the route of administration chosen. Techniques for formulation and administration of the compounds described herein are known to those skilled in the art. Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Pharmaceutical compositions will generally be tailored to the specific intended route of administration.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes may be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

Methods of Use

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a HBV and/or HDV infection.

Some embodiments disclosed herein relate to a method of treating a HBV and/or HDV infection that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of HBV and/or HDV. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of HBV and/or HDV.

In some embodiments, the HBV infection can be an acute HBV infection. In some embodiments, the HBV infection can be a chronic HBV infection.

Some embodiments disclosed herein relate to a method of treating liver cirrhosis that is developed because of a HBV and/or HDV infection that can include administering to a subject suffering from liver cirrhosis and/or contacting a cell infected with the HBV and/or HDV in a subject suffering from liver cirrhosis with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cirrhosis with an effective amount of the compound, or a pharmaceutically acceptable salt thereof. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cirrhosis.

Some embodiments disclosed herein relate to a method of treating liver cancer (such as hepatocellular carcinoma) that is developed because of a HBV and/or HDV infection that can include administering to a subject suffering from the liver cancer and/or contacting a cell infected with the HBV and/or HDV in a subject suffering from the liver cancer with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cancer (such as hepatocellular carcinoma). Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cancer (such as hepatocellular carcinoma).

Some embodiments disclosed herein relate to a method of treating liver failure that is developed because of a HBV and/or HDV infection that can include administering to a subject suffering from liver failure and/or contacting a cell infected with the HBV and/or HDV in a subject suffering from liver failure with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver failure. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver failure.

Various indicators for determining the effectiveness of a method for treating an HBV and/or HDV infection are also known to those skilled in the art. Examples of suitable indicators include, but are not limited to, a reduction in viral load indicated by reduction in HBV DNA (or load) (e.g., reduction <$10^5$ copies/mL in serum), HBV surface antigen (HBsAg) and HBV e-antigen (HBeAg), a reduction in plasma viral load, a reduction in viral replication, a reduction in time to seroconversion (virus undetectable in patient serum), an increase in the rate of sustained viral response to therapy, an improvement in hepatic function, and/or a reduction of morbidity or mortality in clinical outcomes.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

The term "effective amount" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In some embodiments, an effective amount of a compound, or a pharmaceutically acceptable salt thereof, as described herein is an amount that is effective to achieve a sustained virologic response, for example, a sustained viral response 12 month after completion of treatment.

Subjects who are clinically diagnosed with a HBV and/or HDV infection include "naïve" subjects (e.g., subjects not previously treated for HBV and/or HDV) and subjects who have failed prior treatment for HBV and/or HDV ("treatment failure" subjects). Treatment failure subjects include "non-responders" (subjects who did not achieve sufficient reduction in ALT (alanine aminotransferase) levels, for example, subject who failed to achieve more than 1 log 10 decrease from base-line within 6 months of starting an anti-HBV and/or anti-HDV therapy) and "relapsers" (subjects who were previously treated for HBV and/or HDV whose ALT levels have increased, for example, ALT>twice the upper normal limit and detectable serum HBV DNA by hybridization assays). Further examples of subjects include subjects with a HBV and/or HDV infection who are asymptomatic.

In some embodiments, a compound, or a pharmaceutically acceptable salt thereof, as described herein can be provided to a treatment failure subject suffering from HBV and/or HDV. In some embodiments, a compound, or a pharmaceutically acceptable salt thereof, as described herein can be provided to a non-responder subject suffering from HBV and/or HDV. In some embodiments, a compound, or a pharmaceutically acceptable salt thereof, as described herein can be provided to a relapser subject suffering from HBV and/or HDV. In some embodiments, the subject can have HBeAg positive chronic hepatitis B. In some embodiments, the subject can have HBeAg negative chronic hepatitis B. In some embodiments, the subject can have liver cirrhosis. In some embodiments, the subject can be asymptomatic, for example, the subject can be infected with HBV and/or HDV but does not exhibit any symptoms of the viral infection. In some embodiments, the subject can be immunocompromised. In some embodiments, the subject can be undergoing chemotherapy.

Examples of agents that have been used to treat HBV and/or HDV include immunomodulating agents, and nucleosides/nucleotides. Examples of immunomodulating agents include interferons (such as IFN-α and pegylated interferons that include PEG-IFN-α-2a); and examples of nucleosides/nucleotides include lamivudine, telbivudine, adefovir dipivoxil, clevudine, entecavir, tenofovir alafenamide and tenofovir disoproxil. However, some of the drawbacks associated with interferon treatment are the adverse side effects, the need for subcutaneous administration and high cost. Potential advantages of a compound of Formula (I), or a pharmaceutically acceptable salt of any of the foregoing, can be less adverse side effects, delay in the onset of an adverse side effect and/or reduction in the severity of an adverse side effect. A drawback with nucleoside/nucleotide treatment can be the development of resistance, including cross-resistance.

Resistance can be a cause for treatment failure. The term "resistance" as used herein refers to a viral strain displaying a delayed, lessened and/or null response to an anti-viral agent. In some embodiments, a compound, or a pharmaceutically acceptable salt thereof, as described herein can be provided to a subject infected with an HBV and/or HDV strain that is resistant to one or more anti-HBV and/or anti-HDV agents. Examples of anti-viral agents wherein resistance can develop include lamivudine, telbivudine, adefovir dipivoxil, clevudine, entecavir, tenofovir alafenamide and tenofovir disoproxil. In some embodiments, development of resistant HBV and/or HDV strains is delayed when a subject is treated with a compound, or a pharmaceutically acceptable salt thereof, as described herein compared to the development of HBV and/or HDV strains resistant to other HBV and/or HDV anti-viral agents, such as those described.

Previously known compounds, such as those provided in WO 2017/156255, were shown to form adducts with glutathione in in vitro assays. Formation of glutathione adducts can be a signal that a compound has the potential to induce liver injury. Thus, the formation of glutathione adducts can be used as a signal to predict safety. Unexpectedly, compounds described herein, such as many compounds of Formula (I), and pharmaceutically acceptable salts thereof, have been shown not to form adducts with glutathione in in vitro assays. Further, known compounds (for example, those described in WO 2017/156255), have demonstrated potency in a HepG2.2.15 cell based assay with an $EC_{50}$ of >1000 pM. Many compounds described herein, such as compounds of Formula (I), and pharmaceutically acceptable salts thereof, unexpectedly show improved potency in a HepG2.2.15 cell based assay with an $EC_{50}$<1000 pM range. Thus, compounds described herein, including compounds of Formula (I), and pharmaceutically acceptable salts thereof, can be at least 16 times more potent than previously known compounds. In some embodiments, improved potency can lead to a significantly lower dose requirement and therefore improve daily dose burden as well as lead to improved safety margins.

Combination Therapies

In some embodiments, a compound, or a pharmaceutically acceptable salt thereof, as described herein can be used in combination with one or more additional agent(s) for treating and/or inhibiting replication HBV and/or HDV. Additional agents include, but are not limited to, an interferon, nucleoside/nucleotide analogs, a sequence specific oligonucleotide (such as anti-sense oligonucleotide and siRNA), nucleic acid polymers (NAPs, such as nucleic acid polymers that reduce HBsAg levels) an entry inhibitor and/or a small molecule immunomodulator. Examples of additional agents include recombinant interferon alpha 2b, IFN-α, PEG-IFN-α-2a, lamivudine, telbivudine, adefovir dipivoxil, clevudine, entecavir, tenofovir alafenamide and tenofovir disoproxil. Examples of NAPs include, but are not limited to, REP 2139, REP 2165 and those described in U.S. Application No. 62/757,632, filed Nov. 8, 2018, which is hereby incorporated by reference for the purpose of the NAPs described therein.

In some embodiments, a compound, or a pharmaceutically acceptable salt thereof, as described herein can be administered with one or more additional agent(s) together in a single pharmaceutical composition. In some embodiments, a compound, or a pharmaceutically acceptable salt thereof, can be administered with one or more additional agent(s) as two or more separate pharmaceutical compositions. Further, the order of administration of a compound, or a pharmaceutically acceptable salt thereof, as described herein with one or more additional agent(s) can vary.

EXAMPLES

Additional embodiments are disclosed in further detail in the following examples, which are not in any way intended to limit the scope of the claims.

Example 1

N-(3-chloro-4-fluorophenyl)-4-methyl-5-oxo-5,6,7,9-tetrahydropyrazolo[1,5-a]pyrido[4,3-e]pyrimidine-8(4H)-carboxamide (1)

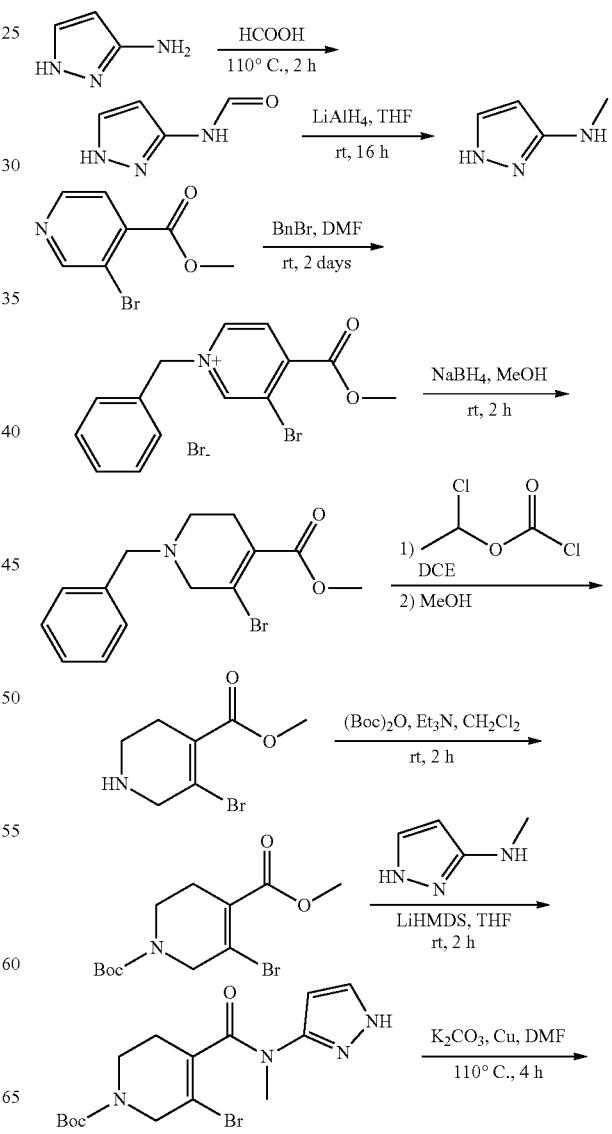

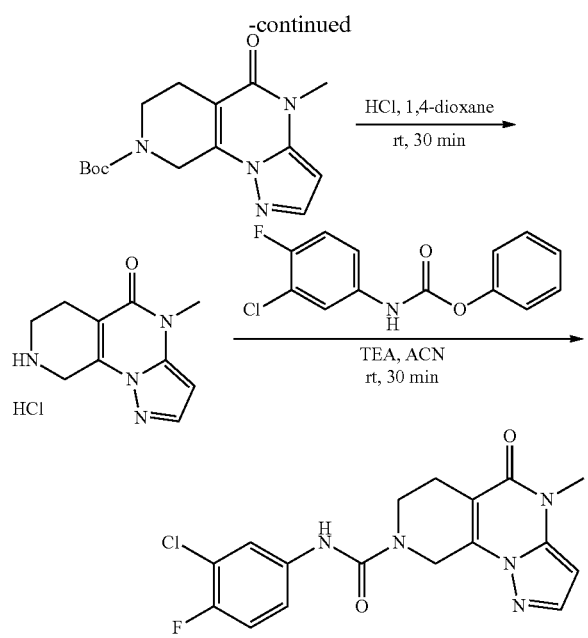

A solution of 1H-pyrazol-3-amine (500 mg, 6.02 mmol, 1.00 eq.) in formic acid (3 mL) was stirred for 2 h at 110° C. and then concentrated under reduced pressure. The solution was triturated in cyclohexane (50 mL). The solids were collected by filtration to afford N-(1H-pyrazol-3-yl)formamide (700 mg, crude) as a white solid. LCMS (ESI, m/z): 112 [M+H]$^+$, RT: 0.384 min.

To a stirred solution of N-(1H-pyrazol-3-yl)formamide (1.40 g, 12.6 mmol, 1.00 eq.) in THF (50 mL) was added lithium aluminum hydride (1.43 g, 37.8 mmol, 3.00 eq.) in batches with stirring at 0° C. The solution was stirred for 16 h at room temperature (rt). The reaction was then quenched with sodium sulfate decahydrate and stirred for 30 min. The mixture was diluted with ethyl acetate (50 mL), and the solids were filtered off. The filtrate was concentrated under reduced pressure. The residue was purified by silica gel column chromatography with CH$_2$Cl$_2$:CH$_3$OH (10:1) to afford N-methyl-1H-pyrazol-3-amine (700 mg, 57% yield) as a light yellow oil. LCMS (ESI, m/z): 98 [M+H]$^+$, RT: 0.167 min.

To a stirred solution of methyl 3-bromopyridine-4-carboxylate (10.0 g, 46.3 mmol, 1.00 eq.) in N,N-dimethylformamide (100 mL) was added benzyl bromide (8.71 g, 50.9 mmol, 1.10 eq.). The solution was stirred for 2 days at rt. The solution was triturated in acetone (300 mL) and stirred at 0° C. for 0.5 h. The solids were collected by filtration to afford product 1-benzyl-3-bromo-4-(methoxycarbonyl) pyridin-1-ium bromide (12.0 g, 67% yield) as a white solid. LCMS (ESI, m/z): 306 [M-Br]$^+$, RT: 0.618 min.

To a stirred solution of 1-benzyl-3-bromo-4-(methoxycarbonyl)pyridin-1-ium bromide (5.00 g, 12.9 mmol, 1.00 eq.) in CH$_3$OH (50 mL) was added sodium borohydride (2.44 g, 64.6 mmol, 5.00 eq.) in batches with stirring at 0° C. The solution was stirred for 2 h at rt, and the reaction was quenched with water (30 mL). The mixture was extracted with ethyl acetate (2×50 mL). The combined organic layers were washed with brine (2×50 mL), dried over anhydrous sodium sulfate, filtered and concentrated under reduced pressure. The residue was purified by silica gel column chromatography with ethyl acetate (EA):petroleum ether (PE) (1:50) to afford methyl 1-benzyl-3-bromo-5,6-dihydro-2H-pyridine-4-carboxylate 2.50 g (62% yield) as a light yellow oil. LCMS (ESI, m/z): 310 [M+H]$^+$, RT: 0.754 min.

To a stirred solution of methyl 1-benzyl-3-bromo-5,6-dihydro-2H-pyridine-4-carboxylate (2.40 g, 7.74 mmol, 1.00 eq.) in 1,2-dichloroethane (50 mL) was added chloroethyl chloroformate (1.22 g, 8.53 mmol, 1.10 eq.) dropwise with stirring at 0° C. The solution was stirred for 1 h at 84° C. and then concentrated. Methanol (50 mL) was added to the mixture at rt. The solution was stirring for an additional 1 h at 65° C. and then concentrated. The residue was purified by silica gel column chromatography with CH$_2$Cl$_2$:CH$_3$OH (10:1) to afford methyl 3-bromo-1,2,5,6-tetrahydropyridine-4-carboxylate (1.20 g, 70% yield) as a yellow oil. LCMS (ESI, m/z): 220 [M+H]$^+$, RT: 0.613 min.

To a stirred solution of methyl 3-bromo-1,2,5,6-tetrahydropyridine-4-carboxylate (2.90 g, 13.2 mmol, 1.00 eq.) in CH$_2$Cl$_2$ (20 mL) was added triethylamine (4.00 g, 39.5 mmol, 3.00 eq.). A solution of di-tert-butyl dicarbonate (3.16 g, 14.5 mmol, 1.10 eq.) in dichloromethane (1 mL) was then added dropwise with stirring at 0° C. The solution was stirred for 2 h at rt and then concentrated. The residue was purified by silica gel column chromatography with EA:PE (1:9) to afford 1-tert-butyl 4-methyl 3-bromo-5,6-dihydro-2H-pyridine-1,4-dicarboxylate 3.00 g (71% yield) as a light yellow oil. LCMS (ESI, m/z): 320 [M+H]$^+$, RT: 1.228 min.

To a stirred solution of 1-tert-butyl 4-methyl 3-bromo-5,6-dihydro-2H-pyridine-1,4-dicarboxylate (500 mg, 1.56 mmol, 1.00 eq.) in tetrahydrofuran (10 mL) was added lithium hexamethyldisilazide (4.7 mL, 4.70 mmol, 3.00 eq., 1 mol/L in THF) and N-methyl-1H-pyrazol-3-amine (167 mg, 1.72 mmol, 1.10 eq.). The solution was stirred for 2 h at rt. The reaction was quenched with CH$_3$OH (15 mL), and then the mixture was concentrated under reduced pressure. The crude product was purified by reverse flash chromatography with the following gradient conditions: column C$_{18}$; mobile phase, ACN:H$_2$O=(40%:60%); detector, 254 nm to afford tert-butyl 3-bromo-4-[methyl(1H-pyrazol-3-yl)carbamoyl]-5,6-dihydro-2H-pyridine-1-carboxylate (240 mg, 40% yield) as a light yellow oil. LCMS (ESI, m/z): 385[M+H]$^+$, RT: 1.063 min.

To a solution of tert-butyl 3-bromo-4-[methyl(1H-pyrazol-3-yl)carbamoyl]-5,6-dihydro-2H-pyridine-1-carboxylate (380 mg, 0.986 mmol, 1.00 eq.) in N,N-dimethylformamide (5.00 mL) was added potassium carbonate (273 mg, 1.97 mmol, 2.00 eq.) and copper (125 mg, 1.97 mmol, 2.00 eq.). The solution was stirred for 4 h at 110° C. The solids were filtered off, and the filtration was concentrated under reduced pressure. The crude product was purified by reverse flash chromatography with the following gradient conditions: column C$_{18}$; mobile phase, ACN:H$_2$O=(40%:60%); detector, 254 nm to afford tert-butyl 7-methyl-8-oxo-2,3,7,12-tetraazatricyclo[7.4.0.0ˆ[2,6]]trideca-1(9),3,5-triene-12-carboxylate (130 mg, 43% yield) as a light yellow oil. LCMS (ESI, m/z): 305 [M+H]$^+$, RT: 1.112 min.

The mixture of tert-butyl 7-methyl-8-oxo-2,3,7,12-tetraazatricyclo[7.4.0.0ˆ[2,6]]trideca-1(9),3,5-triene-12-carboxylate (130 mg, 0.427 mmol, 1.00 eq.) in HCl in 1,4-dioxane (2.00 mL, 4 mol/L) was stirred for 30 min at rt and then concentrated under reduced pressure to afford 7-methyl-2,3,7,12-tetraazatricyclo[7.4.0.0ˆ[2,6]]trideca-1(9),3,5-trien-8-one hydrochloride salt (120 mg, crude) as a light yellow solid. LCMS (ESI, m/z): 205 [M+H—HCl]$^+$, RT: 0.648 min.

To a stirred solution of 7-methyl-2,3,7,12-tetraazatricyclo [7.4.0.0ˆ[2,6]]trideca-1(9),3,5-trien-8-one hydrochloride salt (150 mg, 0.623 mmol, 1.00 eq.) in acetonitrile (8 mL) was added phenyl N-(3-chloro-4-fluorophenyl)carbamate (215 mg, 0.808 mmol, 1.30 eq.) and triethylamine (743 mg, 7.345 mmol, 11.8 eq.). The solution was stirred for 30 min at rt and then concentrated under reduced pressure. The crude product was purified by Prep-HPLC with the following conditions: Column: XBridge Prep OBD $C_{18}$ Column, 30×150 mm 5 □m; Mobile Phase A: Water (10 mmol/L $NH_4HCO_3$), Mobile Phase B: ACN; Flow rate: 60 mL/min; Gradient: 28% B to 45% B in 10 min; 254&220 nm to afford N-(3-chloro-4-fluorophenyl)-7-methyl-8-oxo-2,3,7,12-tetraazatricyclo[7.4.0.0^[2,6]]trideca-1(9),3,5-triene-12-carboxamide (compound 1, 28.0 mg, 10% yield) as a white solid. LCMS (ESI, m/z): 376 [M+H]$^+$, RT: 1.608 min. $^1$H NMR (400 MHz, DMSO-$d_6$) δ 9.04 (s, 1H), 7.87 (d, J=2.0 Hz, 1H), 7.75 (dd, J=6.8, 2.6 Hz, 1H), 7.48-7.40 (m, 1H), 7.31 (t, J=9.1 Hz, 1H), 6.23 (d, J=2.1 Hz, 1H), 4.83 (s, 2H), 3.75 (t, J=5.7 Hz, 2H), 3.47 (s, 3H), 2.53-2.50 (s, 2H).

Example 2

4-benzyl-N-(3-chloro-4-fluorophenyl)-5-oxo-5,6,7,9-tetrahydropyrazolo[1,5-a]pyrido[4,3-e]pyrimidine-8(4H)-carboxamide (2)

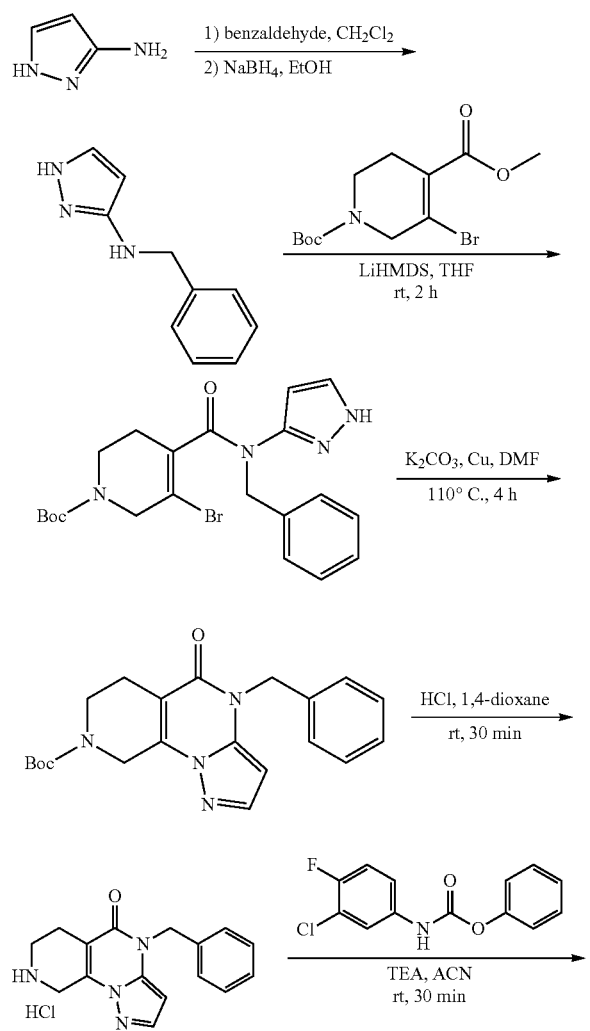

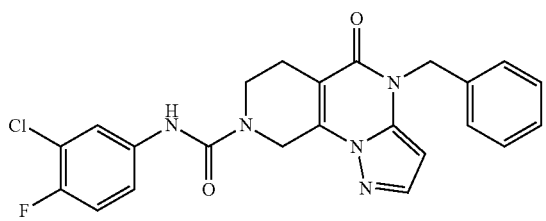

To a stirred solution of 1H-pyrazol-3-amine (1.50 g, 18.1 mmol, 1.00 eq.) in $CH_2Cl_2$ (20 mL) was added benzaldehyde (2.11 g, 19.9 mmol, 1.10 eq.), triethylamine (2.01 g, 19.9 mmol, 1.10 eq.). The solution was stirred overnight at rt and then concentrated under reduced pressure. The residue was dissolved in EtOH (30 mL), and sodium borohydride (1.02 g, 27.1 mmol, 1.50 eq.) was then added in batches at 0° C. The solution was allowed to react for 2 h at rt. The reaction was then quenched with water (30 mL), and the mixture was extracted with EA (2×50 mL). The combined organic layers were washed with brine (2×50 mL), dried over anhydrous sodium sulfate, filtered and concentrated under reduced pressure. The residue was purified by silica gel column chromatography with $CH_2Cl_2$:$CH_3OH$ (40:1) to afford N-benzyl-1H-pyrazol-3-amine (1.70 g, 54% yield) as a white solid. LCMS (ESI, m/z): 174 [M+H]$^+$, RT: 0.649 min.

4-benzyl-N-(3-chloro-4-fluorophenyl)-5-oxo-5,6,7,9-tetrahydropyrazolo[1,5-a]pyrido[4,3-e]pyrimidine-8(4H)-carboxamide, compound 2, was prepared as a white solid according to the procedures of Example 1 g) to j) by substituting N-benzyl-1H-pyrazol-3-amine for N-methyl-1H-pyrazol-3-amine. LCMS (ESI, m/z): 452 [M+H]$^+$, RT: 1.630 min. $^1$H NMR (300 MHz, DMSO-$d_6$) δ 9.04 (s, 1H), 7.87-7.72 (m, 2H), 7.45 (s, 1H), 7.38-7.25 (m, 6H), 6.22 (d, J=2.2 Hz, 1H), 5.24 (s, 2H), 4.85 (s, 2H), 3.77 (d, J=5.9 Hz, 2H), 2.59 (s, 2H).

Example 3

8-(4-bromobenzoyl)-4-phenyl-6,7,8,9-tetrahydropyrazolo[1,5-a]pyrido[4,3-e]pyrimidin-5(4H)-one (3)

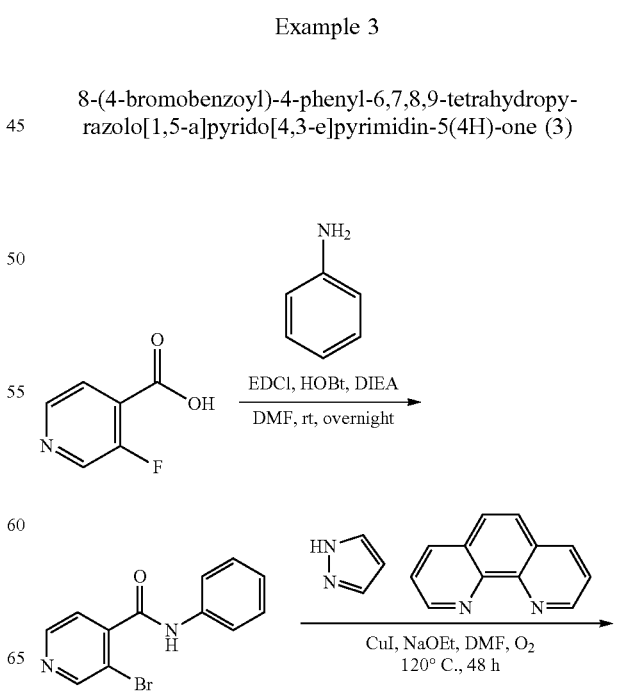

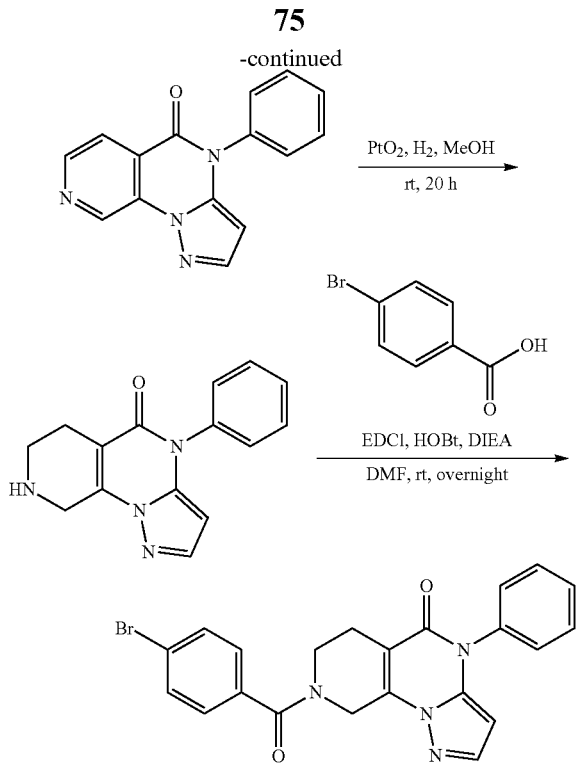

A solution of 3-bromopyridine-4-carboxylic acid (20.0 g, 99.0 mmol, 1.00 eq.), aniline (10.1 g, 108 mmol, 1.10 eq.), 1-(3-dimethylaminopropyl)-3-ethylcarbodiimide hydrochloride (22.7 g, 118 mmol, 1.20 eq.), 1-hydroxybenzotriazole (16.0 g, 118 mmol, 1.20 eq.) and N,N-diisopropylethylamine (38.3 g, 297 mmol, 3.00 eq.) in N,N-dimethylformamide (200 mL) was stirred overnight at rt, and then the reaction was quenched with water (200 mL). The mixture was extracted with EA (3×500 mL). The combined organic layers were washed with brine (100 mL), dried over anhydrous sodium sulfate, filtered and concentrated under reduced pressure. The residue was purified by silica gel column chromatography with EA:PE (45:55) to afford 3-bromo-N-phenylpyridine-4-carboxamide (21.7 g, 79% yield) as an off-white solid. LCMS (ESI, m/z): 277 [M+H]$^+$, RT: 0.824 min.

To a stirred mixture of 3-bromo-N-phenylpyridine-4-carboxamide (2.00 g, 7.21 mmol, 1.00 eq.), pyrazole (0.490 g, 7.217 mmol, 1.00 eq.), 1,10-phenanthroline (0.520 g, 2.88 mmol, 0.40 eq.) and sodium ethoxide (0.980 g, 14.4 mmol, 2.00 eq.) in N,N-dimethylformamide (20 mL) was added cuprous iodide (0.270 g, 1.44 mmol, 0.20 eq.). The mixture was stirred for 48 h at 120° C. under an oxygen atmosphere. The reaction was quenched with water (100 mL). The mixture was extracted with CH$_2$Cl$_2$ (3×100 mL). The combined organic layers were washed with brine (2×100 mL), dried over anhydrous sodium sulfate, filtered and concentrated under reduced pressure. The residue was purified by silica gel column chromatography with EA:PE (6:4) to afford 7-phenyl-2,3,7,12-tetraazatricyclo[7.4.0.0ˆ[2,6]]trideca-1(9),3,5,10,12-pentaen-8-one (1.10 g, 58% yield) as a yellow solid. LCMS (ESI, m/z): 263 [M+H]$^+$, RT: 0.845 min.

To a stirred mixture of 4-phenylpyrazolo[1,5-a]pyrido[4,3-e]pyrimidin-5(4H)-one (340 mg, 0.915 mmol, 1.00 eq.) in MeOH (60 mL) was added platinum dioxide (34.0 mg) under H$_2$ atmosphere (3 atm). The mixture was stirred overnight at rt. The solid was filtered off, and the filtrate was concentrated under reduced pressure to afford 4-phenyl-6,7,8,9-tetrahydropyrazolo[1,5-a]pyrido[4,3-e]pyrimidin-5(4H)-one (330 mg, 96% yield) as a yellow solid. LCMS (ESI, m/z): 267 [M+H]$^+$, RT: 0.647 min.

To a stirred mixture of 7-phenyl-2,3,7,12-tetraazatricyclo[7.4.0.0ˆ[2,6]]trideca-1(9),3,5-trien-8-one (165 mg, 0.620 mmol, 1.00 eq.), 4-bromobenzoic acid (137 mg, 0.682 mmol, 1.10 eq.), 1-ethyl-3-(3-dimethylaminopropyl)carbodiimide hydrochloride (142 mg, 0.744 mmol, 1.20 eq.) and 1-hydroxybenzotriazole (100 mg, 0.744 mmol, 1.20 eq.) in N,N-dimethylformamide (5.0 mL) was added N,N-diisopropylethylamine (240 mg, 1.86 mmol, 3.00 eq.). The mixture was stirred overnight at rt, and then diluted with water (15 mL). The mixture was extracted with CH$_2$Cl$_2$ (3×20 mL). The combined organic layers were washed with brine (2×20 mL), dried over anhydrous sodium sulfate, filtered and concentrated under reduced pressure. The crude product was purified by Prep-HPLC: Column: XBridge Prep C$_{18}$ OBD Column, 19×150 mm 5 μm; Mobile Phase A: Water (10 mmol/L NH$_4$HCO$_3$), Mobile Phase B: ACN; Flow rate: 25 mL/min; Gradient: 35% B to 65% B in 7 min; 220 nm to afford the final compound. The final compound was repurified by Prep A Chiral_SFC: Column: DAICEL DCpak P4VP, 20 mm×250 mm, 5 μm; Mobile Phase A: CO$_2$, Mobile Phase B: IPA (8 mmol/L NH$_3$.MeOH)—HPLC; Flow rate: 40 mL/min; Gradient: 30% B; 254 nm to afford 8-(4-bromobenzoyl)-4-phenyl-6,7,8,9-tetrahydropyrazolo[1,5-a]pyrido[4,3-e]pyrimidin-5(4H)-one (compound 3, 72.5 mg, 26% yield) as a white solid. LCMS (ESI, m/z): 449 [M+H]$^+$, RT: 1.591 min. $^1$H NMR (400 MHz, DMSO-d$_6$) δ 7.87-7.58 (m, 5H), 7.57-7.38 (m, 5H), 5.52-5.32 (m, 1H), 5.09-4.73 (m, 2H), 4.02-3.52 (m, 2H), 2.51 (s, 2H).

Example 4

8-(4-bromo-3-fluorobenzoyl)-4-phenyl-6,7,8,9-tetrahydropyrazolo[1,5-a]pyrido[4,3-e]pyrimidin-5(4H)-one (4)

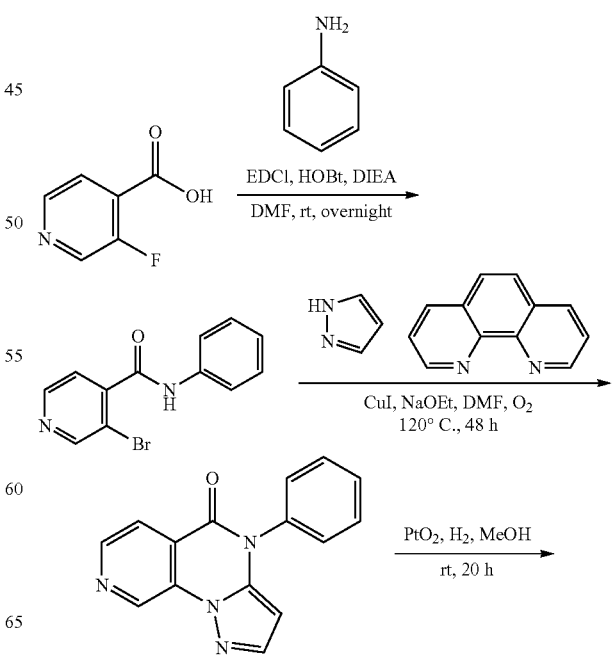

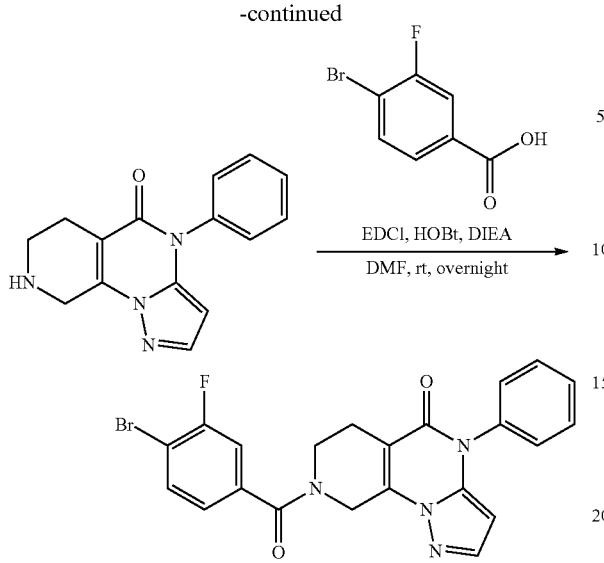

Compound 4 was prepared as a white solid according to the procedures of Example 3 a) to d) by substituting 4-bromo-3-fluorobenzoic acid for 4-bromobenzoic acid. LCMS (ESI, m/z): 467 [M+H]+, RT: 1.632 min. 1H NMR (400 MHz, DMSO-$d_6$) δ 7.97-7.83 (m, 1H), 7.82-7.52 (m, 5H), 7.51-7.41 (m, 2H), 7.40-7.19 (m, 1H), 5.53-5.37 (m, 1H), 5.15-4.70 (m, 2H), 4.01-3.52 (m, 2H), 2.62-2.54 (m, 2H).

Example 5

12-(4-bromo-3-chlorobenzoyl)-7-phenyl-2,3,7,12-tetraazatricyclo[7.4.0.0^[2,6]]trideca-1(9),3,5-trien-8-one (5)

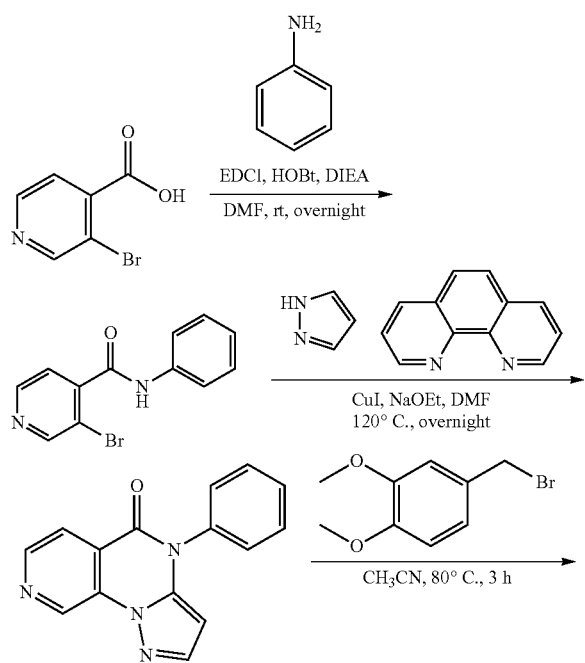

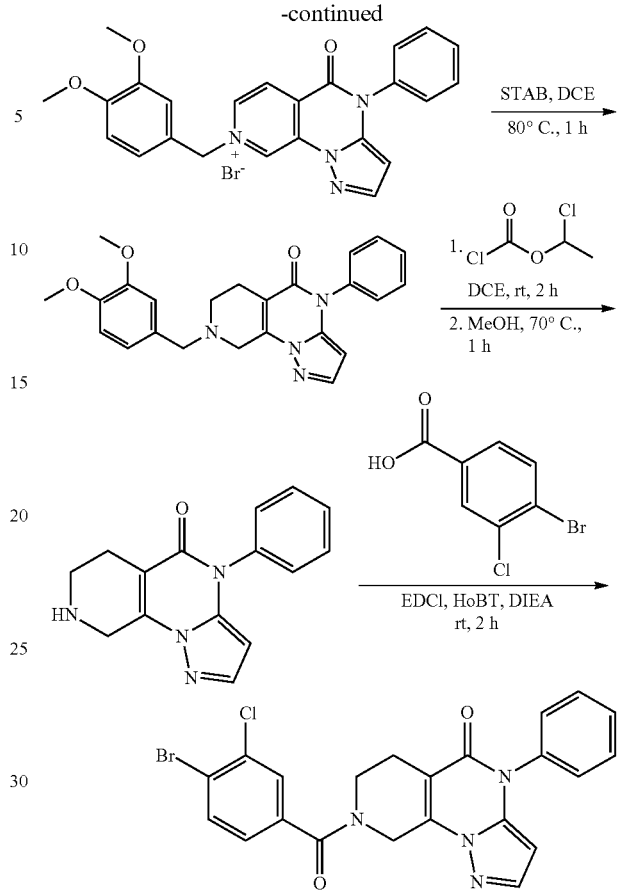

A solution of 3-bromopyridine-4-carboxylic acid (20.0 g, 99.0 mmol, 1.00 eq.), aniline (10.1 g, 108 mmol, 1.10 eq.), 1-(3-dimethylaminopropyl)-3-ethylcarbodiimide hydrochloride (22.7 g, 118 mmol, 1.20 eq.), 1-hydroxybenzotriazole (16.0 g, 118 mmol, 1.20 eq.) and N,N-diisopropylethylamine (38.3 g, 297 mmol, 3.00 eq.) in N,N-dimethylformamide (200 mL) was stirred overnight at rt, and the reaction was then quenched with water (500 mL). The mixture was extracted with EA (3×500 mL). The combined organic layers were washed with brine (100 mL), dried over anhydrous sodium sulfate, filtered and concentrated under reduced pressure. The residue was purified by silica gel column chromatography with EA:PE (45:55) to afford 3-bromo-N-phenylpyridine-4-carboxamide (21.7 g, 79% yield) as an off-white solid. LCMS (ESI, m/z): 277 [M+H]+, RT: 0.824 min.

To a stirred mixture of 3-bromo-N-phenylpyridine-4-carboxamide (2.00 g, 7.21 mmol, 1.00 eq.), pyrazole (0.49 g, 7.217 mmol, 1.00 eq.), 1,10-phenanthroline (0.520 g, 2.88 mmol, 0.400 eq.) and sodium ethoxide (0.980 g, 14.4 mmol, 2.00 eq.) in N,N-dimethylformamide (20 mL) was added cuprous iodide (0.270 g, 1.44 mmol, 0.200 eq.). The mixture was stirred for 48 h at 120° C. under an oxygen atmosphere. The reaction was quenched with water (100 mL), and the mixture was extracted with $CH_2Cl_2$ (3×100 mL). The combined organic layers were washed with brine (2×100 mL), dried over anhydrous sodium sulfate, filtered and concentrated under reduced pressure. The residue was purified by silica gel column chromatography with EA:PE (6:4) to afford 7-phenyl-2,3,7,12-tetraazatricyclo[7.4.0.0^[2,6]]trideca-1(9),3,5,10,12-pentaen-8-one (1.10 g, 58% yield) as a yellow solid. LCMS (ESI, m/z): 263 [M+H]+, RT: 0.845 min.

Into a round-bottom flask were added 7-phenyl-2,3,7,12-tetraazatricyclo[7.4.0.0ˆ[2,6]]trideca-1(9),3,5,10,12-pentaen-8-one (500 mg, 1.90 mmol, 1.00 eq.), 4-(bromomethyl)-1,2-dimethoxybenzene (616 mg, 2.66 mmol, 1.40 eq.) and acetonitrile (5 mL) at rt. The mixture was stirred for 3 h at 80° C. and then concentrated under reduced pressure. The residue was purified by trituration with diethyl ether (10 mL). The precipitated solids were collected by filtration, washed with diethyl ether (3×5 mL) and dried to afford 12-[(3,4-dimethoxyphenyl)methyl]-8-oxo-7-phenyl-2,3,7,12-tetraazatricyclo[7.4.0.0ˆ[2,6]]trideca-1(9),3,5,10,12-pentaen-12-ium bromide 900 mg (crude) as a yellow solid. LCMS (ESI, m/z): 413 [M-Br]+, RT: 0.796 min.

Into a round-bottom flask were added 12-[(3,4-dimethoxyphenyl)methyl]-8-oxo-7-phenyl-2,3,7,12-tetraazatricyclo[7.4.0.0ˆ[2,6]]trideca-1(9),3,5,10,12-pentaen-12-ium bromide (900 mg, 1.82 mmol, 1.00 eq.), sodium triacetoxyborohydride (2.76 g, 13.1 mmol, 7.20 eq.) and 1,2-dichloroethane (10 mL) at rt. The mixture was stirred for 1 h at 80° C., and the reaction was quenched with water (10 mL). The mixture was extracted with CH$_2$Cl$_2$ (3×20 mL). The combined organic layers were washed with brine (2×10 mL), dried over anhydrous sodium sulfate, filtered and concentrated under reduced pressure. The residue was purified by Prep-TLC (silica, PE:EA (1:1)) to afford 12-[(3,4-dimethoxyphenyl)methyl]-7-phenyl-2,3,7,12-tetraazatricyclo[7.4.0.0ˆ[2,6]]trideca-1(9),3,5-trien-8-one (300 mg, 40% yield) as a white solid. LCMS (ESI, m/z): 417 [M+H]+, RT: 0.773 min.

Into a round-bottom flask were added 7-benzyl-12-[(3,4-dimethoxyphenyl)methyl]-2,3,7,12-tetraazatricyclo[7.4.0.0ˆ[2,6]]trideca-1(9),3,5-trien-8-one (300 mg, 0.697 mmol, 1.00 eq.), chloroethyl chloroformate (119 mg, 0.836 mmol, 1.20 eq.) and 1,2-dichloroethane (4 mL) at rt. The mixture was stirred for 2 h at rt and then concentrated under reduced pressure. The mixture was dissolved in MeOH (4 mL) and stirred for 1 h at 70° C. The mixture was concentrated under reduced pressure to afford 7-benzyl-2,3,7,12-tetraazatricyclo[7.4.0.0ˆ[2,6]]trideca-1(9),3,5-trien-8-one 440 mg (crude) as a brown oil. LCMS (ESI, m/z): 267 [M+H]+, RT: 0.647 min.

Into a round-bottom flask were added 7-phenyl-2,3,7,12-tetraazatricyclo[7.4.0.0ˆ[2,6]]trideca-1(9),3,5-trien-8-one (440 mg, 1.65 mmol, 1.00 eq.), 4-bromo-3-chlorobenzoic acid (466 mg, 1.98 mmol, 1.20 eq.), 1-(3-dimethylaminopropyl)-3-ethylcarbodiimide hydrochloride (475 mg, 2.47 mmol, 1.50 eq.), 1-hydroxybenzotriazole (335 mg, 2.47 mmol, 1.50 eq.), N,N-diisopropylethylamine (641 mg, 4.95 mmol, 3.00 eq.) and N,N-dimethylformamide (5 mL) at rt. The mixture was stirred for 2 h at rt. The reaction was quenched with water (20 mL), and the mixture was extracted with EA (3×30 mL). The combined organic layers were washed with brine (3×30 mL), dried over anhydrous sodium sulfate, filtered and concentrated under reduced pressure. The crude product was purified by Prep-HPLC with the following conditions: Column: XBridge Prep OBD C$_{18}$ Column, 30×150 mm 5 μm; Mobile Phase A: Water (10 mmol/L NH$_4$HCO$_3$+0.1% NH$_3$.H$_2$O), Mobile Phase B: ACN; Flow rate: 60 mL/min; Gradient: 20% B to 35% B in 7 min; 254 nm to afford 12-(4-bromo-3-chlorobenzoyl)-7-phenyl-2,3,7,12-tetraazatricyclo[7.4.0.0ˆ[2,6]]trideca-1(9),3,5-trien-8-one (compound 5, 125.8 mg, 15% yield) as a white solid. LCMS (ESI, m/z): 483 [M+H]+, RT: 1.724 min. $^1$H NMR (400 MHz, Chloroform-d) δ 7.74 (d, J=8.4 Hz, 1H), 7.66-7.49 (m, 5H), 7.39 (d, J=7.6 Hz, 2H), 7.26-7.25 (m, 1H), 5.51 (br, 1H), 5.15 (br, 2H), 3.73 (br, 2H), 2.76 (br, 2H).

Example 6

7-benzyl-12-(4-bromo-3-chlorobenzoyl)-2,3,7,12-tetraazatricyclo[7.4.0.0ˆ[2,6]]trideca-1(9),3,5-trien-8-one (6)

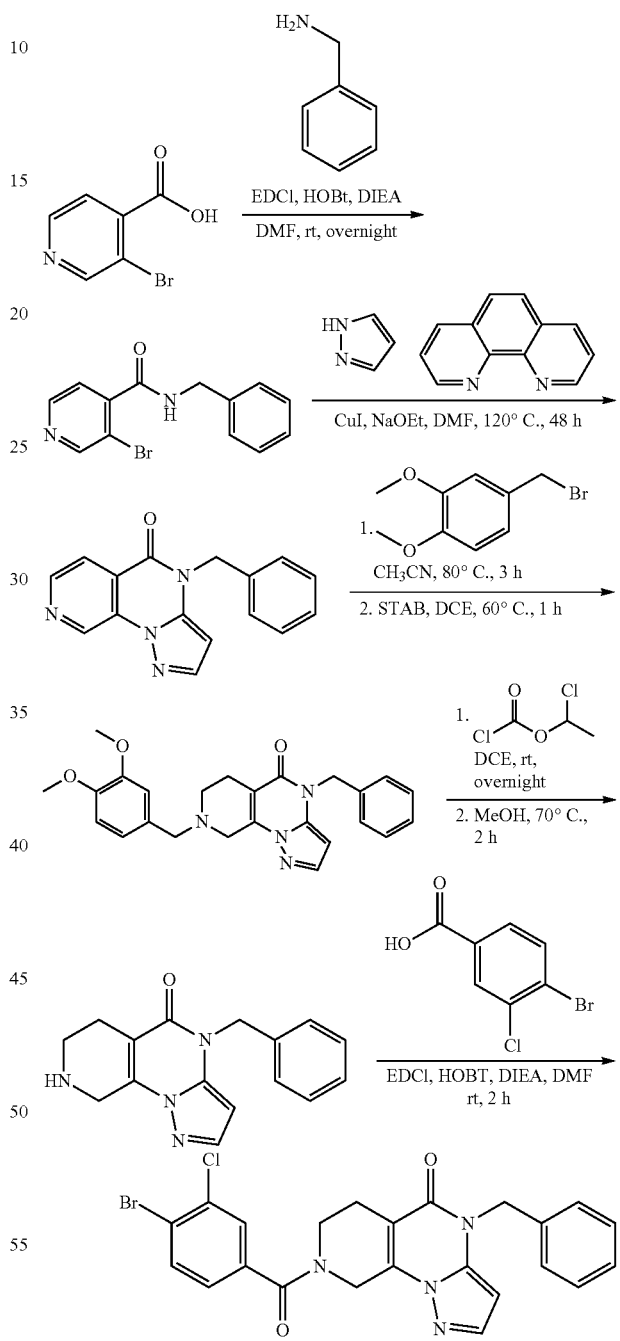

Into a 100-mL round-bottom flask, was placed benzylamine (1.00 g, 9.33 mmol, 1.00 eq.), 3-bromopyridine-4-carboxylic acid (2.07 g, 10.3 mmol, 1.10 eq.), 1-(3-dimethylaminopropyl)-3-ethylcarbodiimide hydrochloride (2.15 g, 11.2 mmol, 1.20 eq.), 1-hydroxybenzotriazole (1.51 g, 11.2 mmol, 1.20 eq.), N,N-dimethylformamide (20 mL), N,N-diisopropylethylamine (3.62 g, 28.0 mmol, 3.00 eq.). The solution was stirred overnight at rt, and the reaction was then quenched with water (100 mL). The mixture was extracted with EA (3×500 mL). The combined organic layers were washed with brine (100 mL), dried over anhydrous sodium sulfate, filtered and concentrated under reduced pressure. The residue was purified by silica gel column chromatography with EA:PE (45:55) to afford N-benzyl-3-bromopyridine-4-carboxamide (1.00 g, 37% yield) as a white solid. LCMS (ESI, m/z): 291 [M+H]$^+$, RT: 0.666 min.

To a stirred solution of N-benzyl-3-bromopyridine-4-carboxamide (1.00 g, 3.44 mmol, 1.00 eq.), 1,10-phenanthroline (0.120 g, 0.666 mmol, 0.19 eq.), pyrazole (0.280 g, 4.12 mmol, 1.20 eq.) and sodium ethoxide (0.470 g, 6.86 mmol, 2.00 eq.) in N,N-dimethylformamide (15 mL) was added cuprous iodide (0.130 g, 0.687 mmol, 0.200 eq.). The mixture was stirred for 48 h at 120° C. under an oxygen atmosphere. The reaction was quenched with water (100 mL), and the mixture was extracted with EA (3×40 mL). The combined organic layers were washed with brine (3×20 mL), dried over anhydrous sodium sulfate, filtered and concentrated under reduced pressure. The residue was purified by silica gel column chromatography with EA:PE (2:1) to afford 7-benzyl-2,3,7,12-tetraazatricyclo[7.4.0.0^[2,6]]trideca-1(9),3,5,10,12-pentaen-8-one (410 mg, 43% yield) as a yellow green solid. LCMS (ESI, m/z): 277 [M+H]$^+$, RT: 0.937 min.

A solution of 7-benzyl-2,3,7,12-tetraazatricyclo[7.4.0.0^[2,6]]trideca-1(9),3,5,10,12-pentaen-8-one (230 mg, 0.832 mmol, 1.00 eq.) and 4-(bromomethyl)-1,2-dimethoxybenzene (269 mg, 1.16 mmol, 1.40 eq.) in acetonitrile (6 mL) was stirred for 3 h at 80° C. The mixture was concentrated under reduced pressure. The residue was washed with diethyl ether (3×10 mL) and then dissolved in 1,2-dichloroethane (6 mL). Sodium triacetoxyborohydride (1.06 g, 4.99 mmol, 6.00 eq.) was added. The mixture was stirred for 1 h at 60° C., and the reaction was then quenched with water (10 mL). The mixture was extracted with CH$_2$Cl$_2$ (3×20 mL). The combined organic layers were washed with brine (2×10 mL), dried over anhydrous sodium sulfate, filtered and concentrated under reduced pressure. The residue was purified by Prep-TLC (silica, PE:EA (1:1)) to afford 7-benzyl-12-[(3,4-dimethoxyphenyl)methyl]-2,3,7,12-tetraazatricyclo[7.4.0.0^[2,6]]trideca-1(9),3,5-trien-8-one (240 mg, 67% yield) as a white solid. LCMS (ESI, m/z): 431 [M+H]$^+$, RT: 0.640 min.

Into a round-bottom flask were added 7-benzyl-12-[(3,4-dimethoxyphenyl)methyl]-2,3,7,12-tetraazatricyclo[7.4.0.0^[2,6]]trideca-1(9),3,5-trien-8-one (100 mg, 0.232 mmol, 1.00 eq.), chloroethyl chloroformate (39.8 mg, 0.279 mmol, 1.20 eq.) and 1,2-dichloroethane (3 mL) at rt. The mixture was stirred overnight at rt and then concentrated under reduced pressure. The residue was dissolved in methanol (3 mL) and stirred for 2 h at 70° C. The mixture was concentrated under reduced pressure to afford 7-benzyl-2,3,7,12-tetraazatricyclo[7.4.0.0^[2,6]]trideca-1(9),3,5-trien-8-one 70 mg (crude) as a brown oil. LCMS (ESI, m/z): 281 [M+H]$^+$, RT: 0.573 min.

Into a round-bottom flask were added 7-benzyl-2,3,7,12-tetraazatricyclo[7.4.0.0^[2,6]]trideca-1(9),3,5-trien-8-one (70.0 mg, 0.250 mmol, 1.00 eq.), 4-bromo-3-chlorobenzoic acid (70.5 mg, 0.300 mmol, 1.20 eq.), 1-(3-dimethylaminopropyl)-3-ethylcarbodiimide hydrochloride (71.8 mg, 0.375 mmol, 1.50 eq.), 1-hydroxybenzotriazole (50.6 mg, 0.375 mmol, 1.50 eq.), N,N-diisopropylethylamine (96.8 mg, 0.749 mmol, 3.00 eq.) and N,N-dimethylformamide (2 mL) at rt. The mixture was stirred for 2 h at rt, and the reaction was quenched with water (10 mL). The mixture was extracted with EA (3×30 mL). The combined organic layers were washed with brine (3×30 mL), dried over anhydrous sodium sulfate, filtered and concentrated under reduced pressure. The crude product was purified by Prep-HPLC with the following conditions: Column: XBridge Prep OBD C$_{18}$ Column, 30×150 mm 5 μm; Mobile Phase A: Water (10 mmol/L NH$_4$HCO$_3$), Mobile Phase B: ACN; Flow rate: 60 mL/min; Gradient: 46% B to 76% B in 7 min; 220 nm to afford 7-benzyl-12-(4-bromo-3-chlorobenzoyl)-2,3,7,12-tetraazatricyclo[7.4.0.0^[2,6]]trideca-1(9),3,5-trien-8-one (compound 6, 39.9 mg, 32% yield) as an off-white solid. LCMS (ESI, m/z): 497 [M+H]$^+$, RT: 1.605 min. $^1$H NMR (300 MHz, Chloroform-d) δ 7.75-7.61 (m, 3H), 7.36-7.30 (m, 5H), 7.25 (d, J=1.8 Hz, 1H) 5.91 (d, J=1.8 Hz, 1H), 5.25 (s, 2H), 5.10-4.76 (m, 2H), 4.04-3.72 (m, 2H), 2.79 (br, 2H).

Example 7

12-(4-bromo-3-fluorobenzoyl)-4-methyl-7-phenyl-2,3,7,12-tetraazatricyclo[7.4.0.0^[2,6]]trideca-1(9),3,5-trien-8-one (7)

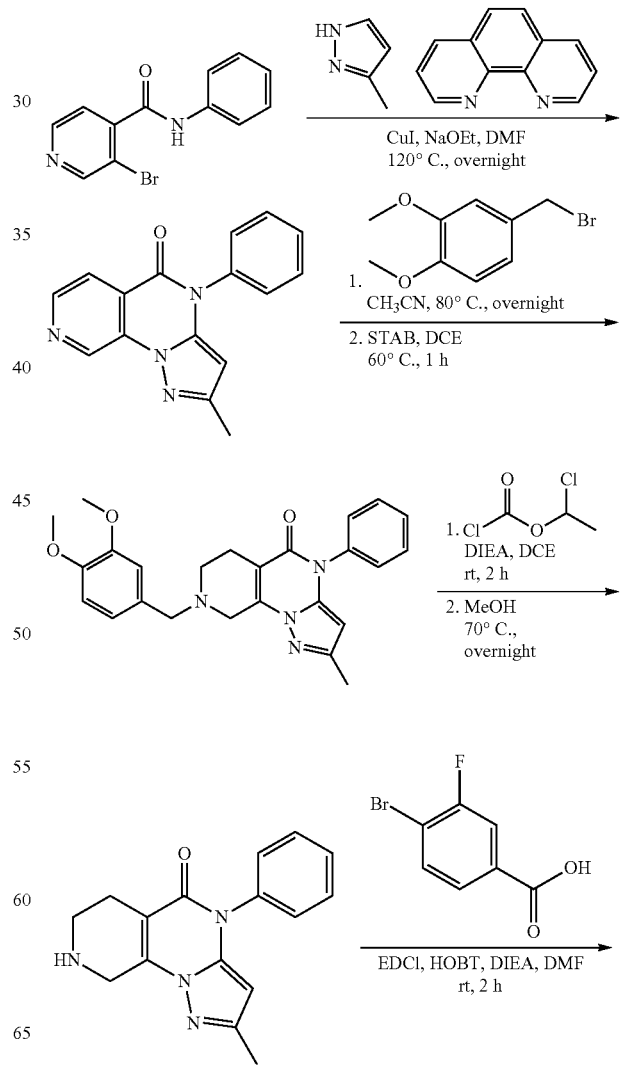

-continued

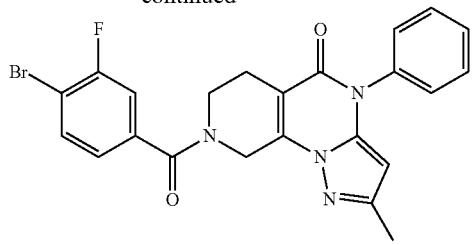

A solution of 3-bromo-N-phenylpyridine-4-carboxamide (1.00 g, 3.61 mmol, 1.00 eq.), 3-methyl-1H-pyrazole (0.300 g, 3.61 mmol, 1.00 eq.), 1,10-phenanthroline (0.260 g, 1.44 mmol, 0.40 eq.), sodium ethoxide (0.490 g, 7.22 mmol, 2.00 eq.) and cuprous iodide (0.140 g, 0.722 mmol, 0.20 eq.) in N,N-dimethylformamide (15 mL) was stirred overnight at 120° C. under an oxygen atmosphere. The reaction was quenched with water (50 mL), and the mixture was extracted with EA (3×50 mL). The combined organic layers were washed with brine (3×50 mL), dried over anhydrous sodium sulfate, filtered and concentrated under reduced pressure. The residue was purified by Prep-TLC (silica, EA) to afford 5-methyl-7-phenyl-2,3,7,12-tetraazatricyclo[7.4.0.0ˆ[2,6]]trideca-1(9),3,5,10,12-pentaen-8-one (440 mg, 44% yield) as a light yellow solid. LCMS (ESI, m/z): 277 [M+H]$^+$, RT: 0.639 min.

A mixture of 4-methyl-7-phenyl-2,3,7,12-tetraazatricyclo[7.4.0.0ˆ[2,6]]trideca-1(9),3,5,10,12-pentaen-8-one (0.440 g, 1.59 mmol, 1.00 eq.) and 4-(bromomethyl)-1,2-dimethoxybenzene (0.478 g, 2.07 mmol, 1.30 eq.) in acetonitrile (5 mL) was stirred overnight at 80° C. and concentrated under reduced pressure. The residue was triturated in diethyl ether (50 mL). The solid was collected by filtration and then dissolved in 1,2-dichloroethane (5 mL). Sodium triacetoxyborohydride (2.03 g, 9.55 mmol, 6.00 eq.) was added, and the mixture was stirred for 1 h at 60° C. The reaction was quenched with water (10 mL). The combined organic layers were washed with brine (3×20 mL), dried over anhydrous sodium sulfate, filtered and concentrated under reduced pressure. The residue was purified by Prep-TLC (silica, EA 100%) to afford 12-[(3,4-dimethoxyphenyl)methyl]-4-methyl-7-phenyl-2,3,7,12-tetraazatricyclo[7.4.0.0ˆ[2,6]]trideca-1(9),3,5-trien-8-one (170 mg, 24% yield) as an off-white solid. LCMS (ESI, m/z): 431 [M+H]$^+$, RT: 0.631 min.

A solution of 12-[(3,4-dimethoxyphenyl)methyl]-4-methyl-7-phenyl-2,3,7,12-tetraazatricyclo[7.4.0.0ˆ[2,6]]trideca-1(9),3,5-trien-8-one (170 mg, 0.395 mmol, 1.00 eq.), chloroethyl chloroformate (67.7 mg, 0.474 mmol, 1.20 eq.) and N,N-diisopropylethylamine (5.10 mg, 0.0390 mmol, 0.10 eq.) in 1,2-dichloroethane (3 mL) was stirred for 2 h at rt and then concentrated under reduced pressure. The residue was dissolved in methanol (3 mL). The mixture was stirred for overnight at 70° C. and then concentrated under reduced pressure to afford 4-methyl-7-phenyl-2,3,7,12-tetraazatricyclo[7.4.0.0ˆ[2,6]]trideca-1(9),3,5-trien-8-one 250 mg (crude) as a brown oil. LCMS (ESI, m/z): 281 [M+H]$^+$, RT: 0.706 min.

A solution of 4-methyl-7-phenyl-2,3,7,12-tetraazatricyclo[7.4.0.0ˆ[2,6]]trideca-1(9),3,5-trien-8-one (250 mg, 0.892 mmol, 1.00 eq.), 4-bromo-3-fluorobenzoic acid (234 mg, 1.07 mmol, 1.20 eq.), 1-(3-dimethylaminopropyl)-3-ethylcarbodiimide hydrochloride (205 mg, 1.07 mmol, 1.20 eq.), 1-hydroxybenzotriazole (144 mg, 1.07 mmol, 1.20 eq.) and N,N-iisopropylethylamine (345 mg, 2.67 mmol, 3.00 eq.) in N,N-dimethylformamide (5 mL) was stirred for 2 h at rt. The reaction was quenched with water (30 mL), and the mixture was extracted with EA (3×25 mL). The combined organic layers were washed with brine (3×20 mL), dried over anhydrous sodium sulfate, filtered and concentrated under reduced pressure. The crude product was purified by Prep-HPLC with the following conditions: Column: XBridge Shield RP$_{18}$ OBD Column, 19 mm×250 mm, 10 µm; Mobile Phase A: Water (10 mmol/L NH$_4$HCO$_3$), Mobile Phase B: ACN; Flow rate: 25 mL/min; Gradient: 39% B to 59% B in 12 min; 220 nm to afford 12-(4-bromo-3-fluorobenzoyl)-4-methyl-7-phenyl-2,3,7,12-tetraazatricyclo[7.4.0.0ˆ[2,6]]trideca-1(9),3,5-trien-8-one (compound 7, 59.9 mg, 13% yield) as a white solid. LCMS (ESI, m/z): 481 [M+H]$^+$, RT: 1.515 min. $^1$H NMR (400 MHz, DMSO-d$_6$) δ 7.85 (d, J=6.8 Hz, 1H), 7.61-7.51 (m, 4H), 7.45-7.30 (m, 3H), 5.30-5.25 (m, 1H), 4.98-4.94 (m, 2H), 3.91-3.60 (m, 2H), 2.56 (s, 2H), 2.15 (s, 3H).

Example 8

12-(4-bromo-3-fluorobenzoyl)-5-methyl-7-phenyl-2,3,7,12-tetraazatricyclo[7.4.0.0ˆ[2,6]]trideca-1(9),3,5-trien-8-one (8)

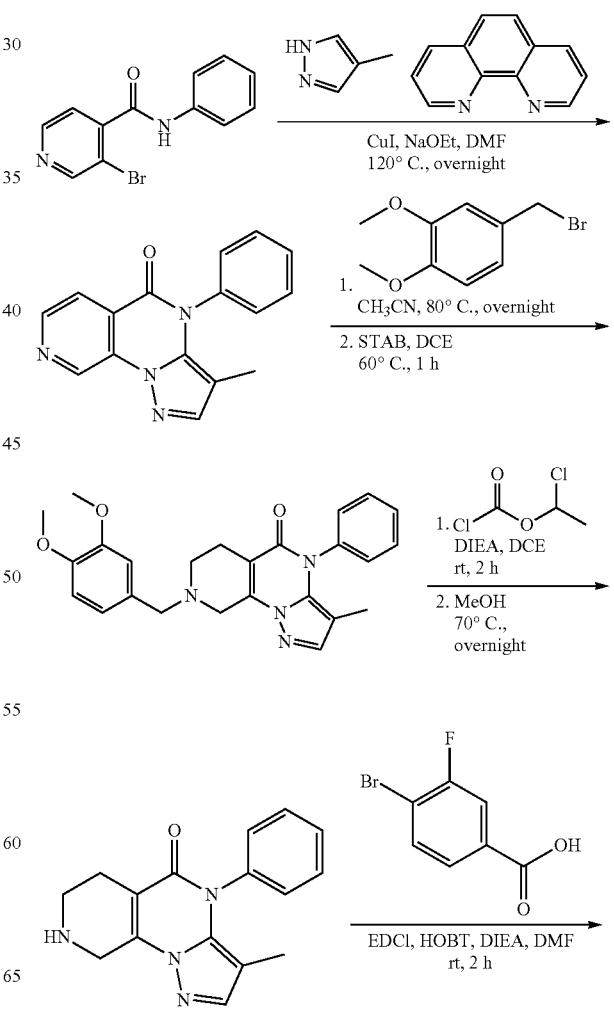

85
-continued
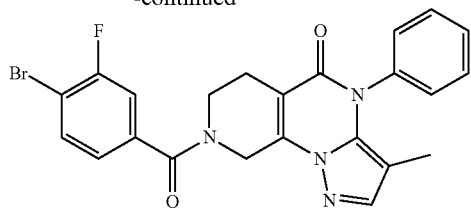
Compound 8 was prepared as a white solid according to the procedures of Example 11 a) to d) by substituting 4-methyl-1H-pyrazole for 3-methyl-1H-pyrazole. LCMS (ESI, m/z): 481 [M+H]+, RT: 1.509 min. $^1$H NMR (400 MHz, DMSO-$d_6$) δ 7.86 (t, J=6.6 Hz, 1H), 7.67-7.56 (m, 5H), 7.43-7.30 (m, 3H), 4.96-4.74 (m, 2H), 3.92-3.60 (m, 2H), 2.56 (s, 2H), 1.20 (s, 3H).
Example 9
5-benzyl-12-(4-bromo-3-fluorobenzoyl)-7-phenyl-2,3,7,12-tetraazatricyclo[7.4.0.0^[2,6]]trideca-1(9),3,5-trien-8-one (9)
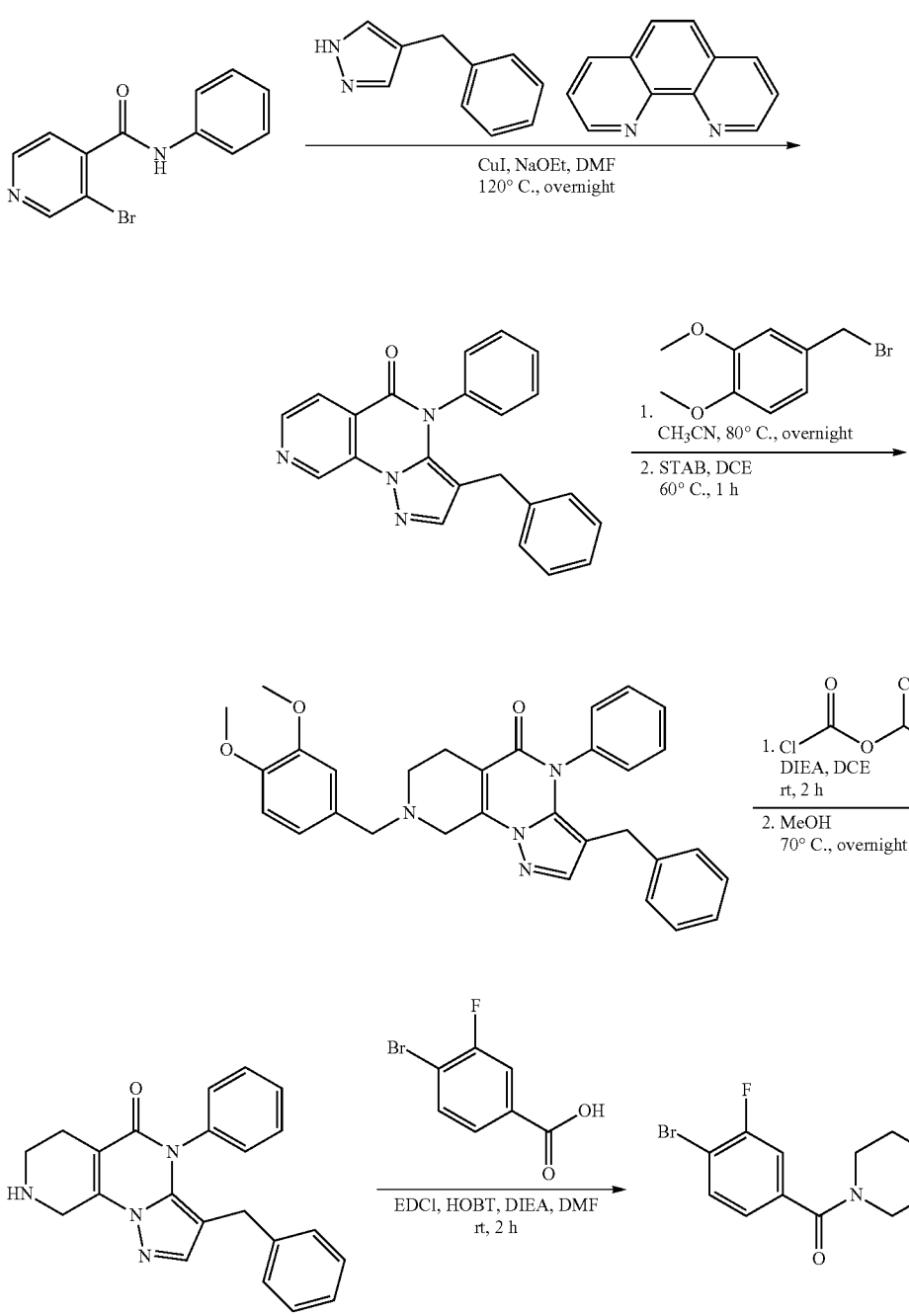

Compound 9 was prepared as an off-white solid according to the procedures of Example 11 a) to d) by substituting 4-benzyl-1H-pyrazole for 3-methyl-1H-pyrazole. LCMS (ESI, m/z): 557 [M+H]+, RT: 1.646 min. $^1$H NMR (300 MHz, DMSO-$d_6$) δ 7.87 (t, J=7.6 Hz, 1H), 7.61 (s, 2H), 7.49-7.42 (m, 3H), 7.40-7.33 (m, 3H), 7.14 (d, J=8.6 Hz, 3H), 6.75 (br, 2H), 4.89 (m, 2H), 3.78 (m, 2H), 2.94 (s, 2H), 2.57 (s, 2H).

Example 10

12-(4-bromo-3-chlorobenzoyl)-5-methyl-7-phenyl-2,3,7,12-tetraazatricyclo[7.4.0.0^[2,6]]trideca-1(9),3,5-trien-8-one (10)

Example 11

4-benzyl-12-(4-bromo-3-chlorobenzoyl)-7-phenyl-2,3,7,12-tetraazatricyclo[7.4.0.0^[2,6]]trideca-1(9),3,5-trien-8-one (11)

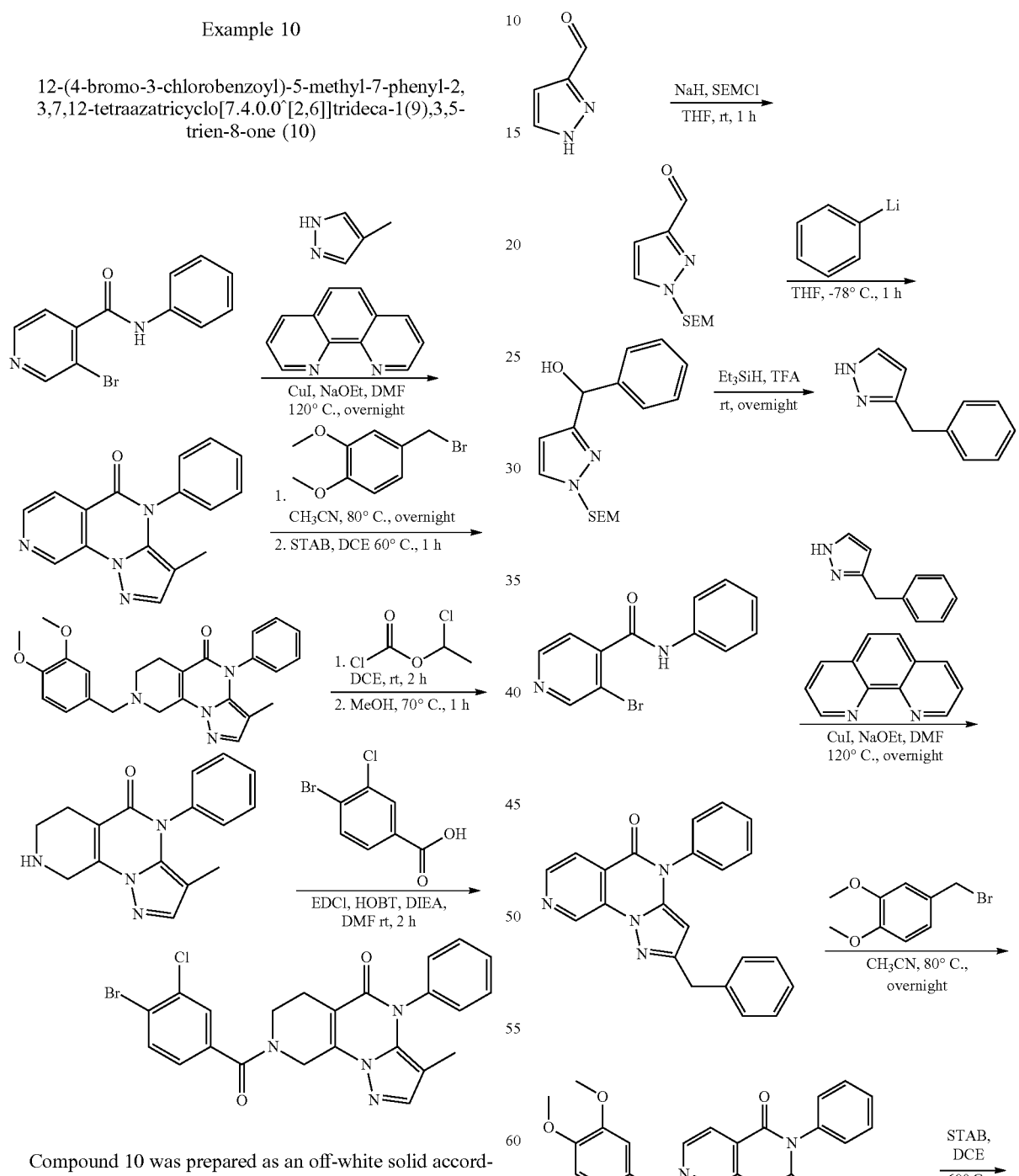

Compound 10 was prepared as an off-white solid according to the procedures of Example 5 b) to f) by substituting 4-methyl-1H-pyrazole for pyrazole. LCMS (ESI, m/z): 497 [M+H]+, RT: 2.473 min. $^1$H NMR (400 MHz, DMSO-$d_6$) δ 7.92 (d, J=8.2 Hz, 1H), 7.81 (m, 1H), 7.67 (br, 1H), 7.56 (t, J=9.2 Hz, 3H), 7.42 (s, 3H), 4.96-4.74 (m, 2H), 3.91-3.61 (m, 2H), 2.55 (s, 2H), 1.21 (s, 3H).

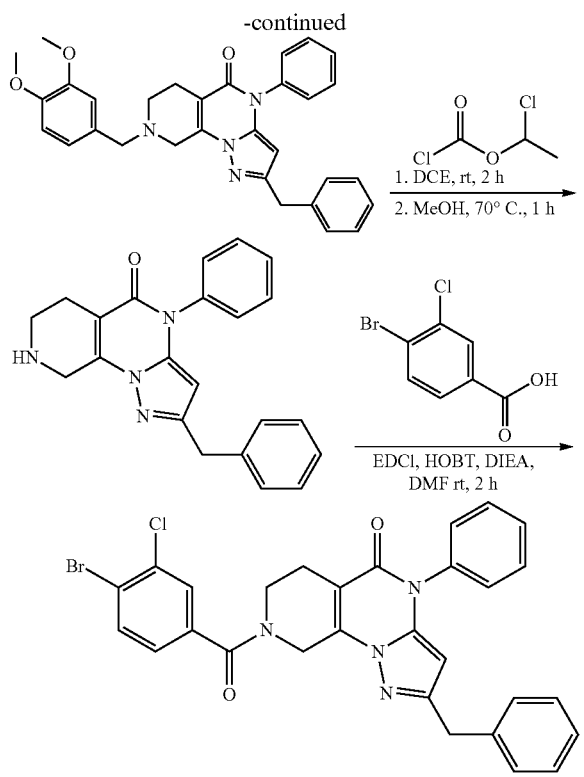

Sodium hydride (3.14 g, 78.5 mmol, 1.89 eq., 60% in mineral oil) was added to a solution of 1H-pyrazole-3-carbaldehyde (4.00 g, 41.6 mmol, 1.00 eq.) in tetrahydrofuran (50 mL) at 0° C. The mixture was stirred for 10 min at 0° C. 2-(Trimethylsilyl)ethoxymethyl chloride (7.63 g, 45.8 mmol, 1.10 eq.) was added dropwise. The mixture was stirred for 1 h at rt. The reaction was quenched with water (100 mL). The mixture was extracted with EA (2×50 mL). The combined organic layers were washed with brine (2×50 mL), dried over anhydrous sodium sulfate, filtered and concentrated under reduced pressure to afford 1-[[2-(trimethylsilyl)ethoxy]methyl]pyrazole-3-carbaldehyde (7.60 g, 81% yield) as a white solid. LCMS (ESI, m/z): 227 [M+H]+, RT: 1.406 min.

Into a 100 mL round-bottom flask were added 1-[[2-(trimethylsilyl)ethoxy]methyl]pyrazole-3-carbaldehyde (4.00 g, 17.6 mmol, 1.00 eq.) and tetrahydrofuran (40 mL) at rt. To the above mixture was added phenyllithium (21.2 mL, 21.2 mmol, 1.20 eq., 1M in THF) dropwise over 10 min at −78° C. The mixture was stirred for 3 h at rt, and the reaction was quenched with water (50 mL). The mixture was extracted with EA (3×100 mL). The combined organic layers were washed with brine (2×50 mL), dried over anhydrous sodium sulfate, filtrated and concentrated under reduced pressure. The residue was purified by silica gel column chromatography with PE:EA (1:1) to afford phenyl (1-[[2-(trimethylsilyl)ethoxy]methyl]pyrazol-3-yl)methanol (2.64 g, 49% yield) as a light yellow solid. LCMS (ESI, m/z): 305 [M+H]+, RT: 1.267 min.

Into a 100 mL round-bottom flask was added phenyl(1-[[2-(trimethylsilyl)ethoxy]methyl]pyrazol-3-yl)methanol (2.60 g, 8.54 mmol, 1.00 eq.), triethylsilane (2.98 g, 25.6 mmol, 3.00 eq.) and trifluoroacetic acid (25 mL) at rt. The mixture was stirred overnight at rt and then concentrated under reduced pressure. The reaction was quenched with water (10 mL), and the mixture was extracted with EA (3×50 mL). The combined organic layers were washed with brine (2×10 mL), dried over anhydrous sodium sulfate, filtrated and concentrated under reduced pressure. The residue was purified by Prep-TLC (silica, EA) to afford 3-benzyl-1H-pyrazole 1.25 g (crude) as a yellow solid. LCMS (ESI, m/z): 159 [M+H]+, RT: 0.588 min.

4-benzyl-12-(4-bromo-3-chlorobenzoyl)-7-phenyl-2,3,7,12-tetraazatricyclo[7.4.0.0^[2,6]]trideca-1(9),3,5-trien-8-one, compound 11, was prepared as an off-white solid according to the procedures of Example 5 b) to f) by substituting 3-benzyl-1H-pyrazole for pyrazole. LCMS (ESI, m/z): 573 [M+H]+, RT: 2.737 min. 1H NMR (400 MHz, Chloroform-d) δ 7.74 (d, J=8.0 Hz, 1H), 7.61 (s, 1H), 7.57-7.44 (m, 3H), 7.41 (d, J=6.8 Hz, 2H), 7.33 (d, J=7.2 Hz, 2H), 7.28-7.17 (m, 4H), 5.26 (s, 1H), 5.12 (br, 2H) 3.94-3.60 (m, 4H), 2.73 (s, 2H).

Example 12

5-benzyl-12-(4-bromo-3-chlorobenzoyl)-7-phenyl-2,3,7,12-tetraazatricyclo[7.4.0.0^[2,6]]trideca-1(9),3,5-trien-8-one (12)

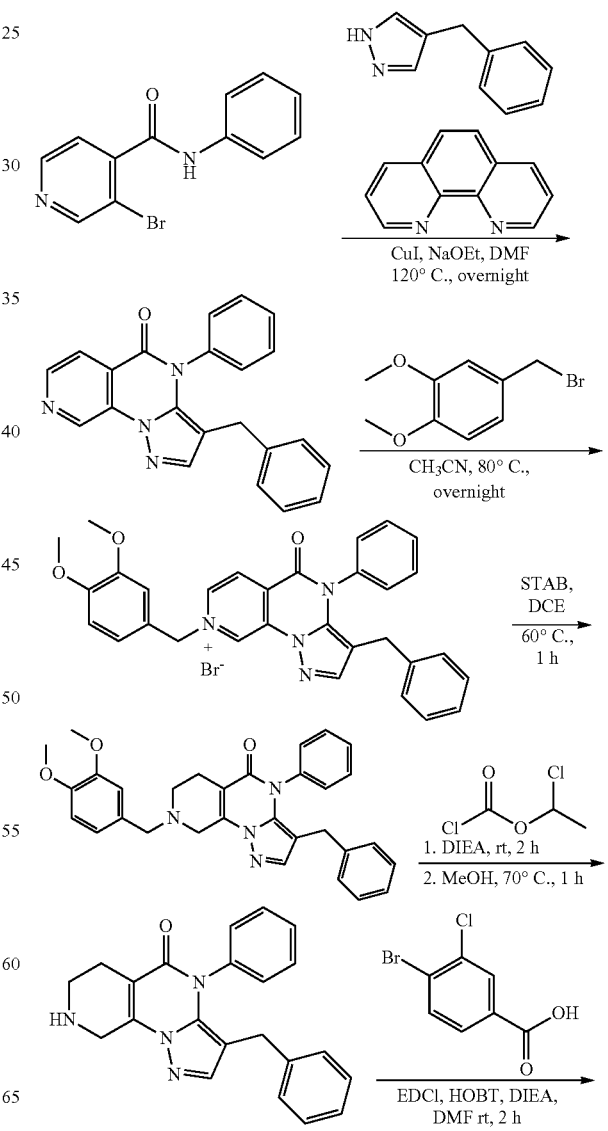

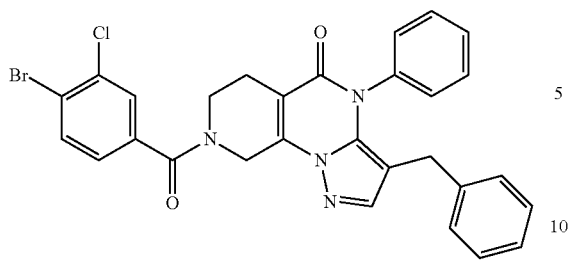

Compound 12 was prepared as a white solid according to the procedures of Example 5 b) to f) by substituting 4-benzyl-1H-pyrazole for pyrazole. LCMS (ESI, m/z): 573 [M+H]+, RT: 1.734 min. $^1$H NMR (400 MHz, DMSO-$d_6$) δ 7.92 (d, J=8.2 Hz, 1H), 7.81 (d, J=19.2 Hz, 1H), 7.60-7.40 (m, 5H), 7.33-7.29 (m, 2H), 7.18-7.10 (m, 3H), 6.79-6.72 (m, 2H), 4.98-4.76 (m, 2H), 3.91-3.61 (m, 2H), 2.93 (d, J=14.8 Hz, 2H), 2.56 (s, 2H).

Example 13

12-(4-bromo-3-chlorobenzoyl)-5-isopropyl-7-phenyl-2,3,7,12-tetraazatricyclo[7.4.0.0^[2,6]]trideca-1(9),3,5-trien-8-one (13)

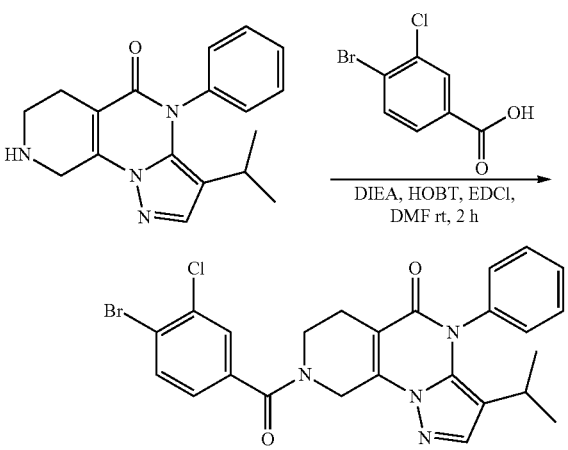

Compound 13 was prepared as a white solid according to the procedures of Example 5 b) to f) by substituting 4-isopropyl-1H-pyrazole for pyrazole. LCMS (ESI, m/z): 525 [M+H]+, RT: 1.659 min. $^1$H NMR (400 MHz, DMSO-$d_6$) δ 7.92 (d, J=8.0 Hz, 1H), 7.85-7.77 (m, 2H), 7.57 (d, J=4.4 Hz, 3H), 7.45 (s, 3H), 4.95-4.73 (m, 2H), 3.90-3.60 (m, 2H), 2.54 (s, 2H), 1.42 (br, 1H), 0.83 (d, J=7.2 Hz, 6H).

Example 14

12-(3,4-dichlorobenzoyl)-N-isopropyl-8-oxo-7-phenyl-2,3,7,12-tetraazatricyclo[7.4.0.0^[2,6]]trideca-1(9),3,5-triene-5-carboxamide (16)

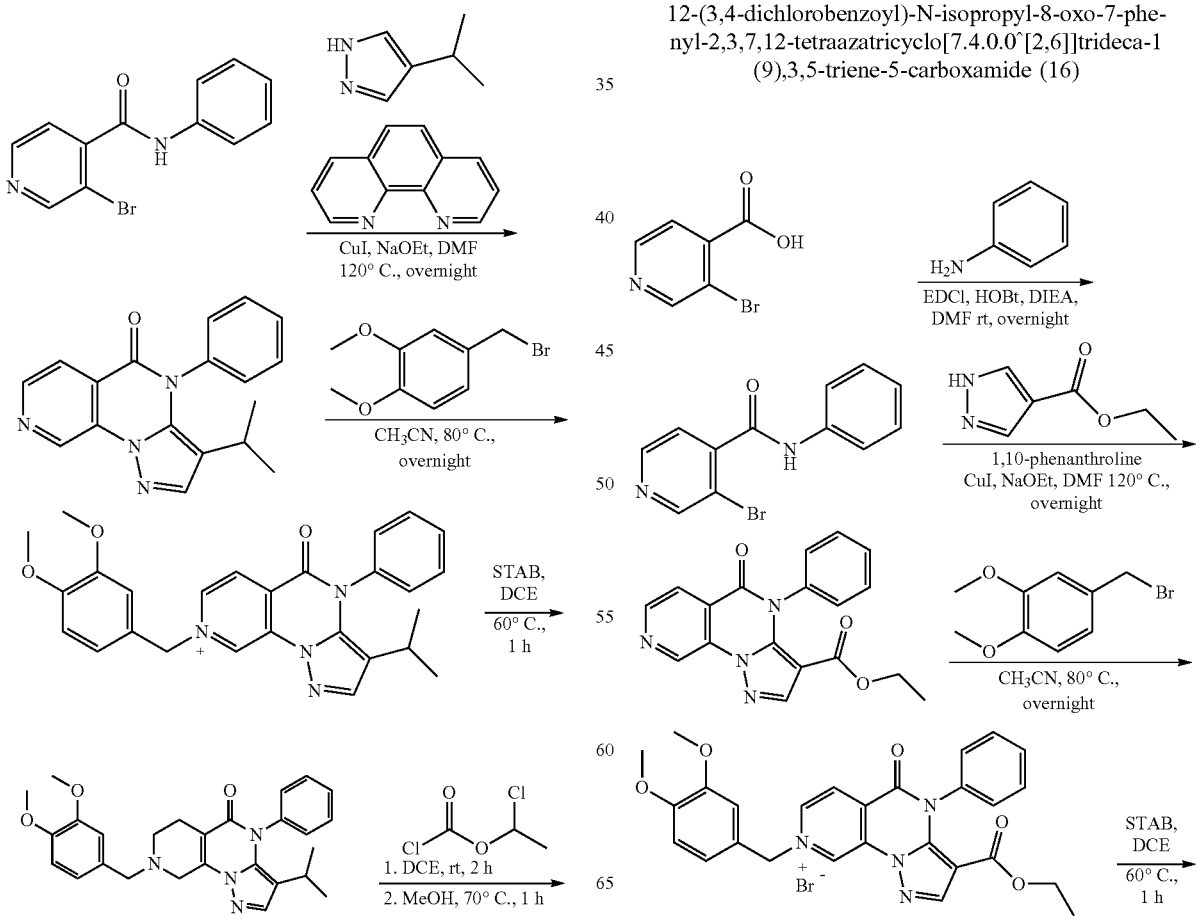

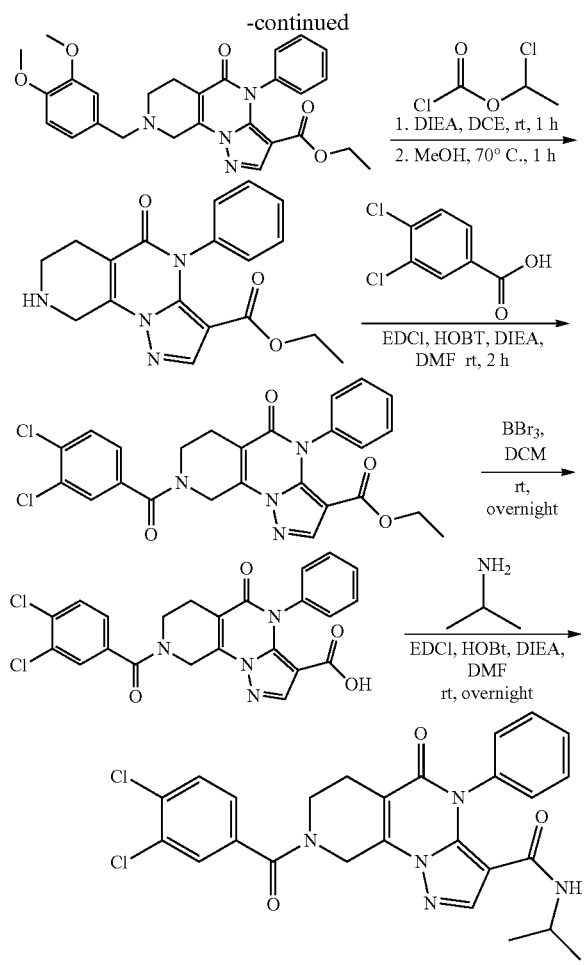

3-bromo-N-phenylpyridine-4-carboxamide: A solution of 3-bromopyridine-4-carboxylic acid (20.0 g, 99.0 mmol, 1.00 eq.), aniline (10.1 g, 108 mmol, 1.10 eq.), N-(3-dimethylaminopropyl)-N'-ethylcarbodiimide hydrochloride (22.8 g, 118 mmol, 1.20 eq.), 1-hydroxybenzotriazole (16.1 g, 118 mmol, 1.20 eq.) and N,N-diisopropylethylamine (38.4 g, 297 mmol, 3.00 eq.) in N,N-dimethylformamide (200 mL) was stirred for overnight at rt. The reaction was quenched with water (200 mL). The mixture was extracted with ethyl acetate (3×500 mL). The organic layers were combined, washed with water (3×200 mL), dried over anhydrous sodium sulfate, filtered and concentrated under reduced pressure. The residue was purified by silica gel column chromatography, eluted with petroleum ether:ethyl acetate (1:1) to afford 3-bromo-N-phenylpyridine-4-carboxamide (21.7 g, 79% yield) as an off-white solid. LCMS (ESI, m/z): 277 [M+H]$^+$.

Ethyl 8-oxo-7-phenyl-2,3,7,12-tetraazatricyclo[7.4.0.0ˆ[2,6]]trideca-1(9),3,5,10,12-pentaene-5-carboxylate: A mixture of 3-bromo-N-phenylpyridine-4-carboxamide (3.00 g, 10.8 mmol, 1.00 eq.), ethyl 1H-pyrazole-4-carboxylate (1.59 g, 11.4 mmol, 1.05 eq.), cuprous iodide (0.412 g, 2.16 mmol, 0.20 eq.), 1,10-phenanthroline (0.390 g, 2.165 mmol, 0.20 eq.), sodium ethoxide (2.21 g, 32.5 mmol, 3.00 eq.) and N,N-dimethylformamide (30 mL) was stirred for overnight at 120° C. under oxygen atmosphere. The mixture was diluted with ethyl acetate (500 mL), washed with water (4×50 mL) and sat. sodium chloride (1×50 mL), dried over anhydrous sodium sulfate, filtered and concentrated under reduced pressure. The residue was purified by silica gel column chromatography, eluted with petroleum ether:ethyl acetate (2:1) to afford ethyl 8-oxo-7-phenyl-2,3,7,12-tetraazatricyclo[7.4.0.0ˆ[2,6]]trideca-1(9),3,5,10,12-pentaene-5-carboxylate (620 mg, 17% yield) as a white solid. LCMS (ESI, m/z): 335 [M+H]$^+$.

12-[(3,4-dimethoxyphenyl)methyl]-5-(ethoxycarbonyl)-8-oxo-7-phenyl-2,3,7,12-tetraazatricyclo[7.4.0.0ˆ[2,6]]trideca-1(9),3,5,10,12-pentaen-12-ium bromide: A mixture of ethyl 8-oxo-7-phenyl-2,3,7,12-tetraazatricyclo[7.4.0.0ˆ[2,6]]trideca-1(9),3,5,10,12-pentaene-5-carboxylate (620 mg, 1.85 mmol, 1.00 eq.), acetonitrile (10 mL) and 4-(bromomethyl)-1,2-dimethoxybenzene (514 mg, 2.22 mmol, 1.20 eq.) was stirred for 4 h at 80° C. and concentrated under reduced pressure to afford 12-[(3,4-dimethoxyphenyl)methyl]-5-(ethoxycarbonyl)-8-oxo-7-phenyl-2,3,7,12-tetraazatricyclo[7.4.0.0ˆ[2,6]]trideca-1(9),3,5,10,12-pentaen-12-ium bromide (1.04 g, crude) as a yellow solid. LCMS (ESI, m/z): 485 [M-Br]$^+$.

Ethyl 12-[(3,4-dimethoxyphenyl)methyl]-8-oxo-7-phenyl-2,3,7,12-tetraazatricyclo[7.4.0.0ˆ[2,6]]trideca-1(9),3,5-triene-5-carboxylate: A mixture of 12-[(3,4-dimethoxyphenyl)methyl]-5-(ethoxycarbonyl)-8-oxo-7-phenyl-2,3,7,12-tetraazatricyclo[7.4.0.0ˆ[2,6]]trideca-1(9),3,5,10,12-pentaen-12-ium bromide (1.04 g, 1.84 mmol, 1.00 eq.), 1,2-dichloroethane (20 mL) and sodium triacetoxyborohydride (1.95 g, 9.20 mmol, 5.00 eq.) was stirred for 1 h at 60° C. The reaction was quenched with water (50 mL). The mixture was extracted with dichloromethane (3×100 mL). The organic layers were combined, washed with water (3×200 mL), dried over anhydrous sodium sulfate, filtered and concentrated under reduced pressure. The residue was purified by silica gel column chromatography, eluted with petroleum ether:ethyl acetate (1:1) to afford ethyl 12-[(3,4-dimethoxyphenyl)methyl]-8-oxo-7-phenyl-2,3,7,12-tetraazatricyclo[7.4.0.0ˆ[2,6]]trideca-1(9),3,5-triene-5-carboxylate (0.730 g, 81% yield) as an off-white solid. LCMS (ESI, m/z): 489 [M+H]$^+$.

Ethyl 8-oxo-7-phenyl-2,3,7,12-tetraazatricyclo[7.4.0.0ˆ[2,6]]trideca-1(9),3,5-triene-5-carboxylate: A mixture of ethyl 12-[(3,4-dimethoxyphenyl)methyl]-8-oxo-7-phenyl-2,3,7,12-tetraazatricyclo[7.4.0.0ˆ[2,6]]trideca-1(9),3,5-triene-5-carboxylate (730 mg, 1.49 mmol, 1.00 eq.), 1,2-dichloroethane (10 mL), N,N-diisopropylethylamine (386 mg, 2.99 mmol, 2.00 eq.) and chloroethyl chloroformate (256 mg, 1.793 mmol, 1.20 eq.) was stirred for 1 h at rt. The mixture was concentrated under reduced pressure, and then methanol (10 mL) was added. The mixture was stirred for 1 h at 70° C. and concentrated under reduced pressure. The residue was purified by silica gel column chromatography, and eluted with dichloromethane:methanol (10:1) to afford ethyl 8-oxo-7-phenyl-2,3,7,12-tetraazatricyclo[7.4.0.0ˆ[2,6]]trideca-1(9),3,5-triene-5-carboxylate (630 mg, crude) as a brown yellow solid. LCMS (ESI, m/z): 339 [M+H]$^+$.

Ethyl 12-(3,4-dichlorobenzoyl)-8-oxo-7-phenyl-2,3,7,12-tetraazatricyclo[7.4.0.0ˆ[2,6]]trideca-1(9),3,5-triene-5-carboxylate: A mixture of 3,4-dichlorobenzoic acid (508 mg, 2.66 mmol, 1.50 eq.), N-(3-dimethylaminopropyl)-N'-ethylcarbodiimide hydrochloride (510 mg, 2.66 mmol, 1.50 eq.), 1-hydroxybenzotrizole (359 mg, 2.66 mmol, 1.50 eq.), N,N-dimethylformamide (10 mL), N,N-diisopropylethylamine (688 mg, 5.32 mmol, 3.00 eq.) and ethyl 8-oxo-7-phenyl-2,3,7,12-tetraazatricyclo[7.4.0.0ˆ[2,6]]trideca-1(9),3,5-triene-5-carboxylate (600 mg, 1.77 mmol, 1.00 eq.) was stirred for 2 h at rt. The mixture was quenched with water (50 mL), and then extracted with ethyl acetate (3×50 mL). The organic layers were combined, washed with water (3×50 mL), dried over anhydrous sodium sulfate, filtered and concentrated under reduced pressure. The residue was purified by silica gel column chromatography, eluted with petroleum ether:ethyl acetate (1:1) to afford ethyl 12-(3,4-dichlorobenzoyl)-8-oxo-7-phenyl-2,3,7,12-tetraazatricyclo[7.4.0.0^[2,6]]trideca-1(9),3,5-triene-5-carboxylate (650 mg, 72% yield) as an off-white solid. LCMS (ESI, m/z): 511 [M+H]+.

12-(3,4-dichlorobenzoyl)-8-oxo-7-phenyl-2,3,7,12-tetraazatricyclo[7.4.0.0^[2,6]]trideca-1(9),3,5-triene-5-carboxylic acid: A mixture of ethyl 12-(3,4-dichlorobenzoyl)-8-oxo-7-phenyl-2,3,7,12-tetraazatricyclo[7.4.0.0^[2,6]]trideca-1(9),3,5-triene-5-carboxylate (400 mg, 0.704 mmol, 1.00 eq.), dichloromethane (5.0 mL) and boron tribromide (5.0 mL) was stirred overnight at rt. The mixture was quenched with ice water (30 mL) at 0° C., and then extracted with ethyl acetate (3×50 mL). The organic layers were combined, washed with water (3×30 mL), dried over anhydrous sodium sulfate, filtered and concentrated under reduced pressure to afford 12-(3,4-dichlorobenzoyl)-8-oxo-7-phenyl-2,3,7,12-tetraazatricyclo[7.4.0.0^[2,6]]trideca-1(9),3,5-triene-5-carboxylic acid (190 mg, crude) as a white solid. LCMS (ESI, m/z): 483 [M+H]+.

12-(3,4-dichlorobenzoyl)-N-isopropyl-8-oxo-7-phenyl-2,3,7,12-tetraazatricyclo[7.4.0.0^[2,6]]trideca-1(9),3,5-triene-5-carboxamide: A mixture of 12-(3,4-dichlorobenzoyl)-8-oxo-7-phenyl-2,3,7,12-tetraazatricyclo[7.4.0.0^[2,6]]trideca-1(9),3,5-triene-5-carboxylic acid (190 mg, 0.393 mmol, 1.00 eq.), N-(3-dimethylaminopropyl)-N'-ethylcarbodiimide hydrochloride (30.2 mg, 0.511 mmol, 1.30 eq.), 1-hydroxybenzotrizole (69.0 mg, 0.511 mmol, 1.30 eq.), N,N-dimethylformamide (5.00 mL), N,N-diisopropylethylamine (254 mg, 1.96 mmol, 5.00 eq.) and isopropylamine (69.7 mg, 1.18 mmol, 3.00 eq.) was stirred overnight at rt. The reaction was quenched with water (50 mL) and then extracted with ethyl acetate (3×50 mL). The organic layers were combined, washed with water (3×50 mL), dried over anhydrous sodium sulfate, filtered and concentrated under reduced pressure. The residue was purified by Prep-TLC (petroleum ether:ethyl acetate=1:10) to afford the crude product. The crude product was purified by Prep-HPLC with the following conditions: Column: XBridge Prep $C_{18}$ OBD Column, 19×150 mm 5 μm; Mobile Phase A: Water (10 mmol/L $NH_4HCO_3$+0.1% $NH_3.H_2O$), Mobile Phase B: ACN; Flow rate: 25 mL/min; Gradient: 35% B to 55% B in 7 min to afford 12-(3,4-dichlorobenzoyl)-N-isopropyl-8-oxo-7-phenyl-2,3,7,12-tetraazatricyclo[7.4.0.0^[2,6]]trideca-1(9),3,5-triene-5-carboxamide (28.4 mg, 14% yield) as a white solid. LCMS (ESI, m/z): 524 [M+H]+. 1H NMR (400 MHz, Chloroform-d) δ 7.87 (s, 1H), 7.62 (s, 1H), 7.60-7.47 (m, 4H), 7.42-7.30 (m, 3H), 5.33-4.61 (m, 3H), 4.21-3.52 (m, 3H), 3.08-2.45 (m, 2H), 0.88 (d, J=6.4 Hz, 6H).

Example 15

N-[12-(3,4-dichlorobenzoyl)-8-oxo-7-phenyl-2,3,7,12-tetraazatricyclo[7.4.0.0^[2,6]]trideca-1(9),3,5-trien-5-yl]-3-methylbutanamide (17)

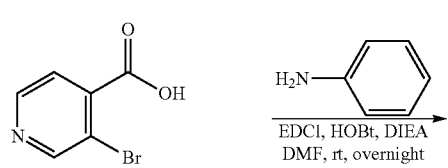

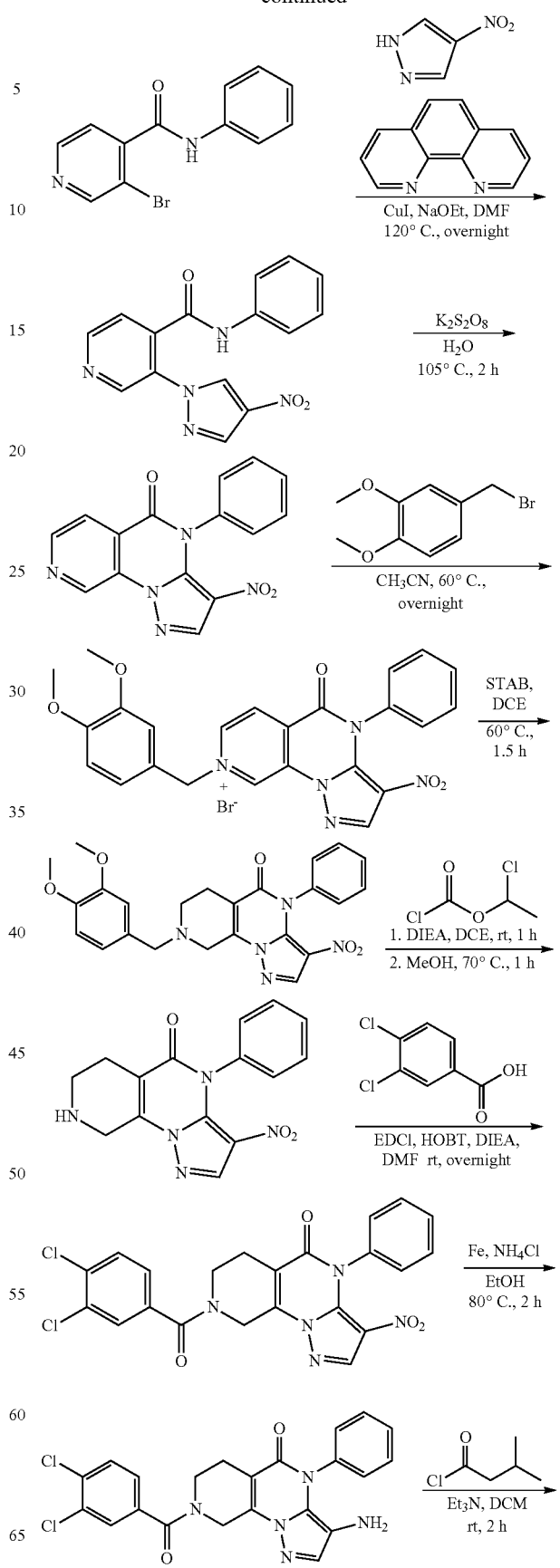

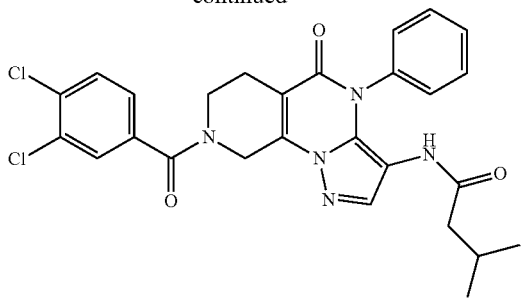

3-bromo-N-phenylpyridine-4-carboxamide: A solution of 3-bromopyridine-4-carboxylic acid (20.0 g, 99.0 mmol, 1.00 eq.), aniline (10.1 g, 108 mmol, 1.10 eq.), N-(3-dimethylaminopropyl)-N'-ethylcarbodiimide hydrochloride (22.8 g, 118 mmol, 1.20 eq.), 1-hydroxybenzotriazole (16.1 g, 118 mmol, 1.20 eq.) and N,N-diisopropylethylamine (38.4 g, 297 mmol, 3.00 eq.) in N,N-dimethylformamide (200 mL) was stirred for overnight at rt. The reaction was quenched with water (200 mL). The mixture was extracted with ethyl acetate (3×500 mL). The organic layers were combined, washed with water (3×200 mL), dried over anhydrous sodium sulfate, filtered and concentrated under reduced pressure. The residue was purified by silica gel column chromatography, eluted with petroleum ether:ethyl acetate (1:1) to afford 3-bromo-N-phenylpyridine-4-carboxamide (21.7 g, 79% yield) as an off-white solid. LCMS (ESI, m/z): 277 [M+H]$^+$.

3-(4-nitropyrazol-1-yl)-N-phenylpyridine-4-carboxamide: A 500 mL 3-necked round-bottom flask was charged with 3-bromo-N-phenylpyridine-4-carboxamide (10.0 g, 36.1 mmol, 1.00 eq.), 4-nitropyrazole (4.90 g, 43.3 mmol, 1.20 eq.), cuprous iodide (1.37 g, 7.22 mmol, 0.200 eq.), 1,10-phenanthroline (1.30 g, 7.22 mmol, 0.200 eq.), N,N-dimethylformamide (150 mL) and sodium ethoxide (7.37 g, 108 mmol, 3.00 eq.). The mixture was stirred for overnight at 120° C. under oxygen atmosphere, and then concentrated under reduced pressure. The mixture was diluted with ethyl acetate (800 mL), washed with water (3×100 mL), dried over anhydrous sodium sulfate, filtered and concentrated under reduced pressure. The residue was purified by silica gel column chromatography, eluted with petroleum ether: ethyl acetate (1:4) to afford 3-(4-nitropyrazol-1-yl)-N-phenylpyridine-4-carboxamide (7.00 g, 63% yield) as an off-white solid. LCMS (ESI, m/z): 310 [M+H]$^+$.

5-nitro-7-phenyl-2,3,7,12-tetraazatricyclo[7.4.0.0ˆ[2,6]]trideca-1(9),3,5,10,12-pentaen-8-one: A 40 mL vial was charged with 3-(4-nitropyrazol-1-yl)-N-phenylpyridine-4-carboxamide (5.00 g, 16.2 mmol, 1.00 eq.), water (100 mL) and potassium persulfate (8.74 g, 32.3 mmol, 2.00 eq.). The mixture was stirred for 2 h at 105° C. and cooled down to rt. The pH value of the mixture was basified to 9 with sat. sodium bicarbonate solution. The mixture was extracted with ethyl acetate (3×300 mL). The organic layers were combined, washed with water (3×200 mL), dried over anhydrous sodium sulfate, filtered and concentrated under reduced pressure. The residue was purified by silica gel column chromatography, eluted with petroleum ether:ethyl acetate (1:1) to afford 5-nitro-7-phenyl-2,3,7,12-tetraazatricyclo[7.4.0.0ˆ[2,6]]trideca-1(9),3,5,10,12-pentaen-8-one (1.55 g, 31% yield) as a light yellow solid. LCMS (ESI, m/z): 308 [M+H]$^+$.

12-[(3,4-dimethoxyphenyl)methyl]-5-nitro-8-oxo-7-phenyl-2,3,7,12-tetraazatricyclo[7.4.0.0ˆ[2,6]]trideca-1(9),3,5,10,12-pentaen-12-ium bromide: A 40 mL vial were added 5-nitro-7-phenyl-2,3,7,12-tetraazatricyclo[7.4.0.0ˆ[2,6]]trideca-1(9),3,5,10,12-pentaen-8-one (1.55 g, 5.05 mmol, 1.00 eq.), acetonitrile (20 mL) and 4-(bromomethyl)-1,2-dimethoxybenzene (1.61 g, 6.96 mmol, 1.38 eq.). The mixture was stirred for overnight at 60° C. and then concentrated reduced pressure to afford 12-[(3,4-dimethoxyphenyl)methyl]-5-nitro-8-oxo-7-phenyl-2,3,7,12-tetraazatricyclo[7.4.0.0ˆ[2,6]]trideca-1(9),3,5,10,12-pentaen-12-ium bromide (2.25 g, crude) as a light yellow solid, which used for next step directly. LCMS (ESI, m/z): 458 [M-Br]$^+$.

12-[(3,4-dimethoxyphenyl)methyl]-5-nitro-7-phenyl-2,3,7,12-tetraazatricyclo[7.4.0.0ˆ[2,6]]trideca-1(9),3,5-trien-8-one: A 100 mL vial was charged with 12-[(3,4-dimethoxyphenyl)methyl]-5-nitro-8-oxo-7-phenyl-2,3,7,12-tetraazatricyclo[7.4.0.0ˆ[2,6]]trideca-1(9),3,5,10,12-pentaen-12-ium bromide (2.25 g, 4.18 mmol, 1.00 eq.), 1,2-dichloroethane (20 mL) and sodium triacetoxyborohydride (5.31 g, 25.1 mmol, 5.99 eq.). The mixture was stirred for 1.5 h at 60° C. The reaction was quenched with water (40 mL). The mixture was extracted with dichloromethane (3×100 mL). The organic layers were combined, washed with water (3×50 mL), dried over anhydrous sodium sulfate, filtered and concentrated under reduced pressure. The residue was purified by silica gel column chromatography, eluted with petroleum ether:ethyl acetate (1:1) to afford 12-[(3,4-dimethoxyphenyl)methyl]-5-nitro-7-phenyl-2,3,7,12-tetraazatricyclo[7.4.0.0ˆ[2,6]]trideca-1(9),3,5-trien-8-one (1.50 g, 78% yield) as a yellow solid. LCMS (ESI, m/z): 484 [M+Na]$^+$.

5-nitro-7-phenyl-2,3,7,12-tetraazatricyclo[7.4.0.0ˆ[2,6]]trideca-1(9),3,5-trien-8-one: A 40 mL vial was charged with 12-[(3,4-dimethoxyphenyl)methyl]-5-nitro-7-phenyl-2,3,7,12-tetraazatricyclo[7.4.0.0ˆ[2,6]]trideca-1(9),3,5-trien-8-one (1.50 g, 3.25 mmol, 1.00 eq.), 1,2-dichloroethane (15 mL), N,N-diisopropylethylamine (0.630 g, 4.88 mmol, 1.50 eq.) and chloroethyl chloroformate (0.510 g, 3.58 mmol, 1.10 eq.). The mixture was stirred for 1 h at rt and then concentrated under reduced pressure. Methanol (15 mL) was added. The mixture was stirred for 1 h at 70° C. and concentrated under reduced pressure to afford 5-nitro-7-phenyl-2,3,7,12-tetraazatricyclo[7.4.0.0ˆ[2,6]]trideca-1(9),3,5-trien-8-one (1.70 g, crude) as a brown solid. LCMS (ESI, m/z): 312 [M+H]$^+$.

12-(3,4-dichlorobenzoyl)-5-nitro-7-phenyl-2,3,7,12-tetraazatricyclo[7.4.0.0ˆ[2,6]]trideca-1(9),3,5-trien-8-one: A 40 mL vial was charged with 3,4-dichlorobenzoic acid (704 mg, 3.68 mmol, 1.50 eq.), N,N-dimethylformamide (12 mL), N-(3-dimethylaminopropyl)-N'-ethylcarbodiimide hydrochloride (706 mg, 3.69 mmol, 1.50 eq.), 1-hydroxybenzotriazole (498 mg, 3.69 mmol, 1.50 eq.), N,N-diisopropylethylamine (952 mg, 7.37 mmol, 3.00 eq.) and 5-nitro-7-phenyl-2,3,7,12-tetraazatricyclo[7.4.0.0ˆ[2,6]]trideca-1(9),3,5-trien-8-one (765 mg, 2.46 mmol, 1.00 eq.). The mixture was stirred for overnight at rt, and the reaction was quenched with water (50 mL). The mixture was extracted with ethyl acetate (3×100 mL). The organic layers were combined, washed with water (3×50 mL), dried over anhydrous sodium sulfate, filtered and concentrated under reduced pressure. The residue was purified by silica gel column chromatography, eluted with petroleum ether:ethyl acetate (1:1) to afford 12-(3,4-dichlorobenzoyl)-5-nitro-7-phenyl-2,3,7,12-tetraazatricyclo[7.4.0.0ˆ[2,6]]trideca-1(9),3,5-trien-8-one (600 mg, 50% yield) as an off-white solid. LCMS (ESI, m/z): 484 [M+H]$^+$.

5-amino-12-(3,4-dichlorobenzoyl)-7-phenyl-2,3,7,12-tetraazatricyclo[7.4.0.0ˆ[2,6]]trideca-1(9),3,5-trien-8-one: A 40 mL vial was charged with 12-(3,4-dichlorobenzoyl)-5-nitro-7-phenyl-2,3,7,12-tetraazatricyclo[7.4.0.0^[2,6]]trideca-1(9),3,5-trien-8-one (600 mg, 1.24 mmol, 1.00 eq.), iron (692 mg, 12.4 mmol, 10.0 eq.), ammonium chloride (663 mg, 12.4 mmol, 10.0 eq.), ethanol (10 mL) and water (2 mL). The mixture was stirred for 2 h at 80° C. The solids were filtered off, and the filtrate was concentrated under reduced pressure. The residue was purified by silica gel column chromatography, eluted with dichloromethane: methanol (10:1) to afford 5-amino-12-(3,4-dichlorobenzoyl)-7-phenyl-2,3,7,12-tetraazatricyclo[7.4.0.0^[2,6]]trideca-1(9),3,5-trien-8-one (290 mg, 52% yield) as a light yellow solid. LCMS (ESI, m/z): 454 [M+H]$^+$.

N-[12-(3,4-dichlorobenzoyl)-8-oxo-7-phenyl-2,3,7,12-tetraazatricyclo[7.4.0.0^[2,6]]trideca-1(9),3,5-trien-5-yl]-3-methylbutanamide: To a stirred solution of 5-amino-12-(3,4-dichlorobenzoyl)-7-phenyl-2,3,7,12-tetraazatricyclo[7.4.0.0^[2,6]]trideca-1(9),3,5-trien-8-one (120 mg, 0.264 mmol, 1.00 eq.) and triethylamine (80.2 mg, 0.792 mmol, 3.00 eq.) in dichloromethane (5.00 mL) was added 3-methylbutanoyl chloride (38.22 mg, 0.317 mmol, 1.20 eq.) dropwise at 0° C. The mixture was stirred for 2 h at rt, and then concentrated under reduced pressure. The crude product was purified by Prep-HPLC with the following conditions: Column: XBridge Prep OBD $C_{18}$ Column, 19×250 mm, 5 µm; Mobile Phase A: Water (10 mmol/L $NH_4HCO_3$+0.1% $NH_3.H_2O$), Mobile Phase B: ACN; Flow rate: 60 mL/min; Gradient: 45% B to 65% B in 7 min to afford N-[12-(3,4-dichlorobenzoyl)-8-oxo-7-phenyl-2,3,7,12-tetraazatricyclo[7.4.0.0^[2,6]]trideca-1(9),3,5-trien-5-yl]-3-methylbutanamide (90.9 mg, 64% yield) as an off-white solid. LCMS (ESI, m/z): 538 [M+H]$^+$. $^1$H NMR (400 MHz, DMSO-$d_6$) δ 8.19 (m, 1H), 7.86-7.72 (m, 3H), 7.57-7.47 (m, 4H), 7.25 (m, 2H), 4.99-4.77 (m, 2H), 3.92-3.61 (m, 2H), 2.56 (m, 2H), 1.68 (m, 1H), 1.38 (m, 2H), 0.74 (d, J=5.6 Hz, 6H).

Example 16

5-(benzylamino)-12-(3,4-dichlorobenzoyl)-7-phenyl-2,3,7,12-tetraazatricyclo[7.4.0.0^[2,6]]trideca-1(9),3,5-trien-8-one (18)

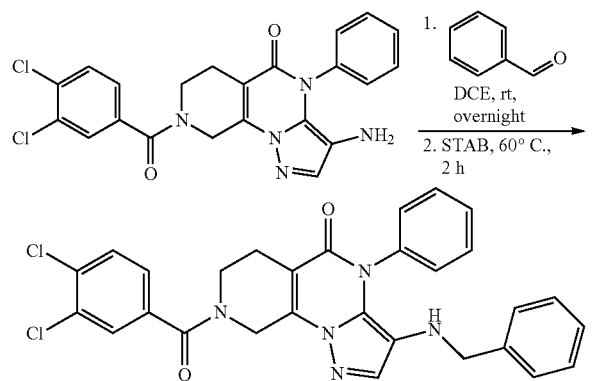

A 40 mL round-bottom flask was charged with 5-amino-12-(3,4-dichlorobenzoyl)-7-phenyl-2,3,7,12-tetraazatricyclo[7.4.0.0^[2,6]]trideca-1(9),3,5-trien-8-one (150 mg, 0.330 mmol, 1.00 eq.), benzaldehyde (42.1 mg, 0.396 mmol, 1.20 eq.) and 1,2-dichloroethane (5 mL) at rt. The mixture was stirred for overnight at rt. Sodium triacetoxyborohydride (420 mg, 1.98 mmol, 6.00 eq.) was then added. The mixture was stirred for 2 h at 60° C., and the reaction was quenched with water (10 ml). The mixture was extracted with dichloromethane (3×40 mL). The organic layers were combined, washed with water (3×50 mL), dried over anhydrous sodium sulfate, filtered and concentrated under reduced pressure. The crude product was purified by Prep-HPLC with the following conditions: Column: XBridge Shield $RP_{18}$ OBD Column, 19×250 mm, 5 µm; Mobile Phase A: Water (10 mmol/L $NH_4HCO_3$), Mobile Phase B: ACN; Flow rate: 25 mL/min; Gradient: 36% B to 56% B in 7 min to afford 5-(benzylamino)-12-(3,4-dichlorobenzoyl)-7-phenyl-2,3,7,12-tetraazatricyclo[7.4.0.0^[2,6]]trideca-1(9),3,5-trien-8-one (31.5 mg, 18% yield) as a light yellow solid. LCMS (ESI, m/z): 544 [M+H]$^+$. $^1$H NMR (400 MHz, DMSO-$d_6$) δ 7.78 (d, J=8.4 Hz, 2H), 7.64-7.44 (m, 7H), 7.22-7.17 (m, 3H), 6.96 (m, 2H), 4.93-4.55 (m, 2H), 3.76-3.59 (m, 4H), 2.54 (s, 2H), 2.30 (m, 1H).

Example 17

5-benzyl-12-(3,4-dichlorobenzoyl)-7-(4-methoxyphenyl)-2,3,7,12-tetraazatricyclo[7.4.0.0^[2,6]]trideca-1(9),3,5-trien-8-one (24)

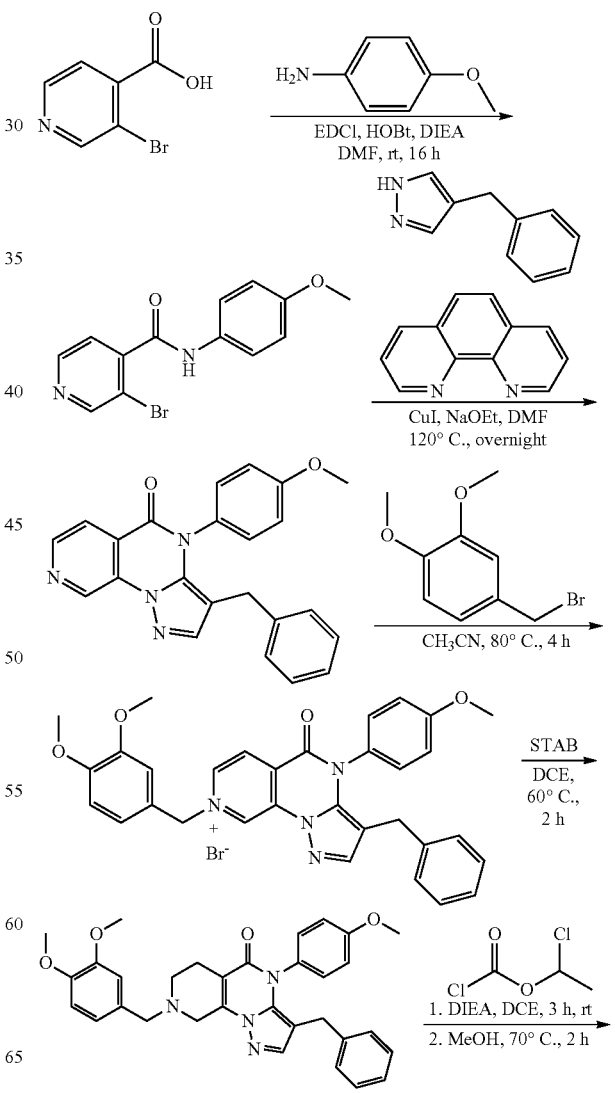

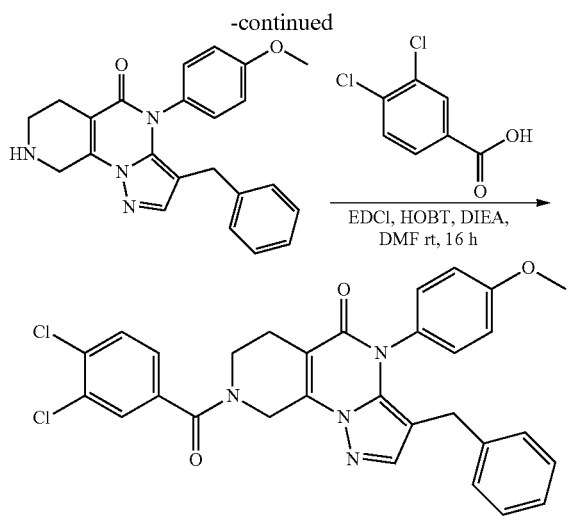

3-bromo-N-(4-methoxyphenyl)pyridine-4-carboxamide: To a stirred solution of 3-bromopyridine-4-carboxylic acid (24.6 g, 122 mmol, 1.50 eq.) and 1-hydroxybenzotriazole (16.5 g, 122 mmol, 1.50 eq.) in N,N-dimethylformamide (120 mL) were added N-(3-dimethylaminopropyl)-N'-ethylcarbodiimide hydrochloride (23.4 g, 122 mmol, 1.50 eq.) and diisopropylethylamine (31.5 g, 244 mmol, 3.00 eq.). The mixture was stirred for 30 minutes at rt. 4-methoxyaniline (10.0 g, 81.2 mmol, 1.00 eq.) was then added. The mixture was stirred for 16 h at rt, and the reaction was quenched with water (600 mL). The solids were collected by filtration and dried to afford 3-bromo-N-(4-methoxyphenyl)pyridine-4-carboxamide (15.0 g, 60% yield) as a light blue solid. LCMS (ESI, m/z): 307 [M+H]$^+$.

5-benzyl-7-(4-methoxyphenyl)-2,3,7,12-tetraazatricyclo[7.4.0.0ˆ[2,6]]trideca-1(9),3,5,10,12-pentaen-8-one: To a stirred solution of 3-bromo-N-(4-methoxyphenyl)pyridine-4-carboxamide (1.50 g, 4.89 mmol, 1.00 eq.) and 4-benzyl-1H-pyrazole (0.850 g, 5.37 mmol, 1.10 eq.) in N,N-dimethylformamide (20 mL) were added 1,10-phenanthroline (0.350 g, 1.94 mmol, 0.40 eq.), cuprous iodide (0.280 g, 1.47 mmol, 0.30 eq.) and sodium ethoxide (1.00 g, 14.6 mmol, 3.00 eq.) at rt under oxygen atmosphere. The mixture was stirred for overnight at 120° C., and the reaction was quenched with water (100 mL). The solids were collected by filtration. The residue was purified by silica gel column chromatography, eluted with petroleum ether:ethyl acetate (3:2) to afford 5-benzyl-7-(4-methoxyphenyl)-2,3,7,12-tetraazatricyclo[7.4.0.0ˆ[2,6]]trideca-1(9),3,5,10,12-pentaen-8-one (340 mg, 18% yield) as a light yellow solid. LCMS (ESI, m/z): 383 [M+H]$^+$.

3-benzyl-8-(3,4-dimethoxybenzyl)-4-(4-methoxyphenyl)-5-oxo-4,5-dihydropyrazolo[1,5-a]pyrido[4,3-e]pyrimidin-8-ium bromide: To a stirred solution of 5-benzyl-7-(4-methoxyphenyl)-2,3,7,12-tetraazatricyclo[7.4.0.0ˆ[2,6]]trideca-1(9),3,5,10,12-pentaen-8-one (340 mg, 0.890 mmol, 1.00 eq.) in acetonitrile (10 mL) was added 4-(bromomethyl)-1,2-dimethoxybenzene (308 mg, 1.33 mmol, 1.50 eq.) at rt under nitrogen atmosphere. The mixture was stirred for 4 h at 80° C. and concentrated under reduced pressure to afford 3-benzyl-8-(3,4-dimethoxybenzyl)-4-(4-methoxyphenyl)-5-oxo-4,5-dihydropyrazolo[1,5-a]pyrido[4,3-e]pyrimidin-8-ium bromide (420 mg, crude) as a dark yellow solid. LCMS (ESI, m/z): 533 [M-Br]$^+$.

5-benzyl-12-[(3,4-dimethoxyphenyl)methyl]-7-(4-methoxyphenyl)-2,3,7,12-tetraazatricyclo[7.4.0.0ˆ[2,6]]trideca-1(9),3,5-trien-8-one: To a stirred solution of 3-benzyl-8-(3,4-dimethoxybenzyl)-4-(4-methoxyphenyl)-5-oxo-4,5-dihydropyrazolo[1,5-a]pyrido[4,3-e]pyrimidin-8-ium bromide (420 mg, 0.684 mmol, 1.00 eq.) in dichloroethane (10 mL) was added sodium triacetoxyborohydride (500 mg, 2.36 mmol, 3.45 eq.) in portions at rt under nitrogen atmosphere. The mixture was stirred for 2 h at 60° C., and the reaction was quenched with water (20 mL). The mixture was extracted with dichloromethane (3×20 mL). The organic layers were combined, washed with water (3×20 mL), dried over anhydrous sodium sulfate, filtered and concentrated under reduced pressure. The residue was purified by silica gel column chromatography, eluted with petroleum ether: ethyl acetate (2:3) to afford 5-benzyl-12-[(3,4-dimethoxyphenyl)methyl]-7-(4-methoxyphenyl)-2,3,7,12-tetraazatricyclo[7.4.0.0ˆ[2,6]]trideca-1(9),3,5-trien-8-one (320 mg, 87% yield) as a brown yellow solid. LCMS (ESI, m/z): 537 [M+H]$^+$.

5-benzyl-7-(4-methoxyphenyl)-2,3,7,12-tetraazatricyclo[7.4.0.0ˆ[2,6]]trideca-1(9),3,5-trien-8-one: To a stirred solution of 5-benzyl-12-[(3,4-dimethoxyphenyl)methyl]-7-(4-methoxyphenyl)-2,3,7,12-tetraazatricyclo[7.4.0.0ˆ[2,6]]trideca-1(9),3,5-trien-8-one (320 mg, 0.596 mmol, 1.00 eq.) and N,N-diisopropylethylamine (154 mg, 1.19 mmol, 2.00 eq.) in dichloroethane (10 mL) was added chloroethyl chloroformate (170 mg, 1.19 mmol, 2.00 eq.) dropwise at 0° C. The mixture was stirred for 3 h at rt and concentrated under reduced pressure. The residue was dissolve in methanol (10 mL). The mixture was stirred for additional 2 h at 70° C. and then concentrated under reduced pressure to afford 5-benzyl-7-(4-methoxyphenyl)-2,3,7,12-tetraazatricyclo[7.4.0.0ˆ[2,6]]trideca-1(9),3,5-trien-8-one (170 mg, crude) as a light brown solid. LCMS (ESI, m/z): 387 [M+H]$^+$.

5-benzyl-12-(3,4-dichlorobenzoyl)-7-(4-methoxyphenyl)-2,3,7,12-tetraazatricyclo[7.4.0.0ˆ[2,6]]trideca-1(9),3,5-trien-8-one: To a stirred solution of 3,4-dichlorobenzoic acid (126 mg, 0.670 mmol, 1.52 eq.) and N,N-diisopropylethylamine (142 mg, 1.10 mmol, 2.50 eq.) in N,N-dimethylformamide (10 mL) was added N-(3-dimethylaminopropyl)-N'-ethylcarbodiimide hydrochloride (92.8 mg, 0.484 mmol, 1.10 eq.) and 1-hydroxybenzotriazole (65.4 mg, 0.484 mmol, 1.10 eq.). The mixture was stirred for 30 minutes at rt. 5-benzyl-7-(4-methoxyphenyl)-2,3,7,12-tetraazatricyclo[7.4.0.0ˆ[2,6]]trideca-1(9),3,5-trien-8-one (170 mg, 0.440 mmol, 1.00 eq.) was then added. The mixture was stirred for 16 h at rt, and the reaction was quenched with water (50 mL). The mixture was extracted with ethyl acetate (3×50 mL). The organic layers were combined, washed with water (3×50 mL), dried over anhydrous sodium sulfate, filtered and concentrated under reduced pressure. The crude product was purified by Prep-HPLC with the following conditions (Column: XBridge Prep OBD $C_{18}$ Column, 19×250 mm, 5 μm; Mobile Phase A: Water (10 mmol/L $NH_4HCO_3$+0.1% $NH_3.H_2O$), Mobile Phase B: ACN; Flow rate: 25 mL/min; Gradient: 61% B to 71% B in 12 min to afford 5-benzyl-12-(3,4-dichlorobenzoyl)-7-(4-methoxyphenyl)-2,3,7,12-tetraazatricyclo[7.4.0.0ˆ[2,6]]trideca-1(9),3,5-trien-8-one (74.0 mg, 30% yield) as an off-white solid. LCMS (ESI, m/z): 559 [M+H]$^+$. $^1$H NMR (300 MHz, Chloroform-d) δ 7.64 (s, 1H), 7.58 (d, J=8.4 Hz, 1H), 7.44-7.35 (m, 2H), 7.22-7.10 (m, 5H), 6.93-6.88 (m, 2H), 6.80 (d, J=6.0 Hz, 2H), 5.14 (m, 2H), 4.01 (m, 1H), 3.81 (s, 3H), 3.76 (m, 1H), 3.11 (s, 2H), 2.76 (m, 2H).

Example 18

5-(benzylamino)-12-(3,4-dichlorobenzoyl)-7-(4-methoxyphenyl)-2,3,7,12-tetraazatricyclo[7.4.0.0^[2,6]]trideca-1(9),3,5-trien-8-one (25)

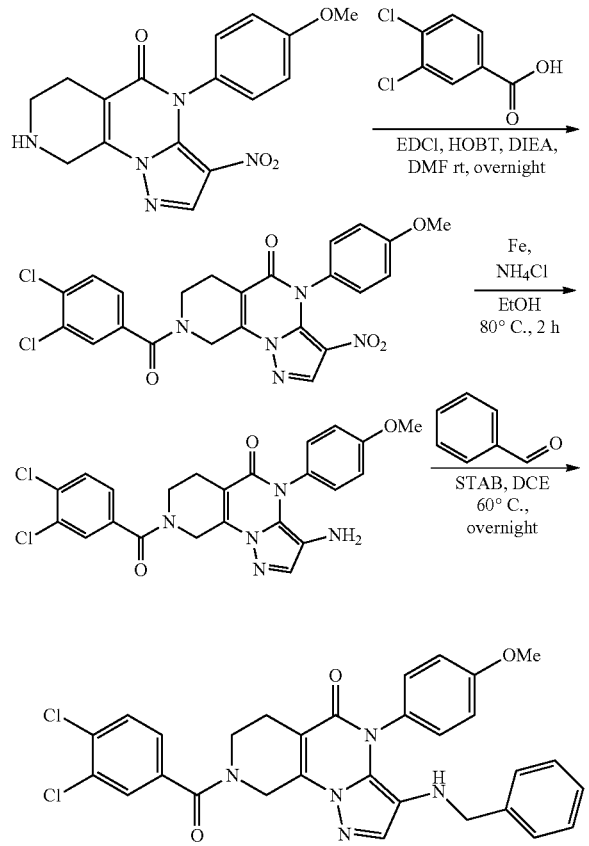

12-(3,4-dichlorobenzoyl)-7-(4-methoxyphenyl)-5-nitro-2,3,7,12-tetraazatricyclo[7.4.0.0^[2,6]]trideca-1(9),3,5-trien-8-one: A 100 mL round-bottom flask was charged with 7-(4-methoxyphenyl)-5-nitro-2,3,7,12-tetraazatricyclo[7.4.0.0^[2,6]]trideca-1(9),3,5-trien-8-one (2.90 g, 8.50 mmol, 1.00 eq., prepared according to the procedures of PH-ALO-BS5E-044), 3,4-dichlorobenzoic acid (1.95 g, 10.2 mmol, 1.20 eq.), N-(3-dimethylaminopropyl)-N'-ethylcarbodiimide hydrochloride (1.95 g, 10.2 mmol, 1.20 eq.), 1-hydroxybenzotriazole (1.38 g, 10.2 mmol, 1.20 eq.), N,N-diisopropylethylamine (3.29 g, 25.5 mmol, 3.00 eq.) and N,N-dimethylformamide (30 mL). The mixture was stirred for overnight at rt, and the reaction was quenched with water (100 mL). The mixture was extracted with ethyl acetate (3×100 mL). The organic layers were combined, washed with water (2×50 mL), dried over anhydrous sodium sulfate, filtered and concentrated under reduced pressure. The residue was purified by silica gel column chromatography, eluted with petroleum ether:ethyl acetate (1:1) to afford 12-(3,4-dichlorobenzoyl)-7-(4-methoxyphenyl)-5-nitro-2,3,7,12-tetraazatricyclo[7.4.0.0^[2,6]]trideca-1(9),3,5-trien-8-one (1.90 g, 43% yield) as an off-white solid. LCMS (ESI, m/z): 514 [M+H]+.

12-(3,4-dichlorobenzoyl)-7-(4-methoxyphenyl)-5-nitro-2,3,7,12-tetraazatricyclo[7.4.0.0^[2,6]]trideca-1(9),3,5-trien-8-one: A 100 mL round-bottom flask was charged with 12-(3,4-dichlorobenzoyl)-7-(4-methoxyphenyl)-5-nitro-2,3,7,12-tetraazatricyclo[7.4.0.0^[2,6]]trideca-1(9),3,5-trien-8-one (1.90 g, 3.70 mmol, 1.00 eq.), iron (2.06 g, 36.9 mmol, 10.0 eq.), ammonium chloride (1.98 g, 36.9 mmol, 10.0 eq.), ethanol (20 mL) and water (4 mL) at rt. The mixture was stirred for 2 h at 80° C. The solids were filtrated off, and the filtrate was concentrated under reduced pressure. The residue was purified by silica gel column chromatography, eluted with dichloromethane:methanol (10:1) to afford 5-amino-12-(3,4-dichlorobenzoyl)-7-(4-methoxyphenyl)-2,3,7,12-tetraazatricyclo[7.4.0.0^[2,6]]trideca-1(9),3,5-trien-8-one (1.50 g, 84% yield) as a light brown solid. LCMS (ESI, m/z): 484 [M+H]+.

5-(benzylamino)-12-(3,4-dichlorobenzoyl)-7-(4-methoxyphenyl)-2,3,7,12-tetraazatricyclo[7.4.0.0^[2,6]]trideca-1(9),3,5-trien-8-one: A 40 mL round-bottom flask was charged with 5-amino-12-(3,4-dichlorobenzoyl)-7-(4-methoxyphenyl)-2,3,7,12-tetraazatricyclo[7.4.0.0^[2,6]]trideca-1(9),3,5-trien-8-one (150 mg, 0.310 mmol, 1.00 eq.), benzaldehyde (39.4 mg, 0.372 mmol, 1.20 eq.) and 1,2-dichloroethane (4.00 mL) at rt. The mixture was stirred for 2 h at rt. Sodium triacetoxyborohydride (394 mg, 1.86 mmol, 6.00 eq.) was added. The mixture was stirred for overnight at 60° C., and the reaction was quenched with water (10 mL). The mixture was extracted with dichloromethane (3×40 mL). The organic layers were combined, washed with water (2×20 mL), dried over anhydrous sodium sulfate, filtered and concentrated under reduced pressure. The crude product was purified by Prep-HPLC with the following conditions, Column: XBridge Prep $C_{18}$ OBD Column, 19×250 mm, 5 µm; Mobile Phase A: Water (10 mmol/L $NH_4HCO_3$+0.1% $NH_3.H_2O$), Mobile Phase B: ACN; Flow rate: 25 mL/min; Gradient: 46% B to 66% B in 7 min to afford 5-(benzylamino)-12-(3,4-dichlorobenzoyl)-7-(4-methoxyphenyl)-2,3,7,12-tetraazatricyclo[7.4.0.0^[2,6]]trideca-1(9),3,5-trien-8-one (48.4 mg, 27% yield) as a light yellow solid. LCMS (ESI, m/z): 574 [M+H]+. 1H NMR (300 MHz, DMSO-$d_6$) δ 7.79 (d, J=8.1 Hz, 2H), 7.64-7.54 (m, 2H), 7.36 (d, J=7.5 Hz, 2H), 7.24 (m, 3H), 7.09-7.00 (m, 4H), 4.93-4.71 (m, 2H), 4.00-3.50 (m, 7H), 2.54 (m, 2H), 2.30 (br s, 1H).

Example 19

4-[5-benzyl-12-(4-bromo-3-chlorobenzoyl)-8-oxo-2,3,7,12-tetraazatricyclo[7.4.0.0^[2,6]]trideca-1(9),3,5-trien-7-yl]-N-methylbenzamide (29)

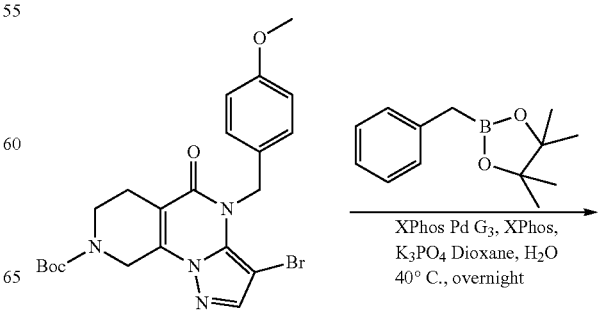

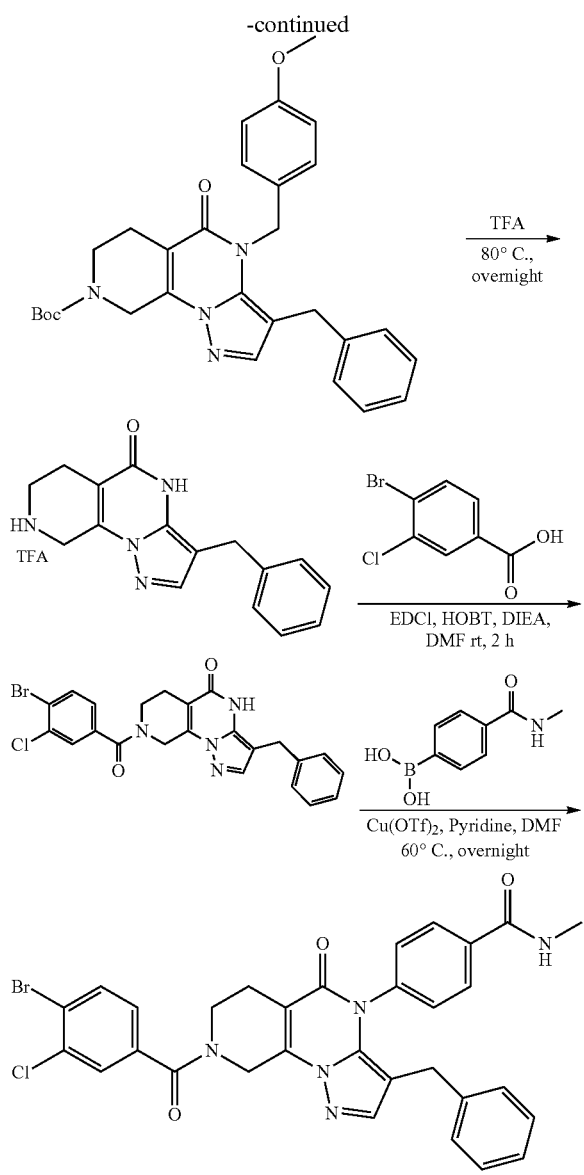

tert-butyl 5-benzyl-7-[(4-methoxyphenyl)methyl]-8-oxo-2,3,7,12-tetraazatricyclo[7.4.0.0^[2,6]]trideca-1(9),3,5-triene-12-carboxylate: A 250 mL round-bottom flask was charged with tert-butyl 5-bromo-7-[(4-methoxyphenyl)methyl]-8-oxo-2,3,7,12-tetraazatricyclo[7.4.0.0^[2,6]]trideca-1(9),3,5-triene-12-carboxylate (15.0 g, 30.6 mmol, 1.00 eq.), 2-benzyl-4,4,5,5-tetramethyl-1,3,2-dioxaborolane (10.7 g, 49.0 mmol, 1.60 eq.), 2-(dicyclohexylphosphino)-2',4',6'-triisopropylbiphenyl (1.46 g, 3.07 mmol, 0.10 eq.), methanesulfonato(2-dicyclohexylphosphino-2',4',6'-tri-i-propyl-1,1'-biphenyl)(2'-amino-1,1'-biphenyl-2-yl)palladium(II) (2.59 g, 3.07 mmol, 0.10 eq.), potassium phosphate (19.5 g, 91.9 mmol, 3.00 eq.), 1,4-dioxane (120 mL) and water (15 mL) at rt. The mixture was stirred for overnight at 40° C. under nitrogen atmosphere, and the reaction was quenched with water (200 mL). The mixture was extracted with ethyl acetate (3×200 mL). The organic layers were combined, washed with water (2×100 mL), dried over anhydrous sodium sulfate, filtered and concentrated under reduced pressure. The residue was purified by silica gel column chromatography, eluted with petroleum ether:ethyl acetate (9:1) to afford tert-butyl 5-benzyl-7-[(4-methoxyphenyl)methyl]-8-oxo-2,3,7,12-tetraazatricyclo[7.4.0.0^[2,6]]trideca-1(9),3,5-triene-12-carboxylate (10.8 g, 70% yield) as an off-white solid. LCMS (ESI, m/z): 501 [M+H]$^+$.

5-benzyl-2,3,7,12-tetraazatricyclo[7.4.0.0^[2,6]]trideca-1(9),3,5-trien-8-one trifluoroacetic acid salt: A 250 mL round-bottom flask was charged with tert-butyl 5-benzyl-7-[(4-methoxyphenyl)methyl]-8-oxo-2,3,7,12-tetraazatricyclo[7.4.0.0^[2,6]]trideca-1(9),3,5-triene-12-carboxylate (10.8 g, 15.6 mmol, 1.00 eq.) and trifluoroacetic acid (100 mL) at rt. The mixture was stirred for overnight at 80° C. and concentrated under reduced pressure to afford 5-benzyl-2,3,7,12-tetraazatricyclo[7.4.0.0^[2,6]]trideca-1(9),3,5-trien-8-one trifluoroacetic acid salt (9.10 g, crude) as a red oil. LCMS (ESI, m/z): 281 [M-CF$_3$COOH+H]$^+$.

5-benzyl-12-(4-bromo-3-chlorobenzoyl)-2,3,7,12-tetraazatricyclo[7.4.0.0^[2,6]]trideca-1(9),3,5-trien-8-one: A 250 mL round-bottom flask was charged with 5-benzyl-2,3,7,12-tetraazatricyclo[7.4.0.0^[2,6]]trideca-1(9),3,5-trien-8-one trifluoroacetic acid salt (9.10 g, 23.1 mmol, 1.00 eq.), 4-bromo-3-chlorobenzoic acid (9.17 g, 38.9 mmol, 1.68 eq.), N-(3-dimethylaminopropyl)-N'-ethylcarbodiimide hydrochloride (9.33 g, 48.7 mmol, 2.11 eq.), 1-hydroxybenzotriazole (6.58 g, 48.7 mmol, 2.11 eq.), N,N-diisopropylethylamine (12.6 g, 97.4 mmol, 4.22 eq.) and N,N-dimethylformamide (10 mL) at rt. The mixture was stirred for 2 h at rt, and the reaction was quenched with water (100 mL). The mixture was extracted with ethyl acetate (3×100 mL). The organic layers were combined, washed with water (2×100 mL), dried over anhydrous sodium sulfate, filtered and concentrated under reduced pressure. The residue was purified by silica gel column chromatography, eluted with ethyl acetate to afford 5-benzyl-12-(4-bromo-3-chlorobenzoyl)-2,3,7,12-tetraazatricyclo[7.4.0.0^[2,6]]trideca-1(9),3,5-trien-8-one (6.70 g, 58% yield) as an off-white solid. LCMS (ESI, m/z): 497 [M+H]$^+$.

5-benzyl-12-(4-bromo-3-chlorobenzoyl)-2,3,7,12-tetraazatricyclo[7.4.0.0^[2,6]]trideca-1(9),3,5-trien-8-one: A 250 mL round-bottom flask was charged with 5-benzyl-12-(4-bromo-3-chlorobenzoyl)-2,3,7,12-tetraazatricyclo[7.4.0.0^[2,6]]trideca-1(9),3,5-trien-8-one (6.70 g, 13.5 mmol, 1.00 eq.), 4-(methylcarbamoyl)phenylboronic acid (2.65 g, 14.8 mmol, 1.10 eq.), cupper(II)trifluoromethansulfonate (4.87 g, 13.5 mmol, 1.00 eq.), pyridine (3.19 g, 40.4 mmol, 3.00 eq.) and N,N-dimethylformamide (50 mL) at rt. The mixture was stirred for two days at 60° C. under oxygen atmosphere, and the reaction was quenched with water (100 mL). The mixture was extracted with ethyl acetate (3×200 mL). The organic layers were combined, washed with water (2×100 mL), dried over anhydrous sodium sulfate, filtered and concentrated under reduced pressure. The crude product was purified by Prep-HPLC with the following conditions, Column: YMC-Actus Triart C$_{18}$, 30×250, 5 μm; Mobile Phase A: Water (10 mmol/L NH$_4$HCO$_3$), Mobile Phase B: ACN; Flow rate: 50 mL/min; Gradient: 60% B to 85% B in 7 min; 220 nm to afford 4-[5-benzyl-12-(4-bromo-3-chlorobenzoyl)-8-oxo-2,3,7,12-tetraazatricyclo[7.4.0.0^[2,6]]trideca-1(9),3,5-trien-7-yl]-N-methylbenzamide (1.9466 g, 23% yield) as an off-white solid. LCMS (ESI, m/z): 630 [M+H]$^+$. $^1$H NMR (300 MHz, Chloroform-d) δ ppm 7.82-7.70 (m, 3H), 7.63 (m, 1H), 7.48 (s, 1H), 7.27-7.21 (m, 2H), 7.19-7.10 (m, 3H), 6.70 (m, 2H), 6.18 (d, J=5.1 Hz, 1H), 5.05 (m, 2H), 3.89 (m, 2H), 3.18-2.99 (m, 5H), 2.75 (br s, 2H).

Example 20

12-(4-bromo-3-chlorobenzoyl)-7-(4-methoxyphenyl)-5-(phenylamino)-2,3,7,12-tetraazatricyclo[7.4.0.0^[2,6]]trideca-1(9),3,5-trien-8-one (32)

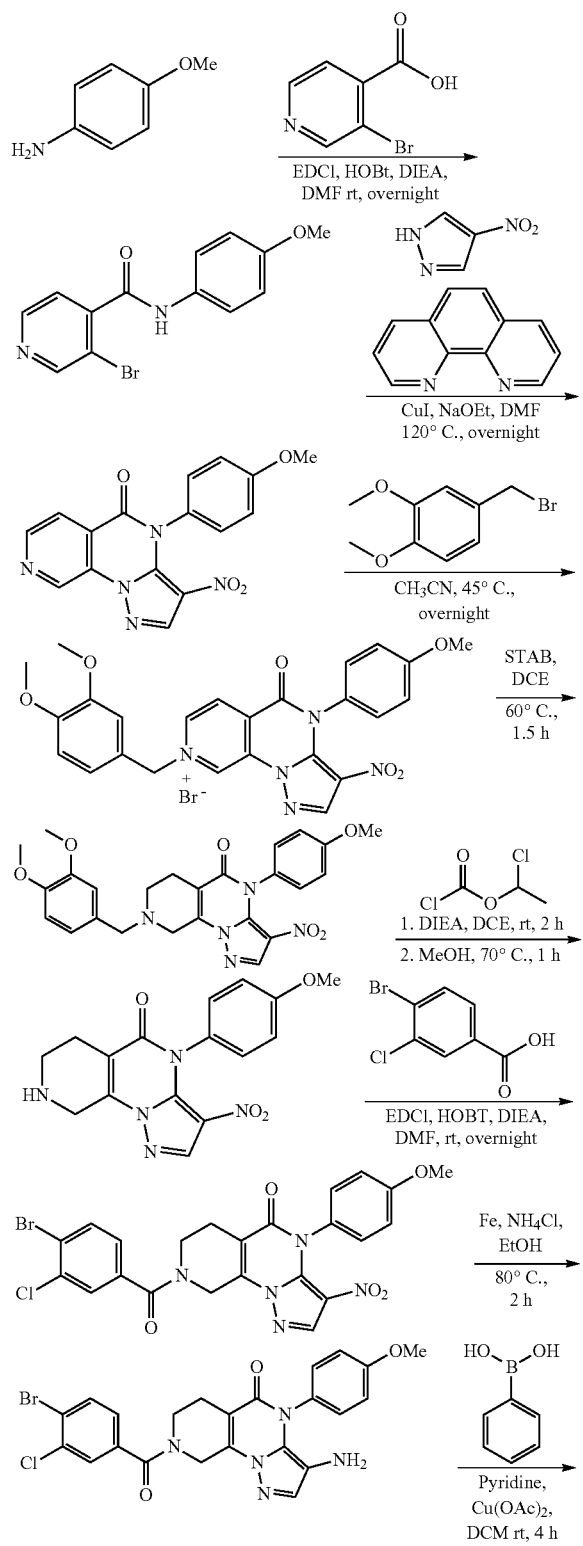

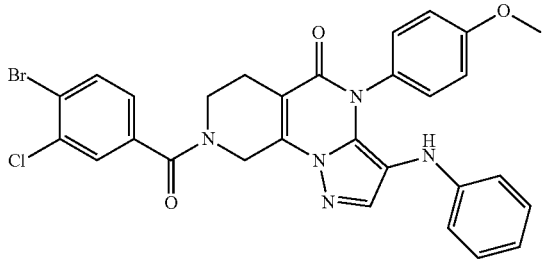

3-bromo-N-(4-methoxyphenyl)pyridine-4-carboxamide: A mixture of p-anisidine (30.0 g, 244 mmol, 1.00 eq.), 3-bromopyridine-4-carboxylic acid (59.1 g, 293 mmol, 1.20 eq.), N-(3-dimethylaminopropyl)-N'-ethylcarbodiimide hydrochloride (53.7 g, 280 mmol, 1.15 eq.), 1-hydroxybenzotrizole (37.9 g, 280 mmol, 1.15 eq.), N,N-diisopropylethylamine (94.5 g, 731 mmol, 3.00 eq.) and N,N-dimethylformamide (300 mL) was stirred for overnight at rt, and the reaction was quenched with ice water (800 mL). The solids were collected by filtration and dried to afford 3-bromo-N-(4-methoxyphenyl)pyridine-4-carboxamide (48.0 g, 64% yield) as a grey solid. LCMS (ESI, m/z): 307 [M+H]$^+$.

7-(4-methoxyphenyl)-5-nitro-2,3,7,12-tetraazatricyclo[7.4.0.0^[2,6]]trideca-1(9),3,5,10,12-pentaen-8-one: A mixture of 3-bromo-N-(4-methoxyphenyl)pyridine-4-carboxamide (10.0 g, 32.6 mmol, 1.00 eq.), 4-nitropyrazole (7.36 g, 65.1 mmol, 2.00 eq.), sodium ethoxide (4.43 g, 65.1 mmol, 2.00 eq.), 1,10-phenanthroline (1.76 g, 9.77 mmol, 0.30 eq.), cuprous iodide (0.931 g, 4.89 mmol, 0.15 eq.) and N,N-dimethylformamide (100 mL) was stirred for overnight at 120° C. under oxygen atmosphere. The mixture was allowed to cool to rt. The reaction was quenched with water (100 mL). The precipitated solids were collected by filtration and washed with water (3×50 mL). The residue was purified by silica gel column chromatography with ethyl acetate: petroleum ether (1:2) to afford 7-(4-methoxyphenyl)-5-nitro-2,3,7,12-tetraazatricyclo[7.4.0.0^[2,6]]trideca-1(9),3,5,10,12-pentaen-8-one (1.80 g, 16% yield) as a yellow solid. LCMS (ESI, m/z): 338 [M+H]$^+$.

12-[(3,4-dimethoxyphenyl)methyl]-7-(4-methoxyphenyl)-5-nitro-8-oxo-2,3,7,12-tetraazatricyclo[7.4.0.0^[2,6]]trideca-1(9),3,5,10,12-pentaen-12-ium bromide: A mixture of 7-(4-methoxyphenyl)-5-nitro-2,3,7,12-tetraazatricyclo[7.4.0.0^[2,6]]trideca-1(9),3,5,10,12-pentaen-8-one (1.00 g, 2.97 mmol, 1.00 eq.), 4-(bromomethyl)-1,2-dimethoxybenzene (1.37 g, 5.93 mmol, 2.00 eq.) and acetonitrile (50 mL) was stirred for overnight at 45° C. The mixture was concentrated under reduced pressure. The residue was dissolved in diethyl ether (50 mL) and stirred for 30 mins. The solids were collected by filtration to afford 12-[(3,4-dimethoxyphenyl)methyl]-7-(4-methoxyphenyl)-5-nitro-8-oxo-2,3,7,12-tetraazatricyclo[7.4.0.0^[2,6]]trideca-1(9),3,5,10,12-pentaen-12-ium bromide (1.50 g, crude) as a yellow solid. LCMS (ESI, m/z): 488 [M-Br]$^+$.

12-[(3,4-dimethoxyphenyl)methyl]-7-(4-methoxyphenyl)-5-nitro-2,3,7,12-tetraazatricyclo[7.4.0.0^[2,6]]trideca-1(9),3,5-trien-8-one: A mixture of 12-[(3,4-dimethoxyphenyl)methyl]-7-(4-methoxyphenyl)-5-nitro-8-oxo-2,3,7,12-tetraazatricyclo[7.4.0.0^[2,6]]trideca-1(9),3,5,10,12-pentaen-12-ium bromide (1.50 g, 2.64 mmol, 1.00 eq.), sodium triacetoxyborohydride (3.36 g, 15.8 mmol, 6.00 eq.) and 1,2-dichloroethane (50 mL) was stirred for 1.5 h at 60° C. The reaction was quenched with water (50 mL) and extracted with dichloromethane (3×50 mL). The combined organic layers were washed with water (3×50 mL), dried over anhydrous sodium sulfate, filtered and concentrated under reduced pressure. The residue was purified by silica gel column chromatography, eluted with ethyl acetate:petroleum ether (2:1) to afford 12-[(3,4-dimethoxyphenyl) methyl]-7-(4-methoxyphenyl)-5-nitro-2,3,7,12-tetraazatricyclo[7.4.0.0^[2,6]]trideca-1(9),3,5-trien-8-one (1.00 g, 76% yield) as a yellow solid. LCMS (ESI, m/z): 492 [M+H]$^+$.

7-(4-methoxyphenyl)-5-nitro-2,3,7,12-tetraazatricyclo[7.4.0.0^[2,6]]trideca-1(9),3,5-trien-8-one: A mixture of 12-[(3,4-dimethoxyphenyl)methyl]-7-(4-methoxyphenyl)-5-nitro-2,3,7,12-tetraazatricyclo[7.4.0.0^[2,6]]trideca-1(9),3,5-trien-8-one (1.00 g, 2.03 mmol, 1.00 eq.), chloroethyl chloroformate (0.436 g, 3.05 mmol, 1.50 eq.), N,N-diisopropylethylamine (0.131 g, 1.02 mmol, 0.50 eq.) and 1,2-dichloroethane (50 mL) was stirred for 2 h at rt and concentrated under reduced pressure. The residue was dissolved in methanol (50 mL) and stirred for additional 1 h at 70° C. The mixture was concentrated under reduced pressure to afford 7-(4-methoxyphenyl)-5-nitro-2,3,7,12-tetraazatricyclo[7.4.0.0^[2,6]]trideca-1(9),3,5-trien-8-one (1.20 g, crude) as a yellow solid. LCMS (ESI, m/z): 342 [M+H]$^+$.

12-(4-bromo-3-chlorobenzoyl)-7-(4-methoxyphenyl)-5-nitro-2,3,7,12-tetraazatricyclo[7.4.0.0^[2,6]]trideca-1(9),3,5-trien-8-one: A mixture of 7-(4-methoxyphenyl)-5-nitro-2,3,7,12-tetraazatricyclo[7.4.0.0^[2,6]]trideca-1(9),3,5-trien-8-one (1.20 g, 3.52 mmol, 1.00 eq.), 4-bromo-3-chlorobenzoic acid (1.24 g, 5.27 mmol, 1.50 eq.), N-(3-dimethylaminopropyl)-N'-ethylcarbodiimide hydrochloride (1.01 g, 5.27 mmol, 1.50 eq.), 1-hydroxybenzotrizole (0.712 g, 5.27 mmol, 1.50 eq.), N,N-diisopropylethylamine (1.36 g, 10.5 mmol, 3.00 eq.) and N,N-dimethylformamide (50 mL) was stirred overnight at rt. The mixture was added ethyl acetate (100 mL) and washed with water (3×50 mL). The organic layer was dried over anhydrous sodium sulfate, filtered and concentrated under reduced pressure. The residue was purified by silica gel column chromatography, eluted with ethyl acetate:petroleum ether (3:1) to afford 12-(4-bromo-3-chlorobenzoyl)-7-(4-methoxyphenyl)-5-nitro-2,3,7,12-tetraazatricyclo[7.4.0.0^[2,6]]trideca-1(9),3,5-trien-8-one (900 mg, 45% yield) as a yellow solid. LCMS (ESI, m/z): 558 [M+H]$^+$.

5-amino-12-(4-bromo-3-chlorobenzoyl)-7-(4-methoxyphenyl)-2,3,7,12-tetraazatricyclo[7.4.0.0^[2,6]]trideca-1(9),3,5-trien-8-one: A mixture of 12-(4-bromo-3-chlorobenzoyl)-7-(4-methoxyphenyl)-5-nitro-2,3,7,12-tetraazatricyclo[7.4.0.0^[2,6]]trideca-1(9),3,5-trien-8-one (600 mg, 1.07 mmol, 1.00 eq.), iron (300 mg, 5.37 mmol, 5.00 eq.), ammonium chloride (287 mg, 5.37 mmol, 5.00 eq.), ethanol (50 mL) and water (10 mL) was stirred for 2 h at 80° C. The solids were filtered off, and the filter cake was washed with ethanol (3×30 mL). The filtrate was concentrated under reduced pressure. The residue was added water (50 mL) and extracted with dichloromethane (3×50 mL). The combined organic layers were washed with water (3×50 mL), dried over anhydrous sodium sulfate, filtered and concentrated under reduced pressure to afford 5-amino-12-(4-bromo-3-chlorobenzoyl)-7-(4-methoxyphenyl)-2,3,7,12-tetraazatricyclo[7.4.0.0^[2,6]]trideca-1(9),3,5-trien-8-one (570 mg, crude) as a brown yellow solid. LCMS (ESI, m/z): 528 [M+H]$^+$.

12-(4-bromo-3-chlorobenzoyl)-7-(4-methoxyphenyl)-5-(phenylamino)-2,3,7,12-tetraazatricyclo[7.4.0.0^[2,6]]trideca-1(9),3,5-trien-8-one: A mixture of 5-amino-12-(4-bromo-3-chlorobenzoyl)-7-(4-methoxyphenyl)-2,3,7,12-tetraazatricyclo[7.4.0.0^[2,6]]trideca-1(9),3,5-trien-8-one (130 mg, 0.246 mmol, 1.00 eq.), phenyl boronic acid (45.0 mg, 0.369 mmol, 1.50 eq.), pyridine (38.9 mg, 0.492 mmol, 2.00 eq.), cupric acetate (67.0 mg, 0.369 mmol, 1.50 eq.) and dichloromethane (10 mL) was stirred for 4 h at rt under oxygen atmosphere. The reaction was quenched with water (30 mL) The mixture was extracted with ethyl acetate (3×30 mL). The organic layers were combined, washed with water (3×30 mL), dried over anhydrous sodium sulfate, filtered and concentrated under reduced pressure. The residue was purified by silica gel column chromatography with ethyl acetate:petroleum ether (3:1) to afford the crude product. The crude product was purified by Pre-HPLC with the following conditions: Column: Xselect CSH $C_{18}$ Column, 30×150 mm, 5 μm; Mobile Phase A: Water (10 mmol/L NH$_4$HCO$_3$+0.1% NH$_3$.H$_2$O), Mobile Phase B: ACN; Flow rate: 60 mL/min; Gradient: 50% B to 70% B in 7 min to afford 12-(4-bromo-3-chlorobenzoyl)-7-(4-methoxyphenyl)-5-(phenylamino)-2,3,7,12-tetraazatricyclo[7.4.0.0^[2,6]]trideca-1(9),3,5-trien-8-one (60.8 mg, 41% yield) as a white solid. LCMS (ESI, m/z): 604 (M+H)$^+$. $^1$H NMR (400 MHz, Chloroform-d) δ 7.79-7.53 (m, 3H), 7.21 (s, 1H), 7.07-6.93 (m, 4H), 6.80-6.63 (m, 3H), 6.17 (d, J=7.9 Hz, 2H), 5.02 (m, 2H), 4.12-3.63 (m, 6H), 2.74 (br s, 2H).

Example 21

4-[12-(4-bromo-3-chlorobenzoyl)-8-oxo-5-[[4-(trifluoromethoxy)phenyl]methyl]-2,3,7,12-tetraazatricyclo[7.4.0.0^[2,6]]trideca-1(9),3,5-trien-7-yl]-N-methylbenzamide (35)

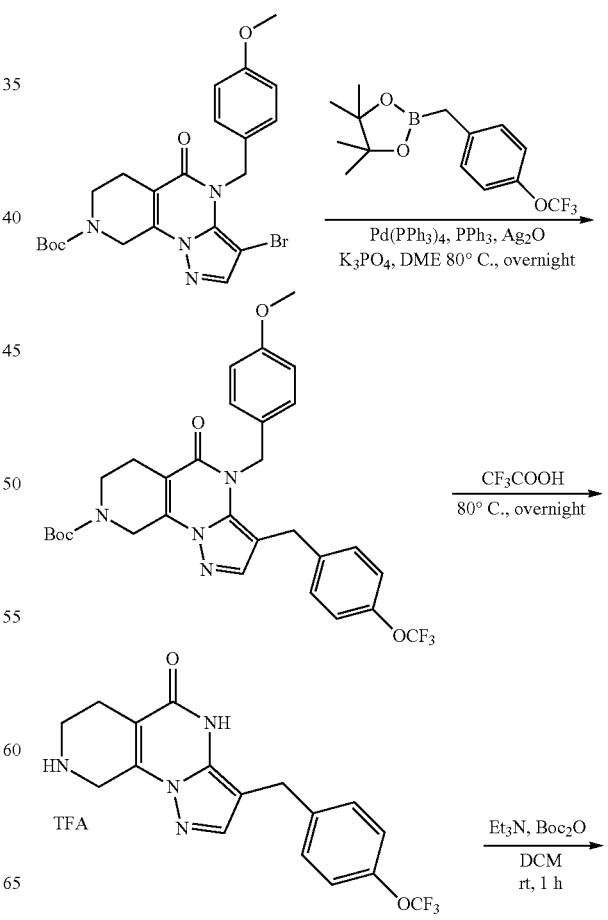

-continued

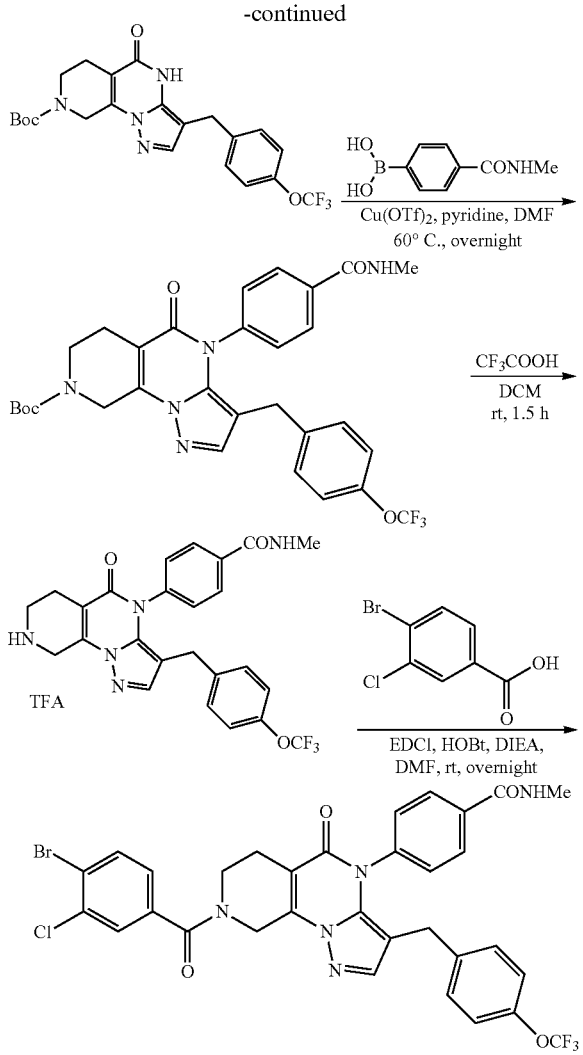

tert-butyl 7-[(4-methoxyphenyl)methyl]-8-oxo-5-[[4-(trifluoromethoxy)phenyl]methyl]-2,3,7,12-tetraazatricyclo[7.4.0.0^[2,6]]trideca-1(9),3,5-triene-12-carboxylate: A mixture of tert-butyl 5-bromo-7-[(4-methoxyphenyl)methyl]-8-oxo-2,3,7,12-tetraazatricyclo[7.4.0.0^[2,6]]trideca-1(9),3,5-triene-12-carboxylate (1.00 g, 2.04 mmol, 1.00 eq.), 4,4,5,5-tetramethyl-2-[[4-(trifluoromethoxy)phenyl]methyl]-1,3,2-dioxaborolane (1.23 g, 4.09 mmol, 2.00 eq.), tetrakis(triphenylphosphine)palladium (0.236 g, 0.204 mmol, 0.10 eq.), triphenylphosphine (0.107 g, 0.409 mmol, 0.20 eq.), potassium carbonate (0.650 g, 3.06 mmol, 1.50 eq.), 1,2-dimethoxyethane (20 mL) and silver oxide (0.757 g, 3.27 mmol, 1.60 eq.) was stirred overnight at 80° C. under nitrogen atmosphere. The solids were filtered off, and the filter cake was washed with ethyl acetate (3×20 mL). The mixture was washed with water (3×50 mL). The combined organic layers were dried over anhydrous sodium sulfate, filtered and concentrated under reduced pressure. The residue was purified by silica gel column chromatography, eluted with petroleum ether:ethyl acetate (2:1) to afford the crude product. The crude product was purified by Prep-TLC (petroleum ether:ethyl acetate=2:1) to afford tert-butyl 7-[(4-methoxyphenyl)methyl]-8-oxo-5-[[4-(trifluoromethoxy)phenyl]methyl]-2,3,7,12-tetraazatricyclo[7.4.0.0^[2,6]]trideca-1(9),3,5-triene-12-carboxylate (310 mg, 26% yield) as a white solid. LCMS (ESI, m/z): 585 [M+H]$^+$.

5-[[4-(trifluoromethoxy)phenyl]methyl]-2,3,7,12-tetraazatricyclo[7.4.0.0^[2,6]]trideca-1(9),3,5-trien-8-one trifluoroacetic acid salt: A mixture of tert-butyl 7-[(4-methoxyphenyl)methyl]-8-oxo-5-[[4-(trifluoromethoxy)phenyl]methyl]-2,3,7,12-tetraazatricyclo[7.4.0.0^[2,6]]trideca-1(9),3,5-triene-12-carboxylate (310 mg, 0.530 mmol, 1.00 eq.) and trifluoroacetic acid (6 mL) was stirred for overnight at 80° C. and concentrated under reduced pressure to afford crude 5-[[4-(trifluoromethoxy)phenyl]methyl]-2,3,7,12-tetraazatricyclo[7.4.0.0^[2,6]]trideca-1(9),3,5-trien-8-one trifluoroacetic acid salt (190 mg crude) as brown oil. LCMS (ESI, m/z): 365 [M-CF$_3$COOH+H]$^+$.

tert-butyl 8-oxo-5-[[4-(trifluoromethoxy)phenyl]methyl]-2,3,7,12-tetraazatricyclo[7.4.0.0^[2,6]]trideca-1(9),3,5-triene-12-carboxylate: A mixture of 5-[[4-(trifluoromethoxy)phenyl]methyl]-2,3,7,12-tetraazatricyclo[7.4.0.0^[2,6]]trideca-1(9),3,5-trien-8-one trifluoroacetic acid salt (426 mg, 0.892 mmol, 1.00 eq.), dichloromethane (5 mL), triethylamine (361 mg, 3.57 mmol, 4.00 eq.) and ditertbutyl dicarbonate (292 mg, 1.34 mmol, 1.50 eq.) was stirred for 1 h at rt. The residue was purified by silica gel column chromatography, eluted with petroleum ether:ethyl acetate (1:1) to afford tert-butyl 8-oxo-5-[[4-(trifluoromethoxy)phenyl]methyl]-2,3,7,12-tetraazatricyclo[7.4.0.0^[2,6]]trideca-1(9),3,5-triene-12-carboxylate (350 mg, 84% yield) as a white solid. LCMS (ESI, m/z): 465 [M+H]$^+$.

tert-butyl 7-[4-(methylcarbamoyl)phenyl]-8-oxo-5-[[4-(trifluoromethoxy)phenyl]methyl]-2,3,7,12-tetraazatricyclo[7.4.0.0^[2,6]]trideca-1(9),3,5-triene-12-carboxylate: A mixture of tert-butyl 8-oxo-5-[[4-(trifluoromethoxy)phenyl]methyl]-2,3,7,12-tetraazatricyclo[7.4.0.0^[2,6]]trideca-1(9),3,5-triene-12-carboxylate (350 mg, 0.754 mmol, 1.00 eq.), 4-(methylcarbamoyl)phenylboronic acid (202 mg, 1.13 mmol, 1.50 eq.), copper(II) trifluoromethanesulfonate (272 mg, 0.754 mmol, 1.00 eq.), N,N-dimethylformamide (10 mL) and pyridine (298 mg, 3.77 mmol, 5.00 eq.) was stirred overnight at 60° C. under oxygen atmosphere and diluted with ethyl acetate (200 mL). The mixture was washed with water (4×20 mL), sat. sodium chloride (1×20 mL), dried over anhydrous sodium sulfate, filtered and concentrated under reduced pressure. The residue was purified by Prep-TLC (petroleum ether/ethyl acetate 1:4) to afford tert-butyl 7-[4-(methylcarbamoyl)phenyl]-8-oxo-5-[[4-(trifluoromethoxy)phenyl]methyl]-2,3,7,12-tetraazatricyclo[7.4.0.0^[2,6]]trideca-1(9),3,5-triene-12-carboxylate (200 mg, 44% yield) as a white solid. LCMS (ESI, m/z): 598 [M+H]$^+$.

N-methyl-4-(8-oxo-5-[[4-(trifluoromethoxy)phenyl]methyl]-2,3,7,12-tetraazatricyclo[7.4.0.0^[2,6]]trideca-1(9),3,5-trien-7-yl)benzamide trifluoroacetic acid salt: A mixture of tert-butyl 7-[4-(methylcarbamoyl)phenyl]-8-oxo-5-[[4-(trifluoromethoxy)phenyl]methyl]-2,3,7,12-tetraazatricyclo[7.4.0.0^[2,6]]trideca-1(9),3,5-triene-12-carboxylate (195 mg, 0.294 mmol, 1.00 eq.), dichloromethane (10 mL) and trifluoroacetic acid (1 mL). The mixture was stirred for 1.5 h at rt. The mixture was concentrated under reduced pressure to afford crude N-methyl-4-(8-oxo-5-[[4-(trifluoromethoxy)phenyl]methyl]-2,3,7,12-tetraazatricyclo[7.4.0.0^[2,6]]trideca-1(9),3,5-trien-7-yl)benzamide trifluoroacetic acid salt (170 mg, crude) as light brown oil. LCMS (ESI, m/z): 498 [M+H]$^+$.

4-[12-(4-bromo-3-chlorobenzoyl)-8-oxo-5-[[4-(trifluoromethoxy)phenyl]methyl]-2,3,7,12-tetraazatricyclo[7.4.0.0^[2,6]]trideca-1(9),3,5-trien-7-yl]-N-methylbenzamide: A mixture of 4-bromo-3-chlorobenzoic acid (51.1 mg, 0.217 mmol, 1.30 eq.), N,N-dimethylformamide (3 mL), N-(3-dimethylaminopropyl)-N'-ethylcarbodiimide hydrochloride (41.6 mg, 0.217 mmol, 1.30 eq.), 1-hydroxybenzotrizole (29.3 mg, 0.217 mmol, 1.30 eq.), N,N-diisopropylethylamine (86.2 mg, 0.667 mmol, 4.00 eq.) and N-methyl-4-(8-oxo-5-[[4-(trifluoromethoxy)phenyl]methyl]-2,3,7,12-tetraazatricyclo[7.4.0.0^[2,6]]trideca-1(9),3,5-trien-7-yl)benzamide trifluoro acetic acid salt (102 mg, 0.167 mmol, 1.00 eq.) was stirred overnight at rt and diluted with ethyl acetate (150 mL). The mixture was washed with hydrochloric acid (2×20 mL, aq. 1 mol/L), sat. sodium bicarbonate (2×20 mL), sat. sodium chloride (1×20 mL), dried over anhydrous sodium sulfate, filtered and concentrated under reduced pressure. The crude product was purified by Prep-HPLC with the following conditions: Column: XBridge Prep OBD $C_{18}$ Column, 30×150 mm 5 μm; Mobile Phase A: Water (10 mmol/L $NH_4HCO_3$+0.1% $NH_3.H_2O$), Mobile Phase B: ACN; Flow rate: 60 mL/min; Gradient: 50% B to 70% B in 7 min to afford 4412-(4-bromo-3-chlorobenzoyl)-8-oxo-5-[[4-(trifluoromethoxy)phenyl]methyl]-2,3,7,12-tetraazatricyclo[7.4.0.0^[2,6]]trideca-1(9),3,5-trien-7-yl]-N-methylbenzamide (73.8 mg, 62% yield) as a white solid. LCMS (ESI, m/z): 714 [M+H]$^+$. $^1$H NMR (300 MHz, Chloroform-d) δ 7.79-7.67 (m, 3H), 7.61 (s, 1H), 7.49 (br s, 1H), 7.24 (m, 1H), 7.16 (d, J=8.4 Hz, 2H), 6.96 (d, J=8.1 Hz, 2H), 6.65 (d, J=8.7 Hz, 2H), 6.20 (d, J=4.8 Hz, 1H), 5.35-4.55 (m, 2H), 4.32-3.41 (m, 2H), 3.14 (s, 2H), 3.02 (d, J=4.8 Hz, 3H), 2.72 (br s, 2H).

Example 22

4-(8-(4-bromo-3-chlorobenzoyl)-3-(4-cyanobenzyl)-5-oxo-6,7,8,9-tetrahydropyrazolo[1,5-a]pyrido[4,3-e]pyrimidin-4(5H)-yl)-N-methylbenzamide (43)

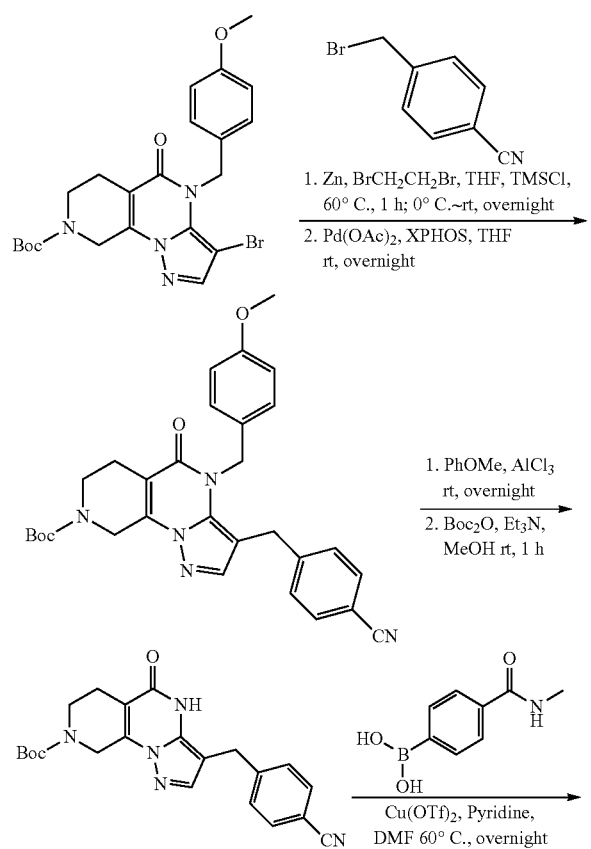

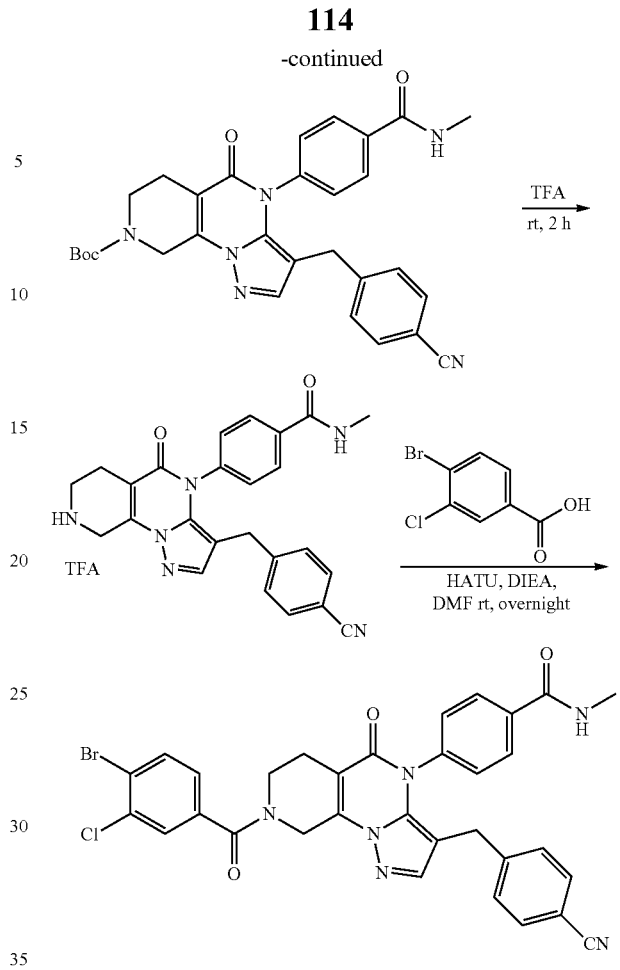

tert-butyl 3-(4-cyanobenzyl)-4-(4-methoxybenzyl)-5-oxo-5,6,7,9-tetrahydropyrazolo[1,5-a]pyrido[4,3-e]pyrimidine-8(4H)-carboxylate: A 40-mL vial was charged with zinc powder (468 mg, 7.15 mmol, 5.00 eq.), tetrahydrofuran (20 mL), dibromoethane (26.9 mg, 0.143 mmol, 0.10 eq.) under nitrogen atmosphere. The mixture was heated to 60° C. Chlorotrimethylsilane (15.5 mg, 0.143 mmol, 0.10 eq.) was added. The solution was stirred for 1 h at 60° C. The reaction was cooled to 0° C. 4-(Bromomethyl)benzonitrile (280 mg, 1.43 mmol, 1.00 eq.) was added. The temperature was increased to rt naturally and stirred for overnight at rt. Tert-butyl 3-bromo-4-(4-methoxybenzyl)-5-oxo-5,6,7,9-tetrahydropyrazolo[1,5-a]pyrido[4,3-e]pyrimidine-8(4H)-carboxylate (700 mg, 1.43 mmol, 1.00 eq.), palladium acetate (32.1 mg, 0.143 mmol, 0.10 eq.) and 2-(dicyclohexylphosphino)-2',4',6'-triisopropylbiphenyl (68.2 mg, 0.143 mmol, 0.10 eq.) were added. The mixture was stirred for overnight at rt under nitrogen atmosphere, and the reaction was quenched with water (50 mL). The mixture was extracted with ethyl acetate (3×50 mL). The organic layers were combined, washed with water (3×50 mL), dried over anhydrous sodium sulfate, filtered and concentrated under reduced pressure. The residue was purified by silica gel column chromatography, eluted with ethyl acetate:hexane (1:1) to afford tert-butyl 3-(4-cyanobenzyl)-4-(4-methoxybenzyl)-5-oxo-5,6,7,9-tetrahydropyrazolo[1,5-a]pyrido[4,3-e]pyrimidine-8(4H)-carboxylate (400 mg, 53% yield) as a yellow solid. LCMS (ESI, m/z): 526 [M+H]$^+$.

tert-butyl 3-(4-cyanobenzyl)-5-oxo-5,6,7,9-tetrahydropyrazolo[1,5-a]pyrido[4,3-e]pyrimidine-8(4H)-carboxylate: A 40-mL round-bottom flask was charged with tert-butyl 3-(4- cyanobenzyl)-4-(4-methoxybenzyl)-5-oxo-5,6,7,9-tetrahydropyrazolo[1,5-a]pyrido[4,3-e]pyrimidine-8(4H)-carboxylate (400 mg, 0.761 mmol, 1.00 eq.), anisole (10 mL) and aluminium chloride (304 mg, 2.28 mmol, 3.00 eq.). The solution was stirred overnight at rt. The mixture was added to a mixture of di-tert-butyl dicarbonate (249 mg, 1.14 mmol, 1.50 eq.), trimethylamine (230 mg, 2.28 mmol, 3.00 eq.) and methanol (20 ml) at 0° C. The solution was stirred for 1 h at rt, and the reaction was quenched with water (50 mL). The mixture was extracted with ethyl acetate (3×50 mL). The organic layers were combined, washed with water (3×50 mL), dried over anhydrous sodium sulfate, filtered and concentrated under reduced pressure. The residue was purified by silica gel column chromatography, eluted with ethyl acetate:hexane (1:1) to afford tert-butyl 3-(4-cyanobenzyl)-5-oxo-5,6,7,9-tetrahydropyrazolo[1,5-a]pyrido[4,3-e]pyrimidine-8(4H)-carboxylate (200 mg, 65% yield) as a yellow solid. LCMS (ESI, m/z): 406 [M+H]$^+$.

tert-butyl 3-(4-cyanobenzyl)-4-(4-(methylcarbamoyl)phenyl)-5-oxo-5,6,7,9-tetrahydropyrazolo[1,5-a]pyrido[4,3-e]pyrimidine-8(4H)-carboxylate: A 40-mL vial was charged with tert-butyl 3-(4-cyanobenzyl)-5-oxo-5,6,7,9-tetrahydropyrazolo[1,5-a]pyrido[4,3-e]pyrimidine-8(4H)-carboxylate (200 mg, 0.493 mmol, 1.00 eq.), 4-(methylcarbamoyl)phenylboronic acid (132 mg, 0.740 mmol, 1.50 eq.), pyridine (195 mg, 2.47 mmol, 5.00 eq.), copper(II) trifluoromethanesulfonate (178 mg, 0.493 mmol, 1.00 eq.) and N,N-dimethylformamide (10 mL). The solution was stirred for overnight at 60° C. under 02 atmosphere. The mixture was diluted with ethyl acetate (50 mL) and washed with water (3×50 mL). The organic layer was dried over anhydrous sodium sulfate, filtered and concentrated under reduced pressure. The residue was purified by silica gel column chromatography, eluted with ethyl acetate to afford tert-butyl 3-(4-cyanobenzyl)-4-(4-(methylcarbamoyl)phenyl)-5-oxo-5,6,7,9-tetrahydropyrazolo[1,5-a]pyrido[4,3-e]pyrimidine-8(4H)-carboxylate (120 mg, 45% yield) as a yellow solid. LCMS (ESI, m/z): 539 [M+H]$^+$.

4-(3-(4-cyanobenzyl)-5-oxo-6,7,8,9-tetrahydropyrazolo[1,5-a]pyrido[4,3-e]pyrimidin-4(5H)-yl)-N-methylbenzamide trifluoroacetic acid salt: A 50-mL round-bottom flask was charged with tert-butyl 3-(4-cyanobenzyl)-4-(4-(methylcarbamoyl)phenyl)-5-oxo-5,6,7,9-tetrahydropyrazolo[1,5-a]pyrido[4,3-e]pyrimidine-8(4H)-carboxylate (120 mg, 0.223 mmol, 1.00 eq.), dichloromethane (20 mL) and trifluoroacetic acid (1 mL). The resulting solution was stirred for 2 h at rt and concentrated under reduced pressure to afford 4-(3-(4-cyanobenzyl)-5-oxo-6,7,8,9-tetrahydropyrazolo[1,5-a]pyrido[4,3-e]pyrimidin-4(5H)-yl)-N-methylbenzamide trifluoroacetic acid salt (98.0 mg, crude) as a yellow solid. LCMS (ESI, m/z): 439 [M-CF$_3$COOH+H]$^+$ 4-(8-(4-bromo-3-chlorobenzoyl)-3-(4-cyanobenzyl)-5-oxo-6,7,8,9-tetrahydropyrazolo[1,5-a]pyrido[4,3-e]pyrimidin-4(5H)-yl)-N-methylbenzamide: A 40-mL vial was charged with 4-(3-(4-cyanobenzyl)-5-oxo-6,7,8,9-tetrahydropyrazolo[1,5-a]pyrido[4,3-e]pyrimidin-4(5H)-yl)-N-methylbenzamide trifluoroacetic acid salt (63.2 mg, 0.114 mmol, 1.00 eq.), 4-bromo-3-chlorobenzoic acid (32.2 mg, 0.137 mmol, 1.20 eq.), O-(7-azabenzotriazol-1-yl)-N,N,N',N'-tetramethyluronium hexafluorophosphate (65.0 mg, 0.171 mmol, 1.50 eq.), N,N-diisopropylethylamine (44.2 mg, 0.342 mmol, 3.00 eq.) and N,N-dimethylformamide (5 mL). The solution was stirred overnight at rt, and the reaction was quenched with water (50 mL). The mixture was extracted with ethyl acetate (3×50 mL). The organic layers were combined, washed with water (3×50 mL), dried over anhydrous sodium sulfate, filtered and concentrated under reduced pressure. The crude product was purified by preparative HPLC using the following gradient conditions: Column: Xselect CSH OBD Column 30×150 mm 5 μm; Mobile Phase A: Water (10 mmol/L NH$_4$HCO$_3$+0.1% NH$_3$.H$_2$O), Mobile Phase B: ACN; Flow rate: 60 mL/min; Gradient: 42% B to 62% B in 7 min to afford 4-(8-(4-bromo-3-chlorobenzoyl)-3-(4-cyanobenzyl)-5-oxo-6,7,8,9-tetrahydropyrazolo[1,5-a]pyrido[4,3-e]pyrimidin-4(5H)-yl)-N-methylbenzamide (20.0 mg, 27% yield) as a white solid. LCMS (ESI, m/z): 655 [M+H]$^+$. $^1$H NMR (300 MHz, Chloroform-d) δ 7.76 (m, 3H), 7.63 (s, 1H), 7.51-7.45 (m, 3H), 7.27 (m, 1H), 7.20 (d, J=8.3 Hz, 2H), 6.79 (d, J=7.9 Hz, 2H), 6.17 (d, J=5.2 Hz, 1H), 5.15 (m, 2H), 3.78 (m, 2H), 3.21 (s, 2H), 3.07 (d, J=4.7 Hz, 3H), 2.75 (br s, 2H).

Example 23

4-[(11R*)-5-benzyl-12-(4-bromo-3-chlorobenzoyl)-11-methyl-8-oxo-2,3,7,12-tetraazatricyclo[7.4.0.0^[2,6]]trideca-1(9),3,5-trien-7-yl]-N-methylbenzamide (71) and 4-[(11S*)-5-benzyl-12-(4-bromo-3-chlorobenzoyl)-11-methyl-8-oxo-2,3,7,12-tetraazatricyclo[7.4.0.0^[2,6]]trideca-1(9),3,5-trien-7-yl]-N-methylbenzamide (72)

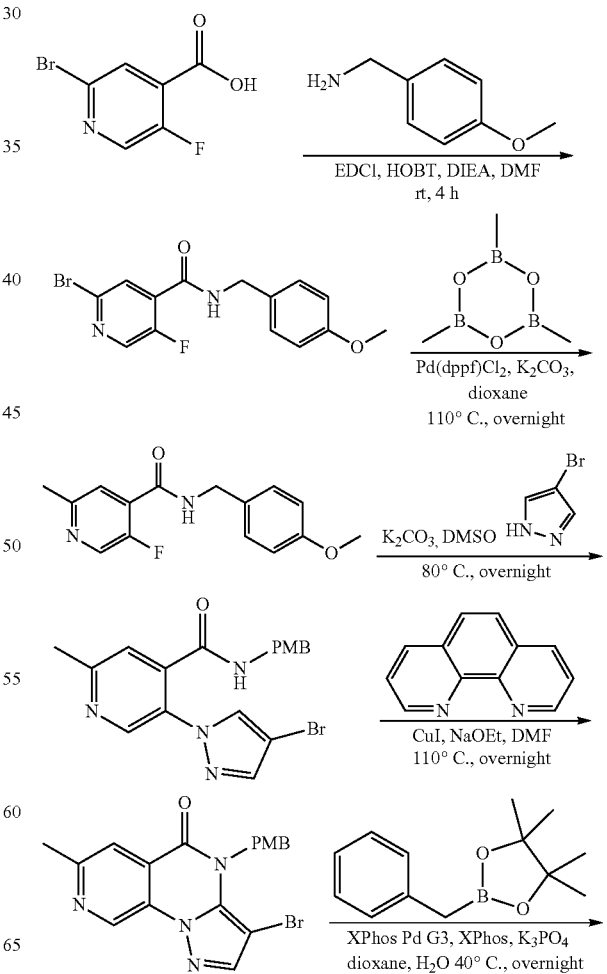

-continued

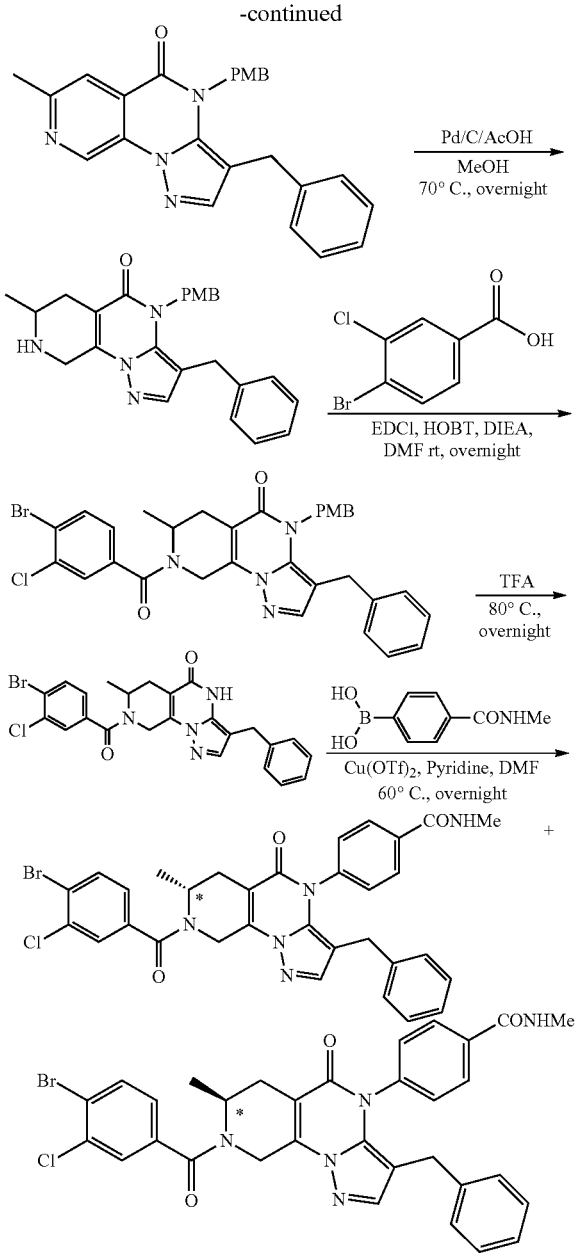

2-bromo-5-fluoro-N-[(4-methoxyphenyl)methyl]pyridine-4-carboxamide: A 100 mL round-bottom flask was charged with 2-bromo-5-fluoropyridine-4-carboxylic acid (10.0 g, 45.5 mmol, 1.00 eq.), (4-methoxyphenyl)methanamine (3.43 g, 25.0 mmol, 1.10 eq.), N-(3-dimethylaminopropyl)-N'-ethylcarbodiimide hydrochloride (13.1 g, 68.2 mmol, 1.50 eq.), 1-Hydroxybenzotriazole (9.21 g, 68.2 mmol, 1.50 eq.), N,N-diisopropylethylamine (17.6 g, 136 mmol, 3.00 eq.) and N,N-dimethylformamide (100 ml). The mixture was stirred for 4 h at rt, and the reaction was quenched with water (100 mL). The mixture was extracted with ethyl acetate (3×200 mL). The combined organic layers were washed with water (3×50 mL), dried over anhydrous sodium sulfate, filtered and concentrated under reduced pressure. The residue was purified by silica gel column chromatography, eluted with petroleum ether:ethyl acetate (1:1) to afford 2-bromo-5-fluoro-N-[(4-methoxyphenyl)methyl]pyridine-4-carboxamide (9.60 g, 62% yield) as an off-white oil. LCMS (ESI, m/z): 339 [M+H]$^+$.

5-fluoro-N-[(4-methoxyphenyl)methyl]-2-methylpyridine-4-carboxamide: A 250 mL round-bottom flask was charged with 2-bromo-5-fluoro-N-[(4-methoxyphenyl)methyl]pyridine-4-carboxamide (9.60 g, 28.3 mmol, 1.00 eq.), 2,4,6-trimethyl-1,3,5,2,4,6-trioxatriborinane (8.53 g, 33.8 mmol, 1.20 eq., 50% in tetrahydrofuran), [1,1'-bis(diphenylphosphino)ferrocene]dichloropalladium(II) (4.14 g, 5.66 mmol, 0.200 eq.), potassium carbonate (11.7 g, 84.9 mmol, 3.00 eq.) and 1,4-dioxane (100 mL) at rt. The mixture was stirred for overnight at 110° C. under nitrogen atmosphere, and the reaction was quenched with water (100 mL). The mixture was extracted with ethyl acetate (3×300 mL). The organic layers were combined, washed with water (3×200 mL), dried over anhydrous sodium sulfate, filtered and concentrated under reduced pressure. The residue was purified by silica gel column chromatography, eluted with ethyl acetate to 5-fluoro-N-[(4-methoxyphenyl)methyl]-2-methylpyridine-4-carboxamide (6.90 g, 89% yield) as a light brown solid. LCMS (ESI, m/z): 275 [M+H]$^+$.

5-(4-bromo-1H-pyrazol-1-yl)-N-(4-methoxybenzyl)-2-methylisonicotinamide: A 250 mL round-bottom flask was charged with 5-fluoro-N-[(4-methoxyphenyl)methyl]-2-methylpyridine-4-carboxamide (6.00 g, 21.9 mmol, 1.00 eq.), dimethyl sulphoxide (60.0 mL), 4-bromopyrazole (3.54 g, 24.1 mmol, 1.10 eq.) and potassium carbonate (9.07 g, 65.6 mmol, 3.00 eq.) at rt. The mixture was stirred for overnight at 80° C. and diluted with water (100 mL). The mixture was extracted with ethyl acetate (3×100 mL). The organic layers were combined, washed with water (3×100 mL), dried over anhydrous sodium sulfate, filtered and concentrated under reduced pressure. The residue was purified by silica gel column chromatography, eluted with petroleum ether:ethyl acetate (1:1) to afford 5-(4-bromo-1H-pyrazol-1-yl)-N-(4-methoxybenzyl)-2-methylisonicotinamide (3.64 g, 41% yield) as a brown solid. LCMS (ESI, m/z): 401 [M+H]$^+$.

3-bromo-4-(4-methoxybenzyl)-7-methylpyrazolo[1,5-a]pyrido[4,3-e]pyrimidin-5(4H)-one: A 100 mL round-bottom flask was charged with 5-(4-bromo-1H-pyrazol-1-yl)-N-(4-methoxybenzyl)-2-methylisonicotinamide (3.64 g, 9.07 mmol, 1.00 eq.), phen (1.31 g, 7.26 mmol, 0.80 eq.), sodium ethoxide (3.09 g, 45.4 mmol, 5.00 eq.), cuprous iodide (0.690 g, 3.63 mmol, 0.40 eq.) and N,N-dimethylformamide (40 mL) at rt. The mixture was stirred for overnight at 110° C. under oxygen atmosphere, and the reaction was quenched with water (50 mL). The mixture was extracted with ethyl acetate (3×50 mL). The organic layers were combined, washed with water (3×50 mL), dried over anhydrous sodium sulfate, filtered and concentrated under reduced pressure. The residue was purified by silica gel column chromatography, eluted with ethyl acetate to afford 3-bromo-4-(4-methoxybenzyl)-7-methylpyrazolo[1,5-a]pyrido[4,3-e]pyrimidin-5(4H)-one (1.50 g, 41% yield) as an off-white solid. LCMS (ESI, m/z): 399 [M+H]$^+$.

5-benzyl-7-[(4-methoxyphenyl)methyl]-11-methyl-2,3,7,12-tetraazatricyclo[7.4.0.0^[2,6]]trideca-1(13),3,5,9,11-pentaen-8-one: A 100 mL round-bottom flask was charged with 5-bromo-7-[(4-methoxyphenyl)methyl]-11-methyl-2,3,7,12-tetraazatricyclo[7.4.0.0^[2,6]]trideca-1(13),3,5,9,11-pentaen-8-one (1.50 g, 3.76 mmol, 1.00 eq.), 2-benzyl-4,4,5,5-tetramethyl-1,3,2-dioxaborolane (0.980 g, 4.49 mmol, 1.20 eq.), methanesulfonato(2-dicyclohexylphosphino-2',4',6'-tri-i-propyl-1,1'-biphenyl)(2'-amino-1,1'-biphenyl-2-yl)palladium(II) (0.320 g, 0.376 mmol, 0.10 eq.), 2-(dicyclohexylphosphino)-2',4',6'-triisopropylbiphenyl (0.180 g, 0.376 mmol, 0.10 eq.), potassium phosphate (2.39 g, 0.0110 mmol, 3.00 eq.), 1,4-dioxane (15 mL) and water (20 mL). The mixture was stirred for overnight at 40° C. under nitrogen atmosphere, and the reaction was quenched with water (30 mL). The mixture was extracted with ethyl acetate (3×100 mL). The combined organic layers were washed with brine (2×40 mL), dried over anhydrous sodium sulfate, filtered and concentrated under reduced pressure. The residue was purified by silica gel column chromatography, eluted with petroleum ether:ethyl acetate (1:1) to afford 5-benzyl-7-[(4-methoxyphenyl)methyl]-11-methyl-2,3,7,12-tetraazatricyclo[7.4.0.0^[2,6]]trideca-1(13),3,5,9,11-pentaen-8-one (950 mg, 61% yield) as a light yellow solid. LCMS (ESI, m/z): 411 [M+H]$^+$.

5-benzyl-7-[(4-methoxyphenyl)methyl]-11-methyl-2,3,7,12-tetraazatricyclo[7.4.0.0^[2,6]]trideca-1(13),3,5,9,11-pentaen-8-one: A 100 mL round-bottom flask was charged with 5-benzyl-7-[(4-methoxyphenyl)methyl]-11-methyl-2,3,7,12-tetraazatricyclo[7.4.0.0^[2,6]]trideca-1(13),3,5,9,11-pentaen-8-one (350 mg, 0.853 mmol, 1.00 eq.), methanol (10.0 mL), 10% Pd/C (45 g) and acetic acid (2.5 mL) at rt. The mixture was stirred for overnight at 70° C. under 3 atm hydrogen atmosphere. The solids were filtered off, and the filtrate was concentrated under reduced pressure. The mixture was diluted with water (10 mL) and acidified to pH to 8 with sat. sodium carbonate. The mixture was extracted with ethyl acetate (3×50 mL). The combined organic layers were washed with water (3×50 mL), dried over anhydrous sodium sulfate, filtered and concentrated under reduced pressure to afford 5-benzyl-7-[(4-methoxyphenyl)methyl]-11-methyl-2,3,7,12-tetraazatricyclo[7.4.0.0^[2,6]]trideca-1(9),3,5-trien-8-one (250 mg, crude) as an off-white solid. LCMS (ESI, m/z): 415 [M+H]$^+$.

5-benzyl-12-(4-bromo-3-chlorobenzoyl)-7-[(4-methoxyphenyl)methyl]-11-methyl-2,3,7,12-tetraazatricyclo[7.4.0.0^[2,6]]trideca-1(9),3,5-trien-8-one: A 40 mL round-bottom flask was charged with 5-benzyl-7-[(4-methoxyphenyl)methyl]-11-methyl-2,3,7,12-tetraazatricyclo[7.4.0.0^[2,6]]trideca-1(9),3,5-trien-8-one (250 mg, 0.603 mmol, 1.00 eq.), 4-bromo-3-chlorobenzoic acid (170 mg, 0.724 mmol, 1.20 eq.), N-(3-dimethylaminopropyl)-N'-ethylcarbodiimide hydrochloride (173 mg, 0.905 mmol, 1.50 eq.), 1-hydroxybenzotriazole (122 mg, 0.905 mmol, 1.50 eq.), N,N-diisopropylethylamine (234 mg, 1.81 mmol, 3.00 eq.) and N,N-dimethylformamide (5 mL). The mixture was stirred for overnight at rt, and the reaction was quenched with water (10 mL). The mixture was extracted with ethyl acetate (3×40 mL). The organic layers were combined were washed with water (3×50 mL), dried over anhydrous sodium sulfate, filtered and concentrated under reduced pressure. The residue was purified by Prep-TLC (petroleum ether:ethyl acetate=1:1) to afford 5-benzyl-12-(4-bromo-3-chlorobenzoyl)-7-[(4-methoxyphenyl)methyl]-11-methyl-2,3,7,12-tetraazatricyclo[7.4.0.0^[2,6]]trideca-1(9),3,5-trien-8-one (200 mg, 52% yield) as a light brown solid. LCMS (ESI, m/z): 631 [M+H]$^+$.

5-benzyl-12-(4-bromo-3-chlorobenzoyl)-7-[(4-methoxyphenyl)methyl]-11-methyl-2,3,7,12-tetraazatricyclo[7.4.0.0^[2,6]]trideca-1(9),3,5-trien-8-one: A 40 mL round-bottom flask was charged with 5-benzyl-12-(4-bromo-3-chlorobenzoyl)-7-[(4-methoxyphenyl)methyl]-11-methyl-2,3,7,12-tetraazatricyclo[7.4.0.0^[2,6]]trideca-1(9),3,5-trien-8-one (200 mg, 0.316 mmol, 1.00 eq.) and trifluoroacetaldehyde (5 mL) at rt. The mixture was stirred for overnight at 80° C. and concentrated under reduced pressure. The residue was purified by Prep-TLC (petroleum ether:ethyl acetate=1:1) to afford 5-benzyl-12-(4-bromo-3-chlorobenzoyl)-7-[(4-methoxyphenyl)methyl]-11-methyl-2,3,7,12-tetraazatricyclo[7.4.0.0^[2,6]]trideca-1(9),3,5-trien-8-one (135 mg, 83% yield) as a light brown solid. LCMS (ESI, m/z): 511 [M+H]$^+$.

5-benzyl-12-(4-bromo-3-chlorobenzoyl)-7-[(4-methoxyphenyl)methyl]-11-methyl-2,3,7,12-tetraazatricyclo[7.4.0.0^[2,6]]trideca-1(9),3,5-trien-8-one: A 100 mL round-bottom flask was charged with 5-benzyl-12-(4-bromo-3-chlorobenzoyl)-7-[(4-methoxyphenyl)methyl]-11-methyl-2,3,7,12-tetraazatricyclo[7.4.0.0^[2,6]]trideca-1(9),3,5-trien-8-one (135 mg, 0.264 mmol, 1.00 eq.), 4-(methylcarbamoyl)phenylboronic acid (51.9 mg, 0.290 mmol, 1.10 eq.), copper(II) trifluoromethanesulfonate (95.4 mg, 0.264 mmol, 1.00 eq.), pyridine (62.6 mg, 0.791 mmol, 3.00 eq.) and N,N-dimethylformamide (10 mL) at rt. The mixture was stirred for overnight at 60° C. under oxygen atmosphere, and the reaction was quenched with water (20 mL). The mixture was extracted with ethyl acetate (3×50 mL). The organic layers were combined were washed with water (3×50 mL), dried over anhydrous sodium sulfate, filtered and concentrated under reduced pressure. The residue was purified by Prep-TLC (petroleum ether:ethyl acetate=1:1) to afford the crude product. The crude product was purified by pre-Chiral-HPLC with the following conditions: Column: CHIRALPAK IA, 2×25 cm, 5 μm; Mobile Phase A: Hex:DCM=3:1 (0.5% 2M NH$_3$-MeOH)—HPLC, Mobile Phase B: EtOH—HPLC; Flow rate: 15 mL/min; Gradient: 50% B to 50% B in 14 min to afford the two enantiomers.

First enantiomer: 4-[(11R*)-5-benzyl-12-(4-bromo-3-chlorobenzoyl)-11-methyl-8-oxo-2,3,7,12-tetraazatricyclo[7.4.0.0^[2,6]]trideca-1(9),3,5-trien-7-yl]-N-methylbenzamide (71) (16.2 mg, 10% yield, the first peak) as a white solid. LCMS (ESI, m/z): 644 [M+H]$^+$, 100% ee. $^1$H NMR (300 MHz, Chloroform-d) δ 7.85-7.70 (m, 3H), 7.62-7.42 (m, 2H), 7.32-7.29 (m, 1H), 7.25-7.11 (m, 5H), 6.80-6.66 (m, 2H), 6.20 (d, J=5.1 Hz, 1H), 5.85 (br, 1H), 4.62-4.32 (m, 2H), 3.15-3.02 (m, 5H), 2.89-2.60 (m, 2H), 1.41-1.27 (m, 3H).

Second enantiomer: 4-[(11S*)-5-benzyl-12-(4-bromo-3-chlorobenzoyl)-11-methyl-8-oxo-2,3,7,12-tetraazatricyclo[7.4.0.0^[2,6]]trideca-1(9),3,5-trien-7-yl]-N-methylbenzamide (72) (24.2 mg, 14% yield, the second peak) as a white solid. LCMS (ESI, m/z): 644 [M+H]$^+$, 100% ee. $^1$H NMR (300 MHz, Chloroform-d) δ 7.85-7.70 (m, 3H), 7.62-7.42 (m, 2H), 7.32-7.29 (m, 1H), 7.25-7.11 (m, 5H), 6.80-6.66 (m, 2H), 6.20 (d, J=5.1 Hz, 1H), 5.85 (br, 1H), 4.62-4.32 (m, 2H), 3.15-3.02 (m, 5H), 2.89-2.60 (m, 2H), 1.41-1.27 (m, 3H).

Example 24

Alternative Synthesis of the Intermediate tert-butyl 3-bromo-4-(4-methoxybenzyl)-5-oxo-5,6,7,9-tetrahydropyrazolo[1,5-a]pyrido[4,3-e]pyrimidine-8(4H)-carboxylate

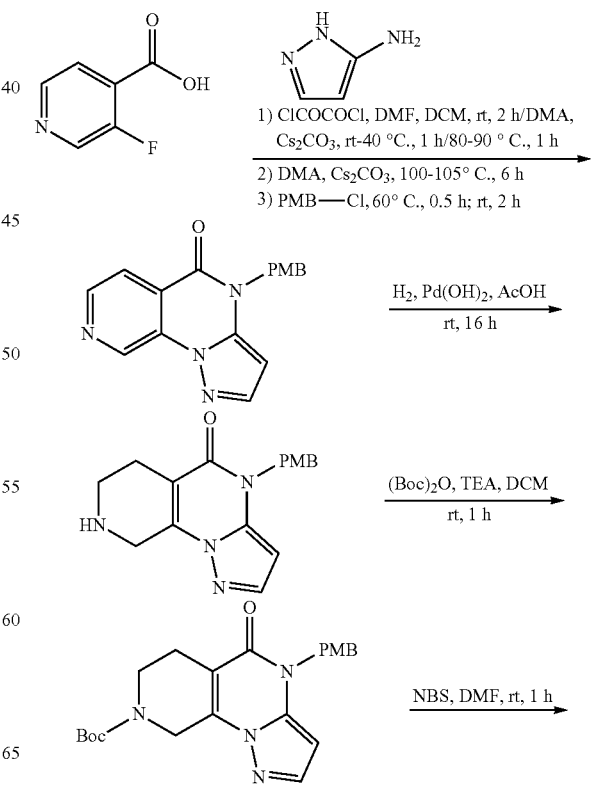

121
-continued

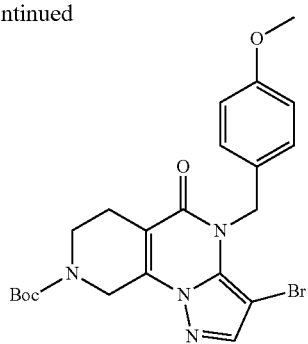

4-(4-methoxy benzyl)pyrazolo[1,5-a]pyrido[4,3-e]pyrimidin-5(4H)-one: 3-Fluoropyridine-4-carboxylic acid (100 g, 0.708 mol, 1.00 eq.) and N,N-dimethylformamide (2.00 mL, 0.0258 mol, 0.04 eq.) was added to dichloromethane (1.00 L), oxalyl chloride (135 g, 1.06 mol, 1.50 eq.) was dropped into slowly at rt. The solution was stirred for 2 h at rt, and then concentrated under reduced pressure to afford the acyl chloride. 2H-pyrazol-3-amine (76.6 g, 0.921 mol, 1.30 eq.) and cesium carbonate (462 g, 1.41 mol, 2.00 eq.) were added to N,N-dimethylacetamide (1.00 L). The acyl chloride which was suspended in N,N-dimethylacetamide (1.00 L) was added in portions at below 40° C. The solution was stirred for 1 h at rt, and for additional 1 h at 80-90° C. Cesium carbonate (231 g, 0.708 mol, 1.00 eq.) was added to mixture, and the mixture was stirred for 1 h at 100-105° C. Another batch of cesium carbonate (231 g, 708 mol, 1.00 eq.) was added, and the mixture was stirred for an additional 5 h at 100-105° C. The mixture was then cooled to 60° C. and used in the next step directly. 4-Methoxybenzyl chloride (66.1 g, 0.422 mol, 0.60 eq.), cesium carbonate (115 g, 0.352 mmol, 0.50 eq.) were added to the mixture. The solution was stirred for 0.5 h at 60° C., and for an additional 2 h at rt. The solids were filtered off, and the filtrate was concentrated under reduced pressure. The residue was dissolved in ethyl acetate (3 L), washed with water (2×2 L). The organic layer was dried by $Na_2SO_4$, filtered and concentrated under reduced pressure. The solids were washed with ethyl acetate and dried to afford product 4-(4-methoxy benzyl)pyrazolo[1,5-a]pyrido[4,3-e]pyrimidin-5(4H)-one (40 g, 19% yield) as a white solid. LCMS (ESI, m/z): 307 [M+H]$^+$.

4-(4-methoxybenzyl)-6,7,8,9-tetrahydropyrazolo[1,5-a]pyrido[4,3-e]pyrimidin-5(4H)-one acetate: A 2-L 3-necked round-bottom flask, was charged with 4-(4-methoxybenzyl)pyrazolo[1,5-a]pyrido[4,3-e]pyrimidin-5(4H)-one (104 g, 0.340 mmol, 1.00 eq.), acetic acid (1.20 L), Pd(OH)$_2$/C (23.8 g). The solution was stirred under 3 atm of $H_2$ at rt for 16 h. The solids were filtered off, and the filtrate was concentrated under reduced pressure to afford 4-(4-methoxybenzyl)-6,7,8,9-tetrahydropyrazolo[1,5-a]pyrido[4,3-e]pyrimidin-5(4H)-one acetate (130 g, crude) as a brown oil. LCMS (ESI, m/z): 311 [M+H]$^+$.

tert-butyl 4-(4-methoxybenzyl)-5-oxo-5,6,7,9-tetrahydropyrazolo[1,5-a]pyrido[4,3-e]pyrimidine-8(4H)-carboxylate: A 2-L round-bottom flask were charged with 4-(4-methoxybenzyl)-6,7,8,9-tetrahydropyrazolo[1,5-a]pyrido[4,3-e]pyrimidin-5(4H)-one acetate (130 g, 0.419 mol, 1.00 eq.), dichloromethane (1.30 L), triethylamine (126 g, 1.24 mol, 2.97 eq.), di-tert-butyl dicarbonate (100 g, 0.458 mol, 1.09 eq.) was added at 0° C. The mixture was stirred for 1 h at rt. The solution was washed with water (1 L), and sat. aq. NaHCO$_3$(0.2 L), dried over anhydrous sodium sulfate and concentrated under reduced pressure. The resulting oil was washed with PE:Et$_2$O (300 mL, 1:1). The solids were collected by filtration to afford tert-butyl 4-(4-methoxybenzyl)-5-oxo-5,6,7,9-tetrahydropyrazolo[1,5-a]pyrido[4,3-e]pyrimidine-8(4H)-carboxylate (116 g, 67% yield) as a brown solid. LCMS (ESI, m/z): 411 [M+H]$^+$.

tert-butyl 3-bromo-4-(4-methoxybenzyl)-5-oxo-5,6,7,9-tetrahydropyrazolo[1,5-a]pyrido[4,3-e]pyrimidine-8(4H)-carboxylate: A 2-L round-bottom flask was charged with tert-butyl 4-(4-methoxybenzyl)-5-oxo-5,6,7,9-tetrahydropyrazolo[1,5-a]pyrido[4,3-e]pyrimidine-8 (4H)-carboxylate (116 g, 283 mmol, 1.00 eq.), N,N-dimethylformamide (1.20 L) and N-bromosuccinimide (50.3 g, 283 mmol, 1 eq.) at 0° C. The solution was stirred for 1 h at rt, and the reaction was quenched with water (6 L) with stirring. The solids were collected by filtration and dried to afford tert-butyl 3-bromo-4-(4-methoxybenzyl)-5-oxo-5,6,7,9-tetrahydropyrazolo[1,5-a]pyrido[4,3-e]pyrimidine-8(4H)-carboxylate (120 g, 87%) of) as a white solid. LCMS: (ESI, m/z): 489 [M+H]$^+$. $^1$H NMR (300 MHz, DMSO-d$_6$) δ 7.96 (s, 1H), 7.15 (d, J=8.7 Hz, 2H), 6.88 (d, J=8.7 Hz, 2H), 5.47 (s, 2H), 4.67 (s, 2H), 3.71 (s, 3H), 3.61 (t, J=5.7 Hz, 2H), 2.47 (s, 2H), 1.44 (s, 9H).

Example 25

Synthesis of Compounds 14, 15, 19-23, 26-28, 30, 31, 33, 34, 36-42, 44-70, 73-91

Compounds 14, 15, 19-23, 26-28, 30, 31, 33, 34, 36-42, 44-70, 73-91 provided in Table A were synthesized using the intermediates and/or protocols of Examples 1-24, using methods and conditions known to those skilled in the art.

TABLE A

| Compound | Cmpd No. | Name | $^1$H NMR | [M + 1]$^+$ |
|---|---|---|---|---|
|  | 14 | 5-benzyl-12-(3,4-dichlorobenzoyl)-7-[(4-methoxyphenyl)methyl]-2,3,7,12-tetrazatricyclo[7.4.0.0^2,6]trideca-1(9),3,5-trien-8-one | (400 MHz, Chloroform-d) δ 7.62-7.35 (m, 3H), 7.35-7.28 (m, 3H), 7.27-7.26 (m, 1H), 7.03-6.87 (m, 4H), 6.87-6.85 (m, 2H), 5.14-4.84 (m, 4H), 3.97-3.72 (m, 7H), 2.74 (s, 2H). | 573.1 |

TABLE A-continued

| Compound | Cmpd No. | Name | ¹H NMR | [M + 1]⁺ |
|---|---|---|---|---|
| | 15 | 12-(3,4-dichlorobenzoyl)-5-(isobutylamino)-7-phenyl-2,3,7,12-tetrazatricyclo[7.4.0.0^2,6]trideca-1(9),3,5-trien-8-one | (400 MHz, Chloroform-d) δ 7.71-7.45 (m, 6H), 7.45-7.38 (m, 2H), 7.38-7.30 (m, 1H), 5.40-4.57 (m, 2H), 4.33-3.40 (m, 2H), 2.90-2.60 (m, 2H), 2.60-2.38 (m, 2H), 1.51-1.40 (m, 1H), 0.65 (d, J = 6.4 Hz, 6H). | 510.05 |
| | 19 | 12-(3,4-dichlorobenzoyl)-N-isobutyl-8-oxo-7-phenyl-2,3,7,12-tetrazatricyclo[7.4.0.0^2,6]trideca-1(9),3,5-triene-5-carboxamide | (400 MHz, DMSO-d6) δ 8.01-7.70 (m, 3H), 7.70-7.50 (m, 2H), 7.50-7.38 (m, 3H), 7.38-7.18 (m, 2H), 5.21-4.40 (m, 2H), 4.20-3.45 (m, 2H), 2.55 (s, 2H), 2.40 (s, 2H), 1.55-1.29 (m, 1H), 0.71 (d, J = 5.6 Hz, 6H). | 538.05 |
| | 20 | N-benzyl-12-(3,4-dichlorobenzoyl)-8-oxo-7-phenyl-2,3,7,12-tetrazatricyclo[7.4.0.0^2,6]trideca-1(9),3,5-triene-5-carboxamide | (400 MHz, DMSO-d6) δ 8.28-8.09 (m, 1H), 8.02 (s, 1H), 7.93-7.74 (m, 2H), 7.66-7.49 (m, 1H), 7.49-7.39 (m, 3H), 7.39-7.24 (m, 5H), 7.24-6.92 (m, 2H), 5.25-4.60 (m, 2H), 4.09-3.73 (m, 3H), 3.63 (s, 1H), 2.58 (s, 2H). | 572.1 |
| | 21 | N-[12-(3,4-dichlorobenzoyl)-7-(4-methoxyphenyl)-8-oxo-2,3,7,12-tetrazatricyclo[7.4.0.0^2,6]trideca-1(9),3,5-trien-5-yl]acetamide | (400 MHz, DMSO-d6) δ 8.35 (s, 1H), 7.79-7.77 (m, 2H), 7.70 (s, 1H), 7.52 (d, J = 15.4 Hz, 1H), 7.15 (s, 2H), 7.02 (d, J = 8.4 Hz, 2H), 4.97 (s, 1H), 4.74 (s, 1H), 3.95 (s, 1H), 3.79 (s, 3H), 3.60 (s, 1H), 2.55 (s, 2H), 1.36 (s, 3H). | 526.2 |
| | 22 | N-[12-(3,4-dichlorobenzoyl)-7-(4-methoxyphenyl)-8-oxo-2,3,7,12-tetrazatricyclo[7.4.0.0^2,6]trideca-1(9),3,5-trien-5-yl]-2-methyl-propanamide | (400 MHz, DMSO-d6) δ 8.19 (s, 1H), 7.79-7.77 (m, 2H), 7.70 (s, 1H), 7.60-7.40 (m, 1H), 7.16 (s, 2H), 6.98 (d, J = 8.8 Hz, 2H), 5.05-4.75 (m, 2H), 3.90 (s, 1H), 3.78 (s, 3H), 3.60 (s, 1H), 2.55 (s, 2H), 1.87 (s, 1H), 0.73 (s, 6H). | 554.25 |

TABLE A-continued

| Compound | Cmpd No. | Name | ¹H NMR | [M + 1]⁺ |
|---|---|---|---|---|
| | 23 | N-[12-(3,4-dichlorobenzoyl)-7-(4-methoxyphenyl)-8-oxo-2,3,7,12-tetrazatricyclo [7.4.0.0 2,6] trideca-1(9),3,5-trien-5-yl]-2-phenyl-acetamide | (400 MHz, DMSO-d6) δ 8.51 (s, 1H), 7.89-7.75 (m, 2H), 7.71 (s, 1H), 7.53 (d, J = 19.2 Hz, 1H), 7.27-7.19 (m, 5H), 7.02 (d, J = 8.9 Hz, 4H), 4.97-4.75 (m, 2H), 3.90 (s, 1H), 3.83 (s, 3H), 3.60 (s, 1H), 2.93 (s, 2H), 2.55 (s, 2H). | 602.25 |
| | 26 | N-[12-(3,4-dichlorobenzoyl)-7-(4-methoxyphenyl)-8-oxo-2,3,7,12-tetrazatricyclo [7.4.0.0 2,6] trideca-1(9),3,5-trien-5-yl] methanesulfonamide | (400 MHz, Chloroform-d) δ 7.78 (s, 1H), 7.61 (s, 1H), 7.57 (s, 1H), 7.55 (s, 1H), 7.34 (d, J = 7.6 Hz, 1H), 7.28 (d, J = 8.8 Hz, 1H), 7.10 (d, J = 8.8 Hz, 2H), 5.11 (br, 2H), 4.79 (s, 1H), 3.88 (s, 4H), 3.74 (br, 1H), 2.74-2.67 (m, 5H). | 562.2 |
| | 27 | 5-benzyl-12-(3,4-dichlorobenzoyl)-7-phenyl-2,3,7,12-tetrazatricyclo [7.4.0.0 2,6] trideca-1(9),3,5-trien-8-one | (300 MHz, DMSO-d6) δ 7.80 (d, J = 8.4 Hz, 2H), 7.61-7.43 (m, 5H), 7.33 (s, 2H), 7.15 (d, J = 7.5 Hz, 3H), 6.75 (s, 2H), 5.11-4.70 (m, 2H), 4.01-3.55 (m, 2H), 2.94 (s, 2H), 2.57 (s, 2H). | 529.25 |
| | 28 | 5-(benzylamino)-12-(4-bromo-3-chloro-benzoyl)-7-(3-methoxyphenyl)-2,3,7,12-tetrazatricyclo [7.4.0.0 2,6] trideca-1(9),3,5-trien-8-one | (300 MHz, Chloroform-d) δ 7.74 (d, J = 8.2 Hz, 1H), 7.62 (s, 1H), 7.44 (t, J = 8.0 Hz, 2H), 7.26 (s, 4H), 7.04 (d, J = 7.8 Hz, 3H), 6.99-6.90 (m, 2H), 5.10 (s, 2H), 3.86 (m, 7H), 2.75 (s, 2H). | 618.20; 620.20 |
| | 30 | N-[12-(4-bromo-3-chloro-benzoyl)-7-(4-methoxyphenyl)-8-oxo-2,3,7,12-tetrazatricyclo [7.4.0.0 2,6] trideca-1(9),3,5-trien-5-yl] benzamide | (400 MHz, DMSO-d6) δ ppm 8.84 (s, 1H), 7.98-7.63 (m, 3H), 7.54-7.25 (m, 6H), 7.16 (s, 2H), 6.77 (d, J = 8.8 Hz, 2H), 4.89 (m, 2H), 3.76 (m, 2H), 3.48 (s, 3H), 2.56 (s, 2H). | 632.00; 634.00 |
| | 31 | N-[12-(4-bromo-3-chloro-benzoyl)-7-(4-methoxyphenyl)-8-oxo-2,3,7,12-tetrazatricyclo [7.4.0.0 2,6] trideca-1(9),3,5-trien-5-yl] benzenesulfonamide | (400 MHz, Chloroform-d) δ ppm 7.73 (d, J = 8.2 Hz, 1H), 7.65-7.44 (m, 7H), 7.23 (s, 1H), 6.99-6.93 (m, 2H), 6.92-6.85 (m, 2H), 5.09 (s, 2H), 4.79 (s, 1H), 3.89-3.71 (m, 5H), 2.69 (s, 2H). | 668.00; 670.00 |

TABLE A-continued

| Compound | Cmpd No. | Name | ¹H NMR | [M + 1]⁺ |
|---|---|---|---|---|
| | 33 | N-[12-(4-bromo-3-chloro-benzoyl)-7-(4-methoxyphenyl)-8-oxo-2,3,7,12-tetrazatricyclo [7.4.0.0 2,6] trideca-1(9),3,5-trien-5-yl]-1-phenyl-methanesulfonamide | (400 MHz, Chloroform-d) δ ppm 7.73 (d, J = 8.2 Hz, 1H), 7.60 (s, 1H), 7.42-7.34 (m, 3H), 7.29 (d, J = 7.0 Hz, 2H), 7.26-7.15 (m, 4H), 7.07-7.01 (m, 2H), 4.95 (m, 2H), 4.60 (s, 1H), 4.08 (s, 2H), 3.91-3.61 (m, 5H), 2.73 (s, 2H). | 682.05; 684.05 |
| | 34 | 4-[5-benzyl-12-(3,4-dichlorobenzoyl)-8-oxo-2,3,7,12-tetrazatricyclo [7.4.0.0 2,6] trideca-1(9),3,5-trien-7-yl]-N-methyl-benzamide | (300 MHz, Chloroform-d) δ ppm 7.81-7.71 (m, 2H), 7.68-7.54 (m, 2H), 7.48 (s, 1H), 7.36 (d, J = 8.3 Hz, 1H), 7.27-7.20 (m, 2H), 7.18-7.11 (m, 3H), 6.70 (s, 2H), 6.22 (d, J = 5.1 Hz, 1H), 5.16 (s, 2H), 3.78 (s, 2H), 3.15-2.98 (m, 5H), 2.75 (s, 2H). | 586.0; 588.0 |
| | 36 | 4-[12-(3,4-dichlorobenzoyl)-8-oxo-5-[[4-(trifluoromethoxy)phenyl]methyl]-2,3,7,12-tetrazatricyclo [7.4.0.0 2,6] trideca-1(9),3,5-trien-7-yl]-N-methyl-benzamide | (300 MHz, Chloroform-d) δ 7.71 (d, J = 8.4 Hz, 2H), 7.62 (s, 1H), 7.56 (d, J = 8.1 Hz, 1H), 7.49 (s, 1H), 7.34 (d, J = 8.1 Hz, 1H), 7.17 (d, J = 8.4 Hz, 2H), 6.96 (d, J = 8.1 Hz, 2H), 6.65 (d, J = 8.4 Hz, 2H), 6.17 (d, J = 4.8 Hz, 1H), 5.29-4.70 (m, 2H), 4.27-3.53 (m, 2H), 3.14 (s, 2H), 3.02 (d, J = 4.8 Hz, 3H), 2.73 (s, 2H). | 670 |
| | 37 | 4-[5-benzyl-12-(4-bromo-3-cyano-benzoyl)-8-oxo-2,3,7,12-tetrazatricyclo [7.4.0.0 2,6] trideca-1(9),3,5-trien-7-yl]-N-methyl-benzamide | (300 MHz, Chloroform-d) δ ppm 7.89-7.71 (m, 4H), 7.66-7.37 (m, 2H), 7.27-7.21 (m, 2H), 7.20-7.10 (m, 3H), 6.70 (s, 2H), 6.17 (d, J = 4.5 Hz, 1H), 5.01 (m, 2H), 3.90 (m, 2H), 3.18-2.97 (m, 5H), 2.76 (s, 2H). | 621.05; 623.05 |
| | 38 | 4-[5-benzyl-12-(4-bromo-3-chloro-benzoyl)-8-oxo-2,3,7,12-tetrazatricyclo [7.4.0.0 2,6] trideca-1(9),3,5-trien-7-yl]-2-chloro-N-methyl-benzamide | (300 MHz, Chloroform-d) δ ppm 7.73 (dd, J = 17.2, 8.1 Hz, 2H), 7.63 (s, 1H), 7.55 (s, 1H), 7.27-7.11 (m, 6H), 6.71 (d, J = 6.7 Hz, 2H), 6.25-6.14 (m, 1H), 5.13 (s, 2H), 3.80 (s, 2H), 3.23 (m, 2H), 3.08 (d, J = 4.8 Hz, 3H), 2.74 (s, 2H). | 664.1 |

TABLE A-continued

| Compound | Cmpd No. | Name | ¹H NMR | [M + 1]⁺ |
|---|---|---|---|---|
| | 39 | 4-[5-anilino-12-(3,4-dichlorobenzoyl)-8-oxo-2,3,7,12-tetrazatricyclo[7.4.0.0 2,6]trideca-1(9),3,5-trien-7-yl]-N-methyl-benzamide | (400 MHz, Chloroform-d) δ 7.83-7.50 (m, 5H), 7.35 (d, J = 8.2 Hz, 1H), 7.16 (d, J = 8.3 Hz, 2H), 6.96 (t, J = 7.7 Hz, 2H), 6.67 (dd, J = 7.9, 6.6 Hz, 1H), 6.09 (d, J = 7.9 Hz, 2H), 6.00 (d, J = 5.1 Hz, 1H), 5.05 (br, 2H), 4.00-3.70 (m, 3H), 3.01 (d, J = 4.8 Hz, 3H), 2.74 (s, 2H). | 587.1 |
| | 40 | 4-[5-anilino-12-(4-bromo-3-chloro-benzoyl)-8-oxo-2,3,7,12-tetrazatricyclo[7.4.0.0 2,6]trideca-1(9),3,5-trien-7-yl]-N-methyl-benzamide | (400 MHz, Chloroform-d) δ 7.83-7.51 (m, 5H), 7.30-7.20 (br, 1H), 7.21-7.11 (m, 2H), 7.02-6.87 (m, 2H), 6.74-6.60 (m, 1H), 6.09 (d, J = 7.9 Hz, 2H), 5.99 (d, J = 5.2 Hz, 1H), 5.04 (m, 2H), 3.82 (m, 2H), 3.01 (d, J = 4.7 Hz, 3H), 2.74 (s, 2H). | 631.10; 633.10 |
| | 41 | 4-[12-(3,4-dichlorobenzoyl)-5-[[4-(difluoromethoxy)phenyl]methylamino]-8-oxo-2,3,7,12-tetrazatricyclo[7.4.0.0 2,6]trideca-1(9),3,5-trien-7-yl]-N-methyl-benzamide | (400 MHz, Chloroform-d) δ 7.92-7.86 (m, 2H), 7.60 (s, 1H), 7.55 (d, J = 8.2 Hz, 1H), 7.49-7.36 (m, 3H), 7.33 (d, J = 8.2 Hz, 1H), 6.98 (q, J = 8.5 Hz, 4H), 6.50 (m, 1H), 6.11 (d, J = 5.2 Hz, 1H), 4.96 (m, 2H), 3.80 (s, 4H), 3.05 (d, J = 4.8 Hz, 3H), 2.72 (s, 2H), 1.74 (s, 1H). | 667.1 |
| | 42 | 4-[5-(benzylamino)-12-(3,4-dichlorobenzoyl)-8-oxo-2,3,7,12-tetrazatricyclo[7.4.0.0 2,6]trideca-1(9),3,5-trien-7-yl]-N-methyl-benzamide | (400 MHz, Chloroform-d) δ 7.92-7.84 (m, 2H), 7.60 (s, 1H), 7.54 (d, J = 8.2 Hz, 1H), 7.51-7.37 (m, 3H), 7.33 (d, J = 8.1 Hz, 1H), 7.24 (d, J = 7.5 Hz, 3H), 6.96 (d, J = 6.9 Hz, 2H), 6.08 (d, J = 5.1 Hz, 1H), 4.95 (m, 2H), 3.83 (s, 4H), 3.04 (d, J = 4.9 Hz, 3H), 2.72 (s, 2H), 1.71 (s, 1H). | 601.15 |
| | 44 | 4-[12-(3,4-dichlorobenzoyl)-8-oxo-5-[[4-(trifluoromethoxy)phenyl]methylamino]-2,3,7,12-tetrazatricyclo[7.4.0.0 2,6]trideca-1(9),3,5-trien-7-yl]-N-methyl-benzamide | (300 MHz, Chloroform-d) δ 7.93 (d, J = 8.3 Hz, 2H), 7.71-7.51 (m, 2H), 7.50-7.30 (m, 4H), 7.12 (d, J = 8.2 Hz, 2H), 7.01 (d, J = 8.4 Hz, 2H), 6.19 (d, J = 4.9 Hz, 1H), 5.30-4.60 (m, 2H), 4.20-3.60 (m, 4H), 3.07 (d, J = 4.6 Hz, 3H), 2.74 (s, 2H), 1.81 (m, 1H). | 685 |

TABLE A-continued

| Compound | Cmpd No. | Name | ¹H NMR | [M + 1]⁺ |
|---|---|---|---|---|
| | 45 | 4-[12-(4-bromo-3-chloro-benzoyl)-8-oxo-5-[[4-(trifluoromethoxy)phenyl]methylamino]-2,3,7,12-tetrazatricyclo[7.4.0.0 2,6]trideca-1(9),3,5-trien-7-yl]-N-methyl-benzamide | (400 MHz, Chloroform-d) δ 7.96-7.85 (m, 2H), 7.72 (d, J = 8.2 Hz, 1H), 7.59 (s, 1H), 7.51-7.36 (m, 3H), 7.23 (d, J = 2.2 Hz, 1H), 7.09 (d, J = 8.0 Hz, 2H), 6.99 (d, J = 8.3 Hz, 2H), 6.17 (d, J = 5.0 Hz, 1H), 5.20-4.60 (m, 2H), 4.20-3.60 (m, 4H), 3.05 (d, J = 4.8 Hz, 3H), 2.72 (s, 2H). | 729.20; 731.20 |
| | 46 | 4-[12-(4-bromo-3-chloro-benzoyl)-5-[[4-(difluoromethoxy)phenyl]methylamino]-8-oxo-2,3,7,12-tetrazatricyclo[7.4.0.0 2,6]trideca-1(9),3,5-trien-7-yl]-N-methyl-benzamide | (400 MHz, Chloroform-d) δ 7.89 (d, J = 8.3 Hz, 2H), 7.72 (d, J = 8.2 Hz, 1H), 7.59 (s, 1H), 7.42 (d, J = 8.3 Hz, 3H), 7.24 C 7.18 (m, 1H), 6.97 (m, 4H), 6.49 (m, 1H), 6.18 (d, J = 5.0 Hz, 1H), 5.20-4.60 (m, 2H), 4.20-3.60 (m, 4H), 3.04 (d, J = 4.8 Hz, 3H), 2.71 (s, 2H) | 711.20; 713.20 |
| | 47 | 4-[5-(benzylamino)-12-(4-bromo-3-chloro-benzoyl)-8-oxo-2,3,7,12-tetrazatricyclo[7.4.0.0 2,6]trideca-1(9),3,5-trien-7-yl]-N-methyl-benzamide | (400 MHz, Chloroform-d) δ 7.93-7.84 (m, 2H), 7.72 (d, J = 8.2 Hz, 1H), 7.60 (s, 1H), 7.51-7.34 (m, 3H), 7.25-7.17 (m, 4H), 6.97 (d, J = 6.8 Hz, 2H), 6.11 (s, 1H), 5.20-4.80 (m, 2H), 4.20-3.60 (s, 4H), 3.04 (d, J = 4.8 Hz, 3H), 2.71 (s, 2H). | 645.20; 647.20 |
| | 48 | 4-[5-[(4-cyanophenyl)methyl]-12-(3,4-dichlorobenzoyl)-8-oxo-2,3,7,12-tetrazatricyclo[7.4.0.0 2,6]trideca-1(9),3,5-trien-7-yl]-N-methyl-benzamide | (400 MHz, Chloroform-d) δ 7.76-7.70 (m, 2H), 7.61 (s, 1H), 7.56 (d, J = 8.2 Hz, 1H), 7.49 (s, 1H), 7.42 (d, J = 8.0 Hz, 2H), 7.34 (d, J = 8.3 Hz, 1H), 7.21-7.13 (m, 2H), 6.76 (d, J = 7.8 Hz, 2H), 6.19 (d, J = 4.9 Hz, 1H), 5.03 (m, 2H), 3.87 (m, 2H), 3.18 (s, 2H), 3.04 (d, J = 4.6 Hz, 3H), 2.73 (s, 2H). | 611.15 |
| | 49 | 4-[5-(benzylamino)-12-(4-bromo-3-chloro-benzoyl)-8-oxo-2,3,7,12-tetrazatricyclo[7.4.0.0 2,6]trideca-1(9),3,5-trien-7-yl]benzamide | (400 MHz, DMSO-d6) δ 8.11 (s, 1H), 8.03 (d, J = 8.1 Hz, 2H), 7.89 (d, J = 8.2 Hz, 1H), 7.82-7.59 (m, 2H), 7.46 (m, 4H), 7.16 (m, 3H), 6.91 (m, 2H), 4.81-5.02 (m, 2H), 3.92-3.53 (m, 4H), 2.55 (m, 3H). | 631.05; 633.05 |

TABLE A-continued

| Compound | Cmpd No. | Name | ¹H NMR | [M + 1]⁺ |
|---|---|---|---|---|
| | 50 | 4-[5-(benzylamino)-12-(3,4-dichlorobenzoyl)-8-oxo-2,3,7,12-tetrazatricyclo [7.4.0.0 2,6] trideca-1(9),3,5-trien-7-yl] benzamide | (400 MHz, DMSO-d6) δ 8.12 (s, 1H), 8.03 (d, J = 8.1 Hz, 2H), 7.85-7.72 (m, 2H), 7.57 (m, 5H), 7.16 (s, 3H), 6.91 (s, 2H), 4.81 (m, 2H), 3.89 (s, 1H), 3.73-3.53 (m, 3H), 2.55 | 587.15 |
| | 51 | 4-[5-[(4-cyanophenyl)methylamino]-12-(3,4-dichlorobenzoyl)-8-oxo-2,3,7,12-tetrazatricyclo [7.4.0.0 2,6] trideca-1(9),3,5-trien-7-yl]-N-methyl-benzamide | (300 MHz, Chloroform-d) δ 7.95 (d, J = 8.2 Hz, 2H), 7.68-7.52 (m, 4H), 7.48 (d, J = 8.2 Hz, 2H), 7.35 (d, J = 7.9 Hz, 2H), 7.12 (d, J = 7.9 Hz, 2H), 6.36 (s, 1H), 5.20-4.70 (m, 2H), 4.20-3.50 (m, 4H), 3.08 (d, J = 4.6 Hz, 3H), 2.74 (s, 2H). | 626.1 |
| | 52 | 4-[5-[[4-(2-amino-2-oxo-ethoxy)phenyl]methylamino]-12-(4-bromo-3-chloro-benzoyl)-8-oxo-2,3,7,12-tetrazatricyclo [7.4.0.0 2,6] trideca-1(9),3,5-trien-7-yl]-N-methyl-benzamide | (300 MHz, Chloroform-d) δ 7.92 (d, J = 8.3 Hz, 2H), 7.74 (d, J = 8.2 Hz, 1H), 7.62 (s, 1H), 7.46 (m, 3H), 7.25 (s, 1H), 6.96 (s, 2H), 6.81 (d, J = 8.5 Hz, 2H), 6.62 (s, 1H), 6.33 (s, 1H), 5.72 (s, 1H), 5.20-4.70 (m, 2H), 4.47 (s, 2H), 4.10-3.70 (m, 4H), 3.08 (d, J = 4.7 Hz, 3H), 2.74 (s, 2H). | 720.1 |
| | 53 | 4-[5-[[4-(2-amino-2-oxo-ethoxy)phenyl]methylamino]-12-(3,4-dichlorobenzoyl)-8-oxo-2,3,7,12-tetrazatricyclo [7.4.0.0 2,6] trideca-1(9),3,5-trien-7-yl]-N-methyl-benzamide | (300 MHz, DMSO-d6) δ 8.60 (d, J = 4.8 Hz, 1H), 8.00 (d, J = 8.2 Hz, 2H), 7.78 (d, J = 8.3 Hz, 2H), 7.71-7.28 (m, 6H), 7.03-6.61 (m, 4H), 4.83 (m, 2H), 4.35 (s, 2H), 3.88 (m, 1H), 3.60 (s, 3H), 2.85 (d, J = 4.4 Hz, 3H), 2.55 (s, 2H). | 674.2 |
| | 54 | 4-[12-(4-bromo-3-chloro-benzoyl)-5-(4-fluoroanilino)-8-oxo-2,3,7,12-tetrazatricyclo [7.4.0.0 2,6] trideca-1(9),3,5-trien-7-yl]-N-methyl-benzamide | (400 MHz, Chloroform-d) δ 7.77-7.58 (m, 5H), 7.30-7.20 (m, 1H), 7.20-7.11 (m, 2H), 6.67 (t, J = 8.7 Hz, 2H), 6.09-5.93 (m, 3H), 5.30-4.70 (m, 2H), 4.15-3.58 (m, 3H), 3.02 (d, J = 4.8 Hz, 3H), 2.74 (s, 2H). | 651.05 |

TABLE A-continued

| Compound | Cmpd No. | Name | ¹H NMR | [M + 1]⁺ |
|---|---|---|---|---|
| | 55 | 4-[12-(4-bromo-3-chloro-benzoyl)-5-[(4-cyanophenyl)methylamino]-8-oxo-2,3,7,12-tetrazatricyclo[7.4.0.0 2,6]trideca-1(9),3,5-trien-7-yl]-N-methyl-benzamide | (400 MHz, Chloroform-d) δ 7.97-7.87 (m, 2H), 7.72 (d, J = 8.2 Hz, 1H), 7.64-7.50 (m, 3H), 7.49-7.42 (m, 2H), 7.34 (s, 1H), 7.25-7.21 (m, 1H), 7.09 (d, J = 8.0 Hz, 2H), 6.20 (d, J = 5.1 Hz, 1H), 5.20-4.80 (m, 2H), 4.10-3.60 (m, 4H), 3.06 (d, J = 4.8 Hz, 3H), 2.72 (s, 2H), 1.90 (s, 1H). | 672.1 |
| | 56 | 4-[5-benzyl-12-(5-bromopyridine-2-carbonyl)-8-oxo-2,3,7,12-tetrazatricyclo[7.4.0.0 2,6]trideca-1(9),3,5-trien-7-yl]-N-methyl-benzamide | (400 MHz, Chloroform-d) δ 8.70 (m, 1H), 7.98 (dd, J = 8.3, 2.2 Hz, 1H), 7.78-7.66 (m, 3H), 7.49 (s, 1H), 7.21 (t, J = 8.2 Hz, 2H), 7.17-7.08 (m, 3H), 6.67 (m, 2H), 6.17 (d, J = 5.1 Hz, 1H), 5.20 (d, J = 2.4 Hz, 2H), 4.09 (t, J = 5.7 Hz, 1H), 3.93 (t, J = 5.6 Hz, 1H), 3.10-3.00 (m, 5H), 2.80 (s, 2H). | 599.00 (Br pattern) |
| | 57 | 4-[12-(4-bromo-3-cyano-benzoyl)-8-oxo-5-[rac-(1R)-1-phenylethyl]-2,3,7,12-tetrazatricyclo[7.4.0.0 2,6]trideca-1(9),3,5-trien-7-yl]-N-methyl-benzamide | (300 MHz, Chloroform-d) δ 7.98-7.92 (m, 1H), 7.88-7.69 (m, 3H), 7.60 (s, 1H), 7.49-7.35 (m, 2H), 7.20-7.01 (m, 3H), 6.80-6.74 (m, 1H), 6.58 (s, 2H), 6.27 (s, 1H), 5.30-4.70 (m, 2H), 4.25-3.50 (m, 2H), 3.05 (m, 4H), 2.72 (s, 2H), 1.49-1.17 (m, 3H). | 637.05 (Br pattern) |
| | 58 | 4-[12-(4-bromo-3-cyano-benzoyl)-8-oxo-5-[rac-(1S)-1-phenylethyl]-2,3,7,12-tetrazatricyclo[7.4.0.0 2,6]trideca-1(9),3,5-trien-7-yl]-N-methyl-benzamide | (300 MHz, Chloroform-d) δ 7.98-7.92 (m, 1H), 7.89-7.51 (m, 4H), 7.49-7.35 (m, 2H), 7.20-7.01 (m, 3H), 6.80-6.74 (m, 1H), 6.58 (s, 2H), 6.27 (s, 1H), 5.30-4.70 (m, 2H), 4.25-3.50 (m, 2H), 3.05 (m, 4H), 2.72 (s, 2H), 1.49-1.17 (m, 3H). | 635.05 (Br pattern) |

TABLE A-continued

| Compound | Cmpd No. | Name | ¹H NMR | [M + 1]⁺ |
|---|---|---|---|---|
| | 59 | 4-[12-(4-bromo-3-chloro-benzoyl)-5-[(4-fluorophenyl)methyl]-8-oxo-2,3,7,12-tetrazatricyclo[7.4.0.0 2,6]trideca-1(9),3,5-trien-7-yl]-N-methyl-benzamide | (300 MHz, Chloroform-d) δ 7.84-7.70 (m, 3H), 7.63 (s, 1H), 7.47 (s, 1H), 7.27-7.19 (m, 3H), 6.85 (t, J = 8.6 Hz, 2H), 6.64 (t, J = 6.9 Hz, 2H), 6.20 (d, J = 5.0 Hz, 1H), 5.15 (m, 2H), 3.77 (m, 2H), 3.06 (m, 5H), 2.75 (s, 2H). | 650.00 (Br pattern) |
| | 60 | 4-[12-(4-bromo-3-cyano-benzoyl)-5-[(4-fluorophenyl)methyl]-8-oxo-2,3,7,12-tetrazatricyclo[7.4.0.0 2,6]trideca-1(9),3,5-trien-7-yl]-N-methyl-benzamide | (300 MHz, Chloroform-d) δ 7.88-7.73 (m, 4H), 7.61 (d, J = 8.5 Hz, 1H), 7.47 (s, 1H), 7.27-7.18 (m, 2H), 6.84 (t, J = 8.6 Hz, 2H), 6.64 (t, J = 6.9 Hz, 2H), 6.25 (d, J = 5.1 Hz, 1H), 5.04 (m, 2H), 3.89 (m, 2H), 3.16-2.93 (m, 5H), 2.76 (s, 2H). | 641.05 (Br pattern) |
| | 61 | 4-[5-benzyl-12-(4-bromo-3-chloro-benzoyl)-8-oxo-2,3,7,12-tetrazatricyclo[7.4.0.0 2,6]trideca-1(9),3,5-trien-7-yl]-N-ethyl-benzamide | (300 MHz, DMSO-d6) δ 8.56 (t, J = 5.5 Hz, 1H), 8.33 (m, 1H), 7.89-7.86 (m, 3H), 7.75 (s, 1H), 7.45-7.17 (m, 8H), 4.56 (m, 2H), 3.93 (m, 3H), 3.55 (s, 1H), 3.34-3.25 (m, 2H), 2.57 (s, 2H), 1.13 (t, J = 7.2 Hz, 3H). | 646.00 (Br, Cl pattern) |
| | 62 | 4-[5-benzyl-12-(4-bromo-3-cyano-benzoyl)-8-oxo-2,3,7,12-tetrazatricyclo[7.4.0.0 2,6]trideca-1(9),3,5-trien-7-yl]-N-ethyl-benzamide | (300 MHz, DMSO-d6) δ 8.56 (t, J = 5.7 Hz, 1H), 8.36 (m, 1H), 8.09 (s, 1H), 8.01 (d, J = 8.4 Hz, 1H), 7.89-7.86 (m, 2H), 7.74 (d, J = 6.6 Hz, 2H), 7.47-7.16 (m, 7H), 4.79-4.32 (m, 2H), 3.93 (m, 3H), 3.54 (s, 1H), 3.31-3.21 (m, 3H), 2.59 (s, 2H), 1.13 (t, J = 7.2 Hz, 3H). | 637.05 (Br pattern) |

TABLE A-continued

| Compound | Cmpd No. | Name | ¹H NMR | [M + 1]⁺ |
|---|---|---|---|---|
| | 63 | 4-[12-(4-bromo-3-cyano-benzoyl)-5-(4-fluoroanilino)-8-oxo-2,3,7,12-tetrazatricyclo[7.4.0.0 2,6]trideca-1(9),3,5-trien-7-yl]-N-methyl-benzamide | (300 MHz, Chloroform-d) δ 7.85 (d, J = 8.4 Hz, 2H), 7.77-7.57 (m, 4H), 7.18 (d, J = 8.4 Hz, 2H), 6.70 (t, J = 8.6 Hz, 2H), 6.05 (m, 3H), 5.20-4.70 (m, 2H), 4.20-3.50 (m, 3H), 3.05 (d, J = 4.8 Hz, 3H), 2.77 (s, 2H). | 642.10 (Br pattern) |
| | 64 | 4-[5-benzyl-12-(4-bromo-3-chloro-benzoyl)-8-oxo-2,3,7,12-tetrazatricyclo[7.4.0.0 2,6]trideca-1(9),3,5-trien-7-yl]-N-isopropyl-benzamide | (400 MHz, DMSO-d6) δ 8.48-8.18 (m, 2H), 7.98-7.73 (m, 4H), 7.41-7.38 (m, 3H), 7.35-7.15 (m, 4H), 4.82-4.40 (m, 2H), 4.18-3.70 (m, 4H), 3.55 (s, 1H), 2.58 (s, 2H), 1.17 (d, J = 6.4 Hz, 6H). | 660.15 (Br pattern) |
| | 65 | 4-[5-benzyl-12-(4-bromo-3-cyano-benzoyl)-8-oxo-2,3,7,12-tetrazatricyclo[7.4.0.0 2,6]trideca-1(9),3,5-trien-7-yl]-N-isopropyl-benzamide | (400 MHz, DMSO-d6) δ 8.42-8.28 (m, 2H), 8.20-8.05 (m, 1H), 8.05-7.95 (m, 1H), 7.92-7.88 (m, 2H), 7.82-7.68 (m, 1H), 7.46-7.20 (m, 6H), 4.68 (s, 1H), 4.44 (s, 1H), 4.20-4.01 (m, 1H), 4.01-3.79 (m, 3H), 3.54 (s, 1H), 2.58 (m, 2H), 1.17 (d, J = 6.4 Hz, 6H). | 651.10 (Br pattern) |
| | 66 | 4-[12-(4-bromo-3-chloro-benzoyl)-5-[(2-fluorophenyl)methylamino]-8-oxo-2,3,7,12-tetrazatricyclo[7.4.0.0 2,6]trideca-1(9),3,5-trien-7-yl]-N-methyl-benzamide | (300 MHz, DMSO-d6) δ 8.58 (d, J = 4.7 Hz, 1H), 8.05-7.87 (m, 3H), 7.85-7.75 (m, 1H), 7.71-7.36 (m, 4H), 7.30-7.15 (m, 1H), 7.12-6.79 (m, 3H), 5.00-4.60 (m, 2H), 3.95-3.50 (m, 4H), 2.84 (d, J = 4.4 Hz, 3H), 2.70-2.51 (m, 2H). | 663.1 |
| | 67 | 4-[12-(4-bromo-3-chloro-benzoyl)-5-[(4-fluorophenyl)methylamino]-8-oxo-2,3,7,12-tetrazatricyclo[7.4.0.0 2,6]trideca-1(9),3,5-trien-7-yl]-N-methyl-benzamide | (300 MHz, DMSO-d6) δ 8.59 (d, J = 4.7 Hz, 1H), 8.05-7.87 (m, 3H), 7.85-7.75 (m, 1H), 7.71-7.36 (m, 4H), 7.05-6.80 (m, 4H), 5.10-4.60 (m, 2H), 4.00-3.50 (m, 4H), 2.84 (d, J = 4.4 Hz, 3H), 2.70-2.51 (m, 2H). | 663.1 |

TABLE A-continued

| Compound | Cmpd No. | Name | ¹H NMR | [M + 1]⁺ |
|---|---|---|---|---|
| | 68 | 4-[5-benzyl-12-(4-bromo-3-chloro-benzoyl)-8-oxo-2,3,7,12-tetrazatricyclo [7.4.0.0 2,6] trideca-1(9),3,5-trien-7-yl]-N-cyclopropyl-benzamide | (400 MHz, CDCl3) δ 7.84-7.78 (m, 2H), 7.78-7.71 (m, 1H), 7.68-7.52 (m, 1H), 7.48-7.31 (m, 4H), 7.28-7.20 (m, 4H), 6.28 (s, 1H), 4.88 (s, 1H), 4.58 (s, 1H), 4.10-3.82 (m, 3H), 3.62 (s, 1H), 2.94-2.82 (m, 1H), 2.82-2.65 (m, 2H), 1.01-0.80 (m, 2H), 0.65-0.43 (m, 2H). | 658.10 (Br, Cl pattern) |
| | 69 | 4-[12-(4-bromo-3-cyano-benzoyl)-5-[(2-fluorophenyl)methylamino]-8-oxo-2,3,7,12-tetrazatricyclo [7.4.0.0 2,6] trideca-1(9),3,5-trien-7-yl]-N-methyl-benzamide | (300 MHz, DMSO-d6) δ 8.59 (d, J = 4.8 Hz, 1H), 8.23-8.07 (m, 1H), 8.07-7.94 (m, 3H), 7.89-7.70 (m, 1H), 7.71-7.43 (m, 3H), 7.29-7.16 (m, 1H), 7.12-6.80 (m, 3H), 5.04-4.61 (m, 2H), 4.02-3.50 (m, 4H), 2.84 (d, J = 4.4 Hz, 3H), 2.67-2.54 (m, 2H). | 656.15 (Br pattern) |
| | 70 | 4-[12-(4-bromo-3-cyano-benzoyl)-5-[(4-fluorophenyl)methylamino]-8-oxo-2,3,7,12-tetrazatricyclo [7.4.0.0 2,6] trideca-1(9),3,5-trien-7-yl]-N-methyl-benzamide | (300 MHz, Chloroform-d) δ 7.97 C 7.87 (m, 2H), 7.83 (d, J = 8.4 Hz, 2H), 7.65 C 7.54 (m, 1H), 7.50 C 7.34 (m, 3H), 6.95 (d, J = 7.1 Hz, 4H), 6.30 C 6.12 (m, 1H), 5.32 C 4.60 (m, 2H), 4.23 C 3.55 (m, 4H), 3.07 (d, J = 4.7 Hz, 3H), 2.75 (s, 2H). | 656.15 (Br pattern) |
| | 73 | 5-[5-benzyl-7-[4-(1H-imidazol-2-yl)phenyl]-8-oxo-2,3,7,12-tetrazatricyclo [7.4.0.0 2,6] trideca-1(9),3,5-triene-12-carbonyl]-2-bromo-benzonitrile | (400 MHz, CDCl3) δ 7.99-7.65 (m, 4H), 7.65-7.51 (m, 1H), 7.41-7.28 (m, 6H), 7.22-7.15 (m, 2H), 7.15-6.91 (m, 2H), 5.05-4.45 (m, 2H), 4.18-3.78 (m, 3H), 3.78-3.42 (m, 1H), 2.85-2.69 (m, 2H). | 632.05 |
| | 74 | 4-[12-(4-bromo-3-chloro-benzoyl)-8-oxo-5-[[rac-(1S)-1-phenylethyl]amino]-2,3,7,12-tetrazatricyclo [7.4.0.0 2,6] trideca-1(9),3,5-trien-7-yl]-N-methyl-benzamide | (300 MHz, Chloroform-d) δ 7.97 (d, J = 7.9 Hz, 2H), 7.72 (d, J = 8.2 Hz, 1H), 7.60 (d, J = 1.9 Hz, 1H), 7.50 (d, J = 7.9 Hz, 2H), 7.31-7.28 (m, 1H), 7.27-7.18 (m, 4H), 7.04 (d, J = 7.0 Hz, 2H), 6.16 (s, 1H), 5.16-4.71 (m, 2H), 4.08-3.59 (m, 3H), 3.13-2.97 (m, 3H), 2.72 (s, 2H), 1.05 (d, J = 6.4 Hz, 3H). | 661.1 |

TABLE A-continued

| Compound | Cmpd No. | Name | ¹H NMR | [M + 1]⁺ |
|---|---|---|---|---|
| | 75 | 4-[5-benzyl-12-(4-bromo-3-chloro-benzoyl)-8-oxo-2,3,7,12-tetrazatricyclo[7.4.0.0 2,6]trideca-1(9),3,5-trien-7-yl]benzamide | (400 MHz, DMSO-d6) δ 8.42-8.19 (m, 1H), 8.00-7.83 (m, 3H), 7.78-7.69 (m, 1H), 7.45-7.19 (m, 8H), 4.75-4.35 (m, 2H), 4.09-3.75 (m, 3H), 3.55 (s, 1H), 2.65-2.55 (m, 2H). | 618.10 (Br, Cl pattern) |
| | 76 | 4-[5-benzyl-12-(4-bromo-3-cyano-benzoyl)-8-oxo-2,3,7,12-tetrazatricyclo[7.4.0.0 2,6]trideca-1(9),3,5-trien-7-yl]-N-cyclopropyl-benzamide | (400 MHz, CDCl3) δ 7.95-7.75 (m, 4H), 7.75-7.50 (m, 1H), 7.48-7.28 (m, 5H), 7.25-7.15 (m, 2H), 6.42 (s, 1H), 5.01-3.38 (m, 2H), 4.15-3.85 (m, 3H), 3.62 (s, 1H), 2.95-2.81 (m, 2H), 2.85-2.55 (m, 1H). | 649.15 (Br pattern) |
| | 77 | 5-benzyl-12-(4-bromo-3-chloro-benzoyl)-7-(4-pyrazol-1-ylphenyl)-2,3,7,12-tetrazatricyclo[7.4.0.0 2,6]trideca-1(9),3,5-trien-8-one | (400 MHz, CDCl3) δ 7.98-7.90 (m, 1H), 7.75-7.67 (m, 4H), 7.67-7.51 (m, 1H), 7.42-7.28 (m, 7H), 7.28-7.19 (m, 2H), 6.48 (s, 1H), 4.98-4.50 (m, 2H), 4.10-3.85 (m, 3H), 3.62 (s, 1H), 2.85-2.55 (m, 2H). | 641.00 (Br, Cl pattern) |
| | 78 | 5-[5-benzyl-8-oxo-7-(4-pyrazol-1-ylphenyl)-2,3,7,12-tetrazatricyclo[7.4.0.0 2,6]trideca-1(9),3,5-triene-12-carbonyl]-2-bromo-benzonitrile | (400 MHz, CDCl3) δ 8.14-7.90 (m, 1H), 7.88-7.78 (m, 5H), 7.69-7.48 (m, 1H), 7.48-7.28 (m, 5H), 7.28 C 7.20 (m, 1H), 6.48 (s, 1H), 4.98-4.42 (m, 2H), 4.10-3.90 (m, 3H), 3.62 (s, 1H), 2.76 (m, 2H) | 630.00 (Br pattern) |

TABLE A-continued

| Compound | Cmpd No. | Name | ¹H NMR | [M + 1]⁺ |
|---|---|---|---|---|
| | 79 | 4-[12-(4-bromo-3-chloro-benzoyl)-8-oxo-5-[[rac-(1R)-1-phenylethyl]amino]-2,3,7,12-tetrazatricyclo [7.4.0.0 2,6] trideca-1(9),3,5-trien-7-yl]-N-methyl-benzamide | (300 MHz, Chloroform-d) δ 7.96 (d, J = 8.0 Hz, 2H), 7.72 (d, J = 8.2 Hz, 1H), 7.60 (d, J = 1.9 Hz, 1H), 7.49 (d, J = 8.0 Hz, 2H), 7.30-7.28 (m, 1H), 7.27-7.16 (m, 4H), 7.03 (d, J = 7.2 Hz, 2H), 6.19 (d, J = 4.9 Hz, 1H), 5.17-4.59 (m, 2H), 4.00-3.42 (m, 3H), 3.07 (dd, J = 4.9, 0.9 Hz, 3H), 2.72 (s, 2H), 1.04 (d, J = 6.6 Hz, 3H). | 661.10 (Br, Cl pattern( |
| | 80 | N-methyl-4-[rac-(11S)-5-benzyl-12-(4-bromo-3-cyano-benzoyl)-11-methyl-8-oxo-2,3,7,12-tetrazatricyclo [7.4.0.0 2,6] trideca-1(9),3,5-trien-7-yl] benzamide | (300 MHz, Chloroform-d) δ 7.91-7.69 (m, 4H), 7.63-7.42 (m, 2H), 7.35-7.30 (m, 1H), 7.27-7.09 (m, 4H), 6.72 (t, J = 3.6 Hz, 2H), 6.19 (s, 1H), 6.01-5.18 (br, 1H), 5.01-3.84 (m, 2H), 3.18-3.01 (m, 5H), 2.91-2.61 (m, 2H), 1.46-1.33 (m, 3H). | 637.10 (Br pattern) |
| | 81 | N-methyl-4-[rac-(11R)-5-benzyl-12-(4-bromo-3-cyano-benzoyl)-11-methyl-8-oxo-2,3,7,12-tetrazatricyclo [7.4.0.0 2,6] trideca-1(9),3,5-trien-7-yl] benzamide | (300 MHz, Chloroform-d) δ 7.91-7.69 (m, 4H), 7.63-7.42 (m, 2H), 7.35-7.30 (m, 1H), 7.27-7.09 (m, 4H), 6.72 (t, J = 3.6 Hz, 2H), 6.19 (s, 1H), 6.01-5.18 (br, 1H), 5.01-3.84 (m, 2H), 3.18-3.01 (m, 5H), 2.91-2.61 (m, 2H), 1.46-1.33 (m, 3H). | 637.10 (Br pattern) |
| | 82 | 4-[5-benzyl-12-(4-bromo-3-cyano-benzoyl)-8-oxo-2,3,7,12-tetrazatricyclo [7.4.0.0 2,6] trideca-1(9),3,5-trien-7-yl] benzamide | (400 MHz, CDCl3) δ 7.95-7.72 (m, 4H), 7.65-7.48 (m, 1H), 7.39-7.25 (m, 8H), 6.28-5.45 (m, 2H), 4.98-4.40 (m, 2H), 4.08-3.75 (m, 3H), 3.72-3.38 (m, 1H), 2.95-2.55 (m, 2H). | 609.05 (Br pattern) |
| | 83 | 4-[12-(4-bromo-3-cyano-benzoyl)-8-oxo-5-(1-phenylethylamino)-2,3,7,12-tetrazatricyclo [7.4.0.0 2,6] trideca-1(9),3,5-trien-7-yl]-N-methyl-benzamide | (400 MHz, Chloroform-d) δ 7.95 (d, J = 8.1 Hz, 2H), 7.86-7.73 (m, 2H), 7.61-7.42 (m, 3H), 7.26-7.12 (m, 5H), 7.02 (d, J = 7.3 Hz, 2H), 6.12 (d, J = 5.2 Hz, 1H), 5.14-4.65 (m, 2H), 4.06-3.57 (m, 3H), 3.06 (d, J = 4.9 Hz, 3H), 2.72 (s, 2H), 1.01 (d, J = 6.6 Hz, 3H). | 652.15 (Br pattern) |

TABLE A-continued

| Compound | Cmpd No. | Name | ¹H NMR | [M + 1]⁺ |
|---|---|---|---|---|
| | 84 | 4-[12-(4-bromo-3-cyano-benzoyl)-5-[(4-cyano-2-fluoro-phenyl)methyl]-8-oxo-2,3,7,12-tetrazatricyclo [7.4.0.0 2,6] trideca-1(9),3,5-trien-7-yl]-N-methyl-benzamide | (300 MHz, Chloroform-d) δ 8.03-7.72 (m, 4H), 7.72-7.55 (m, 1H), 7.55-7.35 (m, 1H), 7.34-7.29 (m, 1H), 7.29-7.26 (m, 1H), 7.22-7.10 (m, 1H), 6.88 (t, J = 7.4 Hz, 1H), 6.45-6.15 (m, 1H), 5.35-4.62 (m, 2H), 4.20-3.55 (m, 2H), 3.30-2.99 (m, 5H), 2.99-2.62 (m, 2H). | 664.05 (Br pattern) |
| | 85 | 4-[12-(4-bromo-3-chloro-benzoyl)-5-[(4-cyano-2-fluoro-phenyl)methyl]-8-oxo-2,3,7,12-tetrazatricyclo [7.4.0.0 2,6] trideca-1(9),3,5-trien-7-yl]-N-methyl-benzamide | (300 MHz, Chloroform-d) δ 7.90-7.70 (m, 3H), 7.62 (s, 1H), 7.55-7.38 (m, 1H), 7.32-7.29 (m, 2H), 7.25-7.22 (m, 1H), 7.22-7.19 (m, 1H), 6.88 (t, J = 7.8 Hz, 1H), 6.35-6.10 (m, 1H), 5.39-4.79 (m, 2H), 4.22-3.70 (m, 2H), 3.30-2.91 (m, 5H), 2.91-2.50 (m, 2H). | 675 |
| | 86 | 4-[12-(4-bromo-3-cyano-benzoyl)-5-[(2-fluoro-4-methoxy-phenyl)methyl]-8-oxo-2,3,7,12-tetrazatricyclo [7.4.0.0 2,6] trideca-1(9),3,5-trien-7-yl]-N-methyl-benzamide | (400 MHz, DMSO-d6) δ 8.56 (d, J = 4.5 Hz, 1H), 8.25-7.99 (m, 2H), 7.98-7.70 (m, 3H), 7.55-7.30 (m, 3H), 6.80-6.40 (m, 3H), 5.03-4.60 (m, 2H), 4.10-3.48 (m, 5H), 3.00-2.71 (m, 5H), 2.60-2.58 (m, 2H). | 671.10 (Br pattern) |
| | 87 | 4-[12-(4-bromo-3-chloro-benzoyl)-5-[(2-fluoro-4-methoxy-phenyl)methyl]-8-oxo-2,3,7,12-tetrazatricyclo [7.4.0.0 2,6] trideca-1(9),3,5-trien-7-yl]-N-methyl-benzamide | (300 MHz, Chloroform-d) δ 7.83 (d, J = 8.4 Hz, 2H), 7.75 (d, J = 8.4 Hz, 1H), 7.63 (s, 1H), 7.41 (s, 1H), 7.31-7.30 (m, 1H), 7.30-7.27 (m, 1H), 6.65 (t, J = 8.4 Hz, 1H), 6.59-6.40 (m, 2H), 6.31-6.08 (m, 1H), 5.35-4.60 (m, 2H), 4.25-3.57 (m, 5H), 3.05 (d, J = 4.5 Hz, 3H), 2.95 (s, 2H), 2.85-2.67 (m, 2H). | 680.05 |

TABLE A-continued

| Compound | Cmpd No. | Name | ¹H NMR | [M + 1]⁺ |
|---|---|---|---|---|
| | 88 | 4-[12-(4-bromo-3-chloro-benzoyl)-5-[(4-methoxyphenyl)methyl]-8-oxo-2,3,7,12-tetrazatricyclo[7.4.0.0 2,6]trideca-1(9),3,5-trien-7-yl]-N-methyl-benzamide | (300 MHz, CDCL3) δ 7.79-7.72 (m, 3H), 7.62 (s, 1H), 7.45 (s, 1H), 7.27-7.23 (m, 3H), 6.69 (d, J = 8.4 Hz, 2H), 6.59 (d, J =8 .7 Hz, 2H), 6.18 (d, J = 4.5 Hz, 1H),5.30-4.80 (m, 2H), 3.77-3.73 (m, 1H), 3.73 (s, 3H), 3.05-3.01 (m, 2H), 3.00 (s, 3H), 2.73-2.60 (m, 2H), 1.60-1.56 (m, 1H). | 662.05 |
| | 89 | 4-[12-(4-bromo-3-cyano-benzoyl)-5-[(4-methoxyphenyl)methyl]-8-oxo-2,3,7,12-tetrazatricyclo[7.4.0.0 2,6]trideca-1(9),3,5-trien-7-yl]-N-methyl-benzamide | (400 MHz, DMSO-d6) δ 8.57 (d, J = 4.4 Hz, 1H), 8.18-8.13 (m, 1H), 8.12-8.02 (m, 1H), 7.90-7.75 (m, 3H), 7.58-7.42 (m, 3H), 6.69 C 6.67 (m, 4H), 5.00-4.76 (m, 2H), 3.93-3.80 (m, 1H), 3.68 (s, 3H), 3.68-3.61 (m, 1H), 3.32 (s, 3H), 2.89-2.81 (m, 2H), 2.67-2.50 (m, 2H). | 653.05 |
| | 90 | 5-benzyl-12-(4-bromo-3-chloro-benzoyl)-7-[4-(1H-imidazol-2-yl)phenyl]-2,3,7,12-tetrazatricyclo[7.4.0.0 2,6]trideca-1(9),3,5-trien-8-one | (400 MHz, CDCl3) δ 7.89-7.70 (m, 3H), 7.70-7.51 (m, 1H), 7.45-7.28 (m, 5H), 7.28-7.20 (m, 2H), 7.20-7.12 (m, 2H), 7.12-6.99 (m, 2H), 5.10-4.75 (m, 1H), 4.75-4.35 (m, 1H), 4.19-3.81 (m, 3H), 3.75-3.50 (m, 1H), 2.90-2.45 (m, 2H). | 641.1 |
| | 91 | 3-[5-benzyl-12-(4-bromo-3-chloro-benzoyl)-8-oxo-2,3,7,12-tetrazatricyclo[7.4.0.0 2,6]trideca-1(9),3,5-trien-7-yl]-N-methyl-benzamide | (300 MHz, Chloroform-d) δ 7.89 (d, J = 7.8 Hz, 1H), 7.76 (d, J = 8.1 Hz, 1H), 7.64 (s, 1H), 7.60-7.47 (m, 2H), 7.45-7.39 (m, 1H), 7.37-7.30 (m, 1H), 7.28-7.11 (m, 4H), 6.71 (m, 2H), 5.62 (br s, 1H), 5.35-4.76 (m, 2H), 4.18-3.60 (m, 2H), 3.21 (d, J = 16.8 Hz, 1H), 3.09-2.98 (m, 1H), 2.88 (s, 3H), 2.74 br (s, 2H). | 632.00 (Br pattern) |

Example 26

Synthesis of Compounds 92-112

Compounds 92-112 provided in Table B can be obtained using the intermediates and/or protocols of Examples 1-24, using methods and conditions known to those skilled in the art.

TABLE B

| Structure | Cmpd # | Name |
|---|---|---|
| 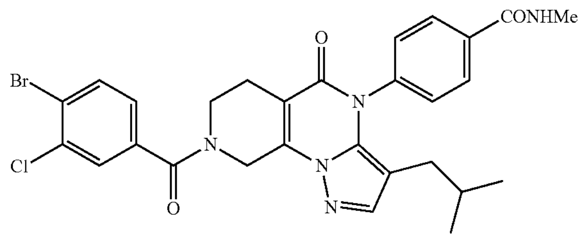 | 92 | 4-(8-(4-bromo-3-chlorobenzoyl)-3-isobutyl-5-oxo-6,7,8,9-tetrahydropyrazolo[1,5-a]pyrido[4,3-e]pyrimidin-4(5H)-yl)-N-methylbenzamide |
| 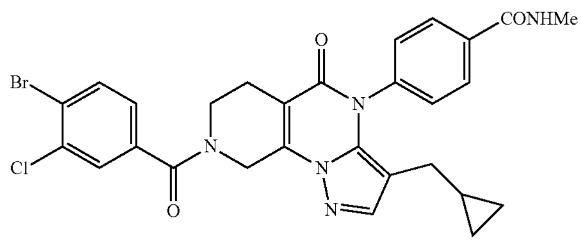 | 93 | 4-(8-(4-bromo-3-chlorobenzoyl)-3-(cyclopropylmethyl)-5-oxo-6,7,8,9-tetrahydropyrazolo[1,5-a]pyrido[4,3-e]pyrimidin-4(5H)-yl)-N-methylbenzamide |
| 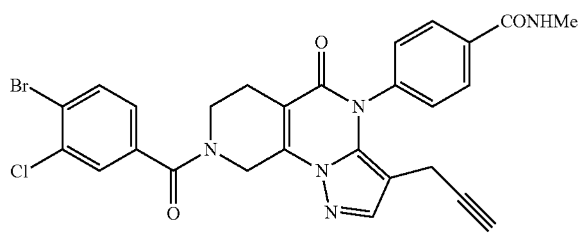 | 94 | 4-(8-(4-bromo-3-chlorobenzoyl)-5-oxo-3-(prop-2-yn-1-yl)-6,7,8,9-tetrahydropyrazolo[1,5-a]pyrido[4,3-e]pyrimidin-4(5H)-yl)-N-methylbenzamide |
| 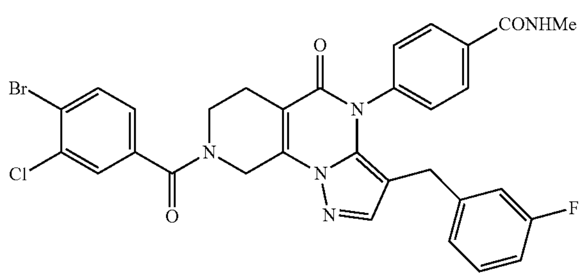 | 95 | 4-(8-(4-bromo-3-chlorobenzoyl)-3-(3-fluorobenzyl)-5-oxo-6,7,8,9-tetrahydropyrazolo[1,5-a]pyrido[4,3-e]pyrimidin-4(5H)-yl)-N-methylbenzamide |
| 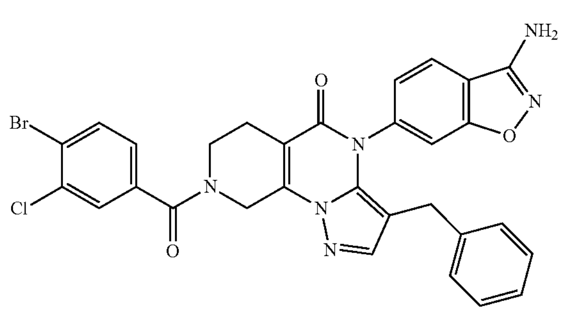 [SMILES: Nc1noc2cc(-n3c(=O)c4c(n5ncc(Cc6ccccc6)c35)CN(C(=O)c3ccc(Br)c(Cl)c3)CC4)ccc12] | 96 | 4-(3-aminobenzo[d]isoxazol-6-yl)-3-benzyl-8-(4-bromo-3-chlorobenzoyl)-6,7,8,9-tetrahydropyrazolo[1,5-a]pyrido[4,3-e]pyrimidin-5(4H)-one |

TABLE B-continued

| Structure | Cmpd # | Name |
|---|---|---|
| 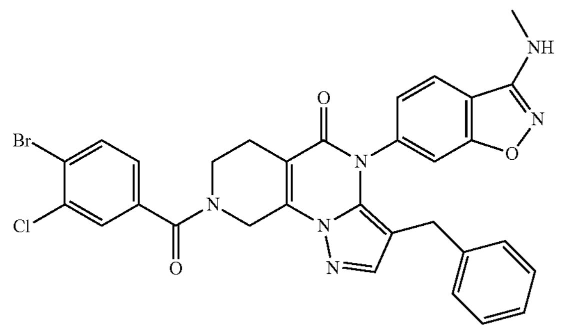 [SMILES: CNc1noc2cc(-n3c(=O)c4c(n5ncc(Cc6ccccc6)c35)CN(C(=O)c3ccc(Br)c(Cl)c3)CC4)ccc12] | 97 | 3-benzyl-8-(4-bromo-3-chlorobenzoyl)-4-(3-(methylamino)benzo[d]isoxazol-6-yl)-6,7,8,9-tetrahydropyrazolo[1,5-a]pyrido[4,3-e]pyrimidin-5(4H)-one |
| 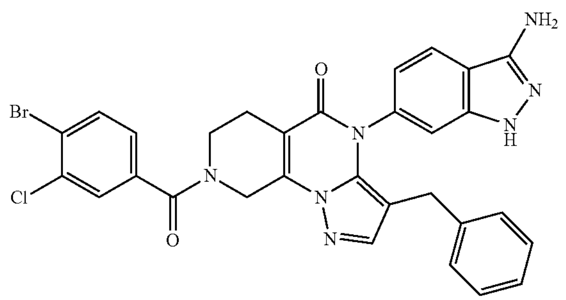 [SMILES: Nc1n[nH]c2cc(-n3c(=O)c4c(n5ncc(Cc6ccccc6)c35)CN(C(=O)c3ccc(Br)c(Cl)c3)CC4)ccc12] | 98 | 4-(3-amino-1H-indazol-6-yl)-3-chlorobenzoyl)-6,7,8,9-tetrahydropyrazolo[1,5-a]pyrido[4,3-e]pyrimidin-5(4H)-one |
| 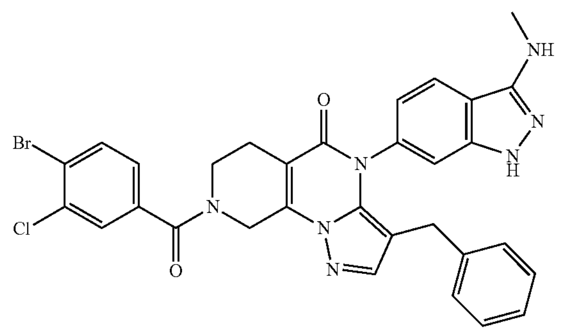 [SMILES: CNc1n[nH]c2cc(-n3c(=O)c4c(n5ncc(Cc6ccccc6)c35)CN(C(=O)c3ccc(Br)c(Cl)c3)CC4)ccc12] | 99 | 3-benzyl-8-(4-bromo-3-chlorobenzoyl)-4-(3-(methylamino)-1H-indazol-6-yl)-6,7,8,9-tetrahydropyrazolo[1,5-a]pyrido[4,3-e]pyrimidin-5(4H)-one |
| 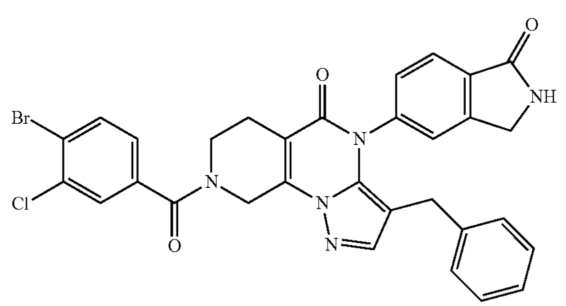 [SMILES: O=C1NCc2cc(-n3c(=O)c4c(n5ncc(Cc6ccccc6)c35)CN(C(=O)c3ccc(Br)c(Cl)c3)CC4)ccc21] | 100 | 3-benzyl-8-(4-bromo-3-chlorobenzoyl)-4-(1-oxoisoindolin-5-yl)-6,7,8,9-tetrahydropyrazolo[1,5-a]pyrido[4,3-e]pyrimidin-5(4H)-one |
| 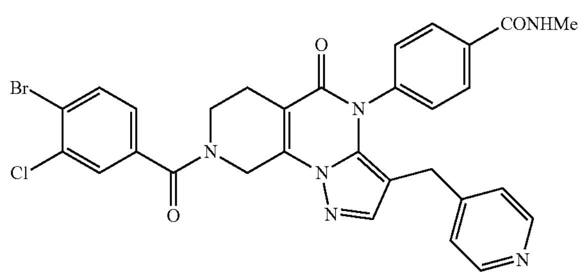 | 101 | 4-(8-(4-bromo-3-chlorobenzoyl)-5-oxo-3-(pyridin-4-ylmethyl)-6,7,8,9-tetrahydropyrazolo[1,5-a]pyrido[4,3-e]pyrimidin-4(5H)-yl)-N-methylbenzamide |

TABLE B-continued

| Structure | Cmpd # | Name |
|---|---|---|
| 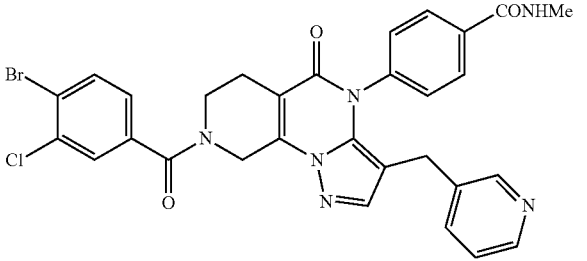 | 102 | 4-(8-(4-bromo-3-chlorobenzoyl)-5-oxo-3-(pyridin-3-ylmethyl)-6,7,8,9-tetrahydropyrazolo[1,5-a]pyrido[4,3-e]pyrimidin-4(5H)-yl)-N-methylbenzamide |
| 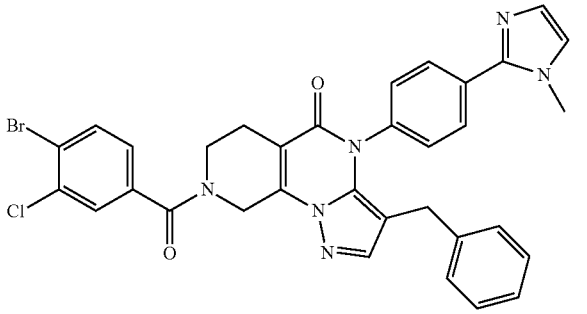 [SMILES: Cn1ccnc1-c1ccc(-n2c(=O)c3c(n4ncc(Cc5ccccc5)c24)CN(C(=O)c2ccc(Br)c(Cl)c2)CC3)cc1] | 103 | 3-benzyl-8-(4-bromo-3-chlorobenzoyl)-4-(4-(1-methyl-1H-imidazol-2-yl)phenyl)-6,7,8,9-tetrahydropyrazolo[1,5-a]pyrido[4,3-e]pyrimidin-5(4H)-one |
| 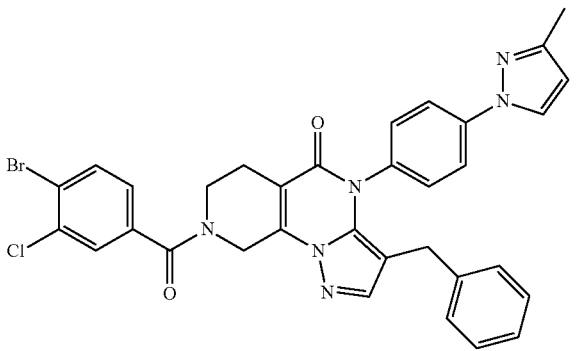 [SMILES: Cc1ccn(-c2ccc(-n3c(=O)c4c(n5ncc(Cc6ccccc6)c35)CN(C(=O)c3ccc(Br)c(Cl)c3)CC4)cc2)n1] | 104 | 3-benzyl-8-(4-bromo-3-chlorobenzoyl)-4-(4-(3-methyl-1H-pyrazol-1-yl)phenyl)-6,7,8,9-tetrahydropyrazolo[1,5-a]pyrido[4,3-e]pyrimidin-5(4H)-one |
| 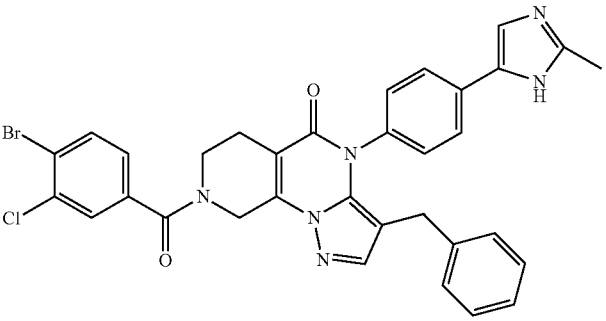 [SMILES: Cc1ncc(-c2ccc(-n3c(=O)c4c(n5ncc(Cc6ccccc6)c35)CN(C(=O)c3ccc(Br)c(Cl)c3)CC4)cc2)[nH]1] | 105 | 3-benzyl-8-(4-bromo-3-chlorobenzoyl)-4-(4-(2-methyl-1H-imidazol-5-yl)phenyl)-6,7,8,9-tetrahydropyrazolo[1,5-a]pyrido[4,3-e]pyrimidin-5(4H)-one |
| 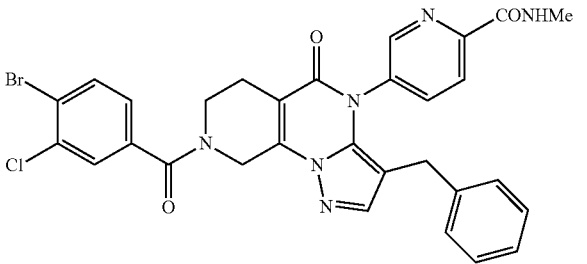 | 106 | 5-(3-benzyl-8-(4-bromo-3-chlorobenzoyl)-5-oxo-6,7,8,9-tetrahydropyrazolo[1,5-a]pyrido[4,3-e]pyrimidin-4(5H)-yl)-N-methylpicolinamide |

TABLE B-continued

| Structure | Cmpd # | Name |
|---|---|---|
| 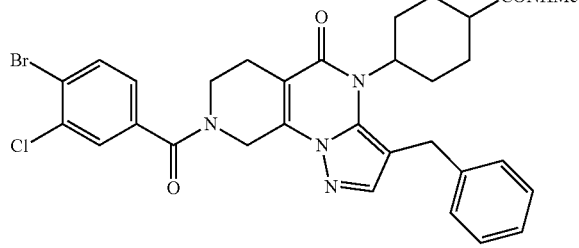 | 107 | 4-(3-benzyl-8-(4-bromo-3-chlorobenzoyl)-5-oxo-6,7,8,9-tetrahydropyrazolo[1,5-a]pyrido[4,3-e]pyrimidin-4(5H)-yl)-N-methylcyclohexane-1-carboxamide |
| 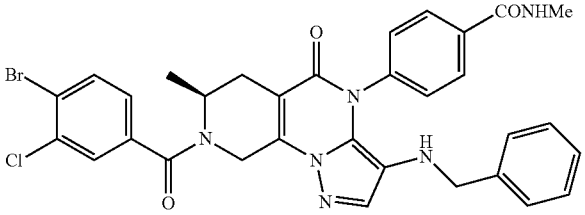 | 108 | (S)-4-(3-(benzylamino)-8-(4-bromo-3-chlorobenzoyl)-7-methyl-5-oxo-6,7,8,9-tetrahydropyrazolo[1,5-a]pyrido[4,3-e]pyrimidin-4(5H)-yl)-N-methylbenzamide |
| 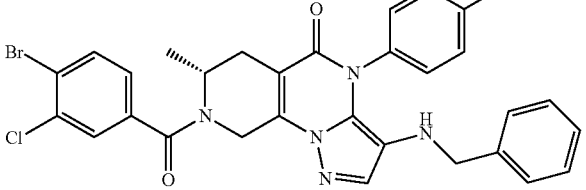 | 109 | (R)-4-(3-(benzylamino)-8-(4-bromo-3-chlorobenzoyl)-7-methyl-5-oxo-6,7,8,9-tetrahydropyrazolo[1,5-a]pyrido[4,3-e]pyrimidin-4(5H)-yl)-N-methylbenzamide |
| 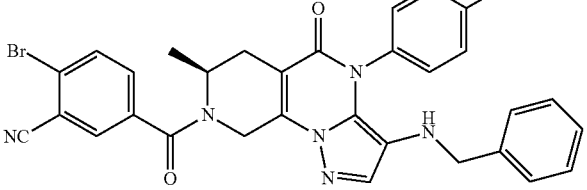 | 110 | (S)-4-(3-(benzylamino)-8-(4-bromo-3-cyanobenzoyl)-7-methyl-5-oxo-6,7,8,9-tetrahydropyrazolo[1,5-a]pyrido[4,3-e]pyrimidin-4(5H)-yl)-N-methylbenzamide |
| 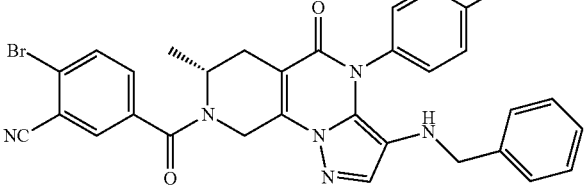 | 111 | (R)-4-(3-(benzylamino)-8-(4-bromo-3-cyanobenzoyl)-7-methyl-5-oxo-6,7,8,9-tetrahydropyrazolo[1,5-a]pyrido[4,3-e]pyrimidin-4(5H)-yl)-N-methylbenzamide |
| 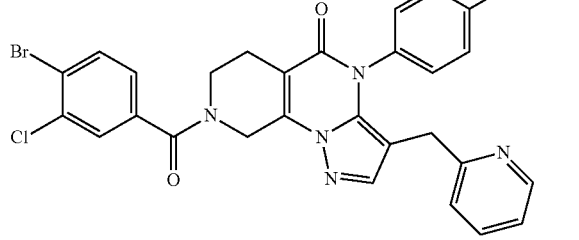 | 112 | 4-(8-(4-bromo-3-chlorobenzoyl)-5-oxo-3-(pyridin-2-ylmethyl)-6,7,8,9-tetrahydropyrazolo[1,5-a]pyrido[4,3-e]pyrimidin-4(5H)-yl)-N-methylbenzamide |

Example A

HBV-DNA Antiviral Assay Using HepG2.117 Cells

The following assay procedure describes the HBV antiviral assay, using HepG2.117 cells, which carry a stably integrated genotype D HBV genome under the control of a Tet-off promoter, and intracellular HBV DNA quantification as endpoint. Cell viability is assessed in parallel by measuring the intracellular ATP content using ATPlite (Perkin Elmer).

On day 0, HepG2.117 cells (which are maintained in routine cell culture with doxycycline present in the medium at a final concentration of 1 μg/mL) were seeded in 96-well plates (white with clear bottom) at a density of $2.0 \times 10^4$ cells/well (0.1 mL/well) in medium without doxycycline to induce pgRNA transcription and subsequent formation of HBV particles. The cells were incubated at 37° C. and 5% $CO_2$.

On day 1, medium was removed from each well, the test articles were diluted in culture medium without doxycycline and 100 μL was added to cell culture wells (9 concentrations, 4-fold dilution). For each plate, 6 untreated (merely DMSO) wells were included. The final concentration of DMSO in the culture medium was 2%. Each plate was prepared in duplicate (one for HBV DNA extraction, one for ATPlite measurement). The cells were incubated at 37° C. and 5% $CO_2$ for 3 days.

On day 4, cell viability was assessed using ATPlite and cell lysates were prepared for HBV DNA extraction and subsequent quantification by qPCR.

HBV DNA Quantification by qPCR

Medium was removed from each well and 100 μL of 0.33% NP-40 in $H_2O$ was added to each well. Plates were sealed, incubated at 4° C. for 5 mins, vortexed extensively and centrifuged briefly. Next, 35 μL of lysate was added to 65 μL QuickExtract DNA Extraction Solution (Epicentre) in a PCR plate for each well. PCR plate was incubated at 65° C. for 6 mins, 98° C. for 2 mins and finally cooled to 4° C. HBV DNA was then quantified by qPCR with HBV-specific primers and probes as specified in Table 1 using the Bio-Rad SSOAdvanced Universal Probes Supermix on a CFX96 machine (Bio-Rad). The PCR cycle program consisted of 95° C. for 3 mins, followed by 40 cycles at 95° C. for 10 sec and 60° C. for 30 sec.

TABLE 1

HBV DNA Primers and Probe for HepG2.117 assay

| Items | Name | Sequence (5' → 3') |
|---|---|---|
| HBV Primer | HBV-forward | GTGTCTGCGGCGTTTTATCA (SEQ ID NO: 1) |
|  | HBV-reverse | GACAAACGGGCAACATACCTT (SEQ ID NO: 2) |
| HBV Probe | HBV probe | FAM/CCTCTKCAT/ZEN/ CCTGCTGCTATGCCTCATC/3IABkFQ/ (SEQ ID NO: 3) |

A DNA standard was prepared by dilution of an IDT gBlock corresponding to the amplicon with concentrations ranging from 10^2 to 10^8 copies/input (i.e. per 4 μL) and used to generate a standard curve by plotting Cq values vs. HBV DNA standard concentration. The quantity of HBV DNA in each sample was determined by interpolating from the standard curve.

Cell Viability

Using the other plates, the cell viability was quantified by ATPlite according to the manufacturer's manual. In brief, 50 μL of cell lysis solution was added to the culture plates and shaken for 5', followed by addition of 50 μL substrate into each well and further shaking. The plates were incubated at room temperature for 10 mins and luminescence signal was subsequently measured on a VarioSkan Lux (ThermoFisher) plate reader.

Data Analysis

Cell viability was calculated as follows: % Cell viability= (luminescence value of test sample)/(average luminescence value of 2% DMSO control)×100%. HBV DNA inhibition was calculated as follows: 100−(HBV DNA copy number of test sample)/(average HBV DNA copy number of 2% DMSO control)×100%. No normalization to entecavir was required due to the excellent dynamic window of this assay. The $CC_{50}$, $EC_{50}$ and $EC_{90}$ values were determined by dose-response curves fitted by GraphPad Prism using "log (agonist) vs. response—Variable slope".

As shown in Table 2, compounds of Formula (I) are active against HBV, where 'A' indicates an $EC_{50} \leq 100$ nM, 'B' indicates an $EC_{50} > 100$ nM and $\leq 500$ nM, 'C' indicates an $EC_{50} > 500$ nM and $\leq 5000$ nM, and 'D' indicates an $EC_{50} > 5000$ nM. Cell viability assessments indicated a large window between effective antiviral concentrations and cytotoxic compound concentrations.

TABLE 2

| Compound | EC50 - HepG2.117 |
|---|---|
| 1 | C |
| 2 | C |
| 3 | D |
| 4 | D |
| 5 | C |
| 6 | C |
| 7 | D |
| 8 | C |
| 9 | B |
| 10 | B |
| 11 | D |
| 12 | B |
| 13 | C |
| 14 | C |
| 15 | D |
| 16 | D |
| 17 | D |
| 18 | C |
| 19 | D |
| 20 | D |
| 21 | D |
| 22 | D |
| 23 | C |
| 24 | B |
| 25 | A |
| 26 | C |
| 27 | A |
| 28 | B |
| 29 | A |
| 30 | B |
| 31 | A |
| 32 | A |
| 33 | C |
| 34 | A |
| 35 | A |
| 36 | B |
| 37 | A |
| 38 | A |
| 39 | A |
| 40 | A |
| 41 | C |
| 42 | A |
| 43 | A |

TABLE 2-continued

| Compound | EC50 - HepG2.117 |
|---|---|
| 44 | B |
| 45 | A |
| 46 | A |
| 47 | A |
| 48 | A |
| 49 | A |
| 50 | A |
| 51 | C |
| 52 | B |
| 53 | C |
| 54 | A |
| 55 | B |
| 56 | C |
| 57 | A |
| 58 | A |
| 59 | A |
| 60 | A |
| 61 | C |
| 62 | C |
| 63 | B |
| 64 | C |
| 65 | C |
| 66 | A |
| 67 | A |
| 68 | D |
| 69 | B |
| 70 | B |
| 71 | A |
| 72 | A |
| 73 | C |
| 74 | A |
| 75 | C |
| 76 | D |
| 77 | D |
| 78 | D |
| 79 | B |
| 80 | B |
| 81 | A |
| 82 | D |
| 83 | B |
| 84 | C |
| 85 | A |
| 86 | B |
| 87 | A |
| 88 | A |
| 89 | A |
| 90 | C |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I), or a pharmaceutically acceptable salt thereof, having the structure:

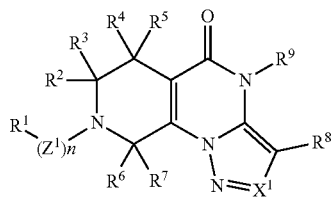

(I)

wherein:

n is 0 or 1;

$Z^1$ is —C(=O)—, —NH—C(=O)— or —O—C(=O)—;

$R^1$ is selected from the group consisting of an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl);

$R^2$ and $R^3$ are independently selected from the group consisting of hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl ($C_{1-4}$ alkyl), an optionally substituted heteroaryl($C_{1-4}$ alkyl) and an optionally substituted heterocyclyl($C_{1-4}$ alkyl);

$R^4$ and $R^5$ are independently selected from the group consisting of hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl ($C_{1-4}$ alkyl), an optionally substituted heteroaryl($C_{1-4}$ alkyl) and an optionally substituted heterocyclyl($C_{1-4}$ alkyl);

$R^6$ and $R^7$ are independently selected from the group consisting of hydrogen, an unsubstituted $C_{1-4}$ alkyl and an unsubstituted $C_{1-4}$ haloalkyl;

$R^8$ is selected from the group consisting of hydrogen, an unsubstituted $C_{1-4}$ alkyl, an unsubstituted $C_{2-4}$ alkenyl, an unsubstituted $C_{2-4}$ alkynyl, an unsubstituted $C_{1-4}$ haloalkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl), an optionally substituted heterocyclyl($C_{1-4}$ alkyl), an optionally substituted N-amido, an optionally substituted N-sulfonamido, —$NR^{10}R^{11}$ and —C(=O)$NR^{12}R^{13}$;

$R^9$ is selected from the group consisting of hydrogen, an unsubstituted $C_{1-4}$ alkyl, an optionally substituted monocyclic $C_{4-6}$ cycloalkyl, an optionally substituted aryl, an optionally substituted heteroaryl, an optionally substituted heterocyclyl, an optionally substituted aryl ($C_{1-4}$ alkyl), an optionally substituted heteroaryl($C_{1-4}$ alkyl) and an optionally substituted heterocyclyl($C_{1-4}$ alkyl);

$R^{10}$ and $R^{12}$ are independently hydrogen or an unsubstituted $C_{1-4}$ alkyl;

$R^{11}$ and $R^{13}$ are independently selected from the group consisting of hydrogen, an unsubstituted $C_{1-4}$ alkyl, an unsubstituted $C_{1-4}$ haloalkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl) and an optionally substituted heterocyclyl($C_{1-4}$ alkyl); or $R^{10}$ and $R^{11}$ are taken together along with the nitrogen to which $R^{10}$ and $R^{11}$ are attached to form an optionally substituted 4- to 8-membered monocyclic heterocyclyl, an optionally substituted 8- to 13-membered fused-bicyclic heterocyclyl or an optionally substituted 7- to 13-membered spiro-bicyclic heterocyclyl;

$R^{12}$ and $R^{13}$ are taken together along with the nitrogen to which $R^{12}$ and $R^{13}$ are attached to form an optionally substituted 4- to 8-membered monocyclic heterocyclyl, an optionally substituted 8- to 13-membered fused-bicyclic heterocyclyl or an optionally substituted 7- to 13-membered spiro-bicyclic heterocyclyl;

$R^2$ and $R^3$ are taken together along with the carbon to which $R^2$ and $R^3$ are attached to form an optionally substituted monocyclic $C_{3-6}$ cycloalkyl or an optionally substituted 3 to 6 member monocyclic heterocyclyl; or $R^4$ and $R^5$ are taken together along with the carbon to which $R^4$ and $R^5$ are attached to form an optionally substituted monocyclic $C_{3-6}$ cycloalkyl or an optionally substituted 3 to 6 member monocyclic heterocyclyl; or $R^2$ and $R^4$ are taken together along with the carbons to which $R^2$ and $R^4$ are each attached to form an optionally monocyclic $C_{5-7}$ cycloalkyl or an optionally substituted 5 to 7 member monocyclic heterocyclyl; or $R^3$ and $R^5$ are taken together along with the carbons to which $R^3$ and $R^5$ are each attached to form an optionally monocyclic $C_{5-7}$ cycloalkyl or an optionally substituted 5 to 7 member monocyclic heterocyclyl; or $R^6$ and $R^7$ are taken together along with the carbon to which $R^6$ and $R^7$ are attached to form an optionally substituted monocyclic $C_{3-4}$ cycloalkyl, an optionally substituted oxetane or an optionally substituted thietane; and $X^1$ is N or $CR^{14}$, wherein $R^{14}$ is hydrogen, cyano, an unsubstituted $C_{1-4}$ alkyl, a substituted $C_{1-4}$ alkyl or an optionally substituted aryl($C_{1-4}$ alkyl), wherein the substituted $C_{1-4}$ alkyl is substituted one or more times with a substituents selected from the group consisting of cyano, halogen, hydroxy and an unsubstituted $C_{1-4}$ alkoxy.

2. The compound of claim 1, wherein n is 1.

3. The compound of claim 2, wherein $Z^1$ is —C(=O)—.

4. The compound of claim 2, wherein $Z^1$ is —NH—C(=O)—.

5. The compound of claim 1, wherein $R^1$ is an optionally substituted aryl.

6. The compound of claim 5, wherein $R^1$ is an optionally substituted phenyl.

7. The compound of claim 1, wherein $R^2$, $R^3$, $R^4$, $R^5$, $R^6$ and $R^7$ are each hydrogen.

8. The compound of claim 1, wherein $X^1$ is N.

9. The compound of claim 1, wherein $X^1$ is $CR^{14}$; and $R^{14}$ is hydrogen.

10. The compound claim 1, wherein $R^8$ is hydrogen, an unsubstituted $C_{1-4}$ alkyl, an unsubstituted $C_{2-4}$ alkynyl, an optionally substituted cycloalkyl($C_{1-4}$ alkyl), an optionally substituted aryl($C_{1-4}$ alkyl), an optionally substituted N-amido or an optionally substituted N-sulfonamido.

11. The compound of claim 1, wherein $R^8$ is —$NR^{10}R^{11}$ or —C(=O)$NR^{12}R^{13}$.

12. The compound of claim 11, wherein $R^{10}$ is hydrogen; and $R^{11}$ is an unsubstituted $C_{1-4}$ alkyl, an unsubstituted $C_{1-4}$ haloalkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl) and an optionally substituted heterocyclyl($C_{1-4}$ alkyl).

13. The compound of claim 11, wherein $R^{12}$ is hydrogen; and $R^{13}$ is an unsubstituted $C_{1-4}$ alkyl, an unsubstituted $C_{1-4}$ haloalkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl) and an optionally substituted heterocyclyl($C_{1-4}$ alkyl).

14. The compound of claim 1, wherein $R^9$ is an unsubstituted $C_{1-4}$ alkyl, an optionally substituted aryl($C_{1-4}$ alkyl), an optionally substituted heteroaryl or an optionally substituted monocyclic $C_{4-6}$ cycloalkyl.

15. The compound of claim 1, wherein the compound is selected from the group consisting of:

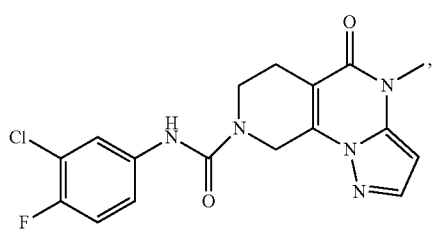

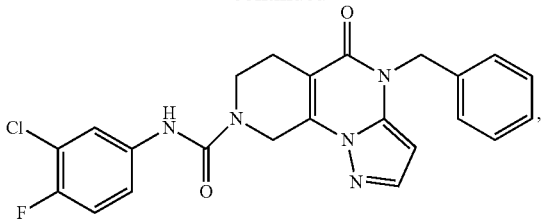

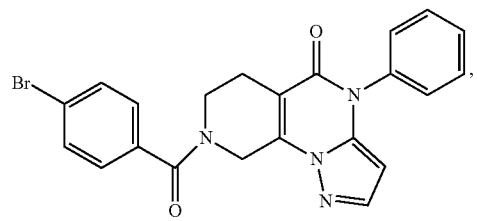

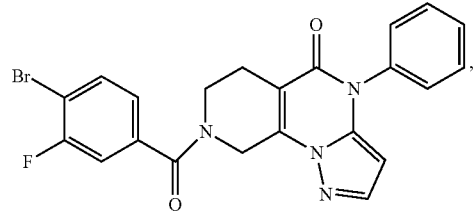

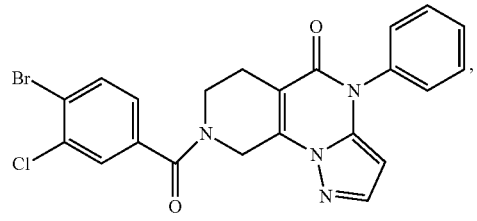

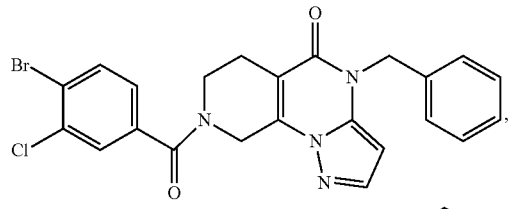

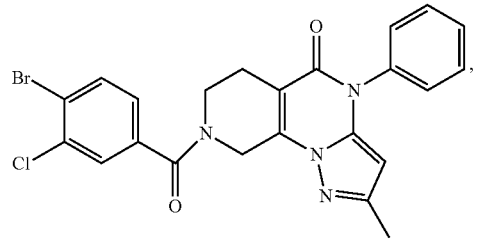

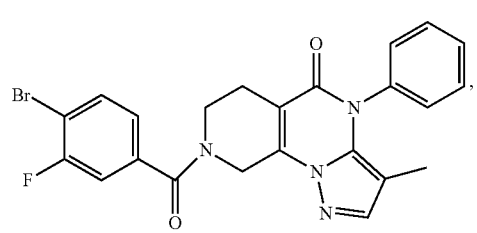

167
-continued
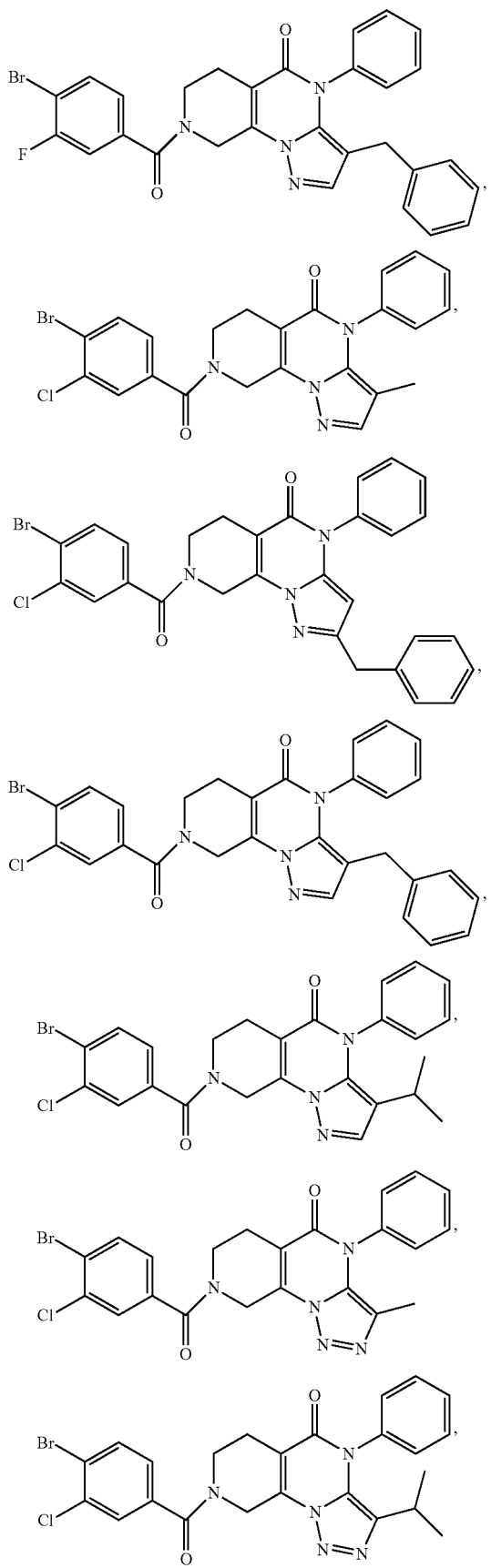
168
-continued
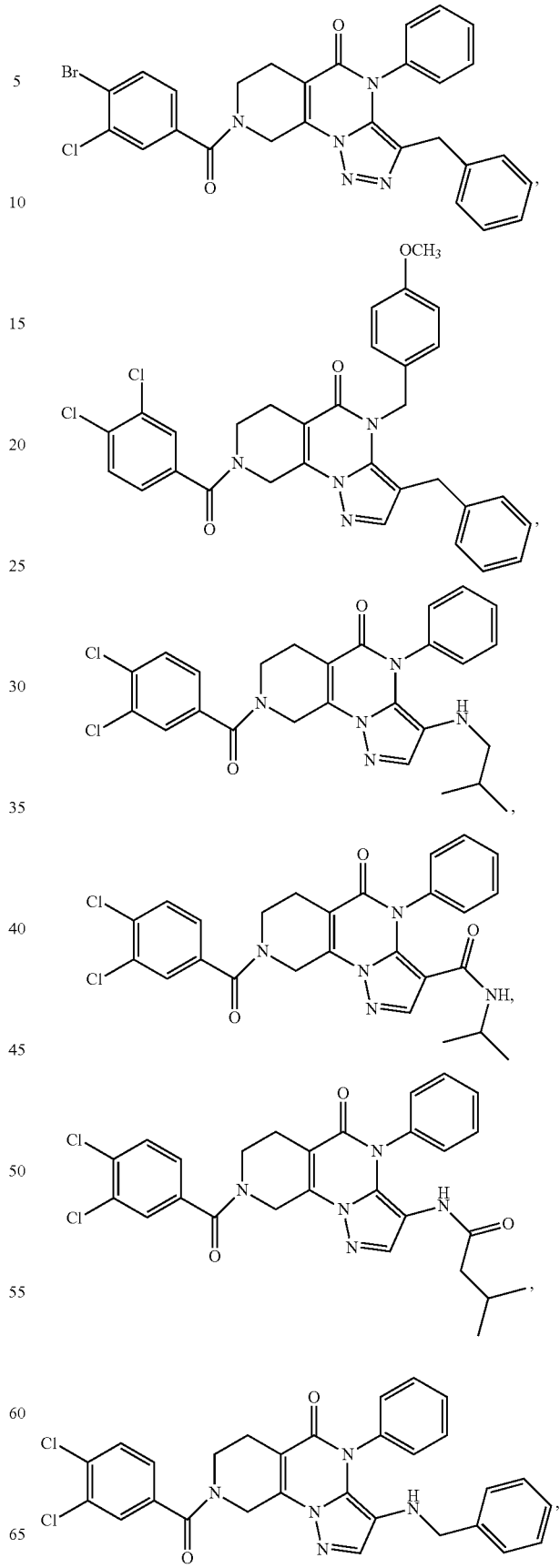

169
-continued
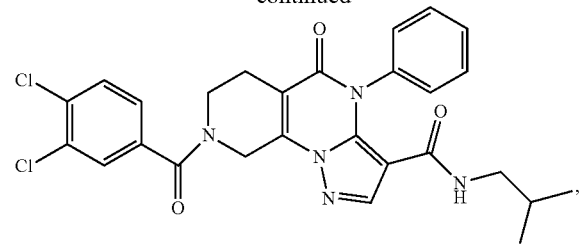
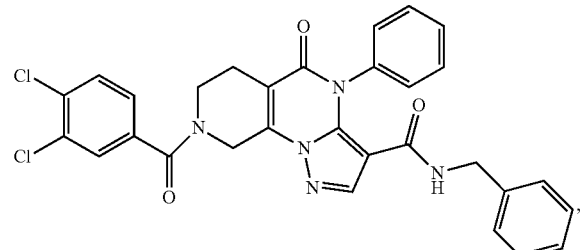
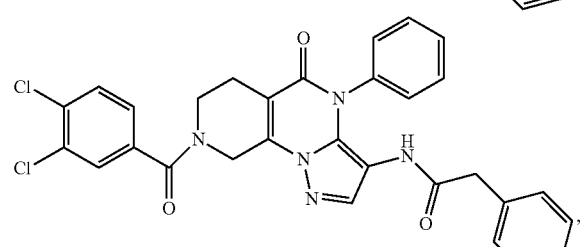
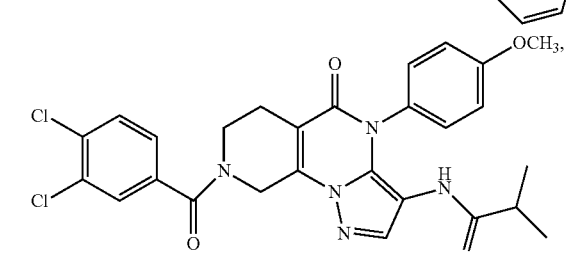
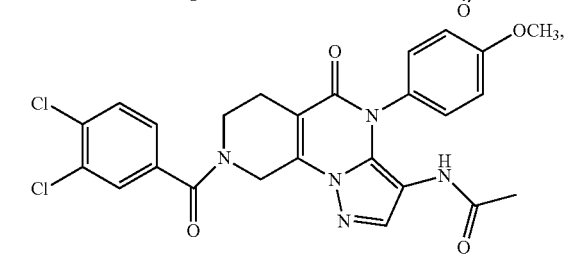
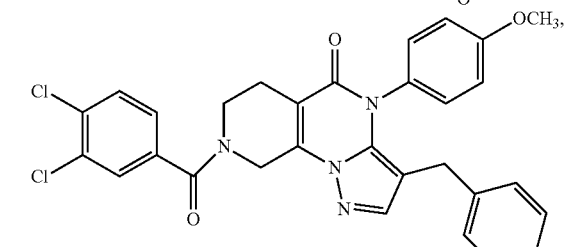
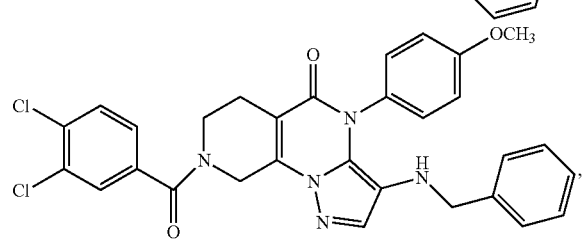
170
-continued
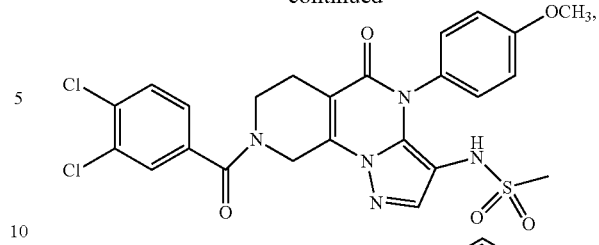
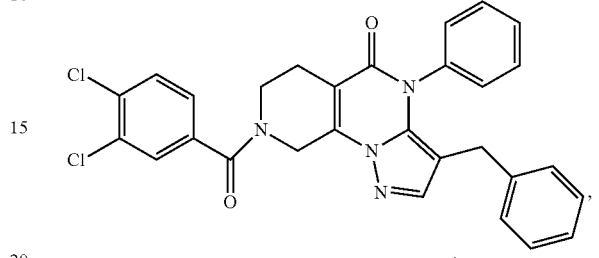
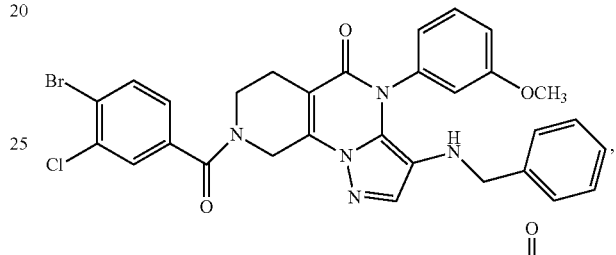
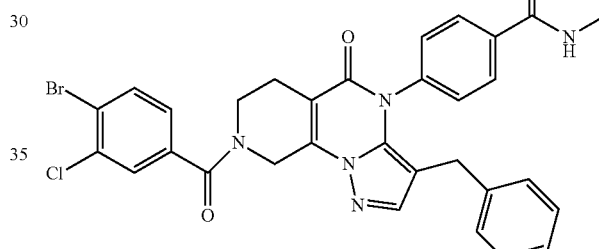
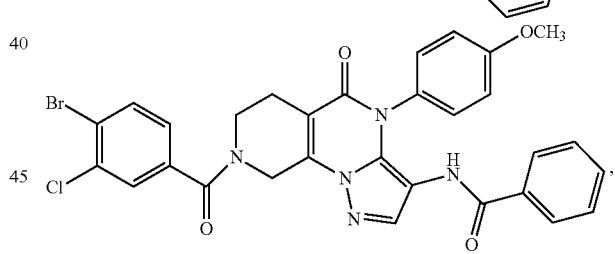
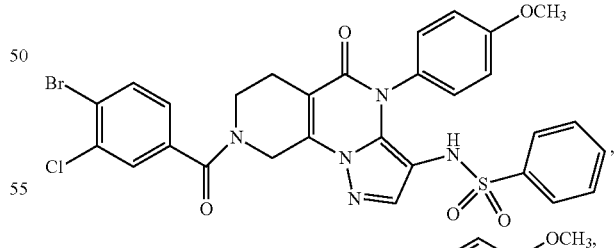
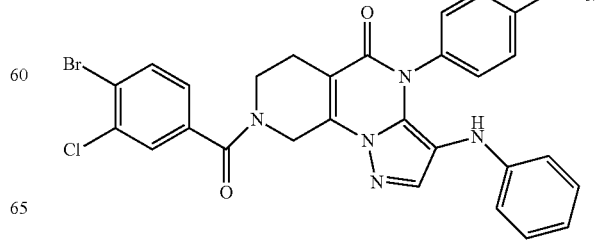

171
-continued
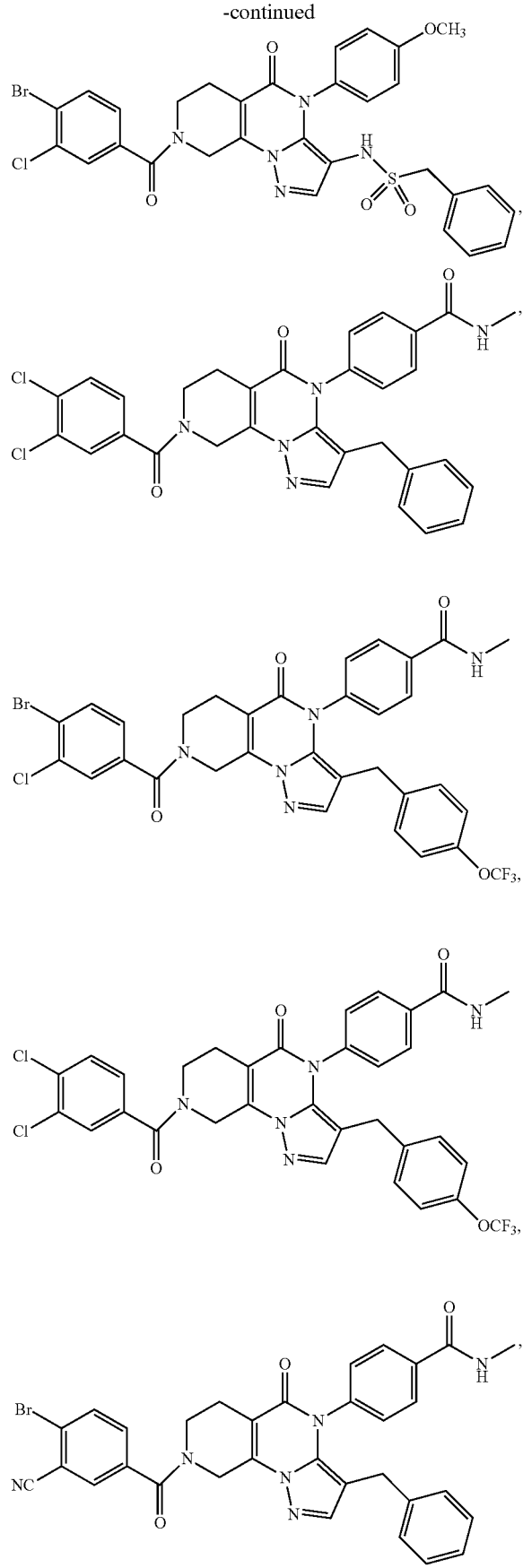
172
-continued
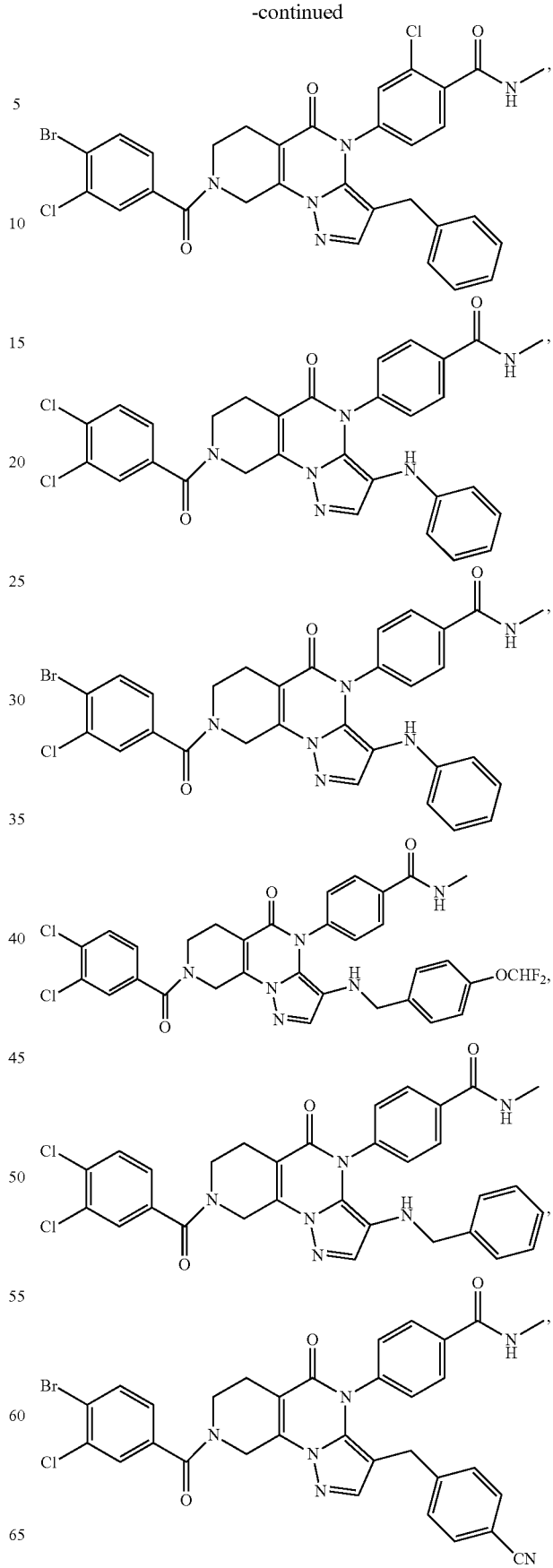

173
-continued
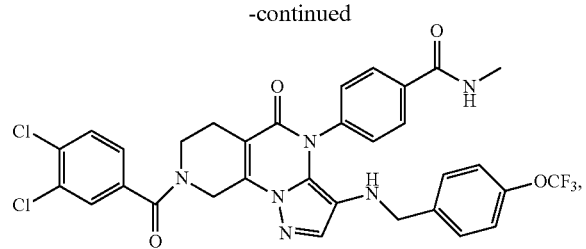
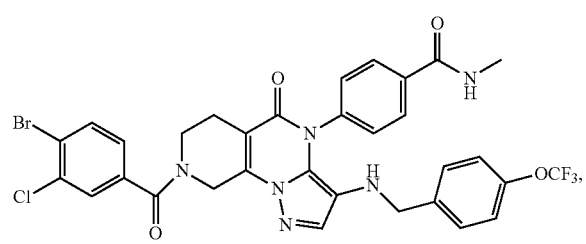
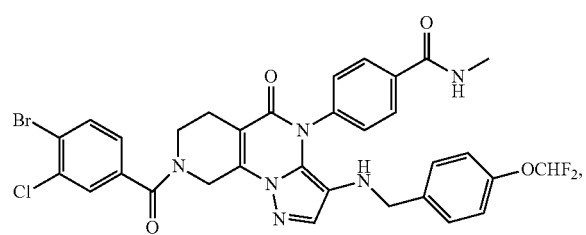
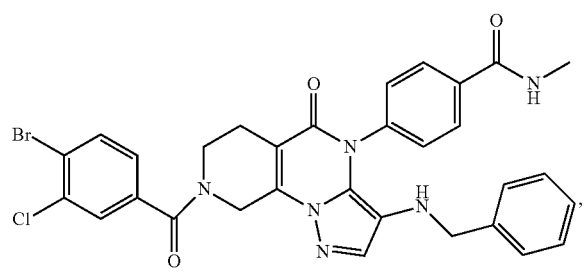
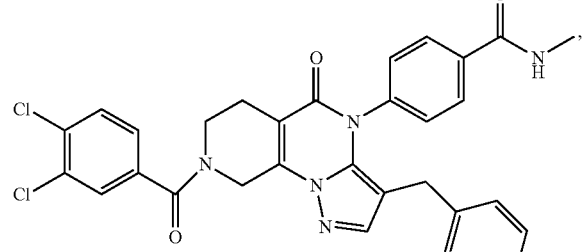
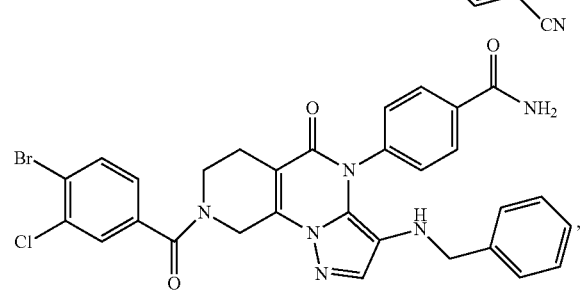
174
-continued
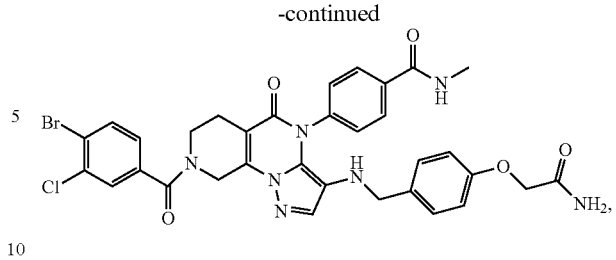
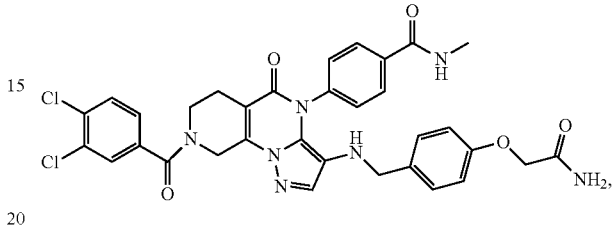
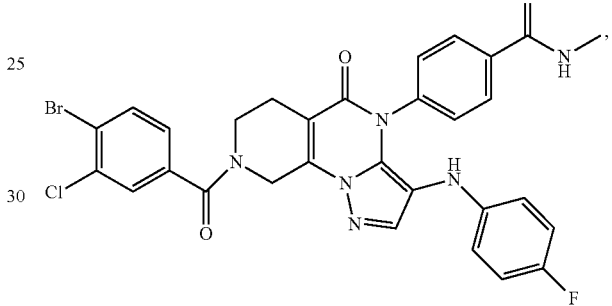
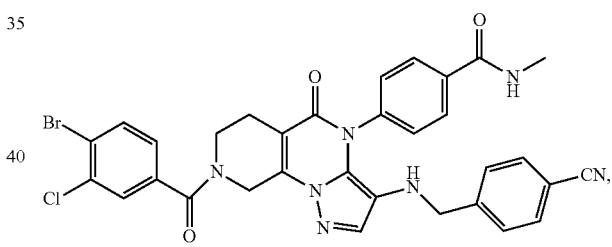
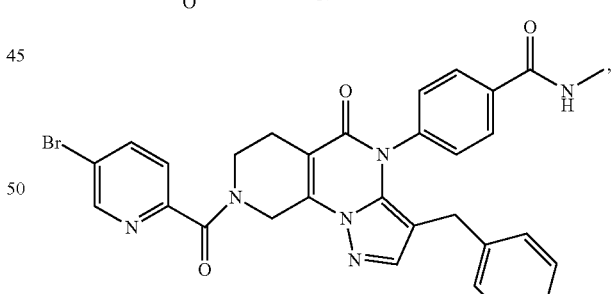
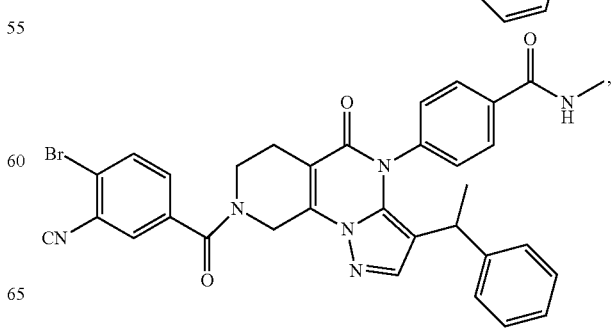

175
-continued
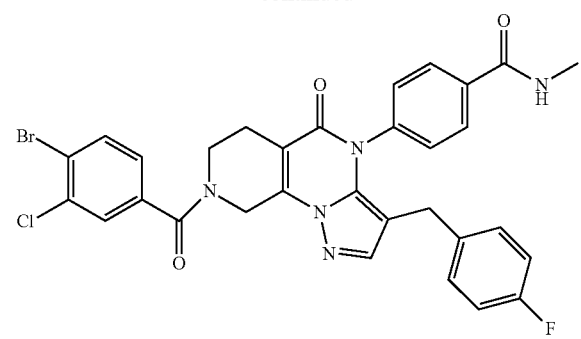
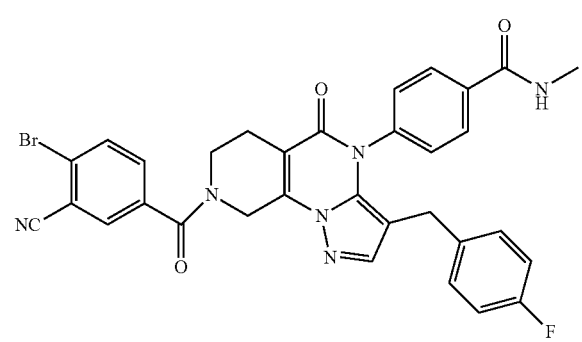
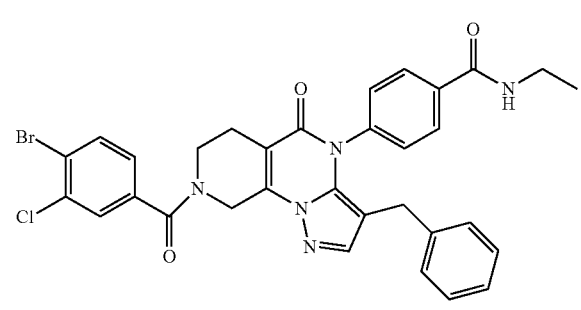
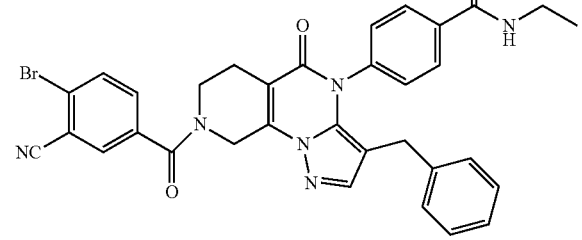
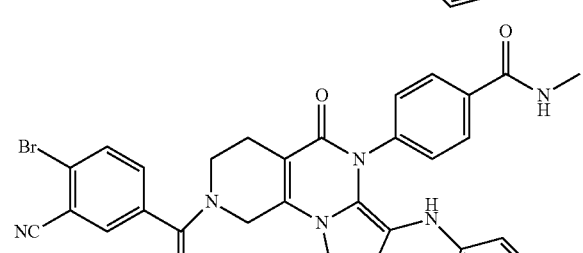
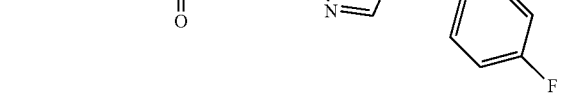
176
-continued
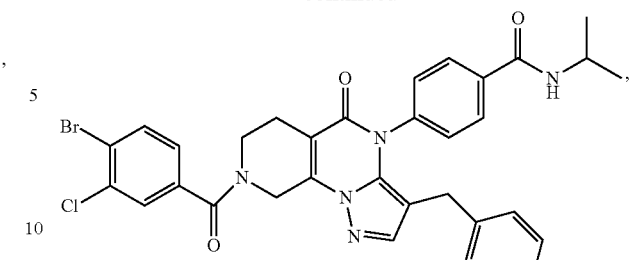
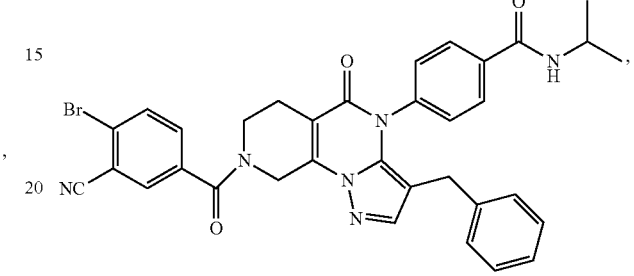
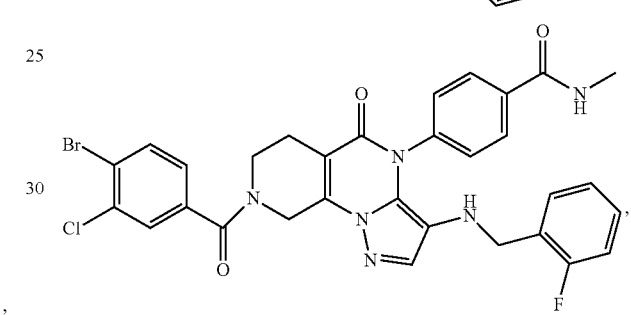
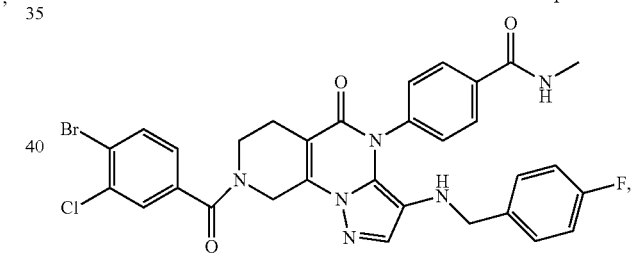
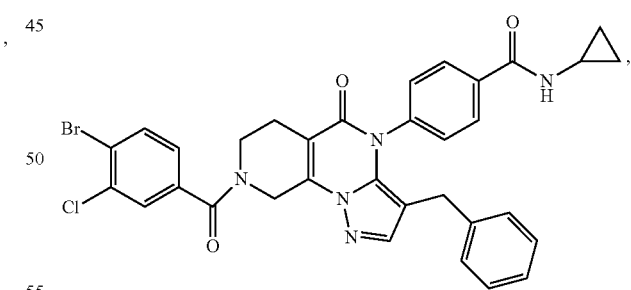
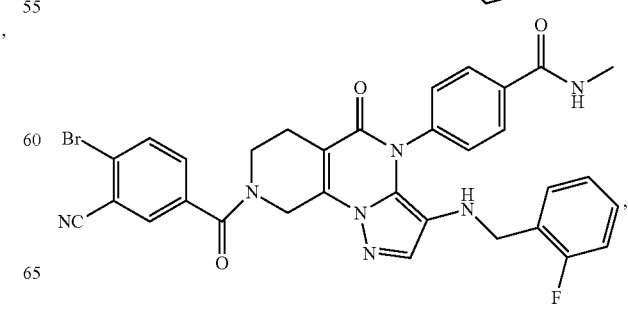

177
-continued
178
-continued
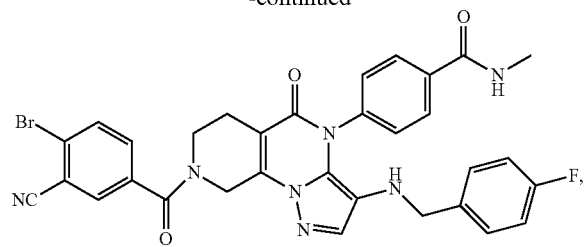
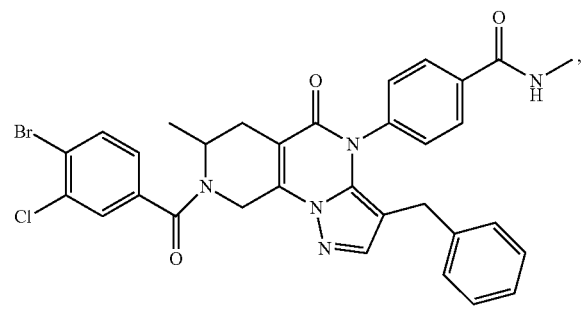
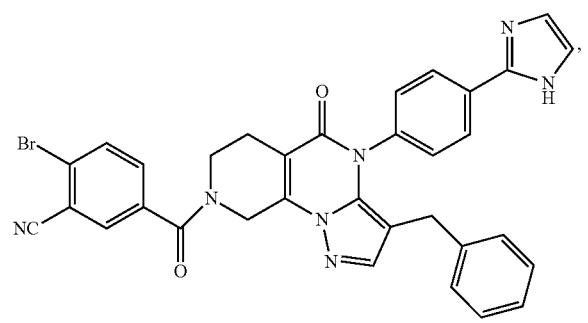
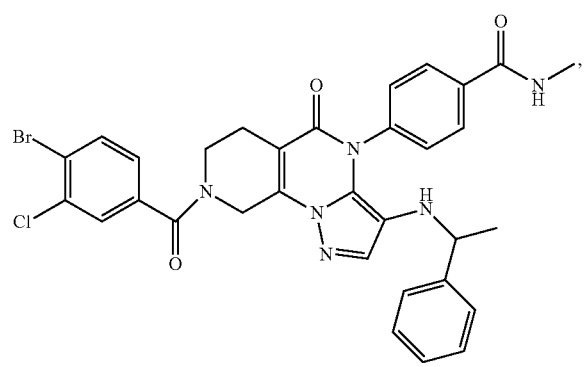
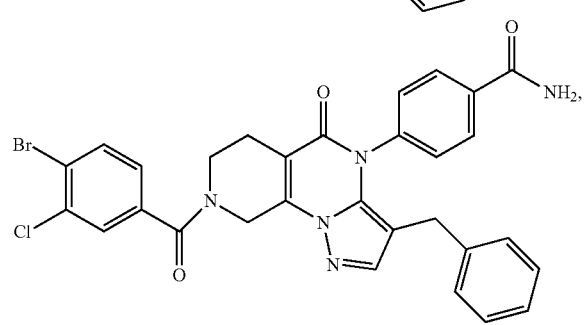
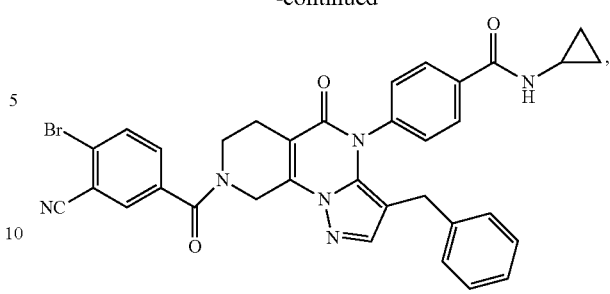

179
-continued
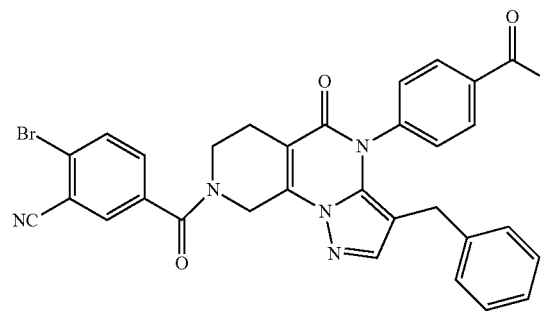
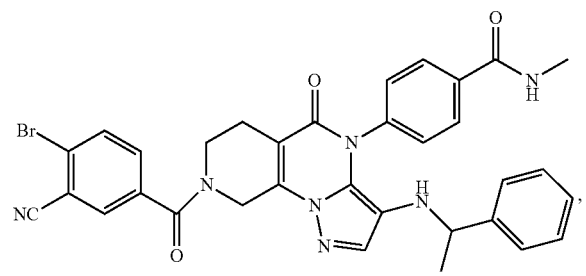
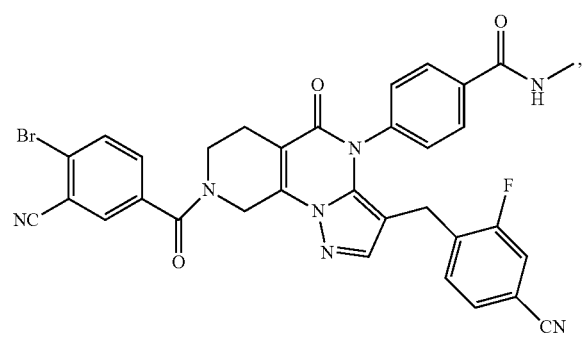
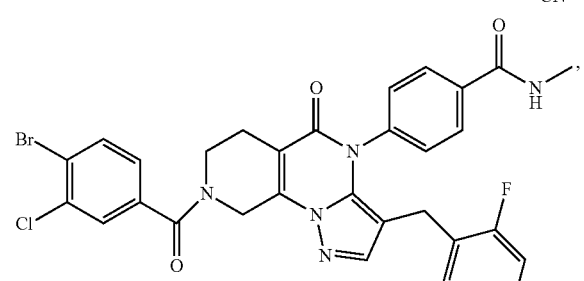
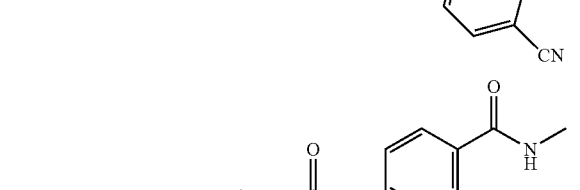
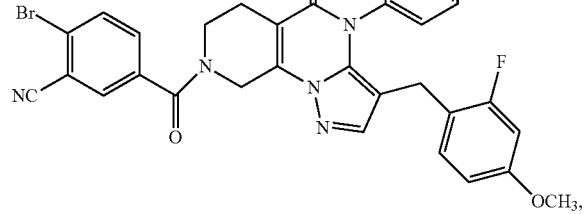
180
-continued
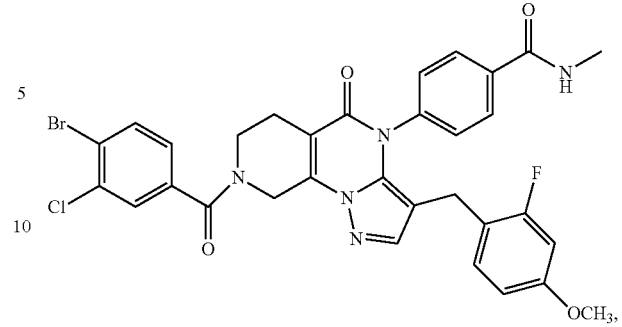
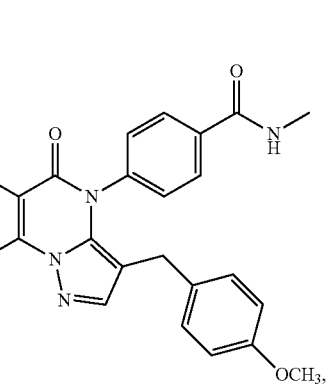
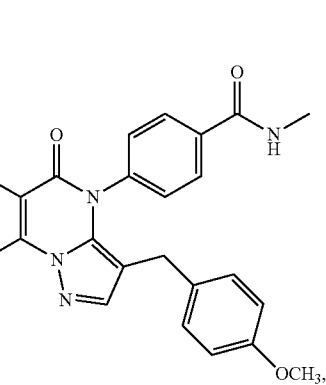
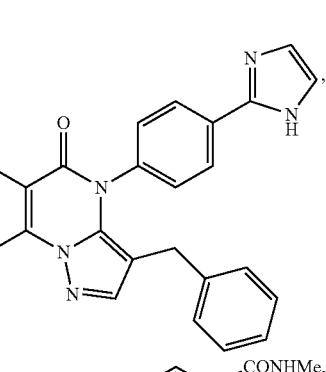
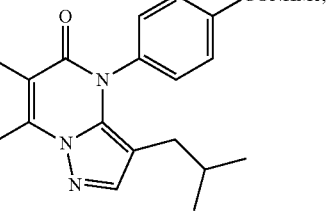

181
-continued
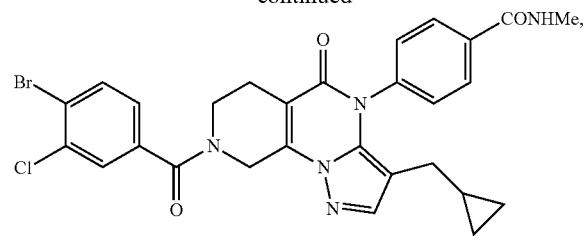
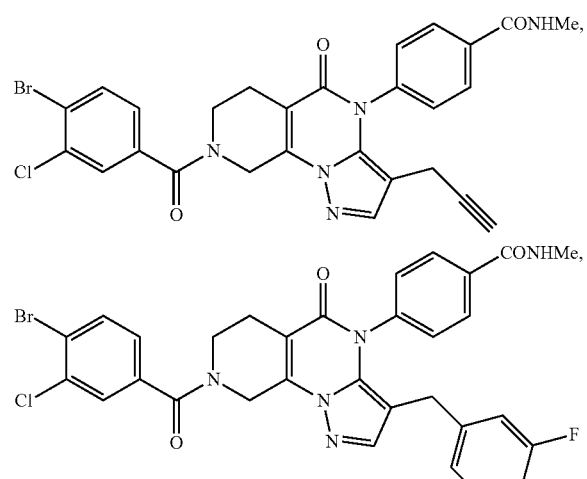
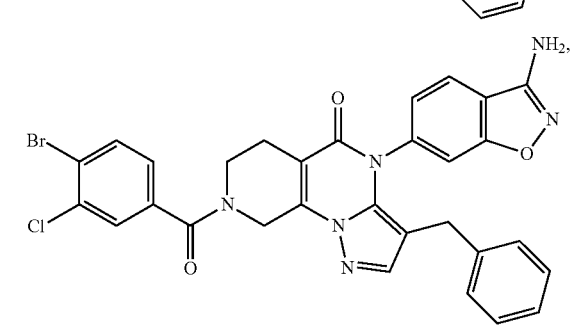
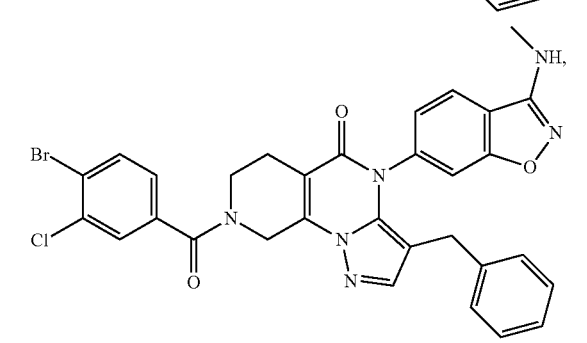
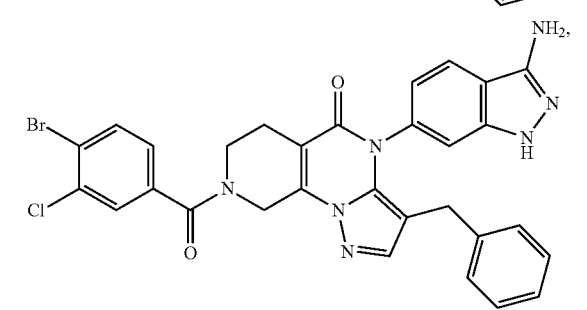
182
-continued
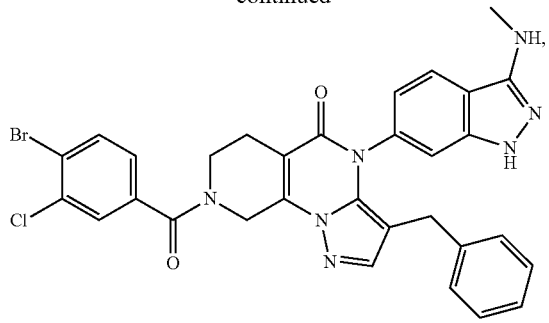
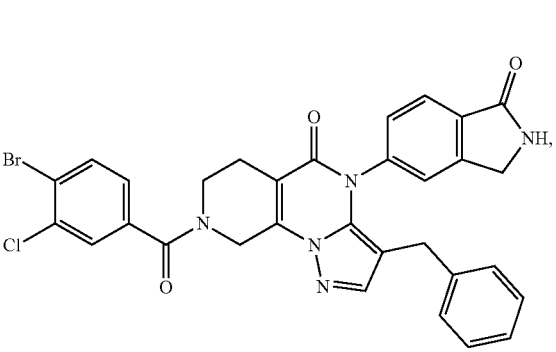
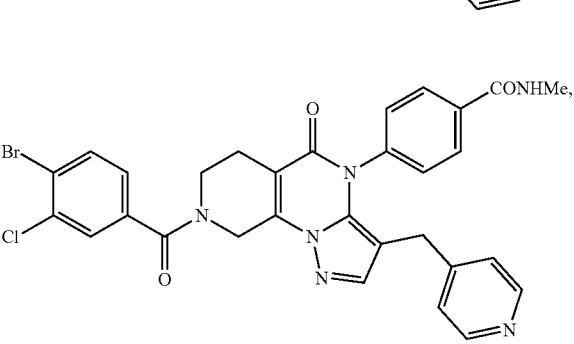
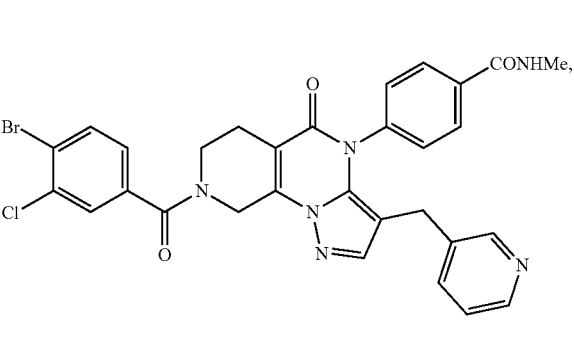
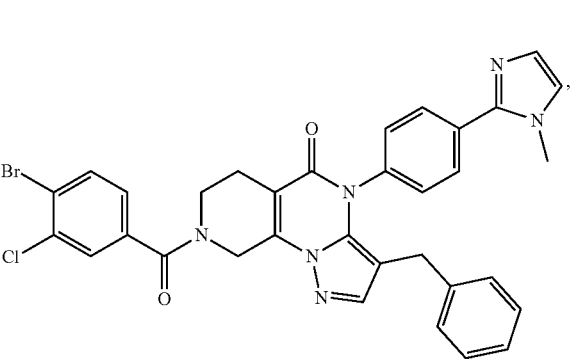

183
-continued
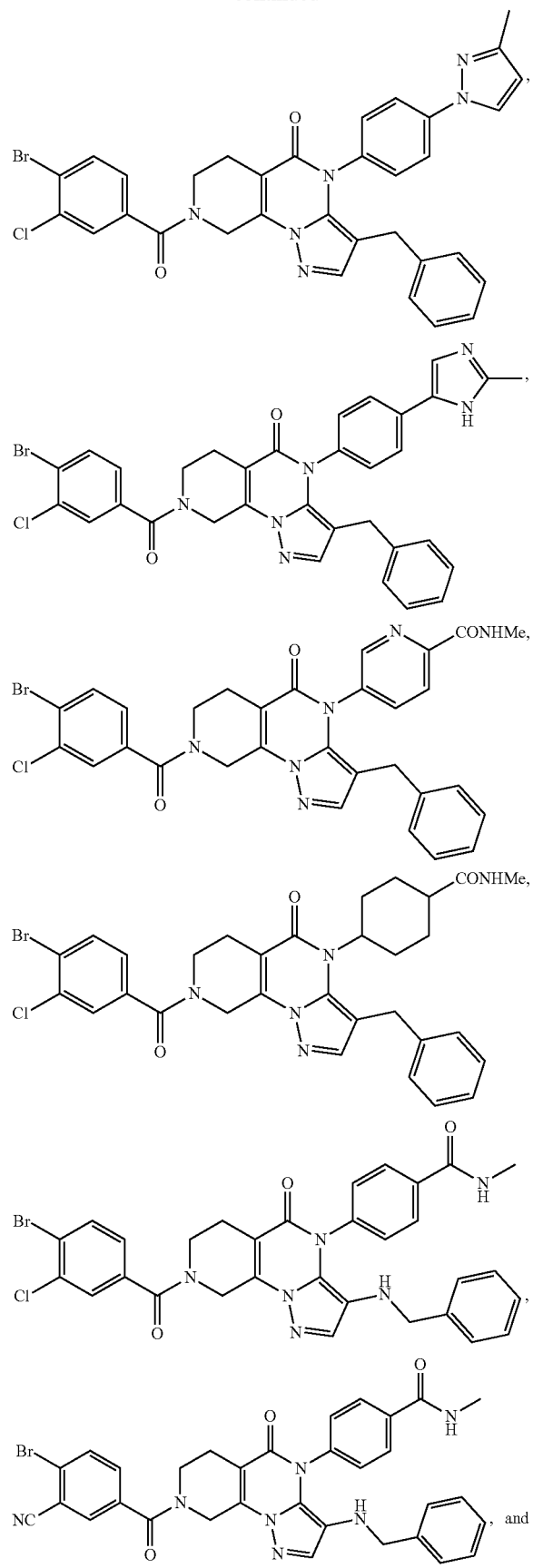
184
-continued
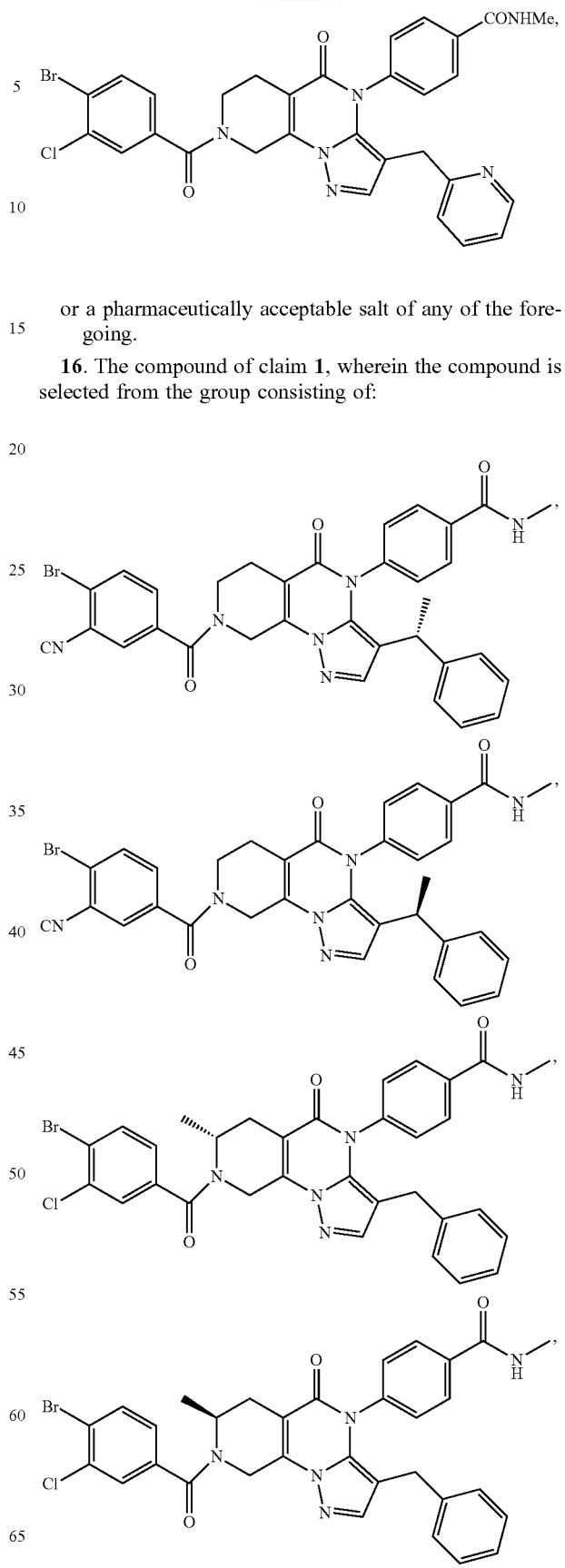
or a pharmaceutically acceptable salt of any of the foregoing.
16. The compound of claim 1, wherein the compound is selected from the group consisting of:

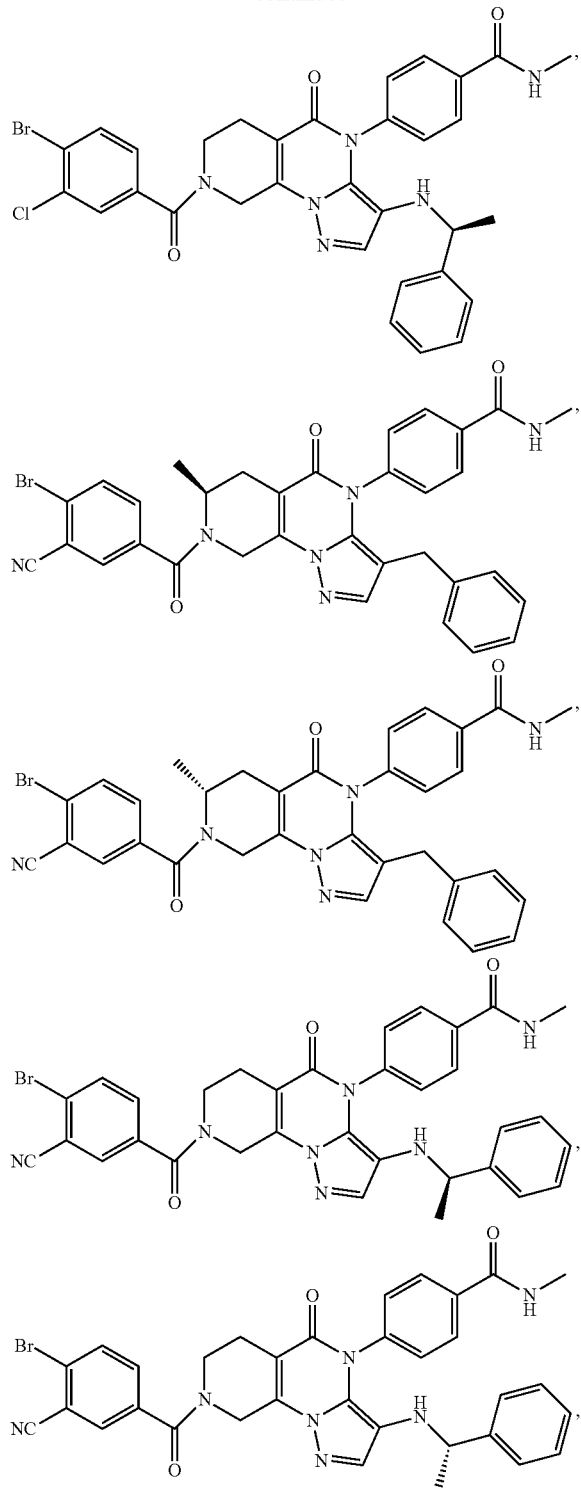

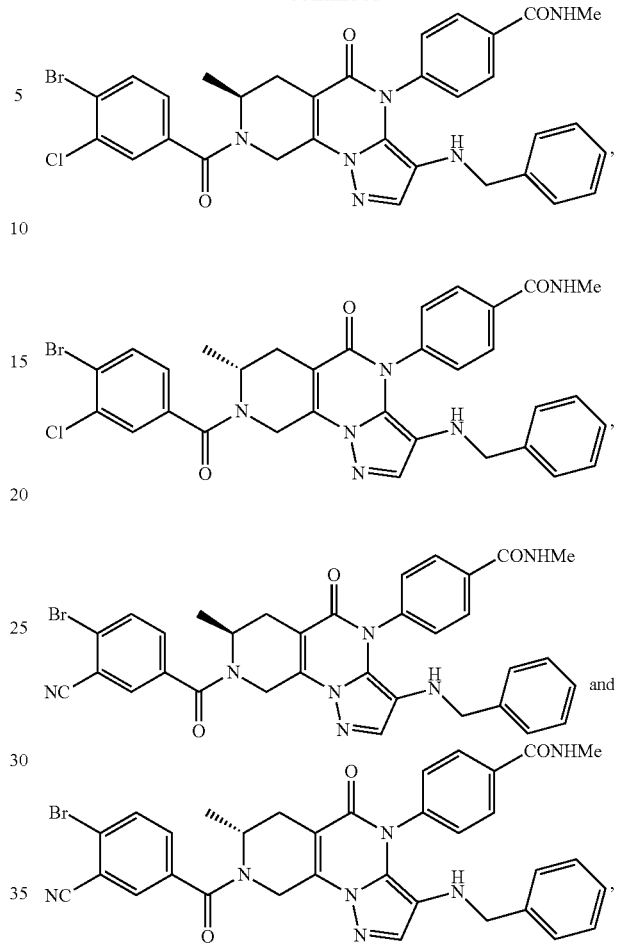

or a pharmaceutically acceptable salt of any of the foregoing.

17. A pharmaceutical composition comprising an effective amount of a compound claim 1, or a pharmaceutically acceptable salt thereof, and excipient.

18. A method for treating hepatitis B in a subject comprising administering to the subject in need thereof an effective amount of a compound of claim 1, or a pharmaceutically acceptable salt thereof, suffering from hepatitis B.

19. A method of claim 18 further comprising treating hepatitis D in a subject suffering from hepatitis D.

20. The method of claim 18, further comprising administering an additional agent selected from the group consisting of an interferon, a nucleoside analog, a nucleotide analog, a sequence specific oligonucleotide, a nucleic acid polymer, an entry inhibitor and a small molecule immunomodulator.

* * * * *

UNITED STATES PATENT AND TRADEMARK OFFICE
CERTIFICATE OF CORRECTION

| | |
|---|---|
| PATENT NO. | : 11,136,321 B2 |
| APPLICATION NO. | : 16/885128 |
| DATED | : October 5, 2021 |
| INVENTOR(S) | : Sandrine Vendeville |

Page 1 of 2

It is certified that error appears in the above-identified patent and that said Letters Patent is hereby corrected as shown below:

In the Specification

Column 19, Line 63, delete "-CHF," and insert -- -CHF$_2$, --.

Column 74, Lines 55-59, delete " 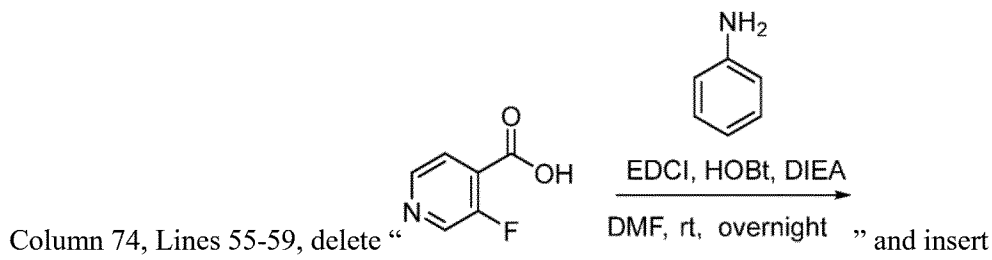 " and insert -- 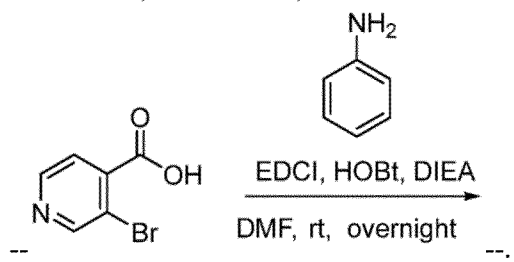 --.

Column 76, Lines 47-53, delete " 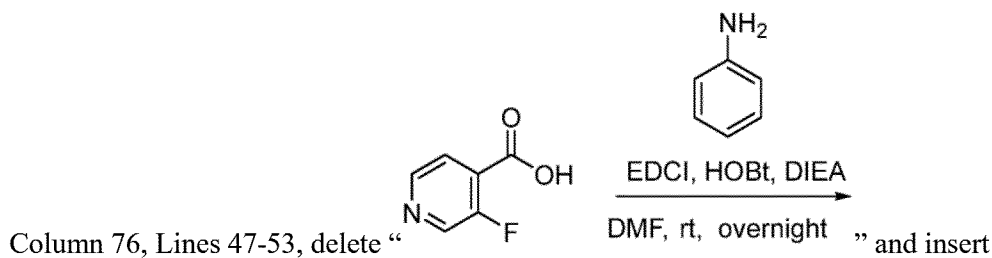 " and insert

Signed and Sealed this
Twelfth Day of September, 2023

Katherine Kelly Vidal
*Director of the United States Patent and Trademark Office*

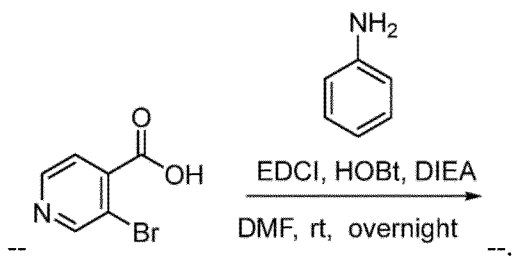
Column 83, Line 66, delete "N,N-iisopropylethylamine" and insert -- N,N-diisopropylethylamine --.
Column 159, Line 21, delete "doxcycyline" and insert -- doxycycline --.
Column 161, Line 5 (Sequence Listing), delete "Artiificial" and insert -- Artificial --.
In the Claims
Column 165, Line 21, Claim 10, after "compound" insert -- of --.
Column 186, Line 43, Claim 17, after "compound" insert -- of --.

SEQUENCE LISTING

```
<160> NUMBER OF SEQ ID NOS: 3

<210> SEQ ID NO 1
<211> LENGTH: 20
<212> TYPE: DNA
<213> ORGANISM: Artiificial Sequence
<220> FEATURE:
<223> OTHER INFORMATION: Synthetic HBV-forward primer

<400> SEQUENCE: 1
gtgtctgcgg cgttttatca                                              20

<210> SEQ ID NO 2
<211> LENGTH: 21
<212> TYPE: DNA
<213> ORGANISM: Artificial Sequence
<220> FEATURE:
<223> OTHER INFORMATION: Synthetic HBV-reverse primer

<400> SEQUENCE: 2
gacaaacggg caacatacct t                                            21

<210> SEQ ID NO 3
<211> LENGTH: 28
<212> TYPE: DNA
<213> ORGANISM: Artificial Sequence
<220> FEATURE:
<223> OTHER INFORMATION: Synthetic HBV-probe
<220> FEATURE:
<221> NAME/KEY: modified_base
<222> LOCATION: 1
<223> OTHER INFORMATION: N=FAM-C
<220> FEATURE:
<221> NAME/KEY: modified_base
<222> LOCATION: 9
<223> OTHER INFORMATION: N=T-ZEN
<220> FEATURE:
```

```
<221> NAME/KEY: modified_base
<222> LOCATION: 28
<223> OTHER INFORMATION: N=C-3IABkFQ

<400> SEQUENCE: 3
nctctkcanc ctgctgctat gcctcatn                                    28
```